US010667501B2

(12) United States Patent
Germaschewski et al.

(10) Patent No.: US 10,667,501 B2
(45) Date of Patent: Jun. 2, 2020

(54) TRANSGENIC NON-HUMAN VERTEBRATE FOR THE IN VIVO PRODUCTION OF DUAL SPECIFICITY IMMUNOGLOBULINS OR HYPERMUTATED HEAVY CHAIN ONLY IMMUNOGLOBULINS

(71) Applicant: Kymab Limited, Cambridge (GB)

(72) Inventors: Volker Germaschewski, Cambridge (GB); E-Chiang Lee, Cambridge (GB); Hanif Ali, Cambridge (GB); Jasper Clube, Cambridge (GB)

(73) Assignee: Kymab Limited, Cambridge (GB)

( * ) Notice: Subject to any disclaimer, the term of this patent is extended or adjusted under 35 U.S.C. 154(b) by 463 days.

(21) Appl. No.: 14/543,359

(22) Filed: Nov. 17, 2014

(65) Prior Publication Data

US 2015/0133641 A1    May 14, 2015

Related U.S. Application Data

(63) Continuation of application No. PCT/GB2013/051280, filed on May 17, 2013.

(30) Foreign Application Priority Data

May 17, 2012   (GB) .................................. 1208708.6

(51) Int. Cl.
    *A01K 67/027*    (2006.01)
    *C12N 15/85*     (2006.01)
    *C07K 16/00*     (2006.01)
    *C07K 16/46*     (2006.01)

(52) U.S. Cl.
    CPC ...... *A01K 67/0278* (2013.01); *A01K 67/0275* (2013.01); *C07K 16/00* (2013.01); *C12N 15/8509* (2013.01); *A01K 2207/15* (2013.01); *A01K 2217/072* (2013.01); *A01K 2217/075* (2013.01); *A01K 2217/15* (2013.01); *A01K 2217/206* (2013.01); *A01K 2227/105* (2013.01); *A01K 2267/01* (2013.01); *C07K 16/462* (2013.01); *C07K 2317/51* (2013.01); *C12N 2015/8518* (2013.01); *C12N 2800/30* (2013.01); *C12N 2800/90* (2013.01)

(58) Field of Classification Search
    CPC .......... A01K 2217/075; A01K 67/0278; A01K 67/0275; A01K 2217/072; A01K 2217/206; A01K 2217/15; A01K 2267/01; A01K 2227/105; A01K 2207/15; C07K 16/00; C07K 16/462; C07K 2317/51; A61K 39/107; C12N 2800/30; C12N 15/8509; C12N 2800/90
    USPC .......... 800/18, 6; 530/387.1, 387.3
    See application file for complete search history.

(56) References Cited

U.S. PATENT DOCUMENTS

| | | |
|---|---|---|
| 4,720,449 A | 1/1988 | Borror et al. |
| 5,169,939 A | 12/1992 | Gefter et al. |
| 5,545,806 A | 8/1996 | Lonberg et al. |
| 5,545,807 A | 8/1996 | Surani et al. |
| 5,565,321 A | 10/1996 | Spriggs et al. |
| 5,633,425 A | 5/1997 | Lonberg et al. |
| 5,770,429 A | 6/1998 | Lonberg et al. |
| 5,789,215 A | 8/1998 | Berns et al. |
| 5,807,715 A | 9/1998 | Morrison et al. |
| 5,939,598 A | 8/1999 | Kucherlapati et al. |
| 5,948,600 A | 9/1999 | Roschger et al. |
| 6,114,598 A | 9/2000 | Kucherlapati et al. |
| 6,130,364 A | 10/2000 | Jakobovits et al. |
| 6,162,963 A | 12/2000 | Kucherlapati et al. |
| 6,319,906 B1 | 11/2001 | Bennett et al. |
| 6,395,487 B1 | 5/2002 | Bradley et al. |
| 6,461,818 B1 | 10/2002 | Bradley et al. |
| 6,596,541 B2 | 7/2003 | Murphy et al. |
| 6,657,103 B1 | 12/2003 | Kucherlapati et al. |
| 6,673,986 B1 | 1/2004 | Kucherlapati et al. |
| 6,713,610 B1 | 3/2004 | Kucherlapati et al. |
| 6,833,268 B1 | 12/2004 | Green et al. |

(Continued)

FOREIGN PATENT DOCUMENTS

| | | |
|---|---|---|
| CA | 2307503 A1 | 11/2001 |
| CA | 2747534 A1 | 6/2010 |

(Continued)

OTHER PUBLICATIONS

Janssen et al., 2006, PNAS (USA) 103:15130-15135.*

(Continued)

*Primary Examiner* — Anne Marie S Wehbe
(74) *Attorney, Agent, or Firm* — Nutter McClennen & Fish LLP

(57) ABSTRACT

The invention relates, in one aspect, generally to novel concept of guided selection of antibody variable domains, combination and expression entirely in vivo. An application is to produce multivalent polypeptides. The present invention relates to multivalent (eg, multispecific) antibodies, antibody chains and polypeptides, as well as heavy chain-only antibodies (H2 antibodies) that are devoid of light chains. The invention further relates to the selection, maturation and production of these in vivo in non-human vertebrates and non-human vertebrate cells. To this end the invention also relates to such non-human vertebrates and cells. The invention also relates to the provision of means to produce and select heavy chain-only antibodies and heavy chains comprising variable domains that have undergone affinity maturation.

6 Claims, 24 Drawing Sheets

Specification includes a Sequence Listing.

(56) References Cited

U.S. PATENT DOCUMENTS

| | | |
|---|---|---|
| 6,914,128 B1 | 7/2005 | Salfeld et al. |
| 6,992,235 B2 | 1/2006 | Bode et al. |
| 6,998,514 B2 | 2/2006 | Bruggemann |
| 7,105,348 B2 | 9/2006 | Murphy et al. |
| 7,119,248 B1 | 10/2006 | Rajewsky et al. |
| 7,205,140 B2 | 4/2007 | Gottschalk et al. |
| 7,205,148 B2 | 4/2007 | Economides et al. |
| 7,294,754 B2 | 11/2007 | Poueymirou et al. |
| 7,435,871 B2 | 10/2008 | Green et al. |
| 7,501,552 B2 | 3/2009 | Lonberg et al. |
| 7,605,237 B2 | 10/2009 | Stevens et al. |
| 7,605,238 B2 | 10/2009 | Korman et al. |
| 7,910,798 B2 | 3/2011 | Tanamach et al. |
| 7,932,431 B2 | 4/2011 | Bruggemann |
| 8,158,419 B2 | 4/2012 | Lonberg et al. |
| 8,502,018 B2 | 8/2013 | Murphy et al. |
| 8,592,644 B2 | 11/2013 | Harriman et al. |
| 8,642,835 B2 | 2/2014 | Macdonald et al. |
| 8,697,940 B2 | 4/2014 | Macdonald et al. |
| 8,754,287 B2 * | 6/2014 | MacDonald ....... A01K 67/0275 800/18 |
| 8,791,323 B2 | 7/2014 | Murphy et al. |
| 8,877,901 B2 | 11/2014 | Govindan |
| 9,253,965 B2 | 2/2016 | Liang et al. |
| 9,434,782 B2 | 9/2016 | Bradley et al. |
| 9,445,581 B2 | 9/2016 | Bradley et al. |
| 9,447,177 B2 | 9/2016 | Bradley et al. |
| 9,504,236 B2 | 11/2016 | Bradley et al. |
| 9,505,827 B2 | 11/2016 | Bradley et al. |
| 9,783,593 B2 | 10/2017 | Bradley et al. |
| 9,783,618 B2 | 10/2017 | Friedrich et al. |
| 9,788,534 B2 | 10/2017 | Bradley et al. |
| 9,896,516 B2 | 2/2018 | Bradley et al. |
| 9,924,705 B2 | 3/2018 | Liang et al. |
| 9,938,357 B2 | 4/2018 | Bradley et al. |
| 9,938,358 B2 | 4/2018 | Bradley et al. |
| 9,963,716 B2 | 5/2018 | Bradley et al. |
| 10,064,398 B2 | 9/2018 | Bradley et al. |
| 10,149,462 B2 | 12/2018 | Lee et al. |
| 10,165,763 B2 | 1/2019 | Bradley et al. |
| 10,226,033 B2 | 3/2019 | Bradley et al. |
| 10,251,377 B2 | 4/2019 | Clube et al. |
| 2002/0088016 A1 | 7/2002 | Bruggemann |
| 2002/0183275 A1 | 12/2002 | Murphy et al. |
| 2003/0108925 A1 | 6/2003 | Dix et al. |
| 2003/0217373 A1 | 11/2003 | Green et al. |
| 2004/0128703 A1 | 7/2004 | Shizuya |
| 2004/0231012 A1 | 11/2004 | Bruggemann |
| 2005/0048621 A1 | 3/2005 | Grasso et al. |
| 2006/0015949 A1 | 1/2006 | Lonberg et al. |
| 2006/0015957 A1 | 1/2006 | Lonberg et al. |
| 2006/0021074 A1 | 1/2006 | Kellermann et al. |
| 2006/0199204 A1 | 9/2006 | Dix et al. |
| 2007/0280945 A1 | 12/2007 | Stevens et al. |
| 2008/0098490 A1 | 4/2008 | Jakobovits et al. |
| 2009/0083870 A1 | 3/2009 | Horn et al. |
| 2009/0083879 A1 | 3/2009 | Dhugga |
| 2009/0093059 A1 | 4/2009 | Baszczynski et al. |
| 2009/0209036 A1 | 8/2009 | Reynaud et al. |
| 2009/0307787 A1 | 12/2009 | Grosveld et al. |
| 2010/0011450 A1 | 1/2010 | Garcia et al. |
| 2010/0069614 A1 | 3/2010 | Houtzager et al. |
| 2010/0146647 A1 | 6/2010 | Logtenberg et al. |
| 2010/0196367 A1 | 8/2010 | Day |
| 2010/0330676 A1 | 12/2010 | Horowitz et al. |
| 2011/0119779 A1 | 5/2011 | Shizuya et al. |
| 2011/0138489 A1 | 6/2011 | Tanamachi et al. |
| 2011/0145937 A1 | 6/2011 | Macdonald et al. |
| 2011/0195454 A1 | 8/2011 | McWhirter et al. |
| 2011/0236378 A1 | 9/2011 | Green et al. |
| 2011/0283376 A1 | 11/2011 | Murphy et al. |
| 2012/0070861 A1 | 3/2012 | Macdonald et al. |
| 2012/0073004 A1 | 3/2012 | Macdonald et al. |
| 2012/0096572 A1 | 4/2012 | Macdonald et al. |
| 2012/0195910 A1 | 8/2012 | Wu et al. |
| 2012/0204278 A1 | 8/2012 | Bradley et al. |
| 2012/0233715 A1 | 9/2012 | Kuroiwa et al. |
| 2012/0322108 A1 | 12/2012 | Macdonald et al. |
| 2013/0039850 A1 | 2/2013 | Lonberg et al. |
| 2013/0096287 A1 | 4/2013 | Macdonald et al. |
| 2013/0102031 A1 | 4/2013 | King et al. |
| 2013/0160153 A1 | 6/2013 | Macdonald et al. |
| 2013/0198879 A1 | 8/2013 | McWhirter et al. |
| 2013/0212719 A1 | 8/2013 | Macdonald et al. |
| 2013/0247235 A1 | 9/2013 | McWhirter et al. |
| 2013/0254911 A1 | 9/2013 | Macdonald et al. |
| 2013/0263293 A1 | 10/2013 | Bradley et al. |
| 2013/0323790 A1 | 12/2013 | Macdonald et al. |
| 2013/0323791 A1 | 12/2013 | Macdonald et al. |
| 2013/0326647 A1 | 12/2013 | Macdonald et al. |
| 2013/0333057 A1 | 12/2013 | Macdonald et al. |
| 2014/0017228 A1 | 1/2014 | Macdonald et al. |
| 2014/0041067 A1 | 2/2014 | Bradley et al. |
| 2014/0120582 A1 | 5/2014 | Bradley et al. |
| 2014/0130193 A1 | 5/2014 | Macdonald et al. |
| 2014/0130194 A1 | 5/2014 | Macdonald et al. |
| 2014/0137275 A1 | 5/2014 | Macdonald et al. |
| 2014/0150125 A1 | 5/2014 | Bradley et al. |
| 2014/0150126 A1 | 5/2014 | Bradley et al. |
| 2014/0182003 A1 | 6/2014 | Bradley et al. |
| 2014/0201854 A1 | 7/2014 | Bradley et al. |
| 2014/0201856 A1 | 7/2014 | Bradley et al. |
| 2014/0212416 A1 | 7/2014 | Friedrich et al. |
| 2014/0213773 A1 | 7/2014 | Macdonald et al. |
| 2014/0283150 A1 | 9/2014 | Bradley et al. |
| 2014/0323327 A1 | 10/2014 | Bradley et al. |
| 2014/0325690 A1 | 10/2014 | Bradley et al. |
| 2014/0331339 A1 | 11/2014 | Bradley et al. |
| 2014/0331343 A1 | 11/2014 | Bradley et al. |
| 2014/0331344 A1 | 11/2014 | Friedrich et al. |
| 2014/0359797 A1 | 12/2014 | Bradley et al. |
| 2015/0033369 A1 | 1/2015 | Bradley et al. |
| 2015/0033372 A1 | 1/2015 | Bradley et al. |
| 2015/0037337 A1 | 2/2015 | Friedrich et al. |
| 2015/0040250 A1 | 2/2015 | Bradley et al. |
| 2015/0082466 A1 | 3/2015 | Clube |
| 2015/0113669 A1 | 4/2015 | Bradley et al. |
| 2015/0133641 A1 | 5/2015 | Germaschewski et al. |
| 2015/0196015 A1 | 7/2015 | Macdonald et al. |
| 2015/0334998 A1 | 11/2015 | Bradley et al. |
| 2016/0044900 A1 | 2/2016 | Bradley et al. |
| 2016/0150768 A1 | 6/2016 | Bradley et al. |
| 2016/0219846 A1 | 8/2016 | Liang |
| 2016/0249592 A1 | 9/2016 | Bradley et al. |
| 2016/0345551 A1 | 12/2016 | Bradley et al. |
| 2016/0345552 A1 | 12/2016 | Bradley et al. |
| 2016/0353719 A1 | 12/2016 | Friedrich et al. |
| 2017/0051045 A1 | 2/2017 | Bradley et al. |
| 2017/0071174 A1 | 3/2017 | Bradley et al. |
| 2017/0081423 A1 | 3/2017 | Bradley et al. |
| 2017/0094956 A1 | 4/2017 | Bradley et al. |
| 2017/0096498 A1 | 4/2017 | Bradley et al. |
| 2017/0099815 A1 | 4/2017 | Bradley et al. |
| 2017/0099816 A1 | 4/2017 | Bradley et al. |
| 2017/0099817 A1 | 4/2017 | Bradley et al. |
| 2017/0101482 A1 | 4/2017 | Bradley et al. |
| 2017/0101483 A1 | 4/2017 | Bradley et al. |
| 2017/0105396 A1 | 4/2017 | Bradley et al. |
| 2017/0135327 A1 | 5/2017 | Lee |
| 2017/0320936 A1 | 11/2017 | Bradley et al. |
| 2017/0354131 A1 | 12/2017 | Bradley et al. |
| 2018/0030121 A1 | 2/2018 | Bradley et al. |

FOREIGN PATENT DOCUMENTS

| | | |
|---|---|---|
| CA | 2820824 A1 | 2/2012 |
| DE | 10251918 A1 | 5/2004 |
| EP | 1780272 A1 | 5/2007 |
| EP | 0937140 B1 | 9/2007 |
| EP | 2517557 A2 | 10/2012 |
| EP | 2147594 A1 | 11/2013 |
| EP | 2480676 B1 | 4/2016 |
| GB | 2398784 A | 9/2004 |
| GB | 2403475 A | 1/2005 |

(56) References Cited

FOREIGN PATENT DOCUMENTS

| | | |
|---|---|---|
| JP | 2004524841 A | 8/2004 |
| JP | 2005510253 A | 4/2005 |
| JP | 2008507257 A | 3/2008 |
| JP | 2010512749 A | 4/2010 |
| JP | 2012521211 A | 9/2012 |
| KR | 20050042792 A | 5/2005 |
| WO | WO-9004036 A1 | 4/1990 |
| WO | WO-9100906 A1 | 1/1991 |
| WO | WO-9110741 A1 | 7/1991 |
| WO | WO-1992003918 A1 | 3/1992 |
| WO | WO-9312227 A1 | 6/1993 |
| WO | WO-9402602 A1 | 2/1994 |
| WO | WO-9404667 A1 | 3/1994 |
| WO | WO-9425585 A1 | 11/1994 |
| WO | WO-9630498 A1 | 10/1996 |
| WO | WO-9824884 A1 | 6/1998 |
| WO | WO-9824893 A2 | 6/1998 |
| WO | WO-9945962 A1 | 9/1999 |
| WO | WO-0026373 A1 | 5/2000 |
| WO | WO-200071585 | 11/2000 |
| WO | WO-0208409 A2 | 1/2002 |
| WO | WO-0236789 A2 | 5/2002 |
| WO | WO-0243478 A2 | 6/2002 |
| WO | WO-0253596 A2 | 7/2002 |
| WO | WO-02059263 A2 | 8/2002 |
| WO | WO-02066630 A1 | 8/2002 |
| WO | WO-02070648 A2 | 9/2002 |
| WO | WO-03006639 A1 | 1/2003 |
| WO | WO-03047336 A2 | 6/2003 |
| WO | WO-03061363 A2 | 7/2003 |
| WO | WO-2004044150 A2 | 5/2004 |
| WO | WO-2004050838 A2 | 6/2004 |
| WO | WO-2005003364 A2 | 1/2005 |
| WO | WO-2005004592 A2 | 1/2005 |
| WO | WO-2005019463 A1 | 3/2005 |
| WO | WO-2005058815 A2 | 6/2005 |
| WO | WO-2005092926 A2 | 10/2005 |
| WO | WO-2006008548 A2 | 1/2006 |
| WO | WO-2006029459 A1 | 3/2006 |
| WO | WO-2006044492 A2 | 4/2006 |
| WO | WO-2006055704 A2 | 5/2006 |
| WO | WO-2006068953 A2 | 6/2006 |
| WO | WO-2006117699 A2 | 11/2006 |
| WO | WO-2006122442 A1 | 11/2006 |
| WO | 2007/096779 A2 † | 8/2007 |
| WO | WO-2007085837 A1 | 8/2007 |
| WO | WO-2007096779 A2 | 8/2007 |
| WO | WO-2007117410 A2 | 10/2007 |
| WO | WO-2007143168 A2 | 12/2007 |
| WO | WO-2008022391 A1 | 2/2008 |
| WO | WO-2008054606 A2 | 5/2008 |
| WO | WO-2008070367 A2 | 6/2008 |
| WO | WO-2008076379 A2 | 6/2008 |
| WO | WO-2008081197 A1 | 7/2008 |
| WO | WO-2008094178 A2 | 8/2008 |
| WO | WO-2008103474 A1 | 8/2008 |
| WO | WO-2008108918 | 9/2008 |
| WO | 2008/122886 A2 † | 10/2008 |
| WO | WO-2008118970 A2 | 10/2008 |
| WO | WO-2008122886 A2 | 10/2008 |
| WO | WO-2008151081 A1 | 12/2008 |
| WO | WO-2009013620 A2 | 1/2009 |
| WO | WO-2009018411 A1 | 2/2009 |
| WO | WO-2009023540 A1 | 2/2009 |
| WO | WO-2009076464 A2 | 6/2009 |
| WO | WO-2009080254 A1 | 7/2009 |
| WO | WO-2009097006 A2 | 8/2009 |
| WO | WO-2009118524 A2 | 10/2009 |
| WO | WO-2009129247 A2 | 10/2009 |
| WO | WO-2009143472 A2 | 11/2009 |
| WO | WO-2009157771 A2 | 12/2009 |
| WO | WO-2010039900 A2 | 4/2010 |
| WO | WO-2010070263 A1 | 6/2010 |
| WO | WO-2010077854 A1 | 7/2010 |
| WO | 2010/097385 A1 † | 9/2010 |
| WO | WO-2010097385 A1 | 9/2010 |
| WO | WO-2010109165 A2 | 9/2010 |
| WO | WO-2010113039 A1 | 10/2010 |
| WO | WO-2011004192 A | 1/2011 |
| WO | WO-2011008093 A1 | 1/2011 |
| WO | WO-2011014469 A1 | 2/2011 |
| WO | WO-2011056864 A1 | 5/2011 |
| WO | WO-2011062206 A1 | 5/2011 |
| WO | WO-2011062207 A1 | 5/2011 |
| WO | WO-2011071957 A1 | 6/2011 |
| WO | WO-2011072204 A1 | 6/2011 |
| WO | WO-2011097603 A1 | 8/2011 |
| WO | WO-2011146121 A1 | 11/2011 |
| WO | WO-2011158009 A1 | 12/2011 |
| WO | WO-2011163311 A1 | 12/2011 |
| WO | WO-2011163314 A1 | 12/2011 |
| WO | WO-2012018764 A1 | 2/2012 |
| WO | WO-2012023053 A2 | 2/2012 |
| WO | WO-2012064682 A1 | 5/2012 |
| WO | WO-2012141798 A1 | 10/2012 |
| WO | WO-2012148873 A2 | 11/2012 |
| WO | WO-2013022782 A1 | 2/2013 |
| WO | WO-2013041844 A2 | 3/2013 |
| WO | WO-2013041845 A2 | 3/2013 |
| WO | WO-2013041846 A2 | 3/2013 |
| WO | WO-2013045916 A1 | 4/2013 |
| WO | WO-2013059230 A1 | 4/2013 |
| WO | WO-2013061078 A1 | 5/2013 |
| WO | WO-2013061098 A2 | 5/2013 |
| WO | WO-2013079953 A1 | 6/2013 |
| WO | WO-2013096142 A1 | 6/2013 |
| WO | WO-2013116609 A1 | 8/2013 |
| WO | WO-2013130981 A1 | 9/2013 |
| WO | WO-2013134263 A1 | 9/2013 |
| WO | WO-2013144567 A1 | 10/2013 |
| WO | WO-2013166236 A1 | 11/2013 |
| WO | WO-2013171505 A2 | 11/2013 |
| WO | WO-2013176772 A1 | 11/2013 |
| WO | WO-2014093622 A2 | 6/2014 |
| WO | WO-2014130690 A1 | 8/2014 |
| WO | WO-2015049517 A2 | 4/2015 |
| WO | WO-2019008123 A2 | 1/2019 |

OTHER PUBLICATIONS

Martensson et al 2007, Current Opin. Immunol. 19:137-142.*
Muramatsu et al. (1999) J. Biol. Chem., vol. 274, 2868-2876.*
1st International MUGEN Conference on Animal Models for Human Immunological Disease, Sep. 10-13, 2006—Athens Greece (Abstracts 1-52), 52 pages.
Adams D.J., et al., "A Genome-Wide, End-Sequenced 129Sv BAC Library Resource for Targeting Vector Construction," Genomics, 2005, vol. 86 (6), pp. 753-758.
Adams D.J., et al., "Contemporary approaches for modifying the mouse genome," Physiological Genomics, vol. 34, 2008, pp. 225-238.
Adams D.J., et al., "Mutagenic Insertion and Chromosome Engineering Resource (MICER)," Nature Genetics, vol. 36 (8), Aug. 2004, pp. 867-871.
Affidavits Evidencing Murphy Slides as Printed Publication, dated Jun. 20, 2016, 84 pages.
Aguilera R.J., et al., "Characterization of immunoglobulin enhancer deletions in murine plasmacytomas," The EMBO Journal, 1985, vol. 4 (13B), pp. 3689-3693.
Ahmed T., "Sanofi-aventis and Regeneron Extend Therapeutic Antibody Agreement," PharmaDeals Review, Nov. 2009, vol. 11, p. 115.
Arnaout R., et al., "High-Resolution Description of Antibody Heavy-Chain Repertoires in Humans," PLoS One, Aug. 2011, vol. 6 (8), pp. e22365-1-e22365-8.
Arthur J.S.C., et al., "Gene-Targeting Vectors," Transgenesis Techniques, Principles and Protocols, Third edition, Chapter 9, 2009 (24 pages, including cover sheet, copyright and preface pages and table of contents), pp. 127-144.
Asenbauer H., et al., "The immunoglobulin lambda light chain enhancer consists of three modules which synergize in activation of transcription," European Journal of Immunology, 1999, vol. 29, pp. 713-724.

(56) References Cited

OTHER PUBLICATIONS

Askew G.R., et al., "Site-Directed Point Mutations in Embryonic Stem Cells: A Gene-Targeting Tag-and-Exchange Strategy," *Molecular and Cellular Biology*, Jul. 1993, vol. 13 (7), pp. 4115-4124.
Atlas of Genetics and Cytogenetics in Oncology and Haematology, VPREB1 (pre-B lymphocyte 1), 5 pages. [Retrieved online at http://atlasgeneticsoncolgy.org/Genes/GC_VPREB1.html on May 25, 2015].
Auerbach W., et al., "Establishment and Chimera Analysis of 129/SvEv- and C57BL/6-Derived Mouse Embryonic Stem Cell Lines," *BioTechniques*, 2000, vol. 29 (5), pp. 1024-1032.
Avery S., Attorney for Applicant, Third-Party Pre-Issuance Submission Under 37 CFR Section 1.290 in U.S. Appl. No. 14/517,755, dated Jun. 26, 2015, 16 pages.
Baer A., et al., "Coping with kinetic and thermodynamic barriers: RMCE, an efficient strategy for the targeted integration of transgenes," *Current Opinions in Biotechnology*, Oct. 2001, vol. 12 (5), pp. 473-480.
Baker A.M., et al., "Adaptation of TCR Expression Vectors for the Construction of Mouse-Human Chimeric MBP-Specific TCR Transgenes," *Journal of Neuroscience Research*, 1996, vol. 45 (4), pp. 487-491.
Baker M.D., et al., "Homologous Recombination Between Transferred and Chromosomal Immunoglobulin Kappa Genes," *Molecular and Cellular Biology*, Oct. 1988, vol. 8 (10), pp. 4041-4047.
Barreto V.M., et al., "AID from bony fish catalyzes class switch recombination," *Journal of Experimental Medicine*, 2005, vol. 202 (6), pp. 733-738.
Bates J.G., et al., "Chromosomal Position of a $V_H$ Gene Segment Determines its Activation and Inactivation as a Substrate for V(D)J Recombination," *Journal of Experimental Medicine*, 2007, vol. 204 (13), pp. 3247-3256.
Beard C., et al., "Efficient Method to Generate Single-Copy Transgenic Mice by Site-Specific Integration in Embryonic Stem Cells," *Genesis*, 2006, vol. 44 (1), pp. 23-28.
Beck E., et al., "Nucleotide Sequence and Exact Localization of the Neomycin Phosphotransferase Gene From Transposon Tn5," *Genesis*, 1982, vol. 19 (3), pp. 327-336.
Beck J.A., et al., "Genealogies of mouse inbred strains," *Nature Genetics*, 2000, vol. 24, pp. 23-25 (with supporting table and chart).
Beerli R.R., et al., "Mining Human Antibody Repertoires," *mAbs*, Jul./Aug. 2010, vol. 2 (4), pp. 365-378.
Bentham, A., Attorneys for Regeneron Pharmaceuticals, Inc., Opposition against EP2421357B1 in the name of Kymab Ltd. pertaining to Application No. 10734546.4, dated Jan. 9, 2017, 13 pages.
Berg D.E., et al., "Inverted Repeats of Tn5 are Transposable Elements," *Proceedings of the National Academy of Sciences U.S.A*, 1982, vol. 79 (8), pp. 2632-2635.
Bethke B., et al., "Segmental Genomic Replacement by Cre-Mediated Recombination: Genotoxic Stress Activation of the p53 Promoter in Single-Copy Transformants," *Nucleic Acids Research*, 1997, vol. 25 (14), pp. 2828-2834.
Bhattacharya P., et al., "Switch Region Identity Plays an Important Role in Ig Class Switch Recombination," *Journal of Immunology*, 2010, vol. 184 (11), pp. 6242-6248.
Billiard F., et al., "Ongoing DII4-Notch Signaling is Required for T-Cell Homeostasis in the Adult Thymus," *European Journal of Immunology*, 2011, vol. 41 (8), pp. 2207-2216.
Birling M.C., et al., "Site-Specific Recombinases for Manipulation of the Mouse Genome," *Transgenesis Techniques, Principles and Protocols*, Third edition, Chapter 16, 2009 (25 pages, including cover sheet, copyright and preface pages and table of contents), pp. 245-263.
Blankenstein T., et al., "Immunoglobulin $V_H$ Region Genes of the Mouse are Organized in Overlapping Clusters," *European Journal of Immunology*, 1987, vol. 17 (9), pp. 1351-1357.
Board of Appeal of the European Patent Office, Datasheet for the Decision of Nov. 9, 2015 for Application No. 02709544.7, Case T 2220/14-3.3.08, 83 pages.
Bode J., et al., "The Transgeneticist's Toolbox: Novel Methods for the Targeted Modification of Eukaryotic Genomes," *Biological Chemistry*, Sep./Oct. 2000, vol. 381 (9-10), pp. 801-813.
Bogen B., et al., "A Rearranged $\lambda_2$ Light Gene Chain Retards but does not Exclude x and $\lambda_1$ Expression," *European Journal of Immunology*, 1991, vol. 21 (10), pp. 2391-2395.
Bolland D.J., et al., "Antisense Intergenic Transcription Precedes Igh D-To-J Recombination and is Controlled by the Intronic Enhancer Eμ," *Molecular and Cellular Biology*, 2007, vol. 27 (15), pp. 5523-5533.
Bonin A., et al., "Isolation, Microinjection, and Transfer of Mouse Blastocysts," *Methods in Molecular Biology*, Chapter 9, 2001, vol. 158, pp. 121-134.
Bornstein, G.G. et al., "Development of a new fully human anti-CD20 monoclonal antibody for the treatment of B-cell malignancies", *Investigational New Drugs*, 2010, vol. 28, pp. 561-574.
Bottaro A., et al., "Deletion of the IgH Intronic Enhancer and Associated Matrix-Attachment Regions Decreases, but does not Abolish, Class Switching at the μ Locus," *International Immunology*, 1998, vol. 10 (6), pp. 799-806.
Bradley A., et al., "Formation of Germ-Line Chimaeras from Embryo-Derived Teratocarcinoma Cell Lines," *Nature*, 1984, vol. 309 (5965), pp. 255-256.
Bransteitter R., et al., "Activation-Induced Cytidine Deaminase Deaminates Deoxycytidine on Single-Stranded DNA but Requires the Action of RNase," *Proceedings of the National Academy of Sciences of the U.S.A.*, Apr. 2003, vol. 100 (7), pp. 4102-4107.
Brault V., et al., "Modeling Chromosomes in Mouse to Explore the Function of Genes, Genomic Disorders, and Chromosomal Organization," *PLoS Genetics*, Jul. 2006, vol. 2 (7), pp. e86-1-e86-9.
Breden F., et al., "Comparison of Antibody Repertoires Produced by HIV-1 Infection, Other Chronic and Acute Infections, and Systemic Autoimmune Disease," *PLoS One*, 2011, vol. 6 (3), pp. e16857.
Brezinschek H.P., et al., "Analysis of the Human $V_H$ Gene Repertoire," *Journal of Clinical Investigation*, 1997, vol. 99 (10), pp. 2488-2501.
Brüggemann M., et al., "A Repertoire of Monoclonal Antibodies with Human Heavy Chains from Transgenic Mice," *Proceedings of the National Academy of Sciences U.S.A*, 1989, vol. 86 (17), pp. 6709-6713.
Brüggemann M., et al., Human Antibody Production in Transgenic Mice: Expression from 100 kb of the Human IgH Locus, *European Journal of Immunology*, May 1991, vol. 21 (5), pp. 1323-1326.
Brüggemann M., et al., "Immunoglobulin Heavy Chain Locus of the Rat: Striking Homology to Mouse Antibody Genes," *Proceedings of the National Academy of Sciences U.S.A*, 1986, vol. 83 (16), pp. 6075-6079.
Brüggemann M., et al., "The Immunogenicity of Chimeric Antibodies," *The Journal of Experimental Medicine*, Dec. 1989, vol. 170 (6), pp. 2153-2157.
Brüggemann M., et al., "Strategies for Expressing Human Antibody Repertoires in Transgenic Mice," *Immunology Today*, Aug. 1996, vol. 17 (8), pp. 391-397.
Brüggemann M., "Human Antibody Expression in Transgenic Mice," *Archivum Immunologiae et Therapia Experimentalis*, 2001, vol. 49 (3), pp. 203-208.
Brüggemann M., "Human Monoclonal Antibodies from Translocus Mice," *Molecular Biology of B Cells*, Chapter 34, 2003, pp. 547-561.
Briney B.S., et al., "Human Peripheral Blood Antibodies with Long HCDR3s are Established Primarily at Original Recombination using a Limited Subset of Germline Genes," *PLoS One*, 2012, vol. 7 (5), pp. e36750-1-e36750-13.
Brocker C.N., et al., "Evolutionary Divergence and Functions of the *ADAM* and *ADAMTS* Gene Families," *Human Genomics*, 2009, vol. 4 (1), pp. 43-55.
Buehr M., et al., "Capture of Authentic Embryonic Stem Cells from Rat Blastocysts," *Cell*, 2008, vol. 135 (7), pp. 1287-1298.
Butler J.E., "Immunoglobulin Diversity, B-Cell and Antibody Repertoire Development in Large Farm Animals," *Revue scientifique et technique (International Office of Epizootics)*, 1998, vol. 17 (7), pp. 43-70.

(56) References Cited

OTHER PUBLICATIONS

Cadiñanos J., et al., "Generation of an Inducible and Optimized PiggyBac Transposon System," *Nucleic Acids Research*, 2007, vol. 35 (12), pp. e87.
Call L.M., et al., "A Cre-lox recombination system for the targeted integration of circular yeast artificial chromosomes into embryonic stem cells," *Human Molecular Genetics*, 2000, vol. 9 (12), pp. 1745-1751.
Carstea A.C., et al., "Germline Competence of Mouse ES and iPS Cell Lines: Chimera Technologies and Genetic Background," *World Journal of Stem Cells*, 2009, vol. 1 (1), pp. 22-29.
Carter T.C., et al., "Standardized Nomenclature for Inbred Strains of Mice," *Cancer Research*, 1952, vol. 12 (8), pp. 602-613.
Casrouge A., et al., "Size Estimate of the $\alpha\beta$ TCR Repertoire of Naive Mouse Splenocytes," *The Journal of Immunology*, 2000, vol. 164 (11), pp. 5782-5787.
Chan A.C., et al., "Therapeutic Antibodies for Autoimmunity and Inflammation," *Nature Reviews Immunology*, 2010, vol. 10 (5), pp. 301-316.
Chen C., et al., "Immunoglobulin Heavy Chain Gene Replacement: A Mechanism of Receptor Editing," *Immunity*, 1995, vol. 3 (6), pp. 747-755.
Chen J., et al., "B Cell Development in Mice that Lack One or Both Immunoglobulin $\kappa$ Light Chain Genes," *The EMBO Journal*, 1993, vol. 12 (3), pp. 821-830.
Chen Y., "PiggyBac Transposon-Mediated, Reversible Gene Transfer in Human Embryonic Stem Cells," *Stem Cells and Development*, Nov. 2010, vol. 19 (6), 9 pages.
Chia R., et al., "The origins and uses of mouse outbred stocks," *Nature Genetics*, 2005, vol. 37 (11), pp. 1181-1186.
Chinese Patent Office, First Office Action (English Translation) for Chinese Application No. 201180039668.1, dated Jan. 3, 2014, 6 pages.
Chinese Patent Office, First Office Action for Chinese Patent Application No. 201180039668.1, dated Jan. 3, 2014, 6 pages.
Chinese Patent Office, Office Action (English Translation) for Chinese Patent Application No. 201380029744.1, dated Nov. 10, 2016, 2 pages.
Chinese Patent Office, Office Action for Chinese Patent Application No. 201380027944.1, dated Nov. 10, 2016, 5 pages.
Chinese Patent Office, Search Report (English Translation), Chinese Patent Application No. 201180039668.1, dated Jan. 3, 2014, 2 pages.
Chinese Patent Office, Search Report, Chinese Patent Application No. 201180039668.1, dated Jan. 3, 2014, 1 page.
Cho C., "Testicular and Epididymal ADAMs: Expression and Function During Fertilization," *Nature Reviews Urology*, 2012, vol. 9 (10), pp. 550-560.
Choi I., et al., "Characterization and Comparative Genomic Analysis of Intronless Adams with Testicular Gene Expression," *Genomics*, 2004, vol. 83 (4), pp. 636-646.
Clark J ., et al., "A Future for Transgenic Livestock," *Nature Reviews Genetics*, 2003, vol. 4 (10), pp. 825-833.
Clark L.A., et al., "Trends in Antibody Sequence Changes During the Somatic Hypermutation Process," *The Journal of Immunology*, 2006, vol. 177 (1), pp. 333-340.
Clark M.R., "IgG Effector Mechanisms," *Chemical Immunology*, 1997, vol. 65, pp. 88-110.
Colbère-Garapin F., et al., "A New Dominant Hybrid Selective Marker for Higher Eukaryotic Cells," *Journal of Molecular Biology*, 1981, vol. 150 (1), pp. 1-14.
Collins F.S., et al., "A Mouse for All Reasons," *Cell*, 2007, vol. 128 (1), pp. 9-13.
Collins A.M., et al., "The reported germline repertoire of human immunoglobulin kappa chain genes is relatively complete and accurate," *Immunogenetics*, 2008, vol. 60, pp. 669-676.
Combriato G., et al., "Regulation of Human Ig$\lambda$ Light Chain Gene Expression by NF-$\kappa$B1," *The Journal of Immunology*, 2002, vol. 168 (3), pp. 1259-1266.

Conrath K., et al., "Camel Single-domain Antibodies as Modular Building Units in Bispecific and Bivalent Antibody Constructs," *The Journal of Biological Chemistry*, 2001, vol. 276 (10), pp. 7346-7350.
Copeland N.G., et al., "Recombineering: A Powerful New Tool for Mouse Functional Genomics," *Nature Reviews Genetics*, 2001, vol. 2 (10), pp. 769-779.
Corbett S.J., et al., "Sequence of the Human Immunoglobulin Diversity (D) Segment Locus: A Systematic Analysis Provides No Evidence for the Use of DIR Segments, Inverted D Segments, "Minor" D Segments or D-D Recombination," *Journal of Molecular Biology*, 1997, vol. 270 (4), pp. 587-597.
Corti D., et al., "A Neutralizing Antibody Selected from Plasma Cells that Binds to Group 1 and Group 2 Influenza A Hemagglutinins," *Science*, 2011, vol. 333 (6044), pp. 850-856.
Crouch E.E., et al., "Regulation of AID expression in the Immune Response," *Journal of Experimental Medicine*, May 2007, vol. 204 (5), pp. 1145-1156.
Cuesta A.M., et al., "Multivalent Antibodies: When Design Surpasses Evolution," *Trends in Biotechnology*, 2010, vol. 28 (7), pp. 355-362.
Davies N.P., et al., "Creation of Mice Expressing Human Antibody Light Chains by Introduction of a Yeast Artificial Chromosome Containing the Core Region of the Human Immunoglobulin $\kappa$ Locus," *Nature Biotechnology*, Aug. 1993, vol. 11 (8), pp. 911-914.
De Bono B., et al., "$V_H$ Gene Segments in the Mouse and Human Genomes," *Journal of Molecular Biology*, 2004, vol. 342 (1), pp. 131-143.
De Kruif J., et al., "Human Immunoglobulin Repertoires Against Tetanus Toxoid Contain a Large and Diverse Fraction of High-Affinity Promiscuous $V_H$ Genes," *Journal of Molecular Biology*, 2009, vol. 387 (3), pp. 548-558.
De Saint Vincent B.R., et al., "Homologous Recombination in Mammalian Cells Mediates Formation of A Functional Gene from Two Overlapping Gene Fragments," *Proceedings of the National Academy of Sciences of the U.S.A*, 1983, vol. 80 (7), pp. 2002-2006.
De Wildt R.M.T., et al., "Analysis of Heavy and Light Chain Pairings Indicates that Receptor Editing Shapes the Human Antibody Repertoire," *Journal of Molecular Biology*, 1999, vol. 285, pp. 895-901.
Dechiara T.M., et al., "Producing Fully ES Cell-Derived Mice from Eight-Cell Stage Embryo Injections," *Methods in Enzymology*, Chapter 16, 2010, vol. 476, pp. 285-294.
Dechiara T.M., et al., "VelociMouse: Fully ES Cell-Derived F0-Generation Mice Obtained from the Injection of ES Cells into Eight-Cell-Stage Embryos," *Methods in Molecular Biology*, Chapter 16, 2009, vol. 530, pp. 311-324.
Declerck P.J., et al., "Generation of Monoclonal Antibodies against autologous Proteins in Gene-inactivated Mice," *The Journal of Biological Chemistry*, Apr. 1995, vol. 270 (15), pp. 8397-8400.
Deftos, M., et al., "Defining the Genetic Origins of Three Rheumatoid Synovium-derived IgG Rheumatoid Factors," *Journal of Clinical Investigations*, Jun. 1994, vol. 93, pp. 2545-2553.
Deng C., et al., "Reexamination of Gene Targeting Frequency as a Function of the Extent of Homology Between the Targeting Vector and the Target Locus," *Molecular and Cellular Biology*, Aug. 1992, vol. 12 (8), pp. 3365-3371.
Denome R.M., et al., "Patterns of Polyadenylation Site Selection in Gene Constructs Containing Multiple Polyadenylation Signals," *Molecular and Cellular Biology*, 1988, vol. 8 (11), pp. 4829-4839.
Di Noia, J.M., et al., "Molecular Mechanisms of Antibody Somatic Hypermutation," *Annual Review of Biochemistry*, 2007, vol. 76, pp. 1-22.
Diez-Roux G., et al., "A High-Resolution Anatomical Atlas of the Transcriptome in the Mouse Embryo," *PLoS Biology*, 2011, vol. 9 (1), pp. 1-13.
Ding L., et al., "Generation of High-Affinity Fully Human Anti-Interleukin-8 Antibodies from its cDNA by Two-Hybrid Screening and Affinity Maturation in Yeast," *Protein Science*, 2010, vol. 9 (10), pp. 1957-1966.
Doetschman T., et al., "Establishment of Hamster Blastocyst-Derived Embryonic Stem (ES) Cells," *Developmental Biology*, 1988, vol. 127 (1), pp. 224-227.

(56) References Cited

OTHER PUBLICATIONS

Doetschman T., et al., "Targeted Mutation of the Hprt Gene in Mouse Embryonic Stem Cells," *Proceedings of the National Academy of Sciences of the U.S.A*, 1988, vol. 85 (22), pp. 8583-8587.
Donohoe M.E., et al., "Transgenic Human λ5 Rescues the Murine λ5 Nullizygous Phenotype," *Journal of Immunology*, 2000, vol. 164, pp. 5269-5276.
Doyle A., et al., "The Construction of Transgenic and Gene Knockout/Knockin Mouse Models of Human Disease," *Transgenic Research*, 2012, vol. 21 (2), pp. 327-349.
Durbin R., "A Map of Human Genome Variation from Population-Scale Sequencing," *Nature*, 1000 Genomes Project Consortium, 2010, vol. 467 (7319), pp. 1061-1073.
Durdik J., et al., "Isotype Switching by a Microinjected μ Immunoglobulin Heavy Chain Gene in Transgenic Mice," *Proceedings of the National Academy of Sciences of the U.S.A*, 1989, vol. 86 (7), pp. 2346-2350.
Ebert A., et al., "The Distal $V_H$ Gene Cluster of the Igh Locus Contains Distinct Regulatory Elements with Pax5 Transcription Factor-Dependent Activity in Pro-B Cells," *Immunity*, Feb. 2011, vol. 34 (2), pp. 175-187.
Edwards D.R., et al., "The ADAM Metalloproteinases," *Molecular Aspects of Medicine*, 2008, vol. 29 (5), pp. 258-289.
Eisener-Dorman A.F., et al., "Cautionary Insights on Knockout Mouse Studies: The Gene or not the Gene?," *Brain, Behavior, and Immunity*, 2009, vol. 23 (3), pp. 318-324.
Ekiert D.C., et al., "A Highly Conserved Neutralizing Epitope on Group 2 Influenza A Viruses," *Science*, 2011, vol. 333 (6044), pp. 843-850.
Engel H., et al., "Expression level of a transgenic λ2 chain results in isotype exclusion and commitment to B1 cells," *European Journal of Immunology*, 1998, vol. 28, pp. 2289-2299.
European Patent Office, Alessandro Brero, Authorized officer, International Search Report for Application No. PCT/GB2012/052296, dated May 17, 2013, 30 pages, together with the Written Opinion of the International Searching Authority.
European Patent Office, Alessandro Brero, Authorized officer, International Search Report for Application No. PCT/GB2012/052297, dated Jun. 19, 2013, 24 pages, together with the Written Opinion of the International Searching Authority.
European Patent Office, Alessandro Brero, Authorized Officer, International Search Report for Application No. PCT/GB2012/052298, dated Jun. 13, 2013, 21 pages, together with the Written Opinion of the International Searching Authority.
European Patent Office, Alessandro Brero, Examiner, Examination Report for Application No. 12762378.3, dated Jun. 8, 2016, 5 pages.
European Patent Office, Alessandro Brero, Examiner, Extended European Search Report for Application No. 16189625.3, dated Nov. 23, 2016, 8 pages.
European Patent Office, Communication pursuant to Rule 114(2) EPC regarding 14772198.9, dated Mar. 30, 2016, 16 pages.
European Patent Office, Laurent Deleu, Examiner, European Search Report for Application No. 12194977.0, dated Jul. 5, 2013, 4 pages.
European Patent Office, F. Chambonnet, Authorized officer, International Search Report for Application No. PCT/GB2012/052380, dated Jan. 3, 2013, 17 pages, together with the Written Opinion of the International Searching Authority.
European Patent Office, Gaby Brouns, Authorized officer, International Search Report for Application No. PCT/GB2012/052956, dated Mar. 1, 2013, 14 pages, together with the Written Opinion of the International Searching Authority.
European Patent Office, Gaby Brouns, Authorized officer, International Search Report for Application No. PCT/GB2012/052960, dated Apr. 29, 2013, 19 pages, together with the Written Opinion of the International Searching Authority.
European Patent Office, Gaby Brouns, Authorized officer, International Search Report for Application No. PCT/GB2013/050682, dated Sep. 25, 2013, 16 pages, together with the Written Opinion of the International Searching Authority.
European Patent Office, Gaby Brouns, Authorized officer, International Search Report for Application No. PCT/GB2013/050683, dated Jul. 9, 2013, 11 pages, together with the Written Opinion of the International Searching Authority.
European Patent Office, Gaby Brouns, Authorized officer, International Search Report for Application No. PCT/GB2013/051280, dated Nov. 15, 2013, 19 pages, together with the Written Opinion of the International Searching Authority.
European Patent Office, Extended European Search Report for Application No. 15188522.5 dated Feb. 2, 2016, 15 pages.
European Patent Office, Examination Report for Application No. 12795841.1, dated Feb. 12, 2016, 5 pages.
European Patent Office, Examination Report for Application No. 13711119.1, dated Dec. 17, 2015, 6 pages.
European Patent Office, Examination Report for Application No. 13711119.1, dated Jul. 13, 2016, 6 pages.
European Patent Office, International Searching Authority, Examiners Report on Allowable Claims for Application No. PCT/GB2010/051122, Jan. 2004, 1 page.
European Patent Office, Examination Report for Application No. 12778780.2, dated Oct. 14, 2016, 3 pages.
European Patent Office, Extended European Search Report for Application No. 14196645.7, dated Jun. 26, 2015, 12 pages.
European Patent Office, Julien Landre, Authorized officer, International Search Report for Application No. PCT/GB2012/052670, dated Feb. 14, 2013, 12 pages, together with the Written Opinion of the International Searching Authority.
European Patent Office, Laurent Deleu, Authorized Officer, International Preliminary Report on Patentability Chapter II for Application No. PCT/GB2010/051122, date of completion Nov. 2, 2011, 33 pages.
European Patent Office, Laurent Deleu, Authorized officer, International Search Report for Application No. PCT/GB2010/051122, dated Sep. 29, 2010, 9 pages, together with the Written Opinion of the International Searching Authority.
European Patent Office, Laurent Deleu, Authorized officer, International Search Report for Application No. PCT/GB2011/050019, dated May 16, 2011, 12 pages, together with the Written Opinion of the International Searching Authority.
European Patent Office, Examination Report for Application No. 12194970.5, dated Sep. 23, 2013, 6 pages.
European Patent Office, Examination Report for Application No. 14176740.0, dated Jun. 6, 2016, 5 pages.
European Patent Office, Examination Report for Application No. 14176740.0, dated Oct. 23, 2015, 5 pages.
European Patent Office, Extended European Search Report for Application No. 12171791.2, dated Jun. 18, 2013, 5 pages.
European Patent Office, Extended European Search Report for Application No. 12171793.8 dated Jun. 21, 2013, 8 pages.
European Patent Office, Extended European Search Report for Application No. 12194970.5, dated Jan. 23, 2013, 9 pages.
European Patent Office, Extended European Search Report for Application No. 12194977.0, dated Jul. 17, 2013, 8 pages.
European Patent Office, Extended European Search Report for Application No. 12195041.4, dated Nov. 18, 2013, 8 pages.
European Patent Office, Extended European Search Report for Application No. 14170196.1, dated Oct. 8, 2014, 8 pages.
European Patent Office, Extended European Search Report for Application No. 14176740.0, dated Oct. 15, 2014, 7 pages.
European Patent Office, Extended European Search Report for Application No. 16151215.7, dated Mar. 16, 2016, 11 pages.
European Patent Office, Notice of opposition to a European patent, pertaining to Application No. 10734546.4, dated Jan. 23, 2013, 41 pages.
European Patent Office, Opposition against EP2421357 Animal Models and Therapeutic Molecules in the name of Kymab Limited pertaining to Application No. 10734546.4, dated Oct. 23, 2013, 44 pages.
European Patent Office, Opposition against EP2517557 Animal Models and Therapeutic Molecules in the name of Kymab Limited pertaining to Application No. 12171793.8, dated Jan. 17, 2017, 39 pages.

(56) References Cited

OTHER PUBLICATIONS

European Patent Office, Statement of Fact and Arguments in Support of Opposition pertaining to Application No. 10734546.4, dated Oct. 22, 2013, 41 pages.
European Patent Office, Invitation to Pay Additional Fees and, Where Applicable, Protest Fee, Application No. PCT/GB2012/052296, dated Jan. 24, 2013, 9 pages.
Evans J.P., "Fertilin β and Other ADAMs as Integrin Ligands: Insights into Cell Adhesion and Fertilization," *Bioessays*, 2001, vol. 23 (7), pp. 628-639.
Featherstone K., et al., "The Mouse Immunoglobulin Heavy Chain V-D Intergenic Sequence Contains Insulators that May Regulate Ordered V(D)J Recombination," *Journal of Biological Chemistry*, 2010, vol. 285 (13), pp. 9327-9338.
Feeney A.J., "Genetic and Epigenetic Control of V Gene Rearrangement Frequency," *Advances in Experimental Medicine and Biology*, Chapter 6, 2009, vol. 650, pp. 73-81.
Fell H.P., "Homologous Recombination in Hybridoma Cells: Heavy Chain Chimeric Antibody Produced by Gene Targeting," *Proceedings of the National Academy of Sciences of the U.S.A*, 1989, vol. 86 (21), pp. 8507-8511.
Feng Y.Q., et al., "Site-Specific Chromosomal Integration in Mammalian Cells: Highly Efficient CRE Recombinase-Mediated Cassette Exchange," *Journal of Molecular Biology*, 1999, vol. 292 (4), pp. 779-785.
Feschotte C., et al., "DNA Transposons and the Evolution of Eukaryotic Genomes," *Annual Review of Genetics*, 2007, vol. 41, pp. 331-368.
Festing, M.F.W., et al., "Revised nomenclature for strain 129 mice," *Mammalian Genome*, 1999, vol. 10, p. 836.
Fleischer B., et al., "Reactivity of Mouse T-Cell Hybridomas Expressing Human Vβ Gene Segments With Staphylococcal and Streptococcal Superantigens," *Infection and Immunity*, Mar. 1996, vol. 64 (3), pp. 987-994.
Folger K.R., et al., "Patterns of Integration of DNA Microinjected into Cultured Mammalian Cells: Evidence for Homologous Recombination Between Injected Plasmid DNA Molecules," *Molecular and Cellular Biology*, 1982, vol. 2 (11), pp. 1372-1387.
Forconi F., et al., "The Normal IGHV1-69-Derived B-Cell Repertoire Contains Stereotypic Patterns Characteristic of Unmutated CLL," *Blood*, 2010, vol. 115 (1), pp. 71-77.
French Patent Office, INPI, Laurent Deleu, Authorized officer, International Search Report for Patent Application No. 1359518, dated Aug. 20, 2014, 3 pages.
Friedrich G., Statement of Dr. Glenn Friedrich, dated Mar. 3, 2016, 4 pages.
Fujieda S., et al., "Multiple Types of Chimeric Germ-Line Ig Heavy Chain Transcripts in Human B Cells: Evidence for Trans-Splicing of Human Ig RNA," *Journal of Immunology*, 1996, vol. 157 (8), pp. 3450-3459.
Fukita Y., et al., "Somatic Hypermutation in the Heavy Chain Locus Correlates with Transcription," *Immunity*, 1998, vol. 9 (1), pp. 105-114.
Gallo M.L., et al., "The Human Immunoglobulin Loci Introduced into Mice: V (D) and J Gene Segment Usage Similar to that of Adult Humans," *European Journal of Immunology*, 2000, vol. 30 (2), pp. 534-540.
Gama Sosa M.A., et al., "Animal Transgenesis: An Overview," *Brain Structure and Function*, 2010, vol. 214 (2-3), pp. 91-109.
Gavilondo J.V., et al., "Antibody Engineering at the Millennium," *BioTechniques*, Jul. 2000, vol. 29 (1), pp. 128-145.
Genbank (D. Muzny et al.), "Rattus norvegicus clone CH230-30N12, * Sequencing in Progress *, 6 unordered pieces," Accession No. AC111740, Nov. 9, 2002, 42 pages. [Retrieved from the Internet: http://www.ncbi.nlm.nih.gov/nuccore/AC111740 on Feb. 28, 2013].
Genbank, "DNA Sequence of the Human Immunoglobulin D Segment Locus," Accession No. x97051.1 S64822, dated Aug. 6, 2014, 29 pages. [Retrieved from the Internet: http://www.ncbi.nlm.nih.gov/nuccore/X97051].
Genbank, "DNA Sequence of the Human Immunoglobulin D Segment Locus," Accession No. x97051.1 S64822, updated Mar. 3, 2015, 26 pages.
Genbank, "*Homo sapiens* immunoglobulin heavy-chain (IGHV2-5) gene, IGHV2-5*10 allele, partial sequence," Accession No. KF698731.1, dated Nov. 18, 2013, 1 page.
Genbank, "Mus musculus strain 129S1/SvImJ chromosome 12 genomic sca locus group 129S1/SvImJ 129S1/SVIMJ_MMCHR12_CTG1," NCBI Reference Sequence No. NT_114985.3, dated May 5, 2014, 1 page.
Gerdes T., et al., "Physical Map of the Mouse λ Light Chain and Related Loci," *Immunogenetics*, 2002, vol. 54 (1), pp. 62-65.
Gerstein R.M., et al., "Isotype Switching of an Immunoglobulin Heavy Chain Transgene Occurs by DNA Recombination Between Different Chromosomes," *Cell*, 1990, vol. 63 (3), pp. 537-548.
Geurts A.M., et al., "Knockout Rats Via Embryo Microinjection of Zinc-Finger Nucleases," *Science*, 2009, vol. 325 (5939), p. 433.
Giallourakis C.C., et al., "Elements Between the IgH Variable (V) and Diversity (D) Clusters Influence Antisense Transcription and Lineage-Specific V(D)J Recombination," *Proceedings of the National Academy of Sciences of the U.S.A.*, 2010, vol. 107 (51), pp. 22207-22212.
Giraldo P., et al., "Size Matters: Use of YACs, BACs and PACs in Transgenic Animals," *Transgenic Research*, 2001, vol. 10 (2), pp. 83-103.
Giusti A.M., et al., "Hypermutation is Observed only in Antibody H Chain V Region Transgenes that have Recombined with Endogenous Immunoglobulin H DNA: Implications for the Location of cis-acting Elements Required for Somatic Mutation," *The Journal of Experimental Medicine*, Mar. 1993, vol. 177 (3), pp. 797-809.
Glanville J., et al., "Naive Antibody Gene-Segment Frequencies are Heritable and Unaltered by Chronic Lymphocyte Ablation," *Proceedings of the National Academy of Sciences of the U.S.A*, Dec. 2011, vol. 108 (50), pp. 20066-20071.
Glaser S. et al., "Current issues in mouse genome engineering," *Nature Genetics*, Nov. 2005, Vo. 37 (11), pp. 1187-1193.
Gluzman Y., "SV40-Transformed Simian Cells Support the Replication of Early SV40 Mutants," *Cell*, 1981, vol. 23 (1), pp. 175-182.
Goldman I.L., et al., "Transgenic Animals in Medicine: Integration and Expression of Foreign Genes, Theoretical and Applied Aspects," *Medical Science Monitor*, 2004, vol. 10 (11), pp. RA274-RA285.
Goodhardt M., et al., "Rearrangement and Expression of Rabbit Immunoglobulin κ Light Chain Gene in Transgenic Mice," *Proceedings of the National Academy of Sciences of the U.S.A.*, 1987, vol. 84 (12), pp. 4229-4233.
Gorman Jr., et al., "The Igκ 3' Enhancer Influences the Ratio of Igκ Versus Igλ B Lymphocytes," *Immunity*, 1996, vol. 5 (3), pp. 241-252.
Gorny M.K., et al., "Human Anti-V3 HIV-1 Monoclonal Antibodies Encoded by the VH5-51/VL Lambda Genes Define a Conserved Antigenic Structure," *PLoS One*, 2011, vol. 6 (12), pp. e27780-1-e27780-10.
Goyenechea B., et al., "Cells Strongly Expressing Igκ Transgenes Show Clonal Recruitment of Hypermutation: A Role for Both MAR and the Enhancers," *EMBO Journal*, 1997, vol. 16 (13), pp. 3987-3994.
Grandea A.G., III., et al., "Human antibodies reveal a protective epitope that is highly conserved among human and nonhuman influenza A viruses," *Proceedings of the National Academy of Sciences of the U.S.A.*, Jul. 2010, vol. 107 (28), pp. 12658-12663.
Gratz S. et al., "Genome Engineering of *Drosophila* with the CRISPR RNA-Guided Cas9 Nuclease," *Genetics*, Aug. 2013, vol. 194, pp. 1029-1035.
Green L.L., "Antibody Engineering via Genetic Engineering of the Mouse: XenoMouse Strains are a Vehicle for the Facile Generation of Therapeutic Human Monoclonal Antibodies," *Journal of Immunological Methods*, Dec. 1999, vol. 231 (1-2), pp. 11-23.
Green L.L., et al., "Antigen-Specific Human Monoclonal Antibodies from Mice Engineered with Human Ig Heavy and Light Chain YACs," *Nature Genetics*, May 1994, vol. 7 (1), pp. 13-21.
Green L.L., et al., "Regulation of B Cell Development by Variable Gene Complexity in Mice Reconstituted with Human Immuno-

(56) References Cited

OTHER PUBLICATIONS globulin Yeast Artificial Chromosomes," *The Journal of Experimental Medicine*, Aug. 1998, vol. 188 (3), pp. 483-495.
Grippo V., et al., "The Heavy Chain Variable Segment Gene Repertoire in Chronic Chagas' Heart Disease," *The Journal of Immunology*, Dec. 2009, vol. 182 (12), pp. 8015-8025.
Grund M., European Patent Attorney, Grund Intellectual Property Group, Third-Party Observations according to Article 115 EPC regarding 11705964.2, dated Apr. 30, 2014, 4 pages.
Grund M., European Patent Attorney, Grund Intellectual Property Group, Third-Party Observations according to Article 115 EPC regarding 11705964.2, dated Aug. 5, 2016, 11 pages.
Grund M., European Patent Attorney, Grund Intellectual Property Group, Third-Party Observations according to Article 115 EPC regarding 11705964.2, dated Feb. 26, 2015, 5 pages.
Grund M., European Patent Attorney, Grund Intellectual Property Group, Third-Party Observations according to Article 115 EPC regarding 11705964.2, dated Oct. 9, 2013, 8 pages.
Grund M., European Patent Attorney, Grund Intellectual Property Group, Third-Party Observations according to Article 115 EPC regarding 12171791.2, dated Aug. 4, 2014, 6 pages.
Grund M., European Patent Attorney, Grund Intellectual Property Group, Third-Party Observations according to Article 115 EPC regarding 12171791.2, dated Dec. 19, 2014, 7 pages.
Grund M., European Patent Attorney, Grund Intellectual Property Group, Third-Party Observations according to Article 115 EPC regarding 12171791.2, dated Feb. 26, 2014, 9 pages.
Grund M., European Patent Attorney, Grund Intellectual Property Group, Third-Party Observations according to Article 115 EPC regarding 12171793.8, dated Jun. 25, 2014, 7 pages.
Grund M., European Patent Attorney, Grund Intellectual Property Group, Third-Party Observations according to Article 115 EPC regarding 12194970.5, dated Apr. 25, 2014, 6 pages.
Grund M., European Patent Attorney, Grund Intellectual Property Group, Third-Party Observations according to Article 115 EPC regarding 12194970.5, dated Aug. 12, 2014, 5 pages.
Grund M., European Patent Attorney, Grund Intellectual Property Group, Third-Party Observations according to Article 115 EPC regarding 12194970.5, dated Mar. 5, 2014, 9 pages.
Grund M., European Patent Attorney, Grund Intellectual Property Group, Third-Party Observations according to Article 115 EPC regarding 12194970.5, dated Nov. 15, 2013, 6 pages.
Grund M., European Patent Attorney, Grund Intellectual Property Group, Third-Party Observations according to Article 115 EPC regarding 12194970.5, dated Sep. 9, 2013, 11 pages.
Grund M., European Patent Attorney, Grund Intellectual Property Group, Third-Party Observations according to Article 115 EPC regarding 12194977.0, dated Mar. 26, 2014, 4 pages.
Grund M., European Patent Attorney, Grund Intellectual Property Group, Third-Party Observations according to Article 115 EPC regarding 12194977.0, dated May 12, 2015, 5 pages.
Grund M., European Patent Attorney, Grund Intellectual Property Group, Third-Party Observations according to Article 115 EPC regarding 12195041.4, dated Jul. 30, 2014, 5 pages.
Grund M., European Patent Attorney, Grund Intellectual Property Group, Third-Party Observations according to Article 115 EPC regarding 12762377.5, dated Feb. 12, 2016, 8 pages.
Grund M., European Patent Attorney, Grund Intellectual Property Group, Third-Party Observations according to Article 115 EPC regarding 12762377.5, dated May 22, 2015, 7 pages.
Grund M., European Patent Attorney, Grund Intellectual Property Group, Third-Party Observations according to Article 115 EPC regarding 12762378.3, dated Feb. 15, 2017, 6 pages.
Grund M., European Patent Attorney, Grund Intellectual Property Group, Third-Party Observations according to Article 115 EPC regarding 12772122.3, dated Mar. 12, 2015, 5 pages.
Grund M., European Patent Attorney, Grund Intellectual Property Group, Third-Party Observations according to Article 115 EPC regarding 12772122.3, dated May 17, 2016, 7 pages.
Grund M., European Patent Attorney, Grund Intellectual Property Group, Third-Party Observations according to Article 115 EPC regarding 12795606.8, dated Aug. 22, 2014, 8 pages.
Grund M., European Patent Attorney, Grund Intellectual Property Group, Third-Party Observations according to Article 115 EPC regarding 12795606.8, dated Feb. 26, 2014, 6 pages.
Grund M., European Patent Attorney, Grund Intellectual Property Group, Third-Party Observations according to Article 115 EPC regarding 12795606.8, dated Mar. 26, 2015, 4 pages.
Grund M., European Patent Attorney, Grund Intellectual Property Group, Third-Party Observations according to Article 115 EPC regarding 13711119.1, dated Dec. 9, 2015, 7 pages.
Grund M., European Patent Attorney, Grund Intellectual Property Group, Third-Party Observations according to Article 115 EPC regarding 13711119.1, dated Jul. 5, 2016, 7 pages.
Grund M., European Patent Attorney, Grund Intellectual Property Group, Third-Party Observations according to Article 115 EPC regarding 13711120.9, dated May 17, 2016, 11 pages.
Grund M., European Patent Attorney, Grund Intellectual Property Group, Third-Party Observations according to Article 115 EPC regarding 14176740.0, dated Aug. 10, 2015, 13 pages.
Grund M., European Patent Attorney, Grund Intellectual Property Group, Third-Party Observations according to Article 115 EPC regarding 14176740.0, dated Nov. 2, 2016, 4 pages.
Grund M., European Patent Attorney, Grund Intellectual Property Group, Third-Party Observations according to Article 115 EPC regarding 16151215.7, dated Mar. 1, 2017, 4 pages.
Grund M., European Patent Attorney, Grund Intellectual Property Group, Third-Party Observations according to Article 115 EPC regarding 16189625.3, dated Mar. 23, 2017, 5 pages.
Grund M., European Patent Attorney, Grund Intellectual Property Group, Third-Party Observations regarding Application No. PCT/GB2012/052297, dated Jan. 17, 2014, 3 pages.
Grund M., European Patent Attorney, Grund Intellectual Property Group, Third-Party Observations regarding Application No. PCT/GB2012/052298, dated Jan. 17, 2014, 4 pages.
Grund M., European Patent Attorney, Grund Intellectual Property Group, Third-Party Observations regarding Application No. PCT/GB2012/052380, dated Jan. 24, 2014, 4 pages.
Grund M., European Patent Attorney, Grund Intellectual Property Group, Third-Party Observations regarding Application No. PCT/GB2012/052956, dated Mar. 26, 2014, 2 pages.
Grund M., European Patent Attorney, Grund Intellectual Property Group, Third-Party Observations regarding Application No. PCT/GB2012/052960, dated Apr. 2, 2014, 3 pages.
Grund M., European Patent Attorney, Grund Intellectual Property Group, Third-Party Observations regarding Application No. PCT/GB2013/050682, dated Jul. 28, 2014, 3 pages.
Grund M., European Patent Attorney, Grund Intellectual Property Group, Third-Party Observations regarding Application No. PCT/GB2013/050683, dated Jul. 28, 2014, 2 pages.
Grund M., European Patent Attorney, Grund Intellectual Property Group, Third-Party Observations regarding Application No. PCT/US2012/026416, dated Jun. 6, 2013, 2 pages.
Gu H., et al., "Independent Control of Immunoglobulin Switch Recombination at Individual Switch Regions Evidenced Through Cre-IoxP-Mediated Gene Targeting," Cell, 1993, vol. 73 (6), pp. 1155-1164.
Guan C., et al., "A Review of Current Large-Scale Mouse Knockout Efforts," *Genesis*, vol. 48, 2010, pp. 73-85.
Guerrero C., et al., "The Bleomycin Resistance Gene of Transposon Tn5 is an Excellent Marker for Transformation of Corynebacteria," *Applied Microbiology and Biotechnology*, 1992, vol. 36 (6), pp. 759-762.
Guirouilh-Barbat J., et al., "Is homologous recombination really an error-free process?", *Frontiers in Genetics*, Jun. 2014, vol. 5 (175), 15 pages.
Guntaka R.V., "Transcription Termination and Polyadenylation in Retroviruses," *Microbiological Reviews*, 1993, vol. 57 (3), pp. 511-521.
Guo Y., et al., "A Preliminary Analysis of the Immunoglobulin Genes in the African Elephant (*Loxodonta africana*)," *PLoS ONE*, Feb. 2011, vol. 6 (2), pp. e16889-1-e16889-14.

(56) References Cited

OTHER PUBLICATIONS

Hagiwara S., "Transgenic Expression of VpreB-3 Under the Control of the Immunoglobulin Heavy Chain Enhancer and SV40 Promoter," *Kobe Journal of Medical Sciences*, 1996, vol. 42 (1), pp. 43-59 (abstract only).
Hamers-Caterman C., et al., "Naturally occurring antibodies devoid of light chains," *Nature*, Jun. 1993, vol. 363, pp. 446-448.
Han C., et al., "Comprehensive Analysis of Reproductive ADAMs: Relationship of ADAM4 and ADAM6 with an ADAM Complex Required for Fertilization in Mice," *Biology of Reproduction*, 2009, vol. 80 (5), pp. 1001-1008.
Harding F.A., et al., "Class Switching in Human Immunoglobulin Transgenic Mice," *Annals of the New York Academy of Sciences*, 1995, vol. 764, pp. 536-546.
Hasty P., et al., "Target Frequency and Integration Pattern for Insertion and Replacement Vectors in Embryonic Stem Cells," *Molecular and Cellular Biology*, 1991, vol. 11 (9), pp. 4509-4517.
Hendricks J., et al., "Organization of the Variable Region of the Immunoglobulin Heavy-Chain Gene Locus of the Rat," *Immunogenetics*, 2010, vol. 62 (7), pp. 479-486.
Herschbach Jarrell B., Third-Party Pre-Issuance Submission Under 37 CFR Section 1.290 in U.S. Appl. No. 14/052,259, dated Aug. 6, 2014, 7 pages.
Hewitt S.L., et al., "Association between the Igk and Igh immunoglobulin loci mediated by the 3' Igk enhancer Induces 'decontraction' of the Igh locus in pre-B cells," *Nature Immunology*, Apr. 2008, vol. 9 (4), pp. 396-404.
Hong J., et al., "Derivation and Characterization of Embryonic Stem Cells Lines Derived from Transgenic Fischer 344 and Dark Agouti Rats," *Stem Cells and Development*, 2012, vol. 21 (6), pp. 1571-1586.
Houdebine L.M., "The Methods to Generate Transgenic Animals and to Control Transgene Expression," *Journal of Biotechnology*, 2002, vol. 98 (2-3), pp. 145-160.
Houdebine L.M., "Transgenic Animal Models in Biomedical Research," *Methods in Molecular Biology*, Chapter 10, 2007, vol. 360, pp. 163-202.
Houldsworth J., et al., "Comparative Genomic Hybridization: An Overview," *The American Journal of Pathology*, Dec. 1994, vol. 145 (6), pp. 1253-1260.
Hsu E., et al., "The plasticity of immunoglobulin gene systems in evolution," *Immunology Reviews*, vol. 210, Apr. 2006, pp. 8-26.
Huang C.C., et al., "Structural Basis of Tyrosine Sulfation and $V_H$-Gene Usage in Antibodies that Recognize the HIV Type 1 Coreceptor-Binding Site on gp120," *Proceedings of the National Academy of Sciences of the U.S.A.*, 2004, vol. 101 (9), pp. 2706-2711.
Huang D., et al., "Sequence Analyses of Three Immunoglobulin G Anti-virus Antibodies Reveal Their Utilization of Autoantibody-related Immunoglobulin Vh Genes, but Not Vλ Genes," *Journal of Clinical Investigations*, Dec. 1992, vol. 90, pp. 2197-2208.
Huber V.C., et al., "Distinct Contributions of Vaccine-Induced Immunoglobulin G1 (IgG1) and IgG2a Antibodies to Protective Immunity Against Influenza," *Clinical and Vaccine Immunology*, 2006, vol. 13 (9), pp. 981-990.
Hudziak R.M., et al., "Establishment of Mammalian Cell Lines Containing Multiple Nonsense Mutations and Functional Suppressor tRNA Genes," *Cell*, 1982, vol. 31 (1), pp. 137-146.
Huovila A.J., et al., "Shedding Light on ADAM Metalloproteinases," *Trends in Biochemical Sciences*, 2005, vol. 30 (7), pp. 413-422.
Iglesias-Ussel M.D., et al., "Forced Expression of AID Facilitates the Isolation of Class Switch Variants from Hybridoma Cells," *Journal of Immunological Methods*, 2006, vol. 316 (1-2), pp. 59-66.
Ivics Z., et al., "The Expanding Universe of Transposon Technologies for Gene and Cell Engineering," *Mobile DNA*, 2010, vol. 1 (1), 15 pages.
Ivics Z., et al., "The Sleeping Beauty Transposable Element: Evolution, Regulation and Genetic Applications," *Current Issues in Molecular Biology*, 2004, vol. 6 (1), pp. 43-55.
Izsvák Z., et al., "Sleeping Beauty Transposition: Biology and Applications for Molecular Therapy," *Molecular Therapy*, 2004, vol. 9 (2), pp. 147-156.
Jacob H.J., et al., "Gene Targeting in the Rat: Advances and Opportunities," *Trends in Genetics*, 2010, vol. 26 (12), pp. 510-518.
Jakobovits A., et al., "From XenoMouse Technology to Panitumumab, the First Fully Human Antibody Product from Transgenic Mice," *Nature Biotechnology*, 2007, vol. 25 (10), pp. 1134-1143.
Jakobovits A., "Production of Fully Human Antibodies by Transgenic Mice," *Current Opinion in Biotechnology*, 1995, vol. 6 (5), pp. 561-566.
Jakobovits A., "The Long-Awaited Magic Bullets: Therapeutic Human Monoclonal Antibodies from Transgenic Mice," *Expert Opinion Investigational Drugs*, 1998, vol. 7 (4), pp. 607-614.
Janeway C.A. et al., "The rearrangement of antigen-receptor gene segments controls lymphocyte development," Immunobiology: The Immune System in Health and Disease, 5th Edition, Aug. 2015, 13 pages. [Retrieved from the Internet: http://www.ncbi.nlm.nih.gov/books/NBK27113/].
Janeway et al., "Structural Variation in Immunoglobulin Constant Regions," *Immunobiology: The Immune System in Health and Disease*, 5th Edition, 2001, 5 pages.
Jasper, P.J., et al., "B lymphocyte deficiency in IgH-transgenic rabbits," *European Journal of Immunology*, 2007, vol. 37, pp. 2290-2299.
Jessen K.A., et al., "Molecular Analysis of Metastasis in a Polyomavirus Middle T Mouse Model: the Role of Osteopontin," *Breast Cancer Research*, 2004, vol. 6 (3), pp. R157-R169.
Johnston C.M., et al., "Complete Sequence Assembly and Characterization of the C57BL/6 Mouse Ig Heavy Chain V Region," *The Journal of Immunology*, 2006, vol. 176 (7), pp. 4221-4234.
Jones, B.T., Attorney for Applicant, Third-Party Pre-Issuance Submission Under 37 CFR Sec. 1.290 in U.S. Appl. No. 15/016,211, filed Oct. 4, 2016, 59 pages.
Jones, B.T., Attorney for Applicant, Third-Party Pre-Issuance Submission Under 37 CFR Sec. 1.290 in U.S. Appl. No. 15/018,670, filed Aug. 12, 2016, 26 pages.
Jones, B.T., Attorney for Applicant, Third-Party Pre-Issuance Submission Under 37 CFR Sec. 1.290 in U.S. Appl. No. 15/095,315, filed Sep. 16, 2016, 26 pages.
Jones, B.T., Attorney for Applicant, Third-Party Pre-Issuance Submission Under 37 CFR Sec. 1.290 in U.S. Appl. No. 15/232,122, filed Mar. 13, 2017, 32 pages.
Jones, B.T., Attorney for Applicant, Third-Party Pre-Issuance Submission Under 37 CFR Sec. 1.290 in U.S. Appl. No. 15/214,963, filed Mar. 2, 2017, 42 pages.
Jones, B.T., Attorney for Applicant, Third-Party Pre-Issuance Submission Under 37 CFR Sec. 1.290 in U.S. Appl. No. 15/360,502, filed May 8, 2017, 40 pages.
Jones B.T., Attorney for Applicant, Third-Party Pre-Issuance Submission Under 37 CFR Sec. 1.290 in U.S. Appl. No. 15/383,196, filed May 8, 2017, 25 pages.
Jones B.T., Attorney for Applicant, Third-Party Pre-Issuance Submission Under 37 CFR Sec. 1.290 in U.S. Appl. No. 15/383,202, filed May 3, 2017, 23 pages.
Jung D., et al., "Mechanism and Control of V(D)J Recombination at the Immunoglobulin Heavy Chain Locus," *Annual Review of Immunology*, 2006, vol. 24, pp. 541-570.
Kaminski D.A., et al., "Antibody Class Switching differs among SJL, C57BL/6 and 129 Mice," *International Immunology*, 2007, vol. 19 (4), pp. 545-556.
Karu A.E., et al., "Recombinant Antibody Technology," *ILAR Journal / National Research Council, Institute of Laboratory Animal Resources*, 1995, vol. 37 (3), pp. 132-141.
Kaushik A., et al., "Novel Insight into Antibody Diversification from Cattle," *Veterinary Immunology and Immunopathology*, 2002, vol. 87 (3-4), pp. 347-350.
Kawasaki K., et al., "One-Megabase Sequence Analysis of the Human Immunoglobulin λ Gene Locus," *Genome Research*, 1997, vol. 7, pp. 250-261.

(56) References Cited

OTHER PUBLICATIONS

Kellermann S., et al., "Developing the Xenomouse® Technology for Evaluating Immunogenicity," AntibOZ 2: An International Forum to Predict the Next Wave of Protein-based Therapies and Immuno Diagnostics, 2004, *AntibOZ 2 Conference*, Australia, 1 page (abstract only).
Kenter A.L., et al., "Three-Dimensional Architecture of the IgH Locus Facilitates Class Switch Recombination," *Annals of the New York Academy of Sciences*, 2012, vol. 1267, pp. 86-94.
Köhrer C., et al., "Import of Amber and Ochre Suppressor tRNAs into Mammalian Cells: a General Approach to Site-Specific Insertion of Amino Acid Analogues into Proteins," *Proceedings of the National Academy of Sciences of the U.S.A.*, 2001, vol. 98 (25), pp. 14310-14315.
Kim J.Y., et al., "CHO Cells in Biotechnology for Production of Recombinant Proteins: Current State and Further Potential," *Applied Microbiology Biotechnology*, 2012, vol. 93 (3), pp. 917-930.
Kim T., et al., "Expression and Relationship of Male Reproductive ADAMs in Mouse," *Biology of Reproduction*, 2006, vol. 74 (4), pp. 744-750.
Kindt T.J. et al., "Organization and Expression of Immunoglobulin Genes," *Immunology*, Sixth edition, Chapter 5, 2007 (36 pages, including cover sheet and copyright page), pp. 111-144.
Kingzette M., et al., "Trans-Chromosomal Recombination within the Ig Heavy Chain Switch Region in B Lymphocytes," *Proceedings of the National Academy of Sciences of the U.S.A.*, 1998, vol. 95 (20), pp. 11840-11845.
Kitamura D., et al., "A B Cell-Deficient Mouse by Targeted Disruption of the Membrane Exon of the Immunoglobulin μ Chain Gene," *Nature*, 1991, vol. 350 (6317), pp. 423-426.
Kondo S., et al., "Highly improved Gene Targeting by Germline-Specific Cas9 Expression in *Drosophila*," *Genetics*, vol. 195, Nov. 2013, pp. 715-721 (Abstract).
Kondo S., et al., "Highly improved Gene Targeting by Germline-Specific Cas9 Expression in *Drosophila*," *Genetics*, vol. 195, Nov. 2013, pp. 715-721.
Kostenuik P.J., et al., "Denosumab, a Fully Human Monoclonal Antibody to RANKL, Inhibits Bone Resorption and Increases BMD in Knock-in Mice that Express Chimeric (Murine/Human) RANKL," *Journal of Bone and Mineral Research*, 2009, vol. 24 (2), pp. 182-195.
Kotzamanis G., et al., "Recombining Overlapping BACs into a Single Larger BAC," *BMC Biotechnology*, 2004, vol. 4 (1), 10 pages.
Kouskoff V., et al., "Cassette Vectors Directing Expression of T Cell Receptor Genes in Transgenic Mice," *Journal of Immunological Methods*, 1995, vol. 180 (2), pp. 273-280.
Krause J.C., et al., "Epitope-Specific Human Influenza Antibody Repertoires Diversify by B Cell Intraclonal Sequence Divergence and Interclonal Convergence," *Journal of Immunology*, 2011, vol. 187 (7), pp. 3704-3711.
Krutskikh A., et al., "Epididymal Protein Rnase10 is Required for Post-Testicular Sperm Maturation and Male Fertility," *The FASEB Journal*, 2012, vol. 26 (10), pp. 4198-4209.
Kucherlapati R.S., et al., "Homologous Recombination Between Plasmids in Mammalian Cells can be Enhanced by Treatment of Input DNA," *Proceedings of the National Academy of Sciences of the U.S.A.*, 1984, vol. 81 (10), pp. 3153-3157.
Kuraoka M., et al., "AID Expression During B-Cell Development: Searching for Answers," *Immunologic Research*, 2011, vol. 49 (1-3), pp. 3-13.
Kuroiwa Y., et al., "Sequential Targeting of the Genes Encoding Immunoglobulin-μ and Prion Protein in Cattle," *Nature Genetics*, 2004, vol. 36 (7), pp. 775-780.
Kuzin I.I., et al, "Requirement for enhancer specificity in immunoglobulin heavy chain locus regulation," *Journal of Immunology*, Jun. 2008, vol. 180 (11), pp. 7443-7450.
Laffleur B., et al., "Production of Human or Humanized Antibodies in Mice," *Methods in Molecular Biology*, Chapter 9, 2012, vol. 901, pp. 149-159.
Largaespada D.A., "Transposon Mutagenesis in Mice," *Methods in Molecular Biology*, vol. 530, 2009, pp. 379-390.
Le Mouellic H., et al., "Pattern of Transcription of the Homeo Gene Hox-3.1 in the Mouse Embryo," *Genes & Development*, 1988, vol. 2 (1), pp. 125-135.
Lee E., et al., "Complete Humanization of the Mouse Immunoglobulin Loci Enables Efficient Therapeutic Antibody Discovery," *Nature Biotechnology*, 2014, vol. 32 (4), pp. 356-363.
Lee E., et al., "The Application of Transgenic Mice for Therapeutic Antibody Discovery," *Methods in Molecular Biology*, Chapter 8, 2012, vol. 901, pp. 137-148.
Lee H., et al., "Human C5aR Knock-in Mice Facilitate the Production and Assessment of Anti-Inflammatory Monoclonal Antibodies," *Nature Biotechnology*, 2006, vol. 24 (10), pp. 1279-1284.
Lefranc M., Appendix 1P, Abbreviations and Useful Data, "Nomenclature of the Human Immunoglobulin Genes," *Current Protocols in Immunology*, 2000, Supp. 40, pp. A.1P.1-A.1P.37.
Lefranc M.P., et al., "IGHJ group," The Immunoglobulin FactsBook, IMGT, the international ImMunoGeneTics database, May 2001, 4 pages (including cover sheet and copyright pages).
Lefranc M.P., et al., Excerpts from "The Immunoglobulin FactsBook," IMGT, the international ImMunoGeneTics database, May 2001, 455 pages.
Lefranc M.P., et al., "Immunoglobulin Lambda (IGL) Genes of Human and Mouse," *Molecular Biology of B Cells*, Chapter 4, p. 47, 2004 (Edtrs. Honjo et al.).
Lefranc M.P., "Nomenclature of the Human Immunoglobulin Heavy (IGH) Genes," *Experimental and Clinical Immunogenetics*, 2001, vol. 18 (2), pp. 100-116.
Lefranc M.P., "Nomenclature of the Human Immunoglobulin Kappa (IGK) Genes," *Experimental and Clinical Immunogenetics*, 2001, vol. 18 (3), pp. 161-174.
Lefranc M.P., "Nomenclature of the Human Immunoglobulin Lambda (IGL) Genes," *Experimental and Clinical Immunogenetics*, 2001, vol. 18 (4), pp. 242-254.
Levin A.M., et al., "Optimizing the affinity and specificity of proteins with molecular display," *Molecular Biosystems*, 2006, vol. 2, pp. 49-57.
Li H., et al., "Genetic Diversity of the Human Immunoglobulin Heavy Chain $V^H$ Region," *Immunological Reviews*, Dec. 2002, vol. 190, pp. 53-68.
Li L., et al., "Transgenic Mice with a Diverse Human T Cell Antigen Receptor Repertoire," *Nature Medicine*, 2010, vol. 16 (9), pp. 1029-1034.
Li M., Second Declaration of Dr. Meng (Amy) Li, dated Sep. 5, 2016, 2 pages.
Li M.A., et al., "Crafting Rat Genomes with Zinc Fingers," *Nature Biotechnology*, 2011, vol. 29 (1), pp. 39-41.
Li P., et al., "Germline Competent Embryonic Stem Cells Derived from Rat Blastocysts," *Cell*, 2008, vol. 135 (7), pp. 1299-1310.
Li X., et al., "The Minimum Internal and External Sequence Requirements for Transposition of the Eukaryotic Transformation Vector PiggyBac," *Molecular Genetics & Genomics*, 2001, vol. 266 (2), pp. 190-198.
Liang Q., et al., "Extensive genomic copy number variation in embryonic stem cells," *Proceedings of the National Academy of Sciences of the U.S.A.*, Nov. 2008, vol. 105 (45), pp. 17453-17456.
Liao J., et al., "Generation of Induced Pluripotent Stem Cell Lines from Adult Rat Cells," *Cell Stem Cell*, 2009, vol. 4 (1), pp. 11-15.
Little M., et al., "Generation of a Large Complex Antibody Library from Multiple Donors," *Journal of Immunological Methods*, 1999, vol. 231 (1-2), pp. 3-9.
Liu L., et al., "Potent and Broad Anti-HIV-1 Activity Exhibited by a Glycosyl-Phosphatidylinositol-Anchored Peptide derived from the CDR H3 of Broadly Neutralizing Antibody PG16," *Journal of Virology*, 2011, vol. 85 (17), pp. 8467-8476.
Lonberg N., "Fully Human Antibodies from Transgenic Mouse and Phage Display Platforms," *Current Opinion in Immunology*, 2008, vol. 20 (4), pp. 450-459.
Lonberg N., "Human Antibodies from Transgenic Animals," Nature Biotechnology, 2005, vol. 23 (9), pp. 1117-1125.
Loveslati B.Y., et al., "A Study of Gm Allotypes and Immunoglobulin Heavy Gamma IGHG Genes in Berbers, Arabs and Sub-Saharan

(56) References Cited

OTHER PUBLICATIONS

Africans from Jerba Island, Tunisia," European Journal of Immunogenetics, 2001, vol. 28 (5), pp. 531-538.
Luby T.M., et al., "The μ Switch Region Tandem Repeats are Important, but not Required, for Antibody Class Switch Recombination," *The Journal of Experimental Medicine*, 2001, vol. 193 (2), pp. 159-168.
Luciw P.A., et al., "Location and Function of Retroviral and SV40 Sequences that Enhance Biochemical Transformation after Microinjection of DNA," *Cell*, 1983, vol. 33 (3), pp. 705-716.
Luo G., et al., "Chromosomal Transposition of a Tc1/Mariner-like Element in Mouse Embryonic Stem Cells," *Proceedings of the National Academy of Sciences of the U.S.A.*, 1998, vol. 95 (18), pp. 10769-10773.
Lyon C., Attorney for Applicant, Third-Party Pre-Issuance Submission Under 37 CFR Sec. 1.290 in U.S. Appl. No. 13/846,672, dated Mar. 17, 2015, 32 pages.
Lyon C., Attorney for Applicant, Third-Party Pre-Issuance Submission Under 37 CFR Sec. 1.290 in U.S. Appl. No. 13/875,892, dated May 5, 2015, 49 pages.
Lyon C., Attorney for Applicant, Third-Party Pre-Issuance Submission Under 37 CFR Sec. 1.290 in U.S. Appl. No. 13/886,511, dated May 5, 2015, 18 pages.
Lyon C., Attorney for Applicant, Third-Party Pre-Issuance Submission Under 37 CFR Sec. 1.290 in U.S. Appl. No. 14/040,405, dated Jan. 16, 2015, 18 pages.
Lyon C., Attorney for Applicant, Third-Party Pre-Issuance Submission Under 37 CFR Sec. 1.290 in U.S. Appl. No. 14/040,427, dated Jan. 16, 2015, 20 pages.
Lyon C., Attorney for Applicant, Third-Party Pre-Issuance Submission Under 37 CFR Sec. 1.290 in U.S. Appl. No. 14/056,434, dated Dec. 15, 2014, 6 pages.
Lyon C., Attorney for Applicant, Third-Party Pre-Issuance Submission Under 37 CFR Sec. 1.290 in U.S. Appl. No. 14/056,700, dated Nov. 28, 2014, 6 pages.
Lyon C., Attorney for Applicant, Third-Party Pre-Issuance Submission Under 37 CFR Sec. 1.290 in U.S. Appl. No. 14/056,707, dated Nov. 28, 2014, 10 pages.
Lyon C., Attorney for Applicant, Third-Party Pre-Issuance Submission Under 37 CFR Sec. 1.290 in U.S. Appl. No. 14/080,630, dated Oct. 31, 2014, 8 pages.
Lyon C., Attorney for Applicant, Third-Party Pre-Issuance Submission Under 37 CFR Sec. 1.290 in U.S. Appl. No. 14/137,902, dated Nov. 13, 2014, 9 pages.
Lyon C., Attorney for Applicant, Third-Party Pre-Issuance Submission Under 37 CFR Sec. 1.290 in U.S. Appl. No. 14/220,080, dated Jul. 28, 2015, 28 pages.
Lyon C., Attorney for Applicant, Third-Party Pre-Issuance Submission Under 37 CFR Sec. 1.290 in U.S. Appl. No. 14/220,095, dated Aug. 4, 2015, 19 pages.
Lyon C., Attorney for Applicant, Third-Party Pre-Issuance Submission Under 37 CFR Sec. 1.290 in U.S. Appl. No. 14/220,099, dated Apr. 29, 2015, 43 pages.
Lyon C., Attorney for Applicant, Third-Party Pre-Issuance Submission Under 37 CFR Sec. 1.290 in U.S. Appl. No. 14/226,706, dated Jul. 28, 2015, 53 pages.
Lyon C., Attorney for Applicant, Third-Party Pre-Issuance Submission Under 37 CFR Sec. 1.290 in U.S. Appl. No. 14/263,158, dated Apr. 29, 2015, 16 pages.
Lyon C., Attorney for Applicant, Third-Party Pre-Issuance Submission Under 37 CFR Sec. 1.290 in U.S. Appl. No. 14/263,176, dated Apr. 29, 2015, 16 pages.
Lyon C., Attorney for Applicant, Third-Party Pre-Issuance Submission Under 37 CFR Sec. 1.290 in U.S. Appl. No. 14/497,054, dated Oct. 21, 2015, 81 pages.
Lyon C., Attorney for Applicant, Third-Party Pre-Issuance Submission Under 37 CFR Sec. 1.290 in U.S. Appl. No. 14/498,685, dated Sep. 18, 2015, 37 pages.
Lyon C., Attorney for Applicant, Third-Party Pre-Issuance Submission Under 37 CFR Sec. 1.290 in U.S. Appl. No. 14/516,461, dated Aug. 4, 2015, 27 pages.
Lyon C., Attorney for Applicant, Third-Party Pre-Issuance Submission Under 37 CFR Sec. 1.290 in U.S. Appl. No. 14/226,698, dated Jun. 3, 2015, 53 pages.
Ma B., et al., "Human Antibody Expression in Transgenic Rats: Comparison of Chimeric IgH Loci with Human $V_H$, D and $J_H$ but Bearing Different Rat C-Gene Regions," *Journal of Immunological Methods*, 2013, vols. 400-401, pp. 78-86.
MacDonald L., Curriculum Vitae of Lynn E. MacDonald, Ph.D., 3 pages.
MacDonald L., Declaration of Lynn E. MacDonald with Exhibits, dated Feb. 3, 2015, relating to International Application No. PCT/US02/04500 (Published as WO02/066630 A1), 13 pages.
Macdonald L., Declaration of Lynne E. Macdonald, dated Jun. 29, 2016, 4 pages.
MacDonald L., et al., Expanded Poster: "Velocigene® Technology Extended to Humanization of Several Megabases of Complex Gene Loci," Sep. 2006, 6 pages.
MacDonald L., et al., Poster (Exhibit IJR-47): "Velocigene® Technology Extended to Humanization of Several Megabases of Complex Gene Loci," and evidence of unavailability, Sep. 2006, 42 pages.
MacDonald L., et al., "Velocigene® Technology Extended to Humanization of Several Megabases of Complex Gene Loci," (Abstract-21) 1st International MUGEN Conference on Animal Models for Human Immunological Disease, Athens Greece, Sep. 10-13, 2006, 1 page.
MacDonald L.E., et al., "Precise and in Situ Genetic Humanization of 6 Mb of Mouse Immunoglobulin Genes," *Proceedings of the National Academy of Sciences of the U.S.A.*, 2014, vol. 111 (14), pp. 5147-5152.
Mack M., et al., "A Small Bispecific Antibody Construct Expressed as a Functional Single-Chain Molecule with High Tumor Cell Cytotoxicity," *Proceedings of the National Academy of Sciences of the U.S.A.*, 1995, vol. 92 (15), pp. 7021-7025.
Magadán S., et al., "Production of Antigen-Specific Human Monoclonal Antibodies: Comparison of Mice Carrying IgH/κ or IgH/κ/λ transloci," *Biotechniques*, 2002, vol. 33 (3), pp. 680, 682, 684 passim.
Magdelaine-Beuzelin C., et al., "Structure-function relationships of the variable domains of monoclonal antibodies approved for cancer treatment," *Critical Reviews in Oncology Hematology*, 2007, vol. 64, pp. 210-225.
Maitta R.W., et al., "Immunogenicity and Efficacy of *Cryptococcus neoformans* Capsular Polysaccharide Glucuronoxylomannan Peptide Mimotope-Protein Conjugates in Human Immunoglobulin Transgenic Mice," *Infection and Immunity*, 2004, vol. 72 (1), pp. 196-208.
Makris J.C., et al., "Mutational Analysis of Insertion Sequence 50 (IS50) and Transposon 5 (Tn5) Ends," *Proceedings of the National Academy of Sciences of the U.S.A.*, 1988, vol. 85 (7), pp. 2224-2228.
Mallender W.D., et al., "Construction, Expression, and Activity of a Bivalent Bispecific Single-Chain Antibody," *The Journal of Biological Chemistry*, 1994, vol. 269 (1), pp. 199-206.
Manis J.P., et al., "Mechanism and Control of Class-Switch Recombination," *Trends in Immunology*, 2002, vol. 23 (1), pp. 31-39.
Marcello M.R., et al., "Lack of Tyrosylprotein Sulfotransferase-2 Activity Results in Altered Sperm-Egg Interactions and Loss of ADAM3 and ADAM6 in Epididymal Sperm," *The Journal of Biological Chemistry*, 2011, vol. 286 (15), pp. 13060-13070.
Marchalonis J.J., et al., "Emergence of the immunoglobulin family: conservation in protein sequence and plasticity in gene organization," *Glycobiology*, vol. 6, 1996, pp. 657-663.
Mårtensson I.L., et al., "Role of the Surrogate Light Chain and the Pre-B-Cell Receptor in Mouse B-Cell Development," *Immunology*, 2000, vol. 101 (4), pp. 435-441.
Martinez C., et al., "The Mouse (*Mus musculus*) Immunoglobulin Kappa Variable (IGKV) Genes and Joining (IGKJ) Segments," *Experimental and Clinical Immunogenetics*, Jul. 1998, vol. 15, pp. 184-193.

(56) References Cited

OTHER PUBLICATIONS

Martínez P., et al., "Antibody Synthesis in Vitro," Encyclopedia of Life Sciences, 2005, pp. 1-8.
Martinez-Jean C., et al., "Nomenclature and Overview of the Mouse (*Mus musculus* and *Mus* sp.) Immunoglobulin Kappa (IGK) Genes," *Experimental and Clinical Immunogenetics*, 2001, vol. 18 (4), pp. 255-279.
Matthews V.B., et al., "A Locus Affecting Immunoglobulin Isotype Selection (Igis1) Maps to the MHC Region in C57BL, BALB/c and NOD Mice," *Immunology and Cell Biology*, 2001, vol. 79 (6), pp. 576-582.
Mattila P.S., et al., "Extensive Allelic Sequence Variation in the J Region of the Human Immunoglobulin Heavy Chain Gene Locus," *European Journal of Immunology*, 1995, vol. 25 (9), pp. 2578-2582.
Maul R.W., et al., "AID and Somatic Hypermutation," *Advances in Immunology*, Chapter 6, 2010, vol. 105, pp. 159-191.
McCreath K.J., et al., "Production of Gene-Targeted Sheep by Nuclear Transfer from Cultured Somatic Cells," *Nature*, 2000, vol. 405 (6790), pp. 1066-1069.
McMurry M.T., et al., "Enhancer Control of Local Accessibility to V(D)J Recombinase," *Molecular and Cellular Biology*, Aug. 1997, vol. 17 (8), pp. 4553-4561.
Mejía J.E., et al., "The Assembly of Large BACs by in Vivo Recombination," *Genomics*, 2000, vol. 70 (2), pp. 165-170.
Mendez M.J., et al., "Functional Transplant of Megabase Human Immunoglobulin Loci Recapitulates Human Antibody Response in Mice," *Nature Genetics*, Feb. 1997, vol. 15 (2), pp. 146-156.
Mester G., European Patent Attorney, Grund Intellectual Property Group, Third-Party Observations according to Article 115 EPC regarding 12778780.2, dated Sep. 30, 2016, 5 pages.
MGI, "Guidelines for Nomenclature of Mouse and Rat Strains," International Committee on Standardized Genetic Nomenclature for Mice / Rat Genome and Nomenclature Committee; Chairpersons: J.T. Eppig and G. Levan, Oct. 2011, 11 pages. [printed: Mar. 6, 2012—http://www.informatics.jax.org/mgihome/nomen/strains.shtml].
Mills F.C., et al., "Enhancer Complexes Located Downstream of Both Human Immunoglobulin Cα Genes," *The Journal of Experimental Medicine*, Sep. 1997, vol. 186 (6), pp. 845-858.
Milner E.C., et al., "Polymorphism and Utilization of Human $V_H$ Genes," *Annals of the New York Academy of Sciences*, 1995, vol. 764, pp. 50-61.
Minaee S., et al., "Mapping and Functional Analysis of Regulatory Sequences in the Mouse λ5-VpreB1 Domain," *Molecular Immunology*, 2005, vol. 42 (11), pp. 1283-1292.
Mir K.U., "Sequencing Genomes: From Individuals to Populations," *Briefings in Functional Genomics & Proteomics*, 2009, vol. 8 (5), pp. 367-378.
Müller U., "Ten Years of Gene Targeting: Targeted Mouse Mutants, from Vector Design to Phenotype Analysis," *Mechanisms of Development*, 1999, vol. 82 (1-2), pp. 3-21.
Moffatt S., et al., "PEGylated J591 mAb loaded in PLGA-PEG-PLGA tri-block copolymer for targeted delivery: In vitro evaluation in human prostate cancer cells," *International Journal of Pharmaceutics*, 2006, vol. 317, pp. 10-13.
Monaco A.P., et al., "YACs, BACs, PACs and MACs: Artificial Chromosomes as Research Tools," *Trends in Biotechnology*, Jul. 1994, vol. 12 (7), pp. 280-286.
Moran N., "Mouse Platforms Jostle for Slice of Humanized Antibody Market," *Nature Biotechnology*, Apr. 2013, vol. 31 (4), pp. 267-268.
Moreau P., et al., "The SV40 72 Base Repair Repeat has a Striking Effect on Gene Expression Both in SV40 and Other Chimeric Recombinants," *Nucleic Acids Research*, 1981, vol. 9 (22), pp. 6047-6068.
Moreno R.D., et al., "The Emerging Role of Matrix Metalloproteases of the ADAM Family in Male Germ Cell Apoptosis," *Spermatogenesis*, 2011, vol. 1 (3), pp. 195-208.
Mortuza F.Y., et al., "Immunoglobulin Heavy-Chain Gene Rearrangement in Adult Acute Lymphoblastic Leukemia Reveals Preferential Usage of $J_H$-Proximal Variable Gene Segments," *Blood*, 2001, vol. 97 (9), pp. 2716-2726.
Mullins L.J., et al., "Transgenesis in the Rat and Larger Mammals," Perspective Series: Molecular Medicine in Genetically Engineered Animals, *Journal of Clinical Investigation*, Apr. 1996, vol. 97 (7), pp. 1557-1560.
Muñoz M., et al., "Constraints to Progress in Embryonic Stem Cells from Domestic Species," *Stem Cell Review and Reports*, 2009, vol. 5, pp. 6-9.
Murphy A., "Declaration of Andrew J. Murphy," including Slide Presentation dated Nov. 3, 2009, at Wellcome Trust Advanced Course: Genetic Manipulation of ES Cells, in Hirixton, UK, entitled "BAC-based Modifications of the Mouse Genome: The Big and the Backward," cited in an IDS in U.S. Appl. No. 14/192,051 of MacDonald et al., dated Oct. 6, 2014, 62 pages.
Murphy A., "VelocImmune: Immunoglobulin Variable Region Humanized Mice," *Recombinant Antibodies for Immunotherapy*, 1st Edition, Chapter 8, 2009, pp. 100-108.
Murphy A.J., et al., "Mice with megabase humanization of their Immunoglobulin Genes Generate Antibodies as Efficiently as Normal Mice," *Proceedings of the National Academy of Sciences of the U.S.A.*, 2014, vol. 111 (14), pp. 5153-5158.
Murphy D., "BAC-based Modifications of the Mouse Genome: The Big and the Backward," The Advanced Course: Genetic Manipulation of ES Cells, dated Nov. 3, 2009, VP Target Discovery, Regeneron Pharmaceuticals, 58 pages.
Murphy K., et al., The Generation of Lymphocyte Antigen Receptors, excerpt from *Janeway's Immunobiology*, Seventh edition, Chapter 4, 2008, p. 158.
Muyrers J.P.P., et al., "Rapid Modification of Bacterial Artificial Chromosomes by ET-Recombination," *Nucleic Acids Research*, 1999, vol. 27 (6), pp. 1555-1557.
Nadel B., et al., "Sequence of the Spacer in the Recombination Signal Sequence Affects V(D)J Rearrangement Frequency and Correlates with Nonrandom Vκ Usage in Vivo," *The Journal of Experimental Medicine*, 1998, vol. 187 (9), pp. 1495-1503.
Nagle M., "Regeneron Helps Make Sanofi Velocimmune to its 'Weak' Pipeline," 2007, 2 pages.
Nandi A.K., et al., "Regulated Expression of Genes Inserted at the Human Chromosomal β-globin Locus by Homologous Recombination," *Proceedings of the National Academy of Sciences of the U.S.A.*, 1988, vol. 85 (11), pp. 3845-3849.
Narayanan K., et al., "Bacterial Artificial Chromosome Mutagenesis Using Recombineering, Article ID: 971296," Journal of Biomedicine and Biotechnology, 2010, vol. 2011, Article ID No. 971296, 10 pages.
Narayanan K., et al., "Efficient and Precise Engineering of a 200 kb β-Globin Human/Bacterial Artificial Chromosome in*E. coli* DH10B using an Inducible Homologous Recombination System," *Gene Therapy*, 1999, vol. 6 (3), pp. 442-447.
Nelson A.L., et al., "Development Trends for Human Monoclonal Antibody Therapeutics," *Nature Reviews Drug Discovery*, 2010, vol. 9 (10), pp. 767-774.
Neuberger M.S., et al., "Isotype Exclusion and Transgene Down-Regulation in Immunoglobulin-λ Transgenic Mice," *Nature*, Mar. 1989, vol. 338 (6213), pp. 350-352.
Neuberger M.S., et al., "Somatic Hypermutation," *Current Opinion in Immunology*, 1995, vol. 7 (2), pp. 248-254.
Neuberger M.S., "Expression and regulation of immunoglobulin heavy chain gene transfected into lymphoid cells," *The EMBO Journal*, 1983, vol. 2 (8), pp. 1373-1378.
New Zealand Patent Office, Simon Maguire, Authorized Officer, Further Examination Report for Patent No. 623756, dated Sep. 9, 2015, 3 pages.
Nicholson I.C., et al., "Antibody Repertoires of Four- and Five-Feature Translocus Mice Carrying Human Immunoglobulin Heavy Chain and κ and λ Light Chain Yeast Artificial Chromosomes," *Journal of Immunology*, 1999, vol. 163 (12), pp. 6898-6906.
Niemann H., et al., "Transgenic Farm Animals: Present and Future," *Revue scientifique et technique (International Office of Epizootics)*, 2005, vol. 24 (1), pp. 285-298.
Nucleotide Sequence RID Y55HBK1W114, accessed Aug. 6, 2014, 2 pages.

(56) References Cited

OTHER PUBLICATIONS

Oancea A.E., et al., "Expression of the (recombinant) Endogenous Immunoglobulin Heavy-Chain Locus Requires the Intronic Matrix Attachment Regions," *Molecular and Cellular Biology*, 1997, vol. 17 (5), pp. 2658-2668.
Oberdoerffer P., et al., "Unidirectional Cre-Mediated Genetic Inversion in Mice using the Mutant IoxP Pair Iox66/Iox71," *Nucleic Acids Research*, 2003, vol. 31 (22), pp. e140-1-e140-7.
Ohlin M., et al., "The Human Antibody Repertoire to Infectious Agents: Implications for Disease Pathogenesis," Molecular Immunology, 2003, vol. 40 (1), pp. 1-11.
Ohm-Laursen L., et al., "Identification of Two New Alleles, IGHV3-23*04 and IGHJ6*04, and the Complete Sequence of the IGHV3-h Pseudogene in the Human Immunoglobulin Locus and their Prevalences in Danish Caucasians," *Immunogenetics*, 2005, vol. 57 (9), pp. 621-627.
Osborn M.J., et al., "High-Affinity IgG Antibodies Develop Naturally in Ig-Knockout Rats Carrying Germline Human IgH/Igκ/Igλ Loci Bearing the Rat $C_H$ Region," *Journal of Immunology*, 2013, vol. 190 (4), pp. 1481-1490.
Osoegawa K., et al., "Bacterial Artificial Chromosome Libraries for Mouse Sequencing and Functional Analysis," *Genome Research*, 2000, vol. 10 (1), pp. 116-128.
Oumard A., et al., "Recommended method for chromosome exploitation: RMCE-based cassette-exchange systems in animal cell biotechnology," *Cytotechnology*, 2006, vol. 50, pp. 93-108.
Parng C.L., et al., "Gene Conversion Contributes to Ig Light Chain Diversity in Cattle," *Journal of Immunology*, 1996, vol. 157 (12), pp. 5478-5486.
Pavlicek A., et al., "Ancient Transposable Elements, Processed Pseudogenes, and Endogenous Retroviruses," *Genomic Disorders*, Chapter 4, 2006, pp. 57-72.
Pear W.S., et al., "Localization of the Rat Immunoglobulin Heavy Chain Locus to Chromosome 6," *Immunogenetics*, 1986, vol. 23 (6), pp. 393-395.
Pelham H., et al., "Expression of a *Drosophila* Heat Shock Protein in Mammalian Cells: Transient Association with Nucleoli After Heat Shock," *Philosophical Transactions of the Royal Society B: Biological Sciences*, 1984, vol. 307 (1132), pp. 301-307.
Pera M.F., et al., "Human embryonic stem cells," *Journal of Cell Science*, 2000, vol. 113, pp. 5-10.
Pérez-Luz S., et al., "Factor VIII mRNA expression from a BAC carrying the intact locus made by homologous recombination," *Genomics*, 2007, vol. 90, pp. 610-619.
Perlot T., et al., "Antisense Transcripts from Immunoglobulin Heavy-Chain Locus V(D)J and Switch Regions," *Proceedings of the National Academy of Sciences of the U.S.A.*, 2008, vol. 105 (10), pp. 3843-3848.
Perlot T., et al., "Cis-Regulatory Elements and Epigenetic Changes control genomic rearrangements of the IgH locus," *Advances in Immunology*, Chapter 1, 2008, vol. 99, pp. 1-32.
Pettersson S., et al., "A second B cell-specific enhancer 3' of the immunoglobulin heavy-chain locus," *Nature*, Mar. 1990, vol. 344, pp. 165-168.
Pettitt S.J., et al., "Agouti C57BL/6N Embryonic Stem Cells for Mmouse Genetic Resources," *Nature Methods*, 2009, vol. 6 (7), pp. 493-495.
Plasterk R.H., et al., "Resident Aliens: the Tc1/Mariner Superfamily of Transposable Elements," *Trends Genetics*, 1999, vol. 15(8), pp. 326-332.
Pobursky K., Third-Party Pre-Issuance Submission Under 37 CFR 1.290 in U.S. Appl. No. 13/843,528, dated Mar. 18, 2014, 14 pages.
Pobursky K., Third-Party Pre-Issuance Submission Under 37 CFR 1.290 in U.S. Appl. No. 13/433,084, dated Apr. 1, 2014, 15 pages.
Pobursky K., Third-Party Pre-Issuance Submission Under 37 CFR 1.290 in U.S. Appl. No. 13/434,361, dated Apr. 1, 2014, 15 pages.
Pobursky K., Third-Party Pre-Issuance Submission Under 37 Cfr 1.290 in U.S. Appl. No. 13/740,727, dated May 27, 2014, 25 pages.

Ponsel D., et al., "High Affinity, Developability and Functional Size: the Holy Grail of Combinatorial Antibody by Library Generation," *Molecules*, 2011, vol. 16 (5), pp. 3675-3700.
Popov A.V., et al., "A Human Immunoglobulin λ Locus is Similarly Well Expressed in Mice and Humans," *The Journal of Experimental Medicine*, 1999, vol. 189 (10), pp. 1611-1620.
Pramanik S., et al., "Segmental Duplication as One of the Driving Forces Underlying the Diversity of the Human Immunoglobulin Heavy Chain Variable Gene Region," *BMC Genomics*, Jan. 2011, vol. 12 (1), p. 78.
Presta L., "Molecular engineering and design of therapeutic antibodies," *Current Opinion in Immunology*, 2008, vol. 20, pp. 460-470.
Primakoff P., et al., "Penetration, Adhesion, and Fusion in Mammalian Sperm-Egg Interaction," *Science*, 2002, vol. 296 (5576), pp. 2183-2185.
Primakoff P., et al., "The ADAM Gene Family: Surface Proteins with Adhesion and Protease Activity," *Trends Genetics*, 2000, vol. 16 (2), pp. 83-87.
Printout of PDF file available from the University of California website presented in support of European opposition in the name of Kymab Ltd. pertaining to Application No. EP12171793.8 as filed on Jan. 19, 2017, 4 pages. [http://www.research.uci.edu/facilities-services/tmf/presentations/Mouse_ES_CellLine].
Prosser H.M., et al., "A Resource of Vectors and ES Cells for Targeted Deletion of MicroRNAs in Mice," *Nature Biotechnology*, 2011, vol. 29 (9), pp. 840-845.
Prosser H.M., et al., "Mosaic Complementation Demonstrates a Regulatory Role for Myosin VIIa in Actin Dynamics of Stereocilia," *Molecular and Cellular Biology*, 2008, vol. 28 (5), pp. 1702-1712.
Pruzina S., et al., "Human Monoclonal Antibodies to HIV-1 gp140 from Mice Bearing YAC-Based Human Immunoglobulin Transloci," *Protein Engineering, Design & Selection*, 2011, vol. 24 (10), pp. 791-799.
Puente X.S., et al., "Comparative Genomic Analysis of Human and Chimpanzee Proteases," *Genomics*, 2005, vol. 86 (6), pp. 638-647.
Qi N.R., et al., "A New Transgenic Rat Model of Hepatic Steatosis and the Metabolic Syndrome," *Hypertension*, 2005, vol. 45 (5), pp. 1004-1011.
Qu S., et al., "Gene Targeting of ErbB3 Using a Cre-Mediated Unidirectional DNA Inversion Strategy," *Genesis*, 2006, vol. 44 (10), pp. 477-486.
Ramírez-Solis R., et al., "Chromosome Engineering in Mice," *Nature*, 1995, vol. 378 (6558), pp. 720-724.
Ramsden D.A., et al., "Conservation of Sequence in Recombination Signal Sequence Spacers," *Nucleic Acids Research*, 1994, vol. 22 (10), pp. 1785-1796.
Ray P., et al., "Ectopic Expression of a c-kit$^{W42}$ Minigene in Transgenic Mice: Recapitulation of W Phenotypes and Evidence for c-kit Function in Melanoblast Progenitors," *Genes & Development*, 1991, vol. 5 (12A), pp. 2265-2273.
Raynard S.J., et al., "Cis-Acting Regulatory Sequences Promote High-Frequency Gene Conversion between Repeated Sequences in Mammalian Ccells," *Nucleic Acids Research*, 2004, vol. 32 (19), pp. 5916-5927.
Reddy S.T., et al., "Monoclonal Antibiotics Isolated without Screening by Analysing the Variable-Gene Repertoire of Plasma Cells," *Nature Biotechnology*, 2010, vol. 28 (9), pp. 965-971.
Regeneron Pharmaceuticals, Inc., et al., "Big Pharma Vies for Mice," *Nature Biotechnology*, 2007, vol. 25 (6), pp. 613.
Regeneron Pharmaceuticals, Inc., Press Release—"Astellas Licenses Regeneron's VelocImmune® Technology for Discovering Human Monoclonal Antibodies," dated Mar. 30, 2007, 2 pages.
Regeneron Pharmaceuticals, Inc., Press Release—"AstraZeneca Licenses Regeneron's VelocImmune® Technology for Discovering Human Monoclonal Antibodies—AstraZeneca Is First Licensee of Novel VelocImmune Technology License Fees Total up to $120 Million Over Six Years," dated Feb. 5, 2007, 2 pages.
Regeneron Pharmaceuticals, Inc., Press Release—"Regeneron Initiates Major Global Collaboration with Sanofi-aventis of Develop and Commercialize Fully-Human Therapeutic Antibodies," dated Nov. 29, 2007, 2 pages.

(56) References Cited

OTHER PUBLICATIONS

Ren S.Y., et al., "Targeted Insertion Results in a Rhombomere 2-Specific Hoxa2 Knockdown and Ectopic Activation of Hoxa1 Expression," *Developmental Dynamics*, 2002, vol. 225 (3), pp. 305-315.
Renaut L., et al., "Affinity Maturation of Antibodies: Optimized Methods to Generate High-Quality ScFv Libraries and Isolate IgG Candidates by High-Throughput Screening," *Antibody Engineering: Methods and Protocols*, Second Edition, Chapter 26, 2012, vol. 907, pp. 451-461.
Retter I., et al., "Sequence and Characterization of the Ig Heavy Chain Constant and Partial Variable Region of the Mouse Strain 129S1," *The Journal of Immunology*, 2007, vol. 179 (4), pp. 2419-2427.
Ricker M., European Patent Attorney, Opposition against EP2421357B1 in the name of Kymab Limited Statement of Facts and Arguments pertaining to Application No. 10734546.4, dated Oct. 23, 2013, 29 pages.
Ristevski S., "Making Better Transgenic Models: Conditional, Temporal, and Spatial Approaches," *Molecular Biotechnology*, 2005, vol. 29 (2), pp. 153-163.
Rivera J., et al., "Genetic Background and the Dilemma of Translating Mouse Studies to Humans," *Immunity*, 2008, vol. 28 (1), pp. 1-4.
Rock E.P., et al., "CDR3 Length in Antigen-specific Immune Receptors", *Journal of Experimental Medicine*, Jan. 1994, vol. 179, pp. 323-328.
Rodríguez C.I., et al., "High-Efficiency Deleter Mice Show that FLPe is an Alternative to Cre-IoxP," *Nature Genetics*, 2000, vol. 25 (2), pp. 139-140.
Rogozin I.B., et al., "Cutting edge: DGYW/WRCH is a Better Predictor of Mmutability at G:C bases in Lg Hypermutation than the Widely Accepted RGYW/WRCY Motif and Probably Reflects a Two-Step Activation-Induced Cytidine Deaminase-Triggered Process," *The Journal of Immunology*, 2004, vol. 172 (6), pp. 3382-3384.
Rosner K., et al., "Third Complementarity-Determining Region of Mutated $V_H$ Immunoglobulin Genes Contains Shorter V, D, J, P, and N Components than Non-Mutated Genes," *Immunology*, 2001, vol. 103 (2), pp. 179-187.
Rourke J., Declaration of Jeffrey Rourke, Registered Patent Attorney for Regeneron Pharmaceuticals, Inc.—In the matter of Patent Acceptance 2011266843 in the Name of Kymab Limited and In the Matter of Opposition thereto by Regeneron Pharmaceuticals, Inc., dated Jan. 29, 2016, 5 pages.
Rusk N., "Making Mice at High Speed," *Nature Methods*, Mar. 2007, vol. 4 (3), pp. 196-197.
Sabbattini P., et al., "Analysis of Mice with Single and Multiple Copies of Transgenes Reveals a Novel Arrangement for the $\lambda 5-V_{preB1}$ Locus Control Region," *Molecular and Cellular Biology*, Jan. 1999, vol. 19 (1), pp. 671-679.
Sakai E., et al., "Recombination and Transcription of the Endogenous Ig Heavy Chain Locus is Effected by the Ig Heavy Chain Intronic Enhancer Core Region in the Absence of the Matrix Attachment Regions," *Proceedings of the National Academy of Sciences of the U.S.A.*, 1999, vol. 96 (4), pp. 1526-1531.
Sarkar A., et al., "Molecular Evolutionary Analysis of the Widespread PiggyBac Transposon Family and Related "Domesticated" Sequences," *Molecular Genetics & Genomics*, 2003, vol. 270 (2), pp. 173-180.
Sasso E.H., et al., "Ethnic Differences of Polymorphism of an Immunoglobulin $V_H 3$ Gene," *Journal of Clinical Investigation*, 1995, vol. 96 (3), pp. 1591-1600.
Sasso E.H., et al., "Expression of the Immunoglobulin $V_H$ Gene 51p1 is Proportional to its Germline Gene Copy Number," *Journal of Clinical Investigation*, 1996, vol. 97 (9), pp. 2074-2080.
Sauer B., et al., "Cre-Stimulated Recombination at IoxP-Containing DNA Sequences Placed into the Mammalian Genome," *Nucleic Acids Research*, 1989, vol. 17 (1), pp. 147-161.
Sauer B., et al., "Site-Specific DNA Recombination in Mammalian Cells by the Cre Recombinase of Bacteriophage P1," *Proceedings of the National Academy of Sciences of the U.S.A.*, 1988, vol. 85 (14), pp. 5166-5170.
Sauer B., "Functional Expression of the cre-lox Site-Specific Recombination System in the Yeast *Saccharomyces cerevisiae*," *Molecular and Cellular Biology*, 1987, vol. 7 (6), pp. 2087-2096.
Scapini P., et al., "Myeloid Cells, BAFF, and IFN-γ Establish an Inflammatory Loop that Exacerbates Autoimmunity in Lyn-Deficient Mice," *The Journal of Experimental Medicine*, Jul. 2010, vol. 207 (8), pp. 1757-1773.
Schlake T., et al., "Use of Mutated FLP Recognition Target (FRT) Sites for the Exchange of Expression Cassettes at Defined Chromosomal Loci," *Biochemistry*, 1994, vol. 33 (43), pp. 12746-12751.
Schnütgen F., et al., "A Directional Strategy for Monitoring Cre-Mediated Recombination at the Cellular Level in the Mouse," *Nature Biotechnology*, 2003, vol. 21 (5), pp. 562-565.
Schonewald, S.L., Attorney for Applicant, Third-Party Pre-Issuance Submission Under 37 CFR Sec. 1.290 in U.S. Appl. No. 14/220,074, dated Jul. 12, 2016, 46 pages.
Schonewald, S.L., Attorney for Applicant, Third-Party Pre-Issuance Submission Under 37 CFR Sec. 1.290 in U.S. Appl. No. 14/750,870, dated Aug. 10, 2016, 34 pages.
Schonewald, S.L., Attorney for Applicant, Third-Party Pre-Issuance Submission Under 37 CFR Sec. 1.290 in U.S. Appl. No. 14/818,162, dated May 24, 2016, 47 pages.
Schonewald, S.L., Attorney for Applicant, Third-Party Pre-Issuance Submission Under 37 CFR Sec. 1.290 in U.S. Appl. No. 14/935,010, dated Aug. 19, 2016, 27 pages.
Schroeder Jr. H.W, et al., "Preferential Utilization of Conserved Immunoglobulin Heavy Chain Variable Gene Segments During Human Fetal Life," *Proceedings of the National Academy of Sciences of the U.S.A.*, 1990, vol. 87 (16), pp. 6146-6150.
Schroeder, Jr. H.W., "Similarity and divergence in the development and expression of the mouse and human antibody repertoires," *Developmental and Comparative Immunology*, vol. 30, 2006, pp. 119-135.
Schröck E., et al., "Comparative Genomic Hybridization (CGH)—Detection of Unbalanced Genetic Aberrations Using Conventional and Micro-Array Techniques," *Current Protocols in Cytometry*, Chapter 8, 2001, Unit 8.12.1, Supplement 18, 30 pages.
Schweinfest C.W., et al., "A Heat-Shock-Inducible Eukaryotic Expression Vector," *Gene*, 1988, vol. 71 (1), pp. 207-210.
Scott C.T., "Mice with a Human Touch," *Nature Biotechnology*, 2007, vol. 25 (10), pp. 1075-1077.
Seals D.F., et al., "The ADAMs Family of Metalloproteases: Multidomain Proteins with Multiple Functions," *Genes & Development*, 2003, vol. 17 (1), pp. 7-30.
Seed B., "Purification of Genomic Sequences from Bacteriophage Libraries by Recombination and Selection in Vivo," *Nucleic Acids Research*, 1983, vol. 11 (8), pp. 2427-2445.
Seidl K.J., et al., "An Expressed neo$^r$ Cassette Provides Required Functions of the 1γ2b Exon for Class Switching," *International Immunology*, 1998, vol. 10 (11), pp. 1683-1692.
Seidl K.J., et al., "Position-Dependent Inhibition of Class-Switch Recombination by PGK-neo$^r$ Cassettes Inserted into the Immunoglobulin Heavy Chain Constant Region Locus," *Proceedings of the National Academy of Sciences of the U.S.A.*, Mar. 1999, vol. 96 (6), pp. 3000-3005.
Sekiguchi J., et al., "The Mechanism of V(D)J Recombination," *Molecular Biology of B Cells*, Chapter 5, 2004, pp. 61-82.
Sen R., et al., "Multiple Nuclear Factors Interact with the Immunoglobulin Enhancer Sequences," *Cell*, 1986, vol. 46 (5), pp. 705-716.
Seong E., et al., "To Knockout in 129 or in C57BL/6: That is the Question," *Trends in Genetics*, 2004, vol. 20 (2), pp. 59-62.
Sequence Listing to WO2008054606A2, 163 pages.
Serwe M., et al., "V(D)J Recombination in B Cells is Impaired but not Blocked by Targeted Deletion of the Immunoglobulin Heavy Chain Intron Enhancer," *The EMBO Journal*, 1993, vol. 12 (6), pp. 2321-2327.

(56) References Cited

OTHER PUBLICATIONS

Sharon J., et al., "Expression of a VHC Kappa Chimaeric Protein in Mouse Myeloma Cells," *Nature*, 1984, vol. 309 (5966), pp. 364-367.
Shaul Y., et al., "Homologous Recombination Between a Defective Virus and a Chromosomal Sequence in Mammalian Cells," *Proceedings of the National Academy of Sciences of the U.S.A.*, 1985, vol. 82 (11), pp. 3781-3784.
Shi B., et al., "Comparative Analysis of Human and Mouse Immunoglobulin Variable Heavy Regions from IMGT/LIGM-DB with IMGT/HighV-QUEST," *Theoretical Biology and Medical Modelling*, 2014, vol. 11, pp. 1-11.
Shi Y.P., et al., "The Mapping of Transgenes by Fluorescence in Situ Hybridization on G-Banded Mouse Chromosomes," *Mammalian Genome*, 1994, vol. 5 (6), pp. 337-341.
Shih H.H., "Discovery Process for Antibody-Based Therapeutics," *Development of Antibody-Based Therapeutics*, Chapter 2, 2012, pp. 9-32.
Shimizu A., et al., "Immunoglobulin Double-Isotype Expression by Trans-mRNA in a Human Immunoglobulin Transgenic Mouse," *Proceedings of the National Academy of Sciences of the U.S.A.*, 1989, vol. 86 (20), pp. 8020-8023.
Shore, D.E., Attorney for Applicant, Third-Party Pre-Issuance Submission Under 37 CFR Sec. 1.290 in U.S. Appl. No. 15/199,575, filed May 31, 2017, 37 pages.
Shultz L.D., et al., "Humanized Mice in Translational Biomedical Research," *Nature Reviews / Immunology*, 2007, vol. 7 (2), pp. 118-130.
Sigmund C.D., "Viewpoint: Are Studies in Genetically Altered Mice Out of Control?," *Arteriosclerosis, Thrombosis, and Vascular Biology*, Jun. 2000, vol. 20 (6), pp. 1425-1429.
Simpson E.M., et al., "Genetic Variation Among 129 Substrains and its Importance for Targeted Mutagenesis in Mice," *Nature Genetics*, 1997, vol. 16 (1), pp. 19-27.
Sirac C., et al., "Role of the Monoclonal κ Chain V Domain and Reversibility of Renal Damage in a Transgenic Model of Acquired Fanconi Syndrome," *Blood*, 2006, vol. 108 (2), pp. 536-543.
Skarnes W.C., et al., "A Conditional Knockout Resource for the Genome-Wide Study of Mouse Gene Function," *Nature*, 2011, vol. 474 (7351), pp. 337-342.
Skoultchi A.I., et al., "Expression of Genes Inserted at the Human β-Globin Locus by Homologous Recombination," *Progress in Clinical and Biological Research*, 1987, vol. 251, pp. 581-594.
Smith K.R., "Gene Transfer in Higher Animals: Theoretical Considerations and Key Concepts," *Journal of Biotechnology*, 2002, vol. 99 (1), pp. 1-22.
Smithies O., "Direct Alteration of a Gene in the Human Genome," *Journal of Inherited Metabolic Disease*, 1986, vol. 9 (Suppl. 1), pp. 92-97.
Smithies O., et al., "Insertion of DNA Sequences into the Human Chromosomal β-Globin Locus by Homologous Recombination," *Nature*, 1985, vol. 317 (6034), pp. 230-234.
Sohn J., et al., "Somatic Hypermutation of an Immunoglobulin μ Heavy Chain Transgene," *The Journal of Experimental Medicine*, 1993, vol. 177 (2), pp. 493-504.
Song K., et al., "Accurate Modification of a Chromosomal Plasmid by Homologous Recombination in Human Cells," *Proceedings of the National Academy of Sciences of the U.S.A.*, 1987, vol. 84 (19), pp. 6820-6824.
Sonoda E., et al., "B Cell Development Under the Condition of Allelic Inclusion," *Immunity*, 1997, vol. 6 (3), pp. 225-233.
Sopher B., et al., "Efficient recombination-based methods for bacterial artificial chromosome fusion and mutagenesis," *Gene*, 2006, vol. 371, pp. 136-143.
Sorrell D.A., et al., "Targeted modification of mammalian genomes," *Biotechnology Advances*, vol. 23, 2005, pp. 431-469.
Soukharev S., et al., "Segmental Genomic Replacement in Embryonic Stem Cells by Double Lox Targeting," *Nucleic Acids Research*, 1999, vol. 27 (18), pp. e21.

Spanopoulou E., et al., "Functional Immunoglobulin Transgenes Guide Ordered B-Cell Differentiation in Rag-1-Deficient Mice," *Genes & Development*, 1994, vol. 8 (9), pp. 1030-1042.
Stavnezer J., et al., "Mechanism and Regulation of Class Switch Recombination," *Annual Review of Immunology*, 2008, vol. 26, pp. 261-292.
Stein R., et al., "Characterization of a humanized IgG4 anti-HLA-DR monoclonal antibody that lacks effector cell functions but retains direct antilymphoma activity and increases the potency of rituximab," *Blood*, Oct. 2006, vol. 108 (8), pp. 2736-2744.
Stephen R., Kymab Limited Statement of Facts and Evidence in opposition to EP2550363, Olswang LLP, dated Sep. 10, 2015, 22 pages.
Stephen R., Olswang, Response to Examination Report dated Jun. 6, 2016 for Application No. 14176740.0, as filed with the European Patent Office on Oct. 10, 2016, 4 pages.
Stephen R., Olswang, Response to Search Report dated Oct. 15, 2014 for Application No. 14176740.0, as filed with the European Patent Office on May 12, 2015, 4 pages.
Stephen R., Olswang, Response to Third-Party Observations dated Aug. 10, 2015 and Examination Report dated Oct. 23, 2015 for Application No. 14176740.0, as filed with the European Patent Office on Apr. 23, 2016, 6 pages.
Stevens S., et al., Expanded Poster: "VelocImmune$^{TM}$: Humanization of immunoglobulin loci using VelociGene® technology," Sep. 2006, 6 pages.
Stevens S., et al., Poster (Exhibit IJR-46): "VelocImmune$^{TM}$: Humanization of immunoglobulin loci using VelociGene® technology," and evidence of unavailability, Sep. 2006, 42 pages.
Stevens S. et al., "VelocImmune: Humanization of Immunoglobulin Loci Using Velocigene Technology," (Abstract-4) Presented at 1st International MUGEN Conference on Animal Models for Human Immunological Disease, Athens, Greece, Sep. 10-13, 2006, 1 page.
Stevens S., "Human Antibody Discovery, VelocImmune—A Novel Platform," *Pharma Focus Asia*, 2008, vol. 8, pp. 72-74.
Storb U., et al., "Physical Linkage of Mouse λ Genes by Pulsed-Field Gel Electrophoresis Suggests that the Rearrangement Process Favors Proximate Target Sequences," *Molecular and Cellular Biology*, 1989, vol. 9 (2), pp. 711-718.
Suárez E., et al., "Rearrangement of Only One Human IGHV Gene is Sufficient to Generate a Wide Repertoire of Antigen Specific Antibody Responses in Transgenic Mice," *Molecular Immunology*, 2006, vol. 43 (11), pp. 1827-1835.
Sun Y., et al., "Repertoire of Human Antibodies against the Polysaccharide Capsule of *Streptococcus pneumoniae* Serotype 6B," *Infection and Immunity*, Mar. 1999, vol. 67 (3), pp. 1172-1179.
Takeda S., et al., "Construction of Chimaeric Processed Immunoglobulin Genes Containing Mouse Variable and Human Constant Region Sequences," *Nature*, Apr. 1985, vol. 314 (6010), pp. 452-454.
Taki S., et al., "Targeted Insertion of a Variable Region Gene into the Immunoglobulin Heavy Chain Locus," *Science*, 1993, vol. 262 (5137), pp. 1268-1271.
Talbot P., et al., "Cell Adhesion and Fertilization: Steps in Oocyte Transport, Sperm-Zona Pellucida Interactions, and Sperm-Egg Fusion," *Biology of Reproduction*, 2003, vol. 68 (1), pp. 1-9.
Tan L.K., et al., "A Human-Mouse Chimeric Immunoglobulin Gene with a Human Variable Region is Expressed in Mouse Myeloma Cells," *Journal of Immunology*, Nov. 1985, vol. 135 (5), pp. 3564-3567.
Tanimoto Y., et al., "Embryonic Stem Cells Derived from C57BL/6J and C57BL/6N Mice," *Comparative Medicine*, Aug. 2008, vol. 58 (4), pp. 347-352.
Taylor L.D., et al., "Human Immunoglobulin Transgenes Undergo Rearrangement, Somatic Mutation and Class Switching in Mice that Lack Endogenous IgM," *International Immunology*, 1994, vol. 6 (4), pp. 579-591.
Te Riele H., et al., "Highly Efficient Gene Targeting in Embryonic Stem Cells through Homologous Recombination with Isogenic DNA Constructs," *Proceedings of the National Academy of Sciences of the U.S.A.*, 1992, vol. 89 (11), pp. 5128-5132.

(56) References Cited

OTHER PUBLICATIONS

The Jackson Laboratory, "Breeding Strategies for Maintaining Colonies of Laboratory Mice," A *Jackson Laboratory Resource Manual*, 2007, pp. 1-29.
Thomas K.R., et al., "High Frequency Targeting of Genes to Specific Sites in the Mammalian Genome," *Cell*, 1986, vol. 44 (3), pp. 419-428.
Thomas K.R., et al., "Introduction of Homologous DNA Sequences into Mammalian Cells Induces Mutations in the Cognate Gene," *Nature*, 1986, vol. 324 (6092), pp. 34-38.
Thomas K.R., et al., "Site-Directed Mutagenesis by Gene Targeting in Mouse Embryo-Derived Stem Cells," *Cell*, 1987, vol. 51 (3), pp. 503-512.
Thykjaer T., et al., "Gene Targeting Approaches Using Positive-Negative Selection and Large Flanking Regions," *Plant Molecular Biology*, 1997, vol. 35 (4), pp. 523-530.
Tomizuka K., et al., "Double Trans-Chromosomic Mice: Maintenance of Two Individual Human Chromosome Fragments Containing Ig Heavy and κ Loci and Expression of Fully Human Antibodies," *Proceedings of the National Academy of Sciences of the U.S.A.*, Jan. 2000, vol. 97 (2), pp. 722-727.
Tonegawa S., "Somatic Generation of Antibody Diversity," *Nature*, Apr. 1983, vol. 302 (5909), pp. 575-581.
Tong C., et al., "Production of p53 gene knockout rats by homologous recombination in embryonic stem cells," *Nature*, Sep. 2010, vol. 467 (7312), pp. 211-213.
Torres R., et al., "Laboratory Protocols for Conditional Gene Targeting", *Institute for Genetics*, University of Cologne, 1997, pp. 37-40.
Tuaillon N., et al., "Human immunoglobulin heavy-chain minilocus recombination in transgenic mice: Gene-segment use in μ and γ transcripts," *Proceedings of the National Academy of Sciences of the U.S.A.*, Apr. 1993, vol. 90, pp. 3720-3724.
Tucker P.W., et al., "Mouse IgA Heavy Chain Gene Sequence: Implications for Evolution of Immunoglobulin Hinge Axons," *Proceedings of the National Academy of Sciences of the U.S.A.*, Dec. 1981, vol. 78 (12), pp. 7684-7688.
Ungrin M.D., et al., "Strict Control of Telomerase Activation Using Cre-Mediated Inversion," *BMC Biotechnology*, 2006, vol. 6, pp. 1-9, 2006.
United Kingdom Intellectual Property Office, Combined Search and Examination Report under Sections 17 and 18(3) for Application No. GB1317410.7, dated Nov. 21, 2013, 8 pages.
United Kingdom Intellectual Property Office, Combined Search and Examination Report under Sections 17 and 18(3) for Application No. GB1317447.9, dated Jan. 14, 2014, 7 pages.
United Kingdom Intellectual Property Office, Corrected Search Report Under Section 17 for Application No. GB1122047.2, dated Apr. 20, 2012, 5 pages.
United Kingdom Intellectual Property Office, Search Report under Section 17 for Application No. GB1116122.1, dated Feb. 2, 2012, 1 page.
Urquhart-Dykes & Lord LLP, Third-Party Observation for Application No. EP20140772198, dated Dec. 14, 2015, 8 pages.
USPTO, Excerpts from U.S. Appl. No. 14/682,859, filed Apr. 9, 2015, including Applicant-initiated Interview Summary; Amendments to the Claims and Information Disclosure Statement, 14 pages.
Valenzuela D.M., et al., "High-Throughput Engineering of the Mouse Genome Coupled with High-Resolution Expression Analysis," *Nature Biotechnology*, 2003, vol. 21 (6), pp. 652-659 and vol. 21 (7), p. 822.
Van Der Weyden L., et al., "Mouse Chromosome Engineering for Modeling Human Disease," *Europe PMC Funders Group*, Author Manuscript, Dec. 2008, 32 pages.
Van Dijk M., Declaration of Marcus Van Dijk with exhibits, Apr. 30, 2016, 139 pages.
Van Loo, P.F., et al., "Surrogate-Light-Chain Silencing Is Not Critical for the Limitation of Pre-B Cell Expansion but Is for the Termination of Constitutive Signaling," *Immunity*, Sep. 2007, vol. 27, pp. 468-480.
Van Snick J.L., et al., "Genetic Control of Rheumatoid Factor Production in the Mouse. Role of Genes Linked to the Immunoglobulin Heavy Chain Locus and to the Major Histocompatibility Complex," *Arthritis and Rheumatism*, Sep. 1983, vol. 26 (9), pp. 1085-1090.
Van Spriel A.B., et al., "Immunotherapeutic Perspective for Bispecific Antibodies," *Immunology Today*, 2000, vol. 21 (8), pp. 391-397.
Vasicek T.J., et al., "Structure and Expression of the Human Immunoglobulin λ Genes," *The Journal of Experimental Medicine*, 1990, vol. 172 (2), pp. 609-620.
Vassilieva S., et al., "Establishment of SSEA-1- and Oct-4-Expressing Rat Embryonic Stem-Like Cell Lines and Effects of Cytokines of the IL-6 Family on Clonal Growth," *Experimental Cell Research*, 2000, vol. 258 (2), pp. 361-373.
Venken K.J., et al., "P[acman]: a BAC Transgenic Platform for Targeted Insertion of Large DNA Fragments in *D. melanogaster,*" *Science*, 2006, vol. 314 (5806), pp. 1747-1751.
Vieira P., et al., "The half-lives of serum immunoglobulins in adult mice," *European Journal of Immunology*, 1988, vol. 18, pp. 313-316.
Vollmer J., et al., "Antigen Contacts by Ni-Reactive TCR: Typical αβ Chain Cooperation Versus α Chain-Dominated Specificity," *International Immunology*, 2000, vol. 12 (12), pp. 1723-1731.
Vora K.A., et al., "Altering the Antibody Repertoire via Transgene Homologous Recombination: Evidence for Global and Clone-Autonomous Regulation of Antigen-Driven B Cell Differentiation," *The Journal of Experimental Medicine*, 1995, vol. 181 (1), pp. 271-281.
Wagner S.D., et al., "Antibodies Generated from Human Immunoglobulin Miniloci in Transgenic Mice," *Nucleic Acids Research*, 1994, vol. 22 (8), pp. 1389-1393.
Wallace H.A.C., et al., "Manipulating the Mouse Genome to Engineer Precise Functional Syntenic Replacements with Human Sequence," *Cell*, 2007, vol. 128 (1), pp. 197-209.
Wang M., et al., "AID Upmutants Isolated Using a High-Throughput Screen Highlight the Immunity/Cancer Balance Limiting DNA Deaminase Activity," *Nature Structural & Molecular Biology*, 2009, vol. 16 (7), pp. 769-776.
Wang M., et al., "Altering the Spectrum of Immunoglobulin V Gene Somatic Hypermutation by Modifying the Active Site of AID," *The Journal of Experimental Medicine*, 2010, vol. 207 (1), pp. 141-153.
Wang T.T., et al., "Catching a Moving Target," *Science*, 2011, vol. 333 (6044), pp. 834-835.
Wang W., et al., "Chromosomal Transposition of PiggyBac in Mouse Embryonic Stem Cells," *Proceedings of the National Academy of Sciences of the U.S.A.*, 2008, vol. 105 (27), pp. 9290-9295.
Wang X., et al., "Recombination, transcription, and diversity of a partially germline-joined VH in a mammal," *Immunogenetics*, 2012, vol. 64, pp. 713-717.
Wang Y., et al., "Many Human Immunoglobulin Heavy-Chain IGHV Gene Polymorphisms have been Reported in Error," *Immunology and Cell Biology*, 2008, vol. 86 (2), pp. 111-115.
Wasserman R., et al., "The Pattern of Joining ($J_H$) Gene Usage in the Human IgH Chain Is Established Predominantly at the B PreCursor Cell Stage," *The Journal of Immunology*, Jul. 1992, vol. 149 (2), pp. 511-516.
Waterhouse P., et al., "Combinatorial Infection and in Vivo Recombination: a Strategy for Making Large Phage Antibody Repertoires," *Nucleic Acids Research*, 1993, vol. 21 (9), pp. 2265-2266.
Waterston R.H., et al., "Initial Sequencing and Comparative Analysis of the Mouse Genome," *Nature*, Dec. 2002, vol. 420 (6915), pp. 520-562.
Webpage corroborating non-confidential nature of 2006 MUGEN Conference, Athens (www.mugen.noe.org), accessed Aug. 9, 2016, 4 pages.
Weichhold G.M., et al., "Megabase Inversions in the Human Genome as Physiological Events," *Nature*, Sep. 1990, vol. 347 (6288), pp. 90-92.

(56) References Cited

OTHER PUBLICATIONS

Weichhold G.M., et al., "The Human Immunoglobulin κ Locus Consists of Two Copies that are Organized in Opposite Polarity," *Genomics*, 1993, vol. 16 (2), pp. 503-511.
Weiner L.M., "Fully Human Therapeutic Monoclonal Antibodies," *Journal of Immunology*, Jan./Feb. 2006, vol. 29 (1), pp. 1-9.
White J.K., et al., "Genome-Wide Generation and Systematic Phenotyping of Knockout Mice Reveals New Roles for Many Genes," *Cell*, 2013, vol. 154 (2), pp. 452-464.
Wikipedia, "Monoclonal antibody," 2008, 8 pages.
Wikipedia, "Polyclonal antibodies," 2008, 5 pages.
Wilke K., et al., "Diagnosis of Haploidy and Triploidy Based on Measurement of Gene Copy Number by Real-Time PCR," *Human Mutation*, 2000, vol. 16 (5), pp. 431-436.
Wilkie T.M., et al., "Analysis of the Integrant in MyK-103 Transgenic Mice in which Males Fail to Transmit the Integrant," *Molecular and Cellular Biology*, 1987, vol. 7 (5), pp. 1646-1655.
Williams G.S., et al., "Unequal $V_H$ Gene Rearrangement Frequency within the Large $V_H$7183 Gene Family is not due to Recombination Signal Sequence Variation, and Mapping of the Genes Shows a Bias of Rearrangement Based on Chromosomal Location," *Journal of Immunology*, 2001, vol. 167 (1), pp. 257-263.
Williams K., Attorney for Applicant, Third-Party Pre-Issuance Submission Under 37 CFR 1.290 in U.S. Appl. No. 14/600,829, dated Apr. 1, 2016, 18 pages.
Williams K., Attorney for Applicant, Third-Party Pre-Issuance Submission Under 37 CFR 1.290 in U.S. Appl. No. 14/679,949, dated Apr. 1, 2016, 18 pages.
Wuerffel R., et al., "S—S Synapsis During Class Switch Recombination is Promoted by Distantly Located Transcriptional Elements and Activation-Induced Deaminase," *Immunity*, Nov. 2007, vol. 27 (5), pp. 711-722.
Xiao X., et al., "Germline-like predecessors of broadly neutralizing antibodies lack measurable binding to HIV-1 envelope glycoproteins: Implications for evasion of immune responses and design of vaccine immunogens," *Biochemical and Biophysical Communications*, 2009, vol. 390, pp. 404-409.
Xu L., et al., "Combinatorial Surrobody Libraries," *Proceedings of the National Academy of Sciences of the U.S.A.*, 2008, vol. 105 (31), pp. 10756-10761.
Xu Y., et al., "Deletion of the Igκ Light Chain Intronic Enhancer/Matrix Attachment Region Impairs but does not Abolish VκJκ Rearrangement," *Immunity*, Apr. 1996, vol. 4 (4), pp. 377-385.
Yamada M., et al., "Preferential Utilization of Specific Immunoglobulin Heavy Chain Diversity and Joining Segments in Adult Human Peripheral Blood B Lymphocytes," *Journal of Experimental Medicine*, Feb. 1991, vol. 173, pp. 395-407.
Yancopoulos G.D., et al., "Preferential Utilization of the Most $J_H$-Proximal $V_H$ Gene Segments in Pre-B-Cell Lines," *Nature*, 1984, vol. 311 (5988), pp. 727-733.
Yang X.W., et al., "Homologous Recombination Based Modification in *Escherichia coli* and Germline Transmission in Transgenic Mice of a Bacterial Artificial Chromosome," *Nature Biotechnology*, Sep. 1997, vol. 15 (9), pp. 859-865.
Yu C.C.K., et al., "Differential Usage of $V_H$ Gene Segments is Mediated by cis Elements," *Journal of Immunology*, 1998, vol. 161 (7), pp. 3444-3454.
Yu Y., et al., "Engineering Chromosomal Rearrangements in Mice," *Nature Reviews Genetics*, 2001, vol. 2 (10), pp. 780-790.
Zemlin M., et al., "Expressed Murine and Human CDR-H3 Intervals of Equal Length Exhibit Distinct Repertoires that Differ in their Amino Acid Composition and Predicted Range of Structures," *Journal of Molecular Biology*, 2003, vol. 334 (4), pp. 733-749.
Zhang X., et al., "Combination of overlapping bacterial artificial chromosones by a two-step recombinogenic engineering method," *Nucleic Acids Research*, 2003, vol. 31 (15), pp. e81-1-e81-6.
Zhang Y., et al., "A New Logic for DNA Engineering Using Recombination in *Escherichia coli*," *Nature Genetics*, 1998, vol. 20 (2), pp. 123-128.
Zhao S., "A Comprehensive BAC Resource," *Nucleic Acids Research*, 2001, vol. 29 (1), pp. 141-143.
Zhao Y., et al., "Physical Mapping of the Bovine Immunoglobulin Heavy Chain Constant Region Gene Locus," *Journal of Biological Chemistry*, Sep. 2003, vol. 278 (37), pp. 35024-35032.
Zheng B., et al., "Engineering Mouse Chromosomes with Cre-IoxP: Range, Efficiency, and Somatic Applications," *Molecular and Cellular Biology*, 2000, vol. 20 (2), pp. 648-655.
Zheng J., et al., "Immunoglobulin Gene Transcripts Have distinctive $V_H DJ_H$ Recombination Characteristics in Human Epithelial Cancer Cells", *Journal of Biological Chemistry*, Mar. 2009, vol. 284 (20), pp. 13610-13619.
Zou X., et al., "Removal of the BiP-Retention Domain in Cμ Permits Surface Deposition and Developmental Progression Without L-Chain," *Molecular Immunology*, 2008, vol. 45 (13), pp. 3573-3579.
Zou X., et al., "Subtle differences in antibody responses and hypermutation of lambda λ chains in mice with a disrupted κ contant region," *European Journal of Immunology*, 1995, vol. 25, pp. 2154-2162.
Zou Y., et al., "Cre-IoxP-Mediated Gene Replacement: a Mouse Strain Producing Humanized Antibodies," *Current Biology*, 1994, vol. 4 (12), pp. 1099-1103.
Baxendale H.E., et al., "Natural human antibodies to pneumococcus have distinctive molecular characteristics and protect against pneumococcal disease," *Clinical and Experimental Immunology*, 2007, vol. 151, pp. 51-60.
D'Eustachio P., et al., "Mouse Chromosome 12," *Mammalian Genome*, 1998, vol. 8, pp. S241-S257.
Forsman A., et al., "Llama Antibody Fragments with Cross-Subtype Human Immunodeficiency Virus Type I (HIV-1)-Neutralizing Properties and High Affinity for HIV-1 gp120," *Journal of Virology*, Dec. 2008, vol. 82 (24), pp. 12069-12081.
Grund M., European Patent Attorney, Grund Intellectual Property Group, Third-Party Observations according to Article 115 EPC regarding 12762377.5, dated Jun. 20, 2017, 4 pages.
Jones B.T., Attorney for Applicant, Third-Party Pre-Issuance Submission Under 37 CFR Sec. 1.290 in U.S. Appl. No. 15/251,969, filed May 4, 2017, 22 pages.
Jones B.T., Attorney for Applicant, Third-Party Pre-Issuance Submission Under 37 CFR Sec. 1.290 in U.S. Appl. No. 15/383,101, filed May 30, 2017, 32 pages.
Jones B.T., Attorney for Applicant, Third-Party Pre-Issuance Submission Under 37 CFR Sec. 1.290 in U.S. Appl. No. 15/383,188, filed May 30, 2017, 33 pages.
Suárez E., et al., "Human monoclonal antibodies produced in transgenic BABκ,λ mice recognising idiotypic immunoglobulins of human lymphoma cells," *Molecular Immunology*, 2004, vol. 41, pp. 519-526.
Zhu Z., et al., "Cross-Reactive HIV-1-Neutralizing Human Monoclonal Antibodies Identified from a Patient with 2F5-Like Antibodies," *Journal of Virology*, Nov. 2011, vol. 85 (21), pp. 11401-11408.
"1st International MUGEN Conference on Animal Models for Human Immunological Disease," Sep. 10-13, 2006—Athens Greece (Scientific Programme & Presentations), Sep. 10-13, 2006, 4 pages.
Adekar S.P., et al., "A Natural Human IgM Antibody that Neutralizes Botulinum Neurotoxin in vivo," *Hybridoma*, 2008, vol. 27 (2), pp. 65-69.
Aizenshtein E., et al., "Immunological complex for enhancement of innate immune response in passive vaccination," *Vaccine*, Jan. 2013, vol. 31 (4), pp. 626-631 [abstract only—1 page].
An Z., Therapeutic Monoclonal Antibodies from Bench to Clinic, 2009, 4 pages.
Australian Intellectual Property Office, Examination Report No. 1 for Standard Patent Application for Application No. 2016244295, dated Aug. 18, 2017, 4 pages.
Australian Intellectual Property Office, Notification of material filed by a third-party for Application No. 2012311288 in the name of Kymab Ltd., Applicant, dated Nov. 20, 2017, 14 pages.
Bentham A., JA Kemp, European Patent Attorney, Statement of Fact and Arguments in Support of Opposition against EP2527557 in the name of Kymab Limited pertaining to Application No. 12171793.8, dated Jan. 11, 2017, 32 pages.

(56) References Cited

OTHER PUBLICATIONS

Bentham A., JA Kemp, Final Written Submissions pertaining to Patent No. 2517557 for Application No. 12171793.8, dated May 17, 2018, 20 pages.
Boyd S.D., et al., "Individual Variation in the Germline Ig Gene Repertoire Inferred from Variable Region Gene Rearrangements," *The Journal of Immunology*, Jun. 2010, vol. 184 (12), pp. 6986-6992.
Bradley A., Declarations of Allan Bradley (Tanamachi/Grosveld), as submitted in U.S. Appl. No. 13/416,684, 5 pages.
Bradley A., Declaration of Allan Bradley (commercial success), with exhibits, as submitted in U.S. Appl. No. 13/416,684, dated Feb. 12, 2015, 15 pages.
Bradley A., Declaration of Allan Bradley (mouse strain), with exhibits, as submitted in U.S. Appl. No. 13/416,684, dated Feb. 12, 2015, 68 pages.
Bradshaw, et al., "*Handbook of Cell Signalling*," 2010, Chapter 5, p. 33 (excerpt).
Bruggemann; M., "The Preparation of Human Antibodies from Mice Harbouring Human Immunoglobulin Loci", *Transgenic Animals. Generation and Use*, 1997, Chapter 58, Part IV, Section A, pp. 397-402 (including cover and copyright pages).
Brüggemann M., et al., "Selection Strategies III: Transgenic Mice," in *Handbook of Therapeutic Antibodies—Technologies, Emerging Developments and Approved Therapeutics*, 2010, Chapter 4, pp. 69-91.
Burton D.R., et al., "Antibody vs. HIV in a clash of evolutionary titans," *Proceedings of the National Academy of Sciences of the U.S.A*, Oct. 2005, vol. 102 (42), pp. 14943-14948.
Calame K., et al., "Regulation of immunoglobulin gene transcription," *Immunoglobulin Genes*, 2nd edition, Chapter 18, 1995, pp. 397-422.
Camboni M., et al., "Active and passive immunization strategies based on the SDPM1 peptide demonstrate pre-clinical efficacy in the APPswePSEN1dE9 mouse model for Alzheimer's disease," *Neurobiology of Disease*, Feb. 2014, vol. 52, pp. 31-43 [abstract only—2 pages].
Canadian Intellectual Property Office, Protest and Submission of Prior Art, Application No. 2,802,591, dated Nov. 13, 2019, 18 pages.
Canadian Intellectual Property Office, Office Action for Application No. 2,857,569, dated Jan. 14, 2019, 6 pages.
Collis A.V.J., et al., "Analysis of the Antigen Combining Site: Correlations Between Length and Sequence Composition of the Hypervariable Loops and the Nature of the Antigen," *Journal of Molecular Biology*, 2003, vol. 325, pp. 337-354.
Davis C.G., et al., "Production of Human Antibodies from Transgenic Mice," *Antibody Engineering, Methods and Protocols, Methods in Mol. Biol.*, Chapter 10, 2004, pp. 191-200.
Delves P.J., et al., "Antibodies," *Chapter 3, Roitt's Essential Immunology*, Eleventh edition, 2006, pp. 37-60.
Dörner T., et al., "Delineation of Selective Influences Shaping the Mutated Expressed Human Ig Heavy Chain Repertoire," *The Journal of Immunology*, Mar. 1998, vol. 160 (6), pp. 2831-2841.
Dörner T., et al., "Analysis of the targeting of the hypermutational machinery and the impact of subsequent selection on the distribution of nucleotide changes in human $V_H DJ_H$ rearrangements," *Immunologic Reviews*, Apr. 1998, vol. 162 (1), pp. 161-171.
Dörner T., et al., "Somatic hypermutation of human immunoglobulin heavy chain genes: targeting of RGYW motifs on both DNA strands," *European Journal of Immunology*, 1998, vol. 28, pp. 3384-3396.
Dübel S., "Therapeutic Antibodies—From Past to Future," in *Handbook of Therapeutic Antibodies—Technologies, Emerging Developments and Approved Therapeutics*, 2010, Chapter 1 (excerpt: pp. 3-5).
European Patent Office, Examination Report for Application No. 13723933.1, dated Jan. 17, 2018, 6 pages.
European Patent Office, Examination Report for Application No. 15188522.5, dated Aug. 11, 2017, 6 pages.
European Patent Office, Examination Report for Application No. 16151215.7, dated Jan. 23, 2017, 5 pages.
European Patent Office, Extended European Search Report for Application No. 17174426.1, dated Sep. 14, 2017, 10 pages.
European Patent Office, Extended European Search Report for Application No. 17196214.5, dated Jan. 2, 2018, 13 pages.
European Patent Office, Extended European Search Report for Application No. 18153171.6, dated Jun. 28, 2018, 15 pages.
European Patent Office, Opposition against EP2604110 Animal Models and Therapeutic Molecules in the name of Kymab Limited pertaining to Application No. 12194777.0, dated Aug. 28, 2017, 73 pages.
European Patent Office, Opposition against EP 2758535 Antibodies, Variable Domains and Chains Tailored for Human Use in the name of Kymab Limited pertaining to Application No. 12772122.3, dated Aug. 9, 2017, 75 pages.
European Patent Office, Opposition against EP2798950 Animal Models and Therapeutic Molecules in the name of Kymab Limited pertaining to Application No. 14170196.1, dated Jan. 18, 2018, 33 pages.
European Patent Office, Irmgard Scheffzyk, Authorized officer, International Search Report for Application No. PCT/EP2018/068309, dated Jan. 15, 2019, 14 pages, together with the Written Opinion of the International Searching Authority.
The International Bureau of WIPO, Third-Party Observations regarding Application No. PCT/EP2018/068309, dated Aug. 14, 2019, 6 pages.
Evans M.J., Declaration of Martin J. Evans, with Appendices, dated Dec. 23, 2016, 99 pages.
Frigerio B., et al., "Antibody Engineering as Opportunity for Selection and Organization of Anti-HIV Therapeutic Agents," *The Open Autoimmunity Journal*, 2010, vol. 2, pp. 127-138.
Genbank, "*Homo sapiens* DNA, immunoglobulin heavy-chain variable region, complete sequence, 5 of 5," Accession No. AB019441.1, dated Jun. 18, 2018, 36 pages.
Genbank, "*Homo sapiens* partial IGHJ6 gene for immunoglobulin heavy joining 6, exon 1, allele 4," AJ879487.1, dated Jul. 26, 2016, 1 page.
Genbank, "Immunoglobulin Heavy Chain Variable Region (*Homo sapiens*)," Accession No. BAA75060, dated Jul. 2, 2008, 1 page.
Giudicelli V., et al., "IMGT/GENE-DB: a comprehensive database for human and mouse immunoglobulin and T cell receptor genes," *Nucleic Acids Research*, 2005, vol. 33, pp. D256-0261.
Goding J.W., "Differences Between Conventional and Monoclonal Serology," *Monoclonal Antibodies: Principles and Practice, Production and Application of Monoclonal Antibodies in Cell Biology, Biochemistry and Immunology*, 1996, Third Edition, Section 7.3, pp. 129-130.
Grund M., European Patent Attorney, Grund Intellectual Property Group, Third-Party Observations according to Article 115 EPC regarding 12171793.8, dated Oct. 10, 2013, 10 pages.
Grund M., European Patent Attorney, Grund Intellectual Property Group, Third-Party Observations according to Article 115 EPC regarding 12171793.8, dated Mar. 17, 2015, 4 pages.
Grund M., European Patent Attorney, Grund Intellectual Property Group, Third-Party Observations according to Article 115 EPC regarding 12171793.8, dated May 22, 2015, 5 pages.
Grund M., European Patent Attorney, Grund Intellectual Property Group, Third-Party Observations according to Article 115 EPC regarding 14781635.9, dated May 18, 2018, 4 pages.
Grund M., European Patent Attorney, Grund Intellectual Property Group, Third-Party Observations according to Article 115 EPC regarding 15188522.5, dated Mar. 13, 2019, 3 pages.
Grund M., European Patent Attorney, Grund Intellectual Property Group, Third-Party Observations according to Article 115 EPC regarding 17196235.0, dated Nov. 27, 2018, 22 pages.
Grund M., European Patent Attorney, Grund Intellectual Property Group, Third-Party Observations according to Article 115 EPC regarding 17174426.1, dated Jun. 27, 2018, 7 pages.
Grund M., European Patent Attorney, Grund Intellectual Property Group, Third-Party Observations according to Article 115 EPC regarding 17174426.1, dated Feb. 11, 2019, 5 pages.

(56) References Cited

OTHER PUBLICATIONS

He Y., et al., "Efficient Isolation of Novel Human Monoclonal Antibodies with Neutralizing Activity Against HIV-1 from Transgenic Mice Expressing Human Ig Loci," *The Journal of Immunology*, 2002, vol. 169, pp. 595-605.

HGNC (HUGO Gene Nomenclature Committee), "Gene Family: Immunoglobulin Heavy Locus at 14q32.33 (IGH)," 4 pages. [retrieved on Jul. 31, 2017 at http://www.genenames.org/cgi-bin/genefamilies/set/349].

Hülseweh B., et al, "Human-like antibodies neutralizing Western equine encephalitis virus," *mAbs*, May/Jun. 2014, vol. 6 (3), pp. 718-727.

Ichihara Y., et al., "Organization of human immunoglobulin heavy chain diversity gene loci," *The EMBO Journal*, 1988, vol. 7, No. 13, pp. 4141-4150.

Imbimbo B.P., et al., "Solanezumab for the treatment of mild-to-moderate Alzheimer's disease," *Expert Review of Clinical Immunology*, Feb. 2012, vol. 8 (2), pp. 135-149 [abstract only—1 page].

IMGT, *the International ImMunoGeneTics Information system database*, IMGT/GENE-DB entry for *Homo sapiens* IGHD3-9, 2007, 2 pages.

IMGT, *the International ImMunoGeneTics Information system database*, "Alignment of alleles: Human IGHJ6," dated Jun. 29, 2011, 1 page.

IMGT, *the International ImMunoGeneTics Information system database*, IMGT/GENE-DB entry for *Homo sapiens* IGHJ6, dated Jul. 26, 2017, version 3.1.17, 4 pages.

IMGT, *the International ImMunoGeneTics Information system database*, "IMGT/GENE-DB reference sequences," Nucleotide sequences of the four human IGHJ6 alleles, dated Jul. 26, 2017, version 3.1.17, 1 page.

IMGT, *the International ImMunoGeneTics Information system database*, "IMGT/GENE-DB reference sequences," Amino acid sequences of the four human IGHJ6 alleles, dated Jul. 26, 2017, version 3.1.17, 7 pages.

Jackson S.M., et al., "Human B Cell Subsets," *Advances in Immunology*, Chapter 5, 2008, vol. 98, pp. 151-224.

Janeway C.A. et al., "Structure of the Antibody Molecule and the Immunoglobulin Genes," excerpts from Immunobiology: The Immune System in Health and Disease, 4th Edition, 1999, 4 pages.

Janssens R., et al., "Generation of Heavy-Chain-only Antibodies in Mice," *Proceedings of the National Academy of Sciences of the U.S.A.*, 2006, vol. 103 (41), pp. 15130-15135.

Japanese Patent Office, Notice of Reasons for Rejection for Application No. 2016-548441, dated Aug. 5, 2019, together with English translation, 12 pages.

Japanese Patent Office, Notice of Reasons for Rejection for Application No. 2017-017360, dated Mar. 19, 2018, together with English translation, 7 pages.

Japanese Patent Office, Notice of Reasons for Rejection for Application No. 2017-021028, dated Dec. 21, 2018, together with English translation, 11 pages.

Japanese Patent Office, Decision of Rejection for Application No. 2017-021028, Decision of Rejection, dated Sep. 9, 2019, together with English translation, 9 pages.

Japanese Patent Office, Notice of Reasons for Rejection for Application No. 2018-088749, dated May 27, 2019, together with English translation, 11 pages.

Jendreyko N., et al., "Intradiabodies, Bispecific, Tetravalent Antibodies for the Simultaneous Functional Knockout of Two Cell Surface Receptors," *The Journal of Biological Chemistry*, 2003, vol. 278 (48), pp. 47812-47819.

Kelley S.K., et al., "Preclinical pharmacokinetics, pharmacodynamics, and activity of a humanized anti-CD40 antibody (SGN-40) in rodents and non-human primates," *British Journal of Pharmacology*, 2006, vol. 148, pp. 1116-1123.

Kim S.J., et al., "Antibody Engineering for the Development of Therapeutic Antibodies," *Mol. Cells*, 2005, vol. 20 (1), pp. 17-29.

Kriangkum J., et al., "Molecular Characterization of Waldenstrom's Macroglobulinemia Reveals Frequent Occurrence of Two B-Cell Clones Having Distinct IgH VDJ Sequences," *Clinical Cancer Research*, Apr. 2007, vol. 13 (7), pp. 2005-2013.

Kumar R., et al., "A novel strategy for efficient production of anti-V3 human scFvs against HIV-1 Glade C," *BMC Biotechnology*, Nov. 2012, vol. 12 (87), 15 pages.

Laventie B., et al., "Heavy Chain-Only Antibodies and Tetravalent Bispecific Antibody Neutralizing *Staphylococcus aureus* Leukotoxins," *Proceedings of the National Academy of Sciences of the U.S.A.*, 2011, vol. 108 (39), pp. 16404-16409.

Lee E-Chiang, Declaration of E-Chiang Lee, Jun. 13, 2016, 8 pages.

Lee E., et al., "Use of IGHJ and IGHD gene mutations in analysis of immunoglobulin sequences for the prognosis of chronic lymphocytic leukemia," *Leukemia Research*, 2007, vol. 31, pp. 1247-1252.

Li Z., et al., "The generation of antibody diversity through somatic hypermutation and class switch recombination," *Genes & Development*, vol. 18, pp. 1-11 (2004).

Lonberg N., et al., "Antigen-specific human antibodies from mice comprising four distinct genetic modifications," Nature, Apr. 1994, vol. 368, pp. 856-859.

Lonberg N., et al., "Human Antibodies from Transgenic Mice," *Intern. Rev. Immunol.*, 1995, vol. 13, pp. 65-93.

Lonberg N., "Human Monoclonal Antibodies from Transgenic Mice," *Therapeutic Antibodies. Handbook of Experimental Pharmacology*, 2008, pp. 69-97.

MacDonald L., Declaration of Lynn E. MacDonald, including Annex 1, dated May 16, 2018, 10 pages.

Mårtensson I.L., et al., "The pre-B-cell receptor," *Current Opinion in Immunology*, 2007, vol. 19, pp. 137-142.

Meier I.D., et al., "Short DNA sequences inserted for gene targeting can accidentally interfere with off-target gene expression," The FASEB Journal, Research Communication, Jun. 2010, vol. 24, pp. 1714-1724.

Missirlis P.I., et al., "A high-throughout screen identifying sequence and promiscuity characteristics of the loxP spacer region in Cre-mediated recombination," BMC Genomics, Apr. 2006, vol. 7(73), 13 pages.

Morrison et al. "Vectors and Approaches for the Eukaryotic Expression of Antibodies and Antibody Fusion Proteins," Chapter 9 of Antibody Engineering, 2nd Edition, 1995.

Muramatsu M., et al., "Specific Expression of Activation-induced Cytidine Deaminase (AID), a Novel Member of the RNA-editing Deaminase Family in Germinal Center B Cells," 1999, The Journal of Biological Chemistry, vol. 274, No. 26, pp. 18470-18476.

Newcombe C., et al., "Antibody production: Polyclonal-derived biotherapeutics," *Journal of Chromatography B*, 2007 vol. 848, pp. 2-7.

O'Dea, T.P., Attorney for Applicant, Third-Party Pre-Issuance Submission Under 37 CFR Sec. 1.290 in U.S. Appl. No. 15/383,342, filed Aug. 7, 2017, 32 pages.

O'Dea, T.P., Attorney for Applicant, Third-Party Pre-Issuance Submission Under 37 CFR Sec. 1.290 in U.S. Appl. No. 15/385,348, filed Jul. 28, 2017, 48 pages.

O'Dea, T.P., Attorney for Applicant, Third-Party Pre-Issuance Submission Under 37 CFR Sec. 1.290 in U.S. Appl. No. 15/385,372, filed Jul. 28, 2017, 48 pages.

Okada A., et al., "The variable region gene assembly mechanism," Immunoglobulin Genes, 2nd edition, Chapter 10, 1995, pp. 205-234.

Pinaud E., et al., "The IgH Locus 3' Regulatory Region: Pulling the Strings from Behind," Advances in Immunology, Chapter 2, 2011, vol. 11, pp. 27-70.

Potter K.N., et al., "Features of the overexpressed V1-69 genes in the unmutated subset of chronic lymphocytic leukemia are distinct from those in the healthy elderly repertoire," *Blood*, Apr. 2003, vol. 101 (8), pp. 3082-3084.

Prak E.T.L, et al., "B cell receptor editing in tolerance and auto-immunity," *Annals of the New York Academy of Sciences*, Jan. 2011, vol. 1217, pp. 96-121.

Raaphorst F.M., et al., "Human Ig heavy chain CDR3 regions in adult bone marrow pre-B cells display an adult phenotype of diversity: evidence for structural selection of $D_H$ amino acid sequences," *International Immunology*, Oct. 1997, vol. 9 (10), pp. 1503-1515.

(56) References Cited

OTHER PUBLICATIONS

Ren L., et al., "Silencing of the immunoglobulin heavy chain locus by removal of all eight constant-region genes in a 200-kb region," *Genomics*, Aug. 2004, vol. 84, pp. 686-695.

Ricker M., European Patent Attorney, Opposition against EP2758535 in the name of Kymab Limited Statement of Facts and Arguments pertaining to Application No. 12772122.3, dated Aug. 9, 2017, 42 pages.

Rudolf M.P., et al., "Molecular basis for nonanaphylactogenicity of a monoclonal anti-IgE antibody," *Journal of Immunology*, Jul. 2010, vol. 165 (2), pp. 813-819.

Ruiz M., et al, "The Human Immunoglobulin Heavy Diversity (IGHD) and Joining (IGHJ) Segments," *Experimental and Clinical Immunogenetics*, 1999, vol. 16, pp. 173-184.

Russell N.D., et al., "Production of Protective Human Antipneumococcal Antibodies by Transgenic Mice with Human Immunoglobulin Loci," *Infection and Immunity*, Apr. 2000, vol. 68 (4), pp. 1820-1826.

Shore D.E., Attorney for Applicant, Third-Party Pre-Issuance Submission Under 37 CFR Sec. 1.290 in U.S. Appl. No. 15/088,805, filed Nov. 17, 2017, 44 pages.

Shore D.E., Attorney for Applicant, Third-Party Pre-Issuance Submission Under 37 CFR Sec. 1.290 in U.S. Appl. No. 15/656,897, filed May 4, 2018, 55 pages.

Shore, D.E., Attorney for Applicant, Third-Party Pre-Issuance Submission Under 37 CFR Sec. 1.290 in U.S. Appl. No. 15/690,183, filed Feb. 28, 2018, 60 pages.

Shore D.E., Attorney for Applicant, Third-Party Pre-Issuance Submission Under 37 CFR Sec. 1.290 in U.S. Appl. No. 15/786,281, filed Jun. 27, 2018, 63 pages.

Shore D.E., Attorney for Applicant, Third-Party Pre-Issuance Submission Under 37 CFR Sec. 1.290 in U.S. Appl. No. 15/786,281, filed Jun. 27, 2018 (Second Submission), 62 pages.

Shore D.E., Attorney for Applicant, Third-Party Pre-Issuance Submission Under 37 CFR Sec. 1.290 in U.S. Appl. No. 15/786,281, filed Jun. 27, 2018 (Third Submission), 53 pages.

Shore D.E., Attorney for Applicant, Third-Party Pre-Issuance Submission Under 37 CFR Sec. 1.290 in U.S. Appl. No. 15/948,709, filed Jan. 10, 2019, 43 pages.

Shore D.E., Attorney for Applicant, Third-Party Pre-Issuance Submission Under 37 CFR Sec. 1.290 in U.S. Appl. No. 15/955,216, dated Feb. 5, 2019, 64 pages.

Siman-Tov D.D., et al., "Differentiation of a passive vaccine and the humoral immune response toward infection: Analysis of phage displayed peptides," *Vaccine*, Jan. 2006, vol. 24, pp. 607-612.

Stephen R., Olswang, Submission in Response to Summons and Preliminary Opinion related to Application No. EP 2517557, as filed with the European Patent Office on May 17, 2018, 4 pages.

Stephen R., Olswang, Response to European Opposition filed by Regeneron Pharmaceuticals, Inc. related to Application No. EP 2517557, dated Jun. 23, 2017, 8 pages.

Stephen R., Olswang, Response to Opposition in the name of Kymab Limited related to EP 2758535 as filed with the European Patent Office on Mar. 22, 2018, 26 pages.

Stephen R., Olswang, Response to Third-Party Observations for Application No. 12171793.8, as filed with the European Patent Office on Apr. 17, 2015, 3 pages.

Sullivan P.M., et al., "Targeted Replacement of the Mouse Apolipoprotein E Gene with the Common Human APOE3 Allele Enhances Diet-induced Hypercholesterolemia and Atherosclerosis" *The Journal of Biological Chemistry*, 1997, vol. 272, No. 2, pp. 17972-17980.

Table S1 (from Breden F., et al., "Comparison of Antibody Repertoires Produced by HIV-1 Infection, Other Chronic and Acute Infections, and Systemic Autoimmune Disease," *PLoS One*, 2011, vol. 6 (3), pp. e16857-1-e16857-11.), 60 pages.

Table S2 (from Breden F., et al., "Comparison of Antibody Repertoires Produced by HIV-1 Infection, Other Chronic and Acute Infections, and Systemic Autoimmune Disease," *PLoS One*, 2011, vol. 6 (3), pp. e16857-1-e16857-11.), 14 pages.

Taylor L.D., et al., "A transgenic mouse that expresses a diversity of human sequence heavy and light chain immunoglobulins," *Nucleic Acids Research*, 1992, vol. 20 (23), pp. 6287-6295.

Zwick M.B., et al., "The Long Third Complementarity-Determining Region of the Heavy Chain Is Important in the Activity of the Broadly Neutralizing Anti-Human Immunodeficiency Virus Type 1 Antibody 2F5," *Journal of Virology*, Mar. 2004, vol. 78 (6), pp. 3155-3161.

U.S. Appl. No. 15/383,353, filed Dec. 19, 2016.
U.S. Appl. No. 15/383,196, filed Dec. 19, 2016, issued Apr. 10, 2018 as U.S. Pat. No. 9,938,357.
U.S. Appl. No. 15/383,202, filed Dec. 19, 2016 issued Apr. 10, 2018 as U.S. Pat. No. 9,938,358.
U.S. Appl. No. 15/385,348, filed Dec. 20, 2016.
U.S. Appl. No. 15/385,372, filed Dec. 20, 2016.
U.S. Appl. No. 15/656,897, filed Jul. 21, 2017.
U.S. Appl. No. 15/690,183, filed Aug. 29, 2017, issued Mar. 12, 2019 as U.S. Pat. No. 10/226,033.
U.S. Appl. No. 15/786,281, filed Oct. 17, 2017.
U.S. Appl. No. 15/948,709, filed Apr. 9, 2018.
U.S. Appl. No. 15/973,376, filed May 7, 2018.
U.S. Appl. No. 15/955,216, filed Apr. 17, 2018.
U.S. Appl. No. 16/216,666, filed Dec. 11, 2018.
U.S. Appl. No. 16/296,033, filed Mar. 7, 2019.
U.S. Appl. No. 16/353,870, filed Mar. 14, 2019.
U.S. Appl. No. 16/725,707, filed Dec. 23, 2019.

Laventie et al., Heavy chain-only antibodies and tetravalent bispecific antibody neutralizing *Staphylococcus aureus* leukotoxins, PNAS, 108(39): 16404-16409, 2011.†

Jendreyko et al., Intrabodies, bispecific, tetravalent antibodies for the simultaneous functional knockout of two cell surface receptors, J. Biol. Chem., 278(48):47812-47819, 2003.†

\* cited by examiner
† cited by third party

SEQUENCE LISTING

```
<160> NUMBER OF SEQ ID NOS: 140

<210> SEQ ID NO 1
<211> LENGTH: 5
<212> TYPE: PRT
<213> ORGANISM: Artificial Sequence
<220> FEATURE:
<221> NAME/KEY: REPEAT
<222> LOCATION: (1)(5)n
<223> OTHER INFORMATION: linker n=1,2,3,4,5,6,7,8,9,10

<400> SEQUENCE: 1

Gly Gly Gly Gly Ser
1               5

<210> SEQ ID NO 2
<211> LENGTH: 16
<212> TYPE: PRT
<213> ORGANISM: Artificial Sequence
<220> FEATURE:
<223> OTHER INFORMATION: linker

<400> SEQUENCE: 2

Ala Lys Thr Thr Pro Lys Leu Glu Glu Gly Glu Phe Ser Glu Ala Arg
1               5                   10                  15

<210> SEQ ID NO 3
<211> LENGTH: 17
<212> TYPE: PRT
<213> ORGANISM: Artificial Sequence
<220> FEATURE:
<223> OTHER INFORMATION: linker

<400> SEQUENCE: 3

Ala Lys Thr Thr Pro Lys Leu Asx Glu Gly Glu Phe Ser Glu Ala Arg
1               5                   10                  15

Val
```

```
<210> SEQ ID NO 4
<211> LENGTH: 9
<212> TYPE: PRT
<213> ORGANISM: Artificial Sequence
<220> FEATURE:
<223> OTHER INFORMATION: linker

<400> SEQUENCE: 4

Ala Lys Thr Thr Pro Lys Leu Gly Gly
1               5

<210> SEQ ID NO 5
<211> LENGTH: 10
<212> TYPE: PRT
<213> ORGANISM: Artificial Sequence
<220> FEATURE:
<223> OTHER INFORMATION: linker

<400> SEQUENCE: 5

Ser Ala Lys Thr Thr Pro Lys Leu Gly Gly
1               5                   10

<210> SEQ ID NO 6
<211> LENGTH: 17
<212> TYPE: PRT
<213> ORGANISM: Artificial Sequence
<220> FEATURE:
<223> OTHER INFORMATION: linker

<400> SEQUENCE: 6

Ala Lys Thr Thr Pro Lys Leu Glu Glu Gly Glu Phe Ser Glu Ala Arg
1               5                   10                  15

Val

<210> SEQ ID NO 7
<211> LENGTH: 6
<212> TYPE: PRT
<213> ORGANISM: Artificial Sequence
<220> FEATURE:
<223> OTHER INFORMATION: linker

<400> SEQUENCE: 7

Ser Ala Lys Thr Thr Pro
1               5

<210> SEQ ID NO 8
<211> LENGTH: 10
<212> TYPE: PRT
<213> ORGANISM: Artificial Sequence
<220> FEATURE:
<223> OTHER INFORMATION: linker

<400> SEQUENCE: 8

Ser Ala Lys Thr Thr Pro Lys Leu Gly Gly
1               5                   10

<210> SEQ ID NO 9
<211> LENGTH: 6
<212> TYPE: PRT
<213> ORGANISM: Artificial Sequence
<220> FEATURE:
<223> OTHER INFORMATION: linker

<400> SEQUENCE: 9

Arg Ala Asp Ala Ala Pro
1               5
```

```
<210> SEQ ID NO 10
<211> LENGTH: 9
<212> TYPE: PRT
<213> ORGANISM: Artificial Sequence
<220> FEATURE:
<223> OTHER INFORMATION: linker

<400> SEQUENCE: 10

Arg Ala Asp Ala Ala Pro Thr Val Ser
 1               5

<210> SEQ ID NO 11
<211> LENGTH: 12
<212> TYPE: PRT
<213> ORGANISM: Artificial Sequence
<220> FEATURE:
<223> OTHER INFORMATION: linker

<400> SEQUENCE: 11

Arg Ala Asp Ala Ala Ala Ala Gly Gly Pro Gly Ser
 1               5                  10

<210> SEQ ID NO 12
<211> LENGTH: 9
<212> TYPE: PRT
<213> ORGANISM: Artificial Sequence
<220> FEATURE:
<221> NAME/KEY: REPEAT
<222> LOCATION: (8) 4, (8)(9) 4
<223> OTHER INFORMATION: linker

<400> SEQUENCE: 12

Arg Ala Asp Ala Ala Ala Ala Gly Ser
 1               5

<210> SEQ ID NO 13
<211> LENGTH: 6
<212> TYPE: PRT
<213> ORGANISM: Artificial Sequence
<220> FEATURE:
<223> OTHER INFORMATION: linker

<400> SEQUENCE: 13

Ser Ala Lys Thr Thr Pro
 1               5

<210> SEQ ID NO 14
<211> LENGTH: 10
<212> TYPE: PRT
<213> ORGANISM: Artificial Sequence
<220> FEATURE:
<223> OTHER INFORMATION: linker

<400> SEQUENCE: 14

Ser Ala Lys Thr Thr Pro Lys Leu Gly Gly
 1               5                  10

<210> SEQ ID NO 15
<211> LENGTH: 18
<212> TYPE: PRT
<213> ORGANISM: Artificial Sequence
<220> FEATURE:
<223> OTHER INFORMATION: linker

<400> SEQUENCE: 15

Ser Ala Lys Thr Thr Pro Lys Leu Glu Asx Gly Glu Phe Ser Glu Ala
 1               5                  10                  15
```

Arg Val

```
<210> SEQ ID NO 16
<211> LENGTH: 5
<212> TYPE: PRT
<213> ORGANISM: Artificial Sequence
<220> FEATURE:
<223> OTHER INFORMATION: linker

<400> SEQUENCE: 16

Ala Asp Ala Ala Pro
1               5

<210> SEQ ID NO 17
<211> LENGTH: 12
<212> TYPE: PRT
<213> ORGANISM: Artificial Sequence
<220> FEATURE:
<223> OTHER INFORMATION: linker

<400> SEQUENCE: 17

Ala Asp Ala Ala Pro Thr Val Ser Ile Phe Pro Pro
1               5                   10

<210> SEQ ID NO 18
<211> LENGTH: 5
<212> TYPE: PRT
<213> ORGANISM: Artificial Sequence
<220> FEATURE:
<223> OTHER INFORMATION: linker

<400> SEQUENCE: 18

Thr Val Ala Ala Pro
1               5

<210> SEQ ID NO 19
<211> LENGTH: 12
<212> TYPE: PRT
<213> ORGANISM: Artificial Sequence
<220> FEATURE:
<223> OTHER INFORMATION: linker

<400> SEQUENCE: 19

Thr Val Ala Ala Pro Ser Val Phe Ile Phe Pro Pro
1               5                   10

<210> SEQ ID NO 20
<211> LENGTH: 6
<212> TYPE: PRT
<213> ORGANISM: Artificial Sequence
<220> FEATURE:
<223> OTHER INFORMATION: linker

<400> SEQUENCE: 20

Gln Pro Lys Ala Ala Pro
1               5

<210> SEQ ID NO 21
<211> LENGTH: 13
<212> TYPE: PRT
<213> ORGANISM: Artificial Sequence
<220> FEATURE:
<223> OTHER INFORMATION: linker

<400> SEQUENCE: 21

Gln Pro Lys Ala Ala Pro Ser Val Thr Leu Phe Pro Pro
```

<210> SEQ ID NO 22
<211> LENGTH: 6
<212> TYPE: PRT
<213> ORGANISM: Artificial Sequence
<220> FEATURE:
<223> OTHER INFORMATION: linker

<400> SEQUENCE: 22

Ala Lys Thr Thr Pro Pro
1               5

<210> SEQ ID NO 23
<211> LENGTH: 13
<212> TYPE: PRT
<213> ORGANISM: Artificial Sequence
<220> FEATURE:
<223> OTHER INFORMATION: linker

<400> SEQUENCE: 23

Ala Lys Thr Thr Pro Pro Ser Val Thr Pro Leu Ala Pro
1               5                   10

<210> SEQ ID NO 24
<211> LENGTH: 6
<212> TYPE: PRT
<213> ORGANISM: Artificial Sequence
<220> FEATURE:
<223> OTHER INFORMATION: linker

<400> SEQUENCE: 24

Ala Lys Thr Thr Ala Pro
1               5

<210> SEQ ID NO 25
<211> LENGTH: 13
<212> TYPE: PRT
<213> ORGANISM: Artificial Sequence
<220> FEATURE:
<223> OTHER INFORMATION: linker

<400> SEQUENCE: 25

Ala Lys Thr Thr Ala Pro Ser Val Tyr Pro Leu Ala Pro
1               5                   10

<210> SEQ ID NO 26
<211> LENGTH: 6
<212> TYPE: PRT
<213> ORGANISM: Artificial Sequence
<220> FEATURE:
<223> OTHER INFORMATION: linker

<400> SEQUENCE: 26

Ala Ser Thr Lys Gly Pro
1               5

<210> SEQ ID NO 27
<211> LENGTH: 13
<212> TYPE: PRT
<213> ORGANISM: Artificial Sequence
<220> FEATURE:
<223> OTHER INFORMATION: linker

<400> SEQUENCE: 27

Ala Ser Thr Lys Gly Pro Ser Val Phe Pro Leu Ala Pro
1               5                   10

<210> SEQ ID NO 28
<211> LENGTH: 15
<212> TYPE: PRT
<213> ORGANISM: Artificial Sequence
<220> FEATURE:
<223> OTHER INFORMATION: linker

<400> SEQUENCE: 28

Gly Gly Gly Gly Ser Gly Gly Gly Gly Ser Gly Gly Gly Gly Ser
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: linker

<400> SEQUENCE: 29

Gly Asx Asn Lys Val Glu Tyr Ala Pro Ala Leu Met Ala Leu Ser
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: linker

<400> SEQUENCE: 30

Gly Pro Ala Lys Glu Leu Thr Pro Leu Lys Glu Ala Lys Val Ser
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: linker

<400> SEQUENCE: 31

Gly His Glu Ala Ala Ala Val Met Gln Val Gln Tyr Pro Ala Ser
1               5                   10                  15

<210> SEQ ID NO 32
<211> LENGTH: 8
<212> TYPE: PRT
<213> ORGANISM: Artificial Sequence
<220> FEATURE:
<223> OTHER INFORMATION: linker

<400> SEQUENCE: 32

Gly Ser Thr Val Ala Ala Pro Ser
1               5

<210> SEQ ID NO 33
<211> LENGTH: 8
<212> TYPE: PRT
<213> ORGANISM: Artificial Sequence
<220> FEATURE:
<223> OTHER INFORMATION: linker

<400> SEQUENCE: 33

Thr Val Ala Ala Pro Ser Gly Ser
1               5

```
<210> SEQ ID NO 34
<211> LENGTH: 10
<212> TYPE: PRT
<213> ORGANISM: Artificial Sequence
<220> FEATURE:
<223> OTHER INFORMATION: linker

<400> SEQUENCE: 34

Gly Ser Thr Val Ala Ala Pro Ser Gly Ser
1               5                   10

<210> SEQ ID NO 35
<211> LENGTH: 5
<212> TYPE: PRT
<213> ORGANISM: Artificial Sequence
<220> FEATURE:
<221> NAME/KEY: REPEAT
<222> LOCATION: (1)(3)n,(4)(5)m
<223> OTHER INFORMATION: linker n=1,2,3,4,5,6,7,8,9,10, m=0,1,2,3,4

<400> SEQUENCE: 35

Pro Ala Ser Gly Ser
1               5

<210> SEQ ID NO 36
<211> LENGTH: 7
<212> TYPE: PRT
<213> ORGANISM: Artificial Sequence
<220> FEATURE:
<221> NAME/KEY: REPEAT
<222> LOCATION: (1)(5)n,(6)(7)m
<223> OTHER INFORMATION: linker n=1,2,3,4,5,6,7,8,9,10, m=0,1,2,3,4

<400> SEQUENCE: 36

Gly Gly Gly Gly Ser Gly Ser
1               5

<210> SEQ ID NO 37
<211> LENGTH: 8
<212> TYPE: PRT
<213> ORGANISM: Artificial Sequence
<220> FEATURE:
<221> NAME/KEY: REPEAT
<222> LOCATION: (1)(5)n,(6)(7)m
<223> OTHER INFORMATION: linker n=1,2,3,4,5,6,7,8,9,10, m=0,1,2,3,4

<400> SEQUENCE: 37

Thr Val Ala Ala Pro Ser Gly Ser
1               5

<210> SEQ ID NO 38
<211> LENGTH: 10
<212> TYPE: PRT
<213> ORGANISM: Artificial Sequence
<220> FEATURE:
<221> NAME/KEY: REPEAT
<222> LOCATION: (1)(2)m, (3)(10)n
<223> OTHER INFORMATION: linker n=1,2,3,4,5,6,7,8,9,10, m=0,1,2,3,4

<400> SEQUENCE: 38

Gly Ser Thr Val Ala Ala Pro Ser Gly Ser
1               5                   10

<210> SEQ ID NO 39
<211> LENGTH: 8
<212> TYPE: PRT
<213> ORGANISM: Artificial Sequence
<220> FEATURE:
```

```
<221> NAME/KEY: REPEAT
<222> LOCATION: (1)(6)n, (7)(8)m
<223> OTHER INFORMATION: linker n=1,2,3,4,5,6,7,8,9,10, m=0,1,2,3,4

<400> SEQUENCE: 39

Pro Ala Val Pro Pro Gly Ser
1               5

<210> SEQ ID NO 40
<211> LENGTH: 8
<212> TYPE: PRT
<213> ORGANISM: Artificial Sequence
<220> FEATURE:
<221> NAME/KEY: REPEAT
<222> LOCATION: (1)(6)n,(7)(8)m
<223> OTHER INFORMATION: linker n=1,2,3,4,5,6,7,8,9,10, m=0,1,2,3,4

<400> SEQUENCE: 40

Thr Val Ser Asp Val Pro Gly Ser
1               5

<210> SEQ ID NO 41
<211> LENGTH: 8
<212> TYPE: PRT
<213> ORGANISM: Artificial Sequence
<220> FEATURE:
<221> NAME/KEY: REPEAT
<222> LOCATION: (1)(6)n,(7)8)m
<223> OTHER INFORMATION: linker n=1,2,3,4,5,6,7,8,9,10, m=0,1,2,3,4

<400> SEQUENCE: 41

Thr Gly Leu Asp Ser Pro Gly Ser
1               5

<210> SEQ ID NO 42
<211> LENGTH: 6
<212> TYPE: PRT
<213> ORGANISM: Artificial Sequence
<220> FEATURE:
<223> OTHER INFORMATION: linker

<400> SEQUENCE: 42

Thr Val Ala Ala Pro Ser
1               5

<210> SEQ ID NO 43
<211> LENGTH: 8
<212> TYPE: PRT
<213> ORGANISM: Artificial Sequence
<220> FEATURE:
<223> OTHER INFORMATION: linker

<400> SEQUENCE: 43

Thr Val Ala Ala Pro Ser Gly Ser
1               5

<210> SEQ ID NO 44
<211> LENGTH: 7
<212> TYPE: PRT
<213> ORGANISM: Artificial Sequence
<220> FEATURE:
<223> OTHER INFORMATION: linker

<400> SEQUENCE: 44

Ala Ser Thr Lys Gly Pro Thr
1               5
```

```
<210> SEQ ID NO 45
<211> LENGTH: 5
<212> TYPE: PRT
<213> ORGANISM: Artificial Sequence
<220> FEATURE:
<221> NAME/KEY: REPEAT
<222> LOCATION: (1)(3)n,(4)(5)m
<223> OTHER INFORMATION: linker n=1,2,3,4,5,6,7,8,9,10, m=0,1,2,3,4,
      p=2,3,4,5,6,7,8,9,10

<400> SEQUENCE: 45

Pro Ala Ser Gly Ser
1               5

<210> SEQ ID NO 46
<211> LENGTH: 7
<212> TYPE: PRT
<213> ORGANISM: Artificial Sequence
<220> FEATURE:
<221> NAME/KEY: REPEAT
<222> LOCATION: (1)(5)p,(6)(7)m
<223> OTHER INFORMATION: linker n=1,2,3,4,5,6,7,8,9,10, m=0,1,2,3,4,
      p=2,3,4,5,6,7,8,9,10

<400> SEQUENCE: 46

Gly Gly Gly Gly Ser Gly Ser
1               5

<210> SEQ ID NO 47
<211> LENGTH: 8
<212> TYPE: PRT
<213> ORGANISM: Artificial Sequence
<220> FEATURE:
<221> NAME/KEY: REPEAT
<222> LOCATION: (1)(6)p,(7)(8)m
<223> OTHER INFORMATION: linker n=1,2,3,4,5,6,7,8,9,10, m=0,1,2,3,4,
      p=2,3,4,5,6,7,8,9,10

<400> SEQUENCE: 47

Thr Val Ala Ala Pro Ser Gly Ser
1               5

<210> SEQ ID NO 48
<211> LENGTH: 10
<212> TYPE: PRT
<213> ORGANISM: Artificial Sequence
<220> FEATURE:
<221> NAME/KEY: REPEAT
<222> LOCATION: (1)(2)m,(3)(10)p
<223> OTHER INFORMATION: linker n=1,2,3,4,5,6,7,8,9,10, m=0,1,2,3,4,
      p=2,3,4,5,6,7,8,9,10

<400> SEQUENCE: 48

Gly Ser Thr Val Ala Ala Pro Ser Gly Ser
1               5                   10

<210> SEQ ID NO 49
<211> LENGTH: 8
<212> TYPE: PRT
<213> ORGANISM: Artificial Sequence
<220> FEATURE:
<221> NAME/KEY: REPEAT
<222> LOCATION: (1)(6)n, (7)(8)m
<223> OTHER INFORMATION: linker n=1,2,3,4,5,6,7,8,9,10, m=0,1,2,3,4,
      p=2,3,4,5,6,7,8,9,10

<400> SEQUENCE: 49

Pro Ala Val Pro Pro Gly Ser
1               5
```

```
<210> SEQ ID NO 50
<211> LENGTH: 8
<212> TYPE: PRT
<213> ORGANISM: Artificial Sequence
<220> FEATURE:
<221> NAME/KEY: REPEAT
<222> LOCATION: (1)(6)n,(7)(8)m
<223> OTHER INFORMATION: linker n=1,2,3,4,5,6,7,8,9,10, m=0,1,2,3,4,
      p=2,3,4,5,6,7,8,9,10

<400> SEQUENCE: 50

Thr Val Ser Asp Val Pro Gly Ser
1               5

<210> SEQ ID NO 51
<211> LENGTH: 8
<212> TYPE: PRT
<213> ORGANISM: Artificial Sequence
<220> FEATURE:
<221> NAME/KEY: REPEAT
<222> LOCATION: (1)(6)n,(7)(8)m
<223> OTHER INFORMATION: linker n=1,2,3,4,5,6,7,8,9,10, m=0,1,2,3,4,
      p=2,3,4,5,6,7,8,9,10

<400> SEQUENCE: 51

Thr Gly Leu Asp Ser Pro Gly Ser
1               5

<210> SEQ ID NO 52
<211> LENGTH: 8
<212> TYPE: PRT
<213> ORGANISM: Artificial Sequence
<220> FEATURE:
<221> NAME/KEY: REPEAT
<222> LOCATION: (1)(6)p,(7)(8)m
<223> OTHER INFORMATION: linker m=0,1,2,3,4,5,6,7,8,9,10
      p=2,3,4,5,6,7,8,9,10

<400> SEQUENCE: 52

Thr Val Ala Ala Pro Ser Gly Ser
1               5

<210> SEQ ID NO 53
<211> LENGTH: 63
<212> TYPE: DNA
<213> ORGANISM: Artificial Sequence
<220> FEATURE:
<223> OTHER INFORMATION: oligonucleotide

<400> SEQUENCE: 53
ggaagcggag agggcagagg aagtctgcta acatgcggtg acgtcgagga gaatcctgga        60
cct                                                                      63

<210> SEQ ID NO 54
<211> LENGTH: 34
<212> TYPE: DNA
<213> ORGANISM: Artificial Sequence
<220> FEATURE:
<223> OTHER INFORMATION: oligonucleotide lox2272/66

<400> SEQUENCE: 54
ataacttcgt ataaagtatc ctatacgaac ggta                                    34

<210> SEQ ID NO 55
<211> LENGTH: 34
<212> TYPE: DNA
<213> ORGANISM: Artificial Sequence
```

```
<220> FEATURE:
<223> OTHER INFORMATION: oligonucleotide lox2272/71

<400> SEQUENCE: 55
taccgttcgt ataaagtatc ctatacgaag ttat                                34

<210> SEQ ID NO 56
<211> LENGTH: 5458
<212> TYPE: DNA
<213> ORGANISM: Artificial Sequence
<220> FEATURE:
<223> OTHER INFORMATION: antibody sequence

<400> SEQUENCE: 56
atctttcagg gacaatgatg cccatgcagg cagcatattt ataatgcaca gtaaacacta      60
ggaggaaaca aggcagtgag agaggaaaga gagcagcgat accgaaaatg tcctcagcga     120
gaagctacca cagaggatga atggagatca agcccacgtg gaaacatggg aaaatgtctc     180 agtattttc cacctaagaa gggagggaga tggggtatgt atacacctcc ctgtcctcac     240
tgattgaggg cttccgaga ggatgctcat tccaggtgct gtgataggcc atgtgtacag     300
gcagggctgc cttctccagc ttcagataga gcagtgagga aaagatatgg ccatgggggg     360
tcagcagaag tacagcaaag ggaaaaggga aagggtagca agagtgacaa ctatattcac     420
cccccccaca cacacacaca cacacacgaa attgtgtatt gcaatccaga actgcttctc     480
tctgaaccta atcttagca agcagtttac cagtaactgc ccttgaaatt caggcccctg     540
gaaaggagca gggggttgtg tacaggctat accacagcag tctgcccacc cttagtgatg     600
catgagtaat gctccctgga ctccccaggt tctagtcttc tcatgtcgat gtagttgatt     660
ccacttccct tgctgcacaa ccaggctggg atgcctgggc agaggcagac atgtgaggta     720
taggggttca aatctgtttc caagttttat ccagcttcaa agcatttctc cgtgtacatg     780
agcggtggct tgacaggaga tggagactct ctttcctgga tgtgaggcaa ggaggcaggc     840
gtctgagtca ggatgatgtc cctactcact gctaaagaga aaagtggctt tgatggtgca     900
gggcagggaa atgcactgag tggtcgccac cctcacagaa gagaaagtgt tcactgacct     960
ggcctttccc cagggcctct ccctcccatt gctttccaga aagccatgat ttttgagagc    1020
cacacctgaa cactcacaaa cattatggtg ggaaaagcag atcagagcat taggcaagtt    1080
gcattacctt ggccttcttc ctttggagac aattgatgtg gggttctaga ttgacccaga    1140
gtttcaagtt tatcctgatt caggcttcaa cagctggagg aagaaacaga gatgttttt    1200 gaagtaaaca gatctagcat tactaatcaa cccttcatac tgatgaccta tgggaaataa    1260
tacccaaggg cagaaaaatg ggcagaataa ggggagcccc aaaccaagac gaagctgctg    1320
cccattgaga ccctgggtat tacagagacc tatagctctg gataatggaa gatctatgag    1380
tggcacaggc gctgaggaat cacagcatca ttatcgtgca tctgcaggga attgcttgta    1440
aatatactgg taattacaaa tgtttaaggt cactacaaat actttggagt gtattaaata    1500
tgcttctgat aaagactgtt tttctcacat gaaacaatgg gaaccatgtg acaatcacag    1560
aggtgttgtt actatagcaa aagggattgt tactctccac atccctttaa gtaacttgaa    1620
ggcctgatag acccacccte taagacttca ttagacattc cctacgaatg gttatactct    1680
cctgtatact cccaatacaa ctctaaaata tattattcca tatagtcctt aggtttgtat    1740
taaagtttga ctttttcct tcaaaatatc tcttgtcaca acagcggctc tagagagaaa    1800
tacattccct ccaggcaaat ctatgctgcg ctggtctgac ctgggaccct ggggacattg    1860
```

```
cccctgtgct gagttactaa gatgagccag ccctgcagct gtgctcagcc tgccccatgc    1920
cctgctgatt gatttgcatg ttccagagca cagcccctg  ccctgaagac ttttttatgg    1980
gctggtcgca ccctgtgcag gagtcagtct cagtcaggac acagcatgga catgagggtc    2040
cccgctcagc tcctggggct cctgctactc tggctccgag gtaaggatgg agaacactag    2100
gaatttactc agccagtgtg ctcagtactg actggaactt cagggaagtt ctctgataac    2160
atgattaata gtaagaatat ttgttttat  gtttccaatc tcaggtgcca gatgtgacat    2220
ccagatgacc cagtctccat cctccctgtc tgcatctgta ggagacagag tcaccatcac    2280
ttgccgggca agtcagagca ttagcagcta tttaaattgg tatcagcaga accagggaa    2340 agcccctaag ctcctgatct atgctgcatc cagtttgcaa agtggggtcc catcaaggtt    2400
cagtggcagt ggatctggga cagatttcac tctcaccatc agcagtctgc aacctgaaga    2460
ttttgcaact tactactgtc aacagagtta cagtaccccg atcaccttcg gccaagggac    2520
acgactggag attaaacgta agtacacttt tctcatcttt ttttatgtgt aagacacagg    2580
ttttcatgtt aggagttaaa gtcagttcag aaaatcttga gaaatggag  agggctcatt    2640 atcagttgac gtggcataca gtgtcagatt ttctgtttat caagctagtg agattagggg    2700 caaaagagg  ctttagttga gaggaaagta attaatacta tggtcaccat ccaagagatt    2760
ggatcgagag ataagcatga gtagttattg agatctgggt ctgactgcag gtagcgtggt    2820
cttctagacg tttaagtggg agatttggag gggatgagga atgaaggaac ttcaggatag    2880
aaaagggctg aagtcaagtt cagctcctaa aatggatgtg ggagcaaact ttgaagataa    2940
actgaatgac ccagaggatg aaacagcgca gatcaaagag gggcctggag ctctgagaag    3000
agaaggagac tcatccgtgt tgagtttcca caagtactgt cttgagtttt gcaataaaag    3060
tgggatagca gagttgagtg agccgtaggc tgagttctct cttttgtctc ctaagttttt    3120
atgactacaa aaatcagtag tatgtcctga ataatcatt  aagctgtttg aaagtatgac    3180
tgcttgccat gtagatacca tggcttgctg aataatcaga agaggtgtga ctcttattct    3240
aaaatttgtc acaaaatgtc aaaatgagag actctgtagg aacgagtcct tgacagacag    3300
ctcaaggggt ttttttcctt tgtctcattt ctacatgaaa gtaaatttga aatgatcttt    3360
tttattataa gagtagaaat acagttgggt ttgaactata tgttttaatg gccacggttt    3420
tgtaagacat ttggtccttt gttttcccag ttattactcg attgtaattt tatatcgcca    3480
gcaatggact gaaacggtcc gcaacctctt ctttacaact gggtgacctc gcggctgtgc    3540
cagccatttg gcgttcaccc tgccgctaag ggccatgtga accccgcgg  tagcatccct    3600 tgctccgcgt ggaccacttt cctgaggcac agtgatagga acagagccac taatctgaag    3660
agaacagaga tgtgacagac tacactaatg tgagaaaaac aaggaaaggg tgacttattg    3720
gagatttcag aaataaaatg catttattat tatattccct tattttaatt ttctattagg    3780
gaattagaaa gggcataaac tgctttatcc agtgttatat taaagctta  atgtatataa    3840 tcttttagag gtaaaatcta cagccagcaa aagtcatggt aaatattctt tgactgaact    3900
ctcactaaac tcctctaaat tatatgtcat attaactggt taaattaata taaatttgtg    3960
acatgacctt aactgttag  gtaggatatt tttcttcatg caaaaatatg actaataata    4020
atttagcaca aaaatatttc ccaatacttt aattctgtga tagaaaaatg tttaactcag    4080
ctactataat cccataattt tgaaaactat ttattagctt ttgtgtttga cccttcccta    4140
gccaaaggca actatttaag gacccttta  aactcttgaa actactttag agtcattaag    4200
ttatttaacc acttttaatt actttaaaat gatgtcaatt ccctttaac  tattaattta    4260
```

```
ttttaagggg ggaaaggctg ctcataattc tattgttttt cttggtaaag aactctcagt    4320
tttcgttttt actacctctg tcacccaaga gttggcatct caacagaggg gactttccga    4380
gaggccatct ggcagttgct taagatcaga agtgaagtct gccagttcct cccaggcagg    4440
tggcccagat tacagttgac ctgttctggt gtggctaaaa attgtcccat gtggttacaa    4500
accattagac cagggtctga tgaattgctc agaatatttc tggacaccca aatacagacc    4560
ctggcttaag gccctgtcca tacagtaggt ttagcttggc tacaccaaag gaagccatac    4620
agaggctaat atcagagtat tcttggaaga gacaggagaa aatgaaagcc agtttctgct    4680
cttaccttat gtgcttgtgt tcagactccc aaacatcagg agtgtcagat aaactggtct    4740
gaatctctgt ctgaagcatg gaactgaaaa gaatgtagtt tcagggaaga aaggcaatag    4800
aaggaagcct gagaatatct tcaaagggtc agactcaatt tactttctaa agaagtagct    4860
aggaactagg gaataactta gaaacaacaa gataacttcg tataaagtat cctatacgaa    4920
cggtaattgt atatatgtgc atcctggccc cattgttcct tatctgtagg gataagcgtg    4980 ctttttttgtg tgtctgtata taacataact gtttacacat aatacactga aatggagccc    5040
ttccttgtta cttcatacca tcctctgtgc ttccttcctc aggggctgat gctgcaccaa    5100
ctgtatccat cttcccacca tccagtgagc agttaacatc tggaggtgcc tcagtcgtgt    5160
gcttcttgaa caacttctac cccaaagaca tcaatgtcaa gtggaagatt gatgcagtg    5220 aacgacaaaa tggcgtcctg aacagttgga ctgatcagga cagcaaagac agcacctaca    5280
gcatgagcag caccctcacg ttgaccaagg acgagtatga acgacataac agctataccct    5340 gtgaggccac tcacaagaca tcaacttcac ccattgtcaa gagcttcaac aggaatgagt    5400
gttagagaca aggtcctga gacgataact tcgtatagga tactttatac gaacggta    5458
```

<210> SEQ ID NO 57
<211> LENGTH: 9
<212> TYPE: PRT
<213> ORGANISM: Artificial Sequence
<220> FEATURE:
<223> OTHER INFORMATION: linker sequence

<400> SEQUENCE: 57

Gly Gly Ser Gly Gly Ser Gly Gly Ser
1               5

<210> SEQ ID NO 58
<211> LENGTH: 18
<212> TYPE: PRT
<213> ORGANISM: Artificial Sequence
<220> FEATURE:
<223> OTHER INFORMATION: linker sequence

<400> SEQUENCE: 58

Val Glu Gly Gly Ser Gly Gly Ser Gly Gly Ser Gly Gly Ser Gly Gly
1               5                   10                  15

Val Asp

<210> SEQ ID NO 59
<211> LENGTH: 5
<212> TYPE: PRT
<213> ORGANISM: Artificial Sequence
<220> FEATURE:
<221> NAME/KEY: REPEAT
<222> LOCATION: (1)(5)3
<223> OTHER INFORMATION: linker sequence

```
<400> SEQUENCE: 59

Gly Gly Gly Gly Ser
1               5

<210> SEQ ID NO 60
<211> LENGTH: 5
<212> TYPE: PRT
<213> ORGANISM: Artificial Sequence
<220> FEATURE:
<221> NAME/KEY: REPEAT
<222> LOCATION: (1)(5)3
<223> OTHER INFORMATION: linker sequence

<400> SEQUENCE: 60

Gly Gly Gly Gly Ser
1               5

<210> SEQ ID NO 61
<211> LENGTH: 5
<212> TYPE: PRT
<213> ORGANISM: Artificial Sequence
<220> FEATURE:
<221> NAME/KEY: REPEAT
<222> LOCATION: (1)(5)2
<223> OTHER INFORMATION: linker sequence

<400> SEQUENCE: 61

Gly Gly Gly Gly Ser
1               5

<210> SEQ ID NO 62
<211> LENGTH: 5
<212> TYPE: PRT
<213> ORGANISM: Artificial Sequence
<220> FEATURE:
<221> NAME/KEY: REPEAT
<222> LOCATION: (1)(5)2
<223> OTHER INFORMATION: linker sequence

<400> SEQUENCE: 62

Gly Gly Gly Gly Ser
1               5

<210> SEQ ID NO 63
<211> LENGTH: 5
<212> TYPE: PRT
<213> ORGANISM: Artificial Sequence
<220> FEATURE:
<223> OTHER INFORMATION: linker sequence

<400> SEQUENCE: 63

Gly Gly Gly Gly Ser
1               5

<210> SEQ ID NO 64
<211> LENGTH: 5
<212> TYPE: PRT
<213> ORGANISM: Artificial Sequence
<220> FEATURE:
<223> OTHER INFORMATION: linker sequence

<400> SEQUENCE: 64

Gly Gly Gly Gly Ser
1               5

<210> SEQ ID NO 65
<211> LENGTH: 5
```

```
<212> TYPE: PRT
<213> ORGANISM: Artificial Sequence
<220> FEATURE:
<223> OTHER INFORMATION: linker sequence

<400> SEQUENCE: 65

Ala Lys Thr Thr Pro
1               5

<210> SEQ ID NO 66
<211> LENGTH: 9
<212> TYPE: PRT
<213> ORGANISM: Artificial Sequence
<220> FEATURE:
<223> OTHER INFORMATION: linker sequence

<400> SEQUENCE: 66

Ala Lys Thr Thr Pro Arg Leu Gly Gly
1               5

<210> SEQ ID NO 67
<211> LENGTH: 8
<212> TYPE: PRT
<213> ORGANISM: Artificial Sequence
<220> FEATURE:
<223> OTHER INFORMATION: linker sequence

<400> SEQUENCE: 67

Glu Glu Gly Glu Phe Ser Glu Ala
1               5

<210> SEQ ID NO 68
<211> LENGTH: 18
<212> TYPE: PRT
<213> ORGANISM: Artificial Sequence
<220> FEATURE:
<223> OTHER INFORMATION: linker sequence

<400> SEQUENCE: 68

Val Glu Gly Gly Ser Gly Gly Ser Gly Gly Ser Gly Gly Ser Gly Gly
1               5                   10                  15

Val Asp

<210> SEQ ID NO 69
<211> LENGTH: 5
<212> TYPE: PRT
<213> ORGANISM: Artificial Sequence
<220> FEATURE:
<223> OTHER INFORMATION: linker sequence

<400> SEQUENCE: 69

Gly Gly Gly Gly Ser
1               5

<210> SEQ ID NO 70
<211> LENGTH: 5
<212> TYPE: PRT
<213> ORGANISM: Artificial Sequence
<220> FEATURE:
<223> OTHER INFORMATION: linker sequence

<400> SEQUENCE: 70

Ala Lys Thr Thr Pro
1               5

<210> SEQ ID NO 71
```

```
<211> LENGTH: 9
<212> TYPE: PRT
<213> ORGANISM: Artificial Sequence
<220> FEATURE:
<223> OTHER INFORMATION: linker sequence

<400> SEQUENCE: 71

Ala Lys Thr Thr Pro Arg Leu Gly Gly
1               5

<210> SEQ ID NO 72
<211> LENGTH: 8
<212> TYPE: PRT
<213> ORGANISM: Artificial Sequence
<220> FEATURE:
<223> OTHER INFORMATION: linker sequence

<400> SEQUENCE: 72

Glu Glu Gly Glu Phe Ser Glu Ala
1               5

<210> SEQ ID NO 73
<211> LENGTH: 18
<212> TYPE: PRT
<213> ORGANISM: Artificial Sequence
<220> FEATURE:
<223> OTHER INFORMATION: linker sequence

<400> SEQUENCE: 73

Val Glu Gly Gly Ser Gly Gly Ser Gly Gly Ser Gly Gly Ser Gly Gly
1               5                   10                  15

Val Asp

<210> SEQ ID NO 74
<211> LENGTH: 54
<212> TYPE: DNA
<213> ORGANISM: Artificial Sequence
<220> FEATURE:
<223> OTHER INFORMATION: linker sequence

<400> SEQUENCE: 74
gtcgaaggtg aagtggagg ttctggtgga agtggaggtt caggtggagt cgac          54

<210> SEQ ID NO 75
<211> LENGTH: 15
<212> TYPE: PRT
<213> ORGANISM: Artificial Sequence
<220> FEATURE:
<223> OTHER INFORMATION: linker sequence

<400> SEQUENCE: 75

Gly Gly Gly Gly Ser Gly Gly Gly Ser Gly Gly Gly Gly Ser
1               5                   10                  15

<210> SEQ ID NO 76
<211> LENGTH: 45
<212> TYPE: DNA
<213> ORGANISM: Artificial Sequence
<220> FEATURE:
<223> OTHER INFORMATION: linker sequence

<400> SEQUENCE: 76
ggtggtggtg gttctggcgg cggcggctcc ggtggtggtg gttct                   45

<210> SEQ ID NO 77
<211> LENGTH: 15
```

<212> TYPE: PRT
<213> ORGANISM: Artificial Sequence
<220> FEATURE:
<223> OTHER INFORMATION: linker

<400> SEQUENCE: 77

Gly Gly Gly Gly Ser Gly Gly Gly Gly Ser Gly Gly Gly Gly Ser
1               5                   10                  15

<210> SEQ ID NO 78
<211> LENGTH: 30
<212> TYPE: DNA
<213> ORGANISM: Artificial Sequence
<220> FEATURE:
<223> OTHER INFORMATION: linker sequence

<400> SEQUENCE: 78
ggcggcggcg gctccggtgg tggtggttct                                    30

<210> SEQ ID NO 79
<211> LENGTH: 5
<212> TYPE: PRT
<213> ORGANISM: Artificial Sequence
<220> FEATURE:
<223> OTHER INFORMATION: linker sequence

<400> SEQUENCE: 79

Gly Gly Gly Gly Ser
1               5

<210> SEQ ID NO 80
<211> LENGTH: 15
<212> TYPE: DNA
<213> ORGANISM: Artificial Sequence
<220> FEATURE:
<223> OTHER INFORMATION: linker sequence

<400> SEQUENCE: 80
ggaggtggtg gatcc                                                    15

<210> SEQ ID NO 81
<211> LENGTH: 5
<212> TYPE: PRT
<213> ORGANISM: Artificial Sequence
<220> FEATURE:
<223> OTHER INFORMATION: linker sequence

<400> SEQUENCE: 81

Ala Lys Thr Thr Pro
1               5

<210> SEQ ID NO 82
<211> LENGTH: 15
<212> TYPE: DNA
<213> ORGANISM: Artificial Sequence
<220> FEATURE:
<223> OTHER INFORMATION: linker sequence

<400> SEQUENCE: 82
gccaaaacaa caccc                                                    15

<210> SEQ ID NO 83
<211> LENGTH: 9
<212> TYPE: PRT
<213> ORGANISM: Artificial Sequence
<220> FEATURE:
<223> OTHER INFORMATION: linker sequence

<400> SEQUENCE: 83

Ala Lys Thr Thr Pro Arg Leu Gly Gly
1               5

<210> SEQ ID NO 84
<211> LENGTH: 8
<212> TYPE: PRT
<213> ORGANISM: Artificial Sequence
<220> FEATURE:
<223> OTHER INFORMATION: linker sequence

<400> SEQUENCE: 84

Glu Glu Gly Glu Phe Ser Glu Ala
1               5

<210> SEQ ID NO 85
<211> LENGTH: 24
<212> TYPE: DNA
<213> ORGANISM: Artificial Sequence
<220> FEATURE:
<223> OTHER INFORMATION: linker sequence

<400> SEQUENCE: 85
gaagaaggtg aattttcaga agca                                          24

<210> SEQ ID NO 86
<211> LENGTH: 9
<212> TYPE: PRT
<213> ORGANISM: Artificial Sequence
<220> FEATURE:
<223> OTHER INFORMATION: linker sequence

<400> SEQUENCE: 86

Gly Gly Ser Gly Gly Ser Gly Gly Ser
1               5

<210> SEQ ID NO 87
<211> LENGTH: 27
<212> TYPE: DNA
<213> ORGANISM: Artificial Sequence
<220> FEATURE:
<223> OTHER INFORMATION: linker sequence

<400> SEQUENCE: 87
ggtggttctg gtggttctgg tggttct                                       27

<210> SEQ ID NO 88
<211> LENGTH: 15
<212> TYPE: PRT
<213> ORGANISM: Artificial Sequence
<220> FEATURE:
<223> OTHER INFORMATION: linker sequence

<400> SEQUENCE: 88

Gly Gly Gly Gly Ser Gly Gly Gly Gly Ser Gly Gly Gly Gly Ser
1               5                   10                  15

<210> SEQ ID NO 89
<211> LENGTH: 45
<212> TYPE: DNA
<213> ORGANISM: Artificial Sequence
<220> FEATURE:
<223> OTHER INFORMATION: linker sequence

<400> SEQUENCE: 89

```
ggtggtggtg gttctggcgg cggcggctcc ggtggtggtg gttct          45
```

<210> SEQ ID NO 90
<211> LENGTH: 15
<212> TYPE: PRT
<213> ORGANISM: Artificial Sequence
<220> FEATURE:
<223> OTHER INFORMATION: linker sequence

<400> SEQUENCE: 90

```
Gly Gly Gly Gly Ser Gly Gly Gly Gly Ser Gly Gly Gly Gly Ser
1               5                   10                  15
```

<210> SEQ ID NO 91
<211> LENGTH: 30
<212> TYPE: DNA
<213> ORGANISM: Artificial Sequence
<220> FEATURE:
<223> OTHER INFORMATION: linker sequence

<400> SEQUENCE: 91

```
ggcggcggcg gctccggtgg tggtggttct                            30
```

<210> SEQ ID NO 92
<211> LENGTH: 5
<212> TYPE: PRT
<213> ORGANISM: Artificial Sequence
<220> FEATURE:
<223> OTHER INFORMATION: linker sequence

<400> SEQUENCE: 92

```
Gly Gly Gly Gly Ser
1               5
```

<210> SEQ ID NO 93
<211> LENGTH: 15
<212> TYPE: DNA
<213> ORGANISM: Artificial Sequence
<220> FEATURE:
<223> OTHER INFORMATION: linker sequence

<400> SEQUENCE: 93

```
ggaggtggtg gatcc                                            15
```

<210> SEQ ID NO 94
<211> LENGTH: 18
<212> TYPE: PRT
<213> ORGANISM: Artificial Sequence
<220> FEATURE:
<223> OTHER INFORMATION: linker sequence

<400> SEQUENCE: 94

```
Val Glu Gly Gly Ser Gly Gly Ser Gly Gly Ser Gly Gly Ser Gly Gly
1               5                   10                  15

Val Asp
```

<210> SEQ ID NO 95
<211> LENGTH: 54
<212> TYPE: DNA
<213> ORGANISM: Artificial Sequence
<220> FEATURE:
<223> OTHER INFORMATION: linker sequence

<400> SEQUENCE: 95

```
gtcgaaggtg gaagtggagg ttctggtgga agtggaggtt caggtggagt cgac    54
```

<210> SEQ ID NO 96
<211> LENGTH: 118
<212> TYPE: PRT
<213> ORGANISM: Artificial Sequence
<220> FEATURE:
<223> OTHER INFORMATION: antibody sequence

<400> SEQUENCE: 96

```
Gln Val Gln Leu Val Glu Ser Gly Gly Val Val Gln Pro Gly Arg
1               5                   10                  15

Ser Leu Arg Leu Ser Cys Ala Ala Ser Gly Phe Lys Phe Ser Gly Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Met Gly Tyr Trp His Phe Asp Leu Trp Gly Arg Gly Thr
            100                 105                 110

Leu Val Thr Val Ser Ser
        115
```

<210> SEQ ID NO 97
<211> LENGTH: 354
<212> TYPE: DNA
<213> ORGANISM: Artificial Sequence
<220> FEATURE:
<223> OTHER INFORMATION: antibody sequence

<400> SEQUENCE: 97

```
caggtgcagc tggtggagtc cggggaggc gtggtccagc ctgggaggtc cctgagactc        60
tcctgtgcag cgtctggatt caagttcagt ggctatggca tgcactgggt ccgccaggct       120
ccaggcaagg gctggagtg gtggcagtt atatggtatg atggaagtaa gaaatactat        180
gtagactccg tgaagggccg cttcaccatc tccagagaca attccaagaa cacgctgtat       240
ctgcaaatga acagcctgag agccgaggac acggctgtgt attactgtgc gagacaaatg       300
ggctactggc acttcgatct ctggggccgt ggcaccctgg tcactgtctc ctca             354
```

<210> SEQ ID NO 98
<211> LENGTH: 108
<212> TYPE: PRT
<213> ORGANISM: Artificial Sequence
<220> FEATURE:
<223> OTHER INFORMATION: antibody sequence

<400> SEQUENCE: 98

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
```

```
            65                  70                  75                  80
Glu Asp Phe Ala Val Tyr Tyr Cys Gln Gln Arg Ser Asn Trp Pro Pro
                    85                  90                  95

Leu Thr Phe Gly Gly Gly Thr Lys Val Glu Ile Lys
                100                 105
```

<210> SEQ ID NO 99
<211> LENGTH: 324
<212> TYPE: DNA
<213> ORGANISM: Artificial Sequence
<220> FEATURE:
<223> OTHER INFORMATION: antibody sequence

<400> SEQUENCE: 99

```
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctccgct cactttcggc   300
ggagggacca aggtggagat caaa                                           324
```

<210> SEQ ID NO 100
<211> LENGTH: 120
<212> TYPE: PRT
<213> ORGANISM: Artificial Sequence
<220> FEATURE:
<223> OTHER INFORMATION: antibody sequence

<400> SEQUENCE: 100

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Lys Phe Ser Pro Tyr
                20                  25                  30

Gly Met His Leu Trp Val Arg Gln Ala Pro Gly Lys Gly Leu Glu Trp
            35                  40                  45

Val Ala Leu Val Ile Trp Tyr Asp Gly Ser Lys Lys Tyr Tyr Val Asp
        50                  55                  60

Ser Val Lys Gly Ile Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Arg Gly Tyr Trp His Phe Asp Leu Ile Trp Gly Arg
            100                 105                 110

Gly Thr Leu Val Thr Val Ser Ser
        115                 120
```

<210> SEQ ID NO 101
<211> LENGTH: 324
<212> TYPE: DNA
<213> ORGANISM: Artificial Sequence
<220> FEATURE:
<223> OTHER INFORMATION: antibody sequence

<400> SEQUENCE: 101

```
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
```

```
aggttcagtg gcagtgggtc tgggacagac ttcactctca ccatcagcag cctagagcct      240
gaagattttg cagtttatta ctgtcagcag cgtagcaact ggcctccgct cactttcggc      300
ggagggacca aggtggagat caaa                                             324
```

<210> SEQ ID NO 102
<211> LENGTH: 112
<212> TYPE: PRT
<213> ORGANISM: Artificial Sequence
<220> FEATURE:
<223> OTHER INFORMATION: antibody sequence
<220> FEATURE:
<221> NAME/KEY: misc_feature
<222> LOCATION: (36)..(36)
<223> OTHER INFORMATION: Xaa = leucine or isoleucine

<400> SEQUENCE: 102

```
Glu Ile Val Leu Thr Gln Ser Pro Ala Thr Leu Ser Leu Ser Pro Gly
1               5                   10                  15

Glu Arg Ala Thr Leu Ser Cys Ile Arg Ala Ser Gln Ser Val Ser Ser
            20                  25                  30

Tyr Leu Ala Xaa Trp Tyr Gln Gln Lys Pro Gly Gln Ala Pro Arg Leu
        35                  40                  45

Leu Ile Tyr Ile Asp Ala Ser Asn Arg Ala Thr Ile Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Arg Ser
                85                  90                  95

Asn Trp Pro Pro Leu Thr Phe Gly Gly Gly Thr Lys Val Glu Ile Lys
            100                 105                 110
```

<210> SEQ ID NO 103
<211> LENGTH: 324
<212> TYPE: DNA
<213> ORGANISM: Artificial Sequence
<220> FEATURE:
<223> OTHER INFORMATION: antibody sequence

<400> SEQUENCE: 103

```
gaaattgtgt tgacacagtc tccagccacc ctgtctttgt ctccagggga aagagccacc       60
ctctcctgca gggccagtca gagtgttagc agctacttag cctggtacca acagaaacct      120
ggccaggctc ccaggctcct catctatgat gcatccaaca gggccactgg catcccagcc      180
aggttcagtg gcagtgggtc tgggacagac ttcactctca ccatcagcag cctagagcct      240
gaagattttg cagtttatta ctgtcagcag cgtagcaact ggcctccgct cactttcggc      300
ggagggacca aggtggagat caaa                                             324
```

<210> SEQ ID NO 104
<211> LENGTH: 119
<212> TYPE: PRT
<213> ORGANISM: Artificial Sequence
<220> FEATURE:
<223> OTHER INFORMATION: antibody sequence

<400> SEQUENCE: 104

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30
```

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 105
<211> LENGTH: 357
<212> TYPE: DNA
<213> ORGANISM: Artificial Sequence
<220> FEATURE:
<223> OTHER INFORMATION: antibody sequence

<400> SEQUENCE: 105
gatatcaaac tgcagcagtc aggggctgaa ctggcaagac ctggggcctc agtgaagatg      60
tcctgcaaga cttctggcta cacctttact aggtacacga tgcactgggt aaaacagagg     120
cctggacagg gtctggaatg gattggatac attaatccta gccgtggtta tactaattac     180
aatcagaagt tcaaggacaa ggccacattg actacagaca atcctccag cacagcctac      240 atgcaactga gcagcctgac atctgaggac tctgcagtct attactgtgc aagatattat     300
gatgatcatt actgccttga ctactggggc caaggcacca ctctcacagt ctcctca        357

<210> SEQ ID NO 106
<211> LENGTH: 119
<212> TYPE: PRT
<213> ORGANISM: Artificial Sequence
<220> FEATURE:
<223> OTHER INFORMATION: antibody sequence

<400> SEQUENCE: 106

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser
        115

<210> SEQ ID NO 107
<211> LENGTH: 357
<212> TYPE: DNA

<213> ORGANISM: Artificial Sequence
<220> FEATURE:
<223> OTHER INFORMATION: antibody sequence

<400> SEQUENCE: 107

```
caggtgcagc tgcagcagtc tggggctgaa ctggcaagac ctggggcctc agtgaagatg      60
tcctgcaagg cttctggcta cacctttact aggtacacga tgcactgggt aaaacagagg     120
cctggacagg gtctggaatg gattggatac attaatccta gccgtggtta tactaattac     180
aatcagaagt tcaaggacaa ggccacattg actacagaca atcctccag cacagcctac      240
atgcaactga gcagcctgac atctgaggac tctgcagtct attactgtgc aagatattat     300
gatgatcatt acagccttga ctactggggc caaggcacca ctctcacagt ctcctca       357
```

<210> SEQ ID NO 108
<211> LENGTH: 106
<212> TYPE: PRT
<213> ORGANISM: Artificial Sequence
<220> FEATURE:
<223> OTHER INFORMATION: antibody sequence

<400> SEQUENCE: 108

```
Asp Ile Gln Leu Thr Gln Ser Pro Ala Ile Met Ser Ala Ser Pro Gly
1               5                   10                  15
Glu Lys Val Thr Met Thr Cys Arg Ala Ser Ser Ser Val Ser Tyr Met
            20                  25                  30
Asn Trp Tyr Gln Gln Lys Ser Gly Thr Ser Pro Lys Arg Trp Ile Tyr
        35                  40                  45
Asp Thr Ser Lys Val Ala Ser Gly Val Pro Tyr Arg Phe Ser Gly Ser
    50                  55                  60
Gly Ser Gly Thr Ser Tyr Ser Leu Thr Ile Ser Ser Met Glu Ala Glu
65                  70                  75                  80
Asp Ala Ala Thr Tyr Tyr Cys Gln Gln Trp Ser Ser Asn Pro Leu Thr
                85                  90                  95
Phe Gly Ala Gly Thr Lys Leu Glu Leu Lys
            100                 105
```

<210> SEQ ID NO 109
<211> LENGTH: 317
<212> TYPE: DNA
<213> ORGANISM: Artificial Sequence
<220> FEATURE:
<223> OTHER INFORMATION: antibody sequence

<400> SEQUENCE: 109

```
gacattcagc tgacccagtc tccagcaatc atgtctgcat ctccagggga gaaggtcacc      60
atgacctgca gagccagttc aagtgtaagt tacatgaact ggtaccagca gaagtcaggc     120
acctccccca aaagatggat ttatgacaca tccaaagtgg cttctggagt cccttatcgc     180
ttcagtggca gtgggtctgg gacctcatac tctctcacaa tcagcagcat ggaggctgaa     240
gatgctgcca cttattactg ccaacagtgg agtagtaacc cgctcacgtt cggtgctggg     300
accaagctgg agctgaa                                                    317
```

<210> SEQ ID NO 110
<211> LENGTH: 106
<212> TYPE: PRT
<213> ORGANISM: Artificial Sequence
<220> FEATURE:
<223> OTHER INFORMATION: antibody sequence

<400> SEQUENCE: 110

Asp Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105

<210> SEQ ID NO 111
<211> LENGTH: 318
<212> TYPE: DNA
<213> ORGANISM: Artificial Sequence
<220> FEATURE:
<223> OTHER INFORMATION: antibody sequence

<400> SEQUENCE: 111
gatatcgtgc tcactcagtc tccagcaatc atgtctgcat ctccagggga gaaggtcacc    60
atgacctgca gtgccagctc aagtgtaagt tacatgaact ggtaccagca gaagtcaggc   120
acctccccca aaagatggat ttatgacaca tccaaactgg cttctggagt ccctgctcac   180
ttcaggggca gtgggtctgg gacctcttac tctctcacaa tcagcggcat ggaggctgaa   240
gatgctgcca cttattactg ccagcagtgg agtagtaacc cattcacgtt cggctcgggg   300
acaaagttgg aaataaac                                                 318

<210> SEQ ID NO 112
<211> LENGTH: 728
<212> TYPE: DNA
<213> ORGANISM: Artificial Sequence
<220> FEATURE:
<223> OTHER INFORMATION: antibody sequence

<400> SEQUENCE: 112
gatatcaaac tgcagcagtc aggggctgaa ctggcaagac ctggggcctc agtgaagatg    60
tcctgcaaga cttctggcta cacctttact aggtacacga tgcactgggt aaaacagagg   120
cctggacagg gtctggaatg gattggatac attaatccta gccgtggtta ctaattacaa   180
aatcagaagt tcaaggacaa ggccacattg actacagaca atcctccag cacagcctac   240 atgcaactga gcagcctgac atctgaggac tctgcagtct attactgtgc aagatattat   300
gatgatcatt actgccttga ctactggggc caaggcacca ctctcacagt ctcctcagtc   360
gaaggtggaa gtggaggttc tggtggaagt ggaggttcag gtggagtcga cgacattcag   420
ctgacccagt ctccagcaat catgtctgca tctccagggg agaaggtcac catgacctgc   480
agagccagtt caagtgtaag ttacatgaac tggtaccagc agaagtcagg cacctcccc   540 aaaagatgga tttatgacac atccaaagtg gcttctggag tcccttatcg cttcagtggc   600
agtgggtctg gaacctcata ctctctcaca atcagcagca tggaggctga agatgctgcc   660
acttattact gccaacagtg gagtagtaac ccgctcacgt tcggtgctgg gaccaagctg   720

```
gagctgaa                                                               728
```

<210> SEQ ID NO 113
<211> LENGTH: 242
<212> TYPE: PRT
<213> ORGANISM: Artificial Sequence
<220> FEATURE:
<223> OTHER INFORMATION: antibody sequence

<400> SEQUENCE: 113

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu
```

<210> SEQ ID NO 114
<211> LENGTH: 120
<212> TYPE: PRT
<213> ORGANISM: Artificial Sequence
<220> FEATURE:
<223> OTHER INFORMATION: antibody sequence

<400> SEQUENCE: 114

```
Glu Val Gln Leu Val Gln Ser Gly Ala Glu Val Lys Lys Pro Gly Glu
1               5                   10                  15

Ser Leu Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
```

```
                    50                  55                  60
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Ser Ala Tyr Tyr Tyr Asp Phe Ala Asp Tyr Trp Gly Gln
            100                 105                 110

Gly Thr Leu Val Thr Val Ser Ser
        115                 120

<210> SEQ ID NO 115
<211> LENGTH: 360
<212> TYPE: DNA
<213> ORGANISM: Artificial Sequence
<220> FEATURE:
<223> OTHER INFORMATION: antibody sequence

<400> SEQUENCE: 115
gaggtccagc tggtacagtc tggagcagag gtgaaaaagc ccggggagtc tctgaaggtt      60
tcctgcaagg catctggata caccttcacc agctactata tgcactgggt gcgacaggcc    120
cctggacaag gcttgagtg gatgggaata atcaaccct gtggtggtag cacaagctac      180
gcacagaagt tccagggcag agtcaccatg acccgggaca cgtccacgag cacagtctac    240
atggagctta gcagcctgag atctgaggac acggccgtgt attactgtgc tagaggtagt    300
gcttattact acgatttgc tgactactgg ggccagggaa ccctggtcac cgtctcctca    360

<210> SEQ ID NO 116
<211> LENGTH: 106
<212> TYPE: PRT
<213> ORGANISM: Artificial Sequence
<220> FEATURE:
<223> OTHER INFORMATION: antibody sequence

<400> SEQUENCE: 116

Gln Pro Val Leu Thr Gln Pro Ser Ser Val Ser Val Ala Pro Gly Gln
  1               5                  10                  15

Thr Ala Thr Ile Ser Cys Gly Gly His Asn Ile Gly Ser Lys Asn Val
             20                  25                  30

His Trp Tyr Gln Gln Arg Pro Gly Gln Ser Pro Val Leu Val Ile Tyr
         35                  40                  45

Gln Asp Asn Lys Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Val Trp Asp Asn Tyr Ser Val Leu
                 85                  90                  95

Phe Gly Gly Gly Thr Lys Leu Thr Val Leu
            100                 105

<210> SEQ ID NO 117
<211> LENGTH: 318
<212> TYPE: DNA
<213> ORGANISM: Artificial Sequence
<220> FEATURE:
<223> OTHER INFORMATION: antibody sequence

<400> SEQUENCE: 117
cagcctgtgc tgactcagcc atcctcggtg tcagtggccc caggacagac ggccacgatc      60
```

```
tcctgtgggg gacacaacat tgggagtaaa aatgtgcact ggtaccagca gaggccaggc    120
cagtcccctg tgttggtcat ttatcaggat aataagcggc cctcaggat ccctgagcga    180 ttctctggct ccaactctgg gaacacagcc actctgacca tcagcgggac ccaggcgatg    240
gatgaggctg actactattg tcaggtgtgg gacaattaca gtgtgctatt cggcggaggg    300
accaagctga ccgtccta                                                  318
```

<210> SEQ ID NO 118
<211> LENGTH: 111
<212> TYPE: PRT
<213> ORGANISM: Artificial Sequence
<220> FEATURE:
<223> OTHER INFORMATION: antibody sequence

<400> SEQUENCE: 118

Asp Ile Gln Ala Val Val Thr Gln Glu Ser Ala Leu Thr Thr Ser Pro
1               5                   10                  15

Gly Glu Thr Val Thr Leu Thr Cys Arg Ser Asn Thr Gly Thr Val Thr
            20                  25                  30

Thr Ser Asn Tyr Ala Asn Trp Val Gln Glu Lys Pro Asp His Leu Phe
        35                  40                  45

Thr Gly Leu Ile Gly His Thr Asn Asn Arg Ala Pro Gly Val Pro Ala
    50                  55                  60

Arg Phe Ser Gly Ser Leu Ile Gly Asp Lys Ala Ala Leu Thr Ile Thr
65                  70                  75                  80

Gly Ala Gln Thr Glu Asp Glu Ala Ile Tyr Phe Cys Ala Leu Trp Tyr
                85                  90                  95

Asn Asn His Trp Val Phe Gly Gly Gly Thr Lys Leu Thr Val Leu
            100                 105                 110

<210> SEQ ID NO 119
<211> LENGTH: 333
<212> TYPE: DNA
<213> ORGANISM: Artificial Sequence
<220> FEATURE:
<223> OTHER INFORMATION: antibody sequence

<400> SEQUENCE: 119

```
gatatccagc tgacccagtc tccagcttct ttggctgtgt ctctagggca gagggccacc    60
atctcctgca aggccagcca aagtgttgat tatgatggtg atagttattt gaactggtac   120
caacagattc caggacagcc acccaaactc ctcatctatg atgcatccaa tctagtttct   180
gggatcccac ccaggtttag tggcagtggg tctgggacag acttcaccct caacatccat   240
cctgtggaga aggtggatgc tgcaacctat cactgtcagc aaagtactga ggatccgtgg   300
acgttcggtg agggaccaa gctcgagatc aaa                                  333
```

<210> SEQ ID NO 120
<211> LENGTH: 117
<212> TYPE: PRT
<213> ORGANISM: Artificial Sequence
<220> FEATURE:
<223> OTHER INFORMATION: antibody sequence

<400> SEQUENCE: 120

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
                35                  40                  45

Gly Asp Ile Tyr Pro Gly Gly Gly Tyr Thr Asn Tyr Asn Glu Lys Phe
 50                  55                  60

Lys Gly Lys Ala Thr Val Thr Ala Asp Thr Ser Ser Arg Thr Ala Tyr
 65                  70                  75                  80

Val Gln Val Arg Ser Leu Thr Ser Glu Asp Ser Ala Val Tyr Phe Cys
                 85                  90                  95

Ala Arg Ser Ala Ser Trp Tyr Phe Asp Val Trp Gly Ala Arg Thr Thr
                100                 105                 110

Val Thr Val Ser Ser
                115

<210> SEQ ID NO 121
<211> LENGTH: 373
<212> TYPE: DNA
<213> ORGANISM: Artificial Sequence
<220> FEATURE:
<223> OTHER INFORMATION: antibody sequence

<400> SEQUENCE: 121
caggtgcagc tgcagcagtc tggggctgag ctggtgaggc ctgggtcctc agtgaagatt      60
tcctgcaagg cttctggcta tgcattcagt agctactgga tgaactgggt gaagcagagg     120
cctggacagg gtcttgagtg gattggacag atttggcctg agatggtga tactaactac      180 aatggaaagt tcaagggtaa agccactctg actgcagacg aatcctccag cacagcctac     240
atgcaactca gcagcctagc atctgaggac tctgcggtct atttctgtgc aagacgggag     300
actacgacgg taggccgtta ttactatgct atggactact ggggccaagg gaccacggtc     360
accgtctcct ccg                                                        373

<210> SEQ ID NO 122
<211> LENGTH: 250
<212> TYPE: PRT
<213> ORGANISM: Artificial Sequence
<220> FEATURE:
<223> OTHER INFORMATION: anntibody sequence

<400> SEQUENCE: 122

Asp Ile Gln Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys Gly
                100                 105                 110

Gly Gly Gly Ser Gly Gly Gly Gly Ser Gly Gly Gly Ser Gln Val
            115                 120                 125

Gln Leu Gln Gln Ser Gly Ala Glu Leu Val Arg Pro Gly Ser Ser Val
        130                 135                 140

```
Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
            165                 170                 175

Ile Trp Pro Gly Asp Gly Asp Thr Asn Tyr Asn Gly Lys Phe Lys Gly
        180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
        210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser
            245                 250
```

```
<210> SEQ ID NO 123
<211> LENGTH: 750
<212> TYPE: DNA
<213> ORGANISM: Artificial Sequence
<220> FEATURE:
<223> OTHER INFORMATION: antibody sequence

<400> SEQUENCE: 123
gatatccagc tgacccagtc tccagcttct ttggctgtgt ctctagggca gagggccacc      60
atctcctgca aggccagcca agtgttgat tatgatggtg atagttattt gaactggtac     120
caacagattc caggacagcc acccaaactc ctcatctatg atgcatccaa tctagtttct     180
gggatcccac ccaggtttag tggcagtggg tctgggacag acttcaccct caacatccat     240
cctgtggaga aggtggatgc tgcaacctat cactgtcagc aaagtactga ggatccgtgg     300
acgttcggtg gagggaccaa gctcgagatc aaaggtggtg gtggttctgg cggcggcggc     360
tccggtggtg gtggttctca ggtgcagctg cagcagtctg gggctgagct ggtgaggcct     420
gggtcctcag tgaagatttc ctgcaaggct tctggctatg cattcagtag ctactggatg     480
aactgggtga agcagaggcc tggacagggt cttgagtgga ttggacagat ttggcctgga     540
gatggtgata ctaactacaa tggaaagttc aagggtaaag ccactctgac tgcagacgaa     600
tcctccagca cagcctacat gcaactcagc agcctagcat ctgaggactc tgcggtctat     660
ttctgtgcaa gacgggagac tacgacggta ggccgttatt actatgctat ggactactgg     720
ggccaaggga ccacggtcac cgtctcctcc                                      750
```

```
<210> SEQ ID NO 124
<211> LENGTH: 15
<212> TYPE: PRT
<213> ORGANISM: Artificial Sequence
<220> FEATURE:
<223> OTHER INFORMATION: antibody sequence

<400> SEQUENCE: 124

Gly Gly Gly Gly Ser Gly Gly Gly Ser Gly Gly Gly Gly Ser
1               5                   10                  15
```

```
<210> SEQ ID NO 125
<211> LENGTH: 250
<212> TYPE: PRT
<213> ORGANISM: Artificial Sequence
<220> FEATURE:
<223> OTHER INFORMATION: antibody sequence

<400> SEQUENCE: 125
```

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
                100                 105                 110

Tyr Trp Gly Gln Gly Thr Thr Val Thr Val Ser Ser Gly Gly Gly Gly
            115                 120                 125

Ser Gly Gly Gly Gly Ser Gly Gly Gly Gly Ser Asp Ile Gln Leu Thr
        130                 135                 140

Gln Ser Pro Ala Ser Leu Ala Val Ser Leu Gly Gln Arg Ala Thr Ile
145                 150                 155                 160

Ser Cys Lys Ala Ser Gln Ser Val Asp Tyr Asp Gly Asp Ser Tyr Leu
                165                 170                 175

Asn Trp Tyr Gln Gln Ile Pro Gly Gln Pro Pro Lys Leu Leu Ile Tyr
            180                 185                 190

Asp Ala Ser Asn Leu Val Ser Gly Ile Pro Pro Arg Phe Ser Gly Ser
        195                 200                 205

Gly Ser Gly Thr Asp Phe Thr Leu Asn Ile His Pro Val Glu Lys Val
    210                 215                 220

Asp Ala Ala Thr Tyr His Cys Gln Gln Ser Thr Glu Asp Pro Trp Thr
225                 230                 235                 240

Phe Gly Gly Gly Thr Lys Leu Glu Ile Lys
                245                 250

<210> SEQ ID NO 126
<211> LENGTH: 750
<212> TYPE: DNA
<213> ORGANISM: Artificial Sequence
<220> FEATURE:
<223> OTHER INFORMATION: antibody sequence

<400> SEQUENCE: 126
caggtgcagc tgcagcagtc tggggctgag ctggtgaggc ctgggtcctc agtgaagatt      60
tcctgcaagg cttctggcta tgcattcagt agctactgga tgaactgggt gaagcagagg     120
cctggacagg gtcttgagtg gattggacag atttggcctg gagatggtga tactaactac     180 aatgaaagt tcaagggtaa agccactctg actgcagacg aatcctccag cacagcctac      240
atgcaactca gcagcctagc atctgaggac tctgcggtct atttctgtgc aagacgggag     300
actacgacgg taggccgtta ttactatgct atggactact ggggccaagg gaccacggtc     360
accgtctcct ccggtggtgg tggttctggc ggcggcggct ccggtggtgg tggttctgat     420
atccagctga cccagtctcc agcttctttg gctgtgtctc tagggcagag ggccaccatc     480
tcctgcaagg ccagccaaag tgttgattat gatggtgata gttatttgaa ctggtaccaa     540
cagattccag gacagccacc caaactcctc atctatgatg catccaatct agtttctggg     600

| | |
|---|---|
| atcccaccca ggtttagtgg cagtgggtct gggacagact tcaccctcaa catccatcct | 660 |
| gtggagaagg tggatgctgc aacctatcac tgtcagcaaa gtactgagga tccgtggacg | 720 |
| ttcggtggag ggaccaagct cgagatcaaa | 750 |

<210> SEQ ID NO 127
<211> LENGTH: 1121
<212> TYPE: DNA
<213> ORGANISM: Artificial Sequence
<220> FEATURE:
<223> OTHER INFORMATION: antibody sequence

<400> SEQUENCE: 127

| | |
|---|---|
| ggtggtggtg gttctggcgg cggcggctcc ggtggtggtg gttctgatat ccagctgacc | 60 |
| cagtctccag cttctttggc tgtgtctcta gggcagaggg ccaccatctc ctgcaaggcc | 120 |
| agccaaagtg ttgattatga tggtgatagt tatttgaact ggtaccaaca gattccagga | 180 |
| cagccaccca aactcctcat ctatgatgca tccaatctag tttctgggat cccacccagg | 240 |
| tttagtggca gtgggtctgg acagacttc accctcaaca tccatcctgt ggagaaggtg | 300 |
| gatgctgcaa cctatcactg tcagcaaagt actgaggatc cgtggacgtt cggtggaggg | 360 |
| accaagctcg agatcaaagg aggtggtgga tccgatatca aactgcagca gtcaggggct | 420 |
| gaactggcaa gacctggggc ctcagtgaag atgtcctgca agacttctgg ctacaccttt | 480 |
| actaggtaca cgatgcactg ggtaaaacag aggcctggac agggtctgga atggattgga | 540 |
| tacattaatc ctagccgtgg ttatactaat acaatcaga agttcaagga caaggccaca | 600 |
| ttgactacag acaaatcctc cagcacagcc tacatgcaac tgagcagcct gacatctgag | 660 |
| gactctgcag tctattactg tgcaagatat tatgatgatc attactgcct tgactactgg | 720 |
| ggccaaggca ccactctcac agtctcctca gtcgaaggtg aagtggagg ttctggtgga | 780 |
| agtggaggtt caggtggagt cgacgacatt cagctgaccc agtctccagc aatcatgtct | 840 |
| gcatctccag gggagaaggt caccatgacc tgcagagcca gttcaagtgt aagttacatg | 900 |
| aactggtacc agcagaagtc aggcacctcc cccaaaagat ggatttatga cacatccaaa | 960 |
| gtggcttctg gagtcccctta tcgcttcagt ggcagtgggt ctgggacctc atactctctc | 1020 |
| acaatcagca gcatggaggc tgaagatgct gccacttatt actgccaaca gtggagtagt | 1080 |
| aacccgctca cgttcggtgc tgggaccaag ctggagctga a | 1121 |

<210> SEQ ID NO 128
<211> LENGTH: 373
<212> TYPE: PRT
<213> ORGANISM: Artificial Sequence
<220> FEATURE:
<223> OTHER INFORMATION: antibody sequence

<400> SEQUENCE: 128

Gly Gly Gly Gly Ser Gly Gly Gly Gly Ser Gly Gly Gly Gly Ser Asp
1               5                   10                  15

Ile Gln Leu Thr Gln Ser Pro Ala Ser Leu Ala Val Ser Leu Gly Gln
            20                  25                  30

Arg Ala Thr Ile Ser Cys Lys Ala Ser Gln Ser Val Asp Tyr Asp Gly
        35                  40                  45

Asp Ser Tyr Leu Asn Trp Tyr Gln Gln Ile Pro Gly Gln Pro Pro Lys
    50                  55                  60

Leu Leu Ile Tyr Asp Ala Ser Asn Leu Val Ser Gly Ile Pro Pro Arg
65                  70                  75                  80

```
Phe Ser Gly Ser Gly Ser Gly Thr Asp Phe Thr Leu Asn Ile His Pro
            85                  90                  95

Val Glu Lys Val Asp Ala Ala Thr Tyr His Cys Gln Gln Ser Thr Glu
        100                 105                 110

Asp Pro Trp Thr Phe Gly Gly Gly Thr Lys Leu Glu Ile Lys Gly Gly
            115                 120                 125

Gly Gly Ser Asp Ile Lys Leu Gln Gln Ser Gly Ala Glu Leu Ala Arg
    130                 135                 140

Pro Gly Ala Ser Val Lys Met Ser Cys Lys Thr Ser Gly Tyr Thr Phe
145                 150                 155                 160

Thr Arg Tyr Thr Met His Trp Val Lys Gln Arg Pro Gly Gln Gly Leu
                165                 170                 175

Glu Trp Ile Gly Tyr Ile Asn Pro Ser Arg Gly Tyr Thr Asn Tyr Asn
            180                 185                 190

Gln Lys Phe Lys Asp Lys Ala Thr Leu Thr Thr Asp Lys Ser Ser Ser
        195                 200                 205

Thr Ala Tyr Met Gln Leu Ser Ser Leu Thr Ser Glu Asp Ser Ala Val
    210                 215                 220

Tyr Tyr Cys Ala Arg Tyr Tyr Asp Asp His Tyr Cys Leu Asp Tyr Trp
225                 230                 235                 240

Gly Gln Gly Thr Thr Leu Thr Val Ser Val Glu Gly Gly Ser Gly
                245                 250                 255

Gly Ser Gly Gly Ser Gly Gly Ser Gly Val Asp Asp Ile Gln Leu
            260                 265                 270

Thr Gln Ser Pro Ala Ile Met Ser Ala Ser Pro Gly Glu Lys Val Thr
    275                 280                 285

Met Thr Cys Arg Ala Ser Ser Ser Val Ser Tyr Met Asn Trp Tyr Gln
290                 295                 300

Gln Lys Ser Gly Thr Ser Pro Lys Arg Trp Ile Tyr Asp Thr Ser Lys
305                 310                 315                 320

Val Ala Ser Gly Val Pro Tyr Arg Phe Ser Gly Ser Gly Ser Gly Thr
                325                 330                 335

Ser Tyr Ser Leu Thr Ile Ser Ser Met Glu Ala Glu Asp Ala Ala Thr
            340                 345                 350

Tyr Tyr Cys Gln Gln Trp Ser Ser Asn Pro Leu Thr Phe Gly Ala Gly
        355                 360                 365

Thr Lys Leu Glu Leu
    370

<210> SEQ ID NO 129
<211> LENGTH: 15
<212> TYPE: PRT
<213> ORGANISM: Artificial Sequence
<220> FEATURE:
<223> OTHER INFORMATION: linker sequence

<400> SEQUENCE: 129

Gly Gly Gly Gly Ser Gly Gly Gly Ser Gly Gly Gly Ser
1               5                   10                  15

<210> SEQ ID NO 130
<211> LENGTH: 45
<212> TYPE: DNA
<213> ORGANISM: Artificial Sequence
<220> FEATURE:
<223> OTHER INFORMATION: linker sequence

<400> SEQUENCE: 130
```

```
ggtggtggtg gttctggcgg cggcggctcc ggtggtggtg gttct              45
```

<210> SEQ ID NO 131
<211> LENGTH: 6
<212> TYPE: PRT
<213> ORGANISM: Artificial Sequence
<220> FEATURE:
<223> OTHER INFORMATION: linker sequence

<400> SEQUENCE: 131

Ser Gly Gly Gly Gly Ser
1               5

<210> SEQ ID NO 132
<211> LENGTH: 18
<212> TYPE: DNA
<213> ORGANISM: Artificial Sequence
<220> FEATURE:
<223> OTHER INFORMATION: linker sequence

<400> SEQUENCE: 132

```
tccggaggtg gtggatcc                                            18
```

<210> SEQ ID NO 133
<211> LENGTH: 18
<212> TYPE: PRT
<213> ORGANISM: Artificial Sequence
<220> FEATURE:
<223> OTHER INFORMATION: linker sequence

<400> SEQUENCE: 133

Val Glu Gly Gly Ser Gly Gly Ser Gly Gly Ser Gly Gly Ser Gly Gly
1               5                   10                  15

Val Asp

<210> SEQ ID NO 134
<211> LENGTH: 54
<212> TYPE: DNA
<213> ORGANISM: Artificial Sequence
<220> FEATURE:
<223> OTHER INFORMATION: linker sequence

<400> SEQUENCE: 134

```
gtcgaaggtg gaagtggagg ttctggtgga agtggaggtt caggtggagt cgac    54
```

<210> SEQ ID NO 135
<211> LENGTH: 110
<212> TYPE: PRT
<213> ORGANISM: Artificial Sequence
<220> FEATURE:
<223> OTHER INFORMATION: antibody sequence

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Lys
            100                 105                 110

<210> SEQ ID NO 136
<211> LENGTH: 330
<212> TYPE: DNA
<213> ORGANISM: Artificial Sequence
<220> FEATURE:
<223> OTHER INFORMATION: antibody sequence

<400> SEQUENCE: 136
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaacgtaag                                     330

<210> SEQ ID NO 137
<211> LENGTH: 119
<212> TYPE: PRT
<213> ORGANISM: Artificial Sequence
<220> FEATURE:
<223> OTHER INFORMATION: antibody sequence

<400> SEQUENCE: 137

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 138
<211> LENGTH: 357
<212> TYPE: DNA
<213> ORGANISM: Artificial Sequence
<220> FEATURE:
<223> OTHER INFORMATION: antibody sequence

<400> SEQUENCE: 138
gatatcaaac tgcagcagtc aggggctgaa ctggcaagac ctggggcctc agtgaagatg     60
tcctgcaaga cttctggcta cacctttact aggtacacga tgcactgggt aaaacagagg    120
cctggacagg gtctggaatg gattggatac attaatccta gccgtggtta tactaattac    180

```
aatcagaagt tcaaggacaa ggccacattg actacagaca aatcctccag cacagcctac        240
atgcaactga gcagcctgac atctgaggac tctgcagtct attactgtgc aagatattat        300
gatgatcatt actgccttga ctactggggc caaggcacca ctctcacagt ctcctca          357

<210> SEQ ID NO 139
<211> LENGTH: 106
<212> TYPE: PRT
<213> ORGANISM: Artificial Sequence
<220> FEATURE:
<223> OTHER INFORMATION: antibody sequence

<400> SEQUENCE: 139

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 140
<211> LENGTH: 318
<212> TYPE: DNA
<213> ORGANISM: Artificial Sequence
<220> FEATURE:
<223> OTHER INFORMATION: antibody sequence

<400> SEQUENCE: 140
gacattcagc tgacccagtc tccagcaatc atgtctgcat ctccagggga gaaggtcacc         60
atgacctgca gagccagttc aagtgtaagt tacatgaact ggtaccagca gaagtcaggc        120
acctccccca aaagatggat ttatgacaca tccaaagtgg cttctggagt cccttatcgc        180
ttcagtggca gtgggtctgg gacctcatac tctctcacaa tcagcagcat ggaggctgaa        240
gatgctgcca cttattactg ccaacagtgg agtagtaacc cgctcacgtt cggtgctggg        300
accaagctgg agctgaaa                                                     318
```

TRANSGENIC NON-HUMAN VERTEBRATE FOR THE IN VIVO PRODUCTION OF DUAL SPECIFICITY IMMUNOGLOBULINS OR HYPERMUTATED HEAVY CHAIN ONLY IMMUNOGLOBULINS

CROSS REFERENCE

This application is a Continuation application of International Application No. PCT/GB2013/051280 filed May 17, 2013, which claims priority to GB 1208708.6 filed May 17, 2012, the contents of both of which are hereby incorporated by reference in their entirety.

SEQUENCE LISTING

The attached sequence is hereby incorporated by reference in its entirety.

The invention relates, in one aspect, generally to novel concept of guided selection of antibody variable domains, combination and expression entirely in vivo. An application is to produce multivalent polypeptides.

The present invention also relates to multivalent (eg, multispecific) antibodies, antibody chains and polypeptides, as well as heavy chain-only antibodies (H2 antibodies) that are devoid of light chains. The invention further relates to the selection, maturation and production of these in vivo in non-human vertebrates and non-human vertebrate cells. To this end the invention also relates to such non-human vertebrates and cells. The invention also relates to the provision of means to produce and select heavy chain-only antibodies and heavy chains comprising variable domains that have undergone affinity maturation.

BACKGROUND

The state of the art provides methods for producing antibodies in vitro (eg, using phage, ribosome or yeast display) or in vivo (eg, using non-human vertebrates (eg, mice and rats) and cells comprising transgenic immunoglobulin loci). Such in vivo systems (eg, Xenomouse™) have used completely human transgenic heavy chain loci which comprise human variable regions (human VH, D and JH gene segments) upstream of human constant regions (eg, human mu upstream of human gamma constant gene segments). Subsequently, it has been discovered that the use of totally human transgenic loci in such in vivo systems is detrimental and B-cell development is hampered, leading to relatively small B-cell compartments and restricted utility for generating antibodies. Later-generation transgenic animals (eg, the Velocimouse™) have been created which have chimaeric heavy chain loci in which a human variable region is upstream of endogenous (eg, mouse or rat) constant regions (ie, mouse mu constant region upstream of gamma constant region, in germline configuration). This enables the harnessing of endogenous control mechanisms for B-cell and antibody development, and as such the extent of problems of totally human transgenic loci are not seen. Methods of constructing transgenic vertebrates and use of these to generate antibodies and nucleic acids thereof following antigen immunisation are known in the art, eg, see U.S. Pat. No. 7,501,552 (Medarex); U.S. Pat. Nos. 5,939,598 & 6,130,364 (Abgenix); WO02066630, WO2011163311 & WO2011163314 (Regeneron); WO2011004192 & WO2011158009 (Kymab Limited); WO2009076464, WO2009143472, EP1414858, WO2009013620A2, WO2010070263A1 & WO2010109165A2 (Harbour Antibodies); EP1399559 (Crescendo Biologics) and WO2010039900 (Ablexis), the disclosures of which are explicitly incorporated herein including, but not limited to, for the purpose of providing the skilled person with guidance of how to make non-human animals bearing transgenic immunoglobulin loci and to inactivate endogenous loci expression.

The art has recognised the desirability of producing artificial combinations of epitope or antigen binding sites and specificities. So, the art has proposed multivalent antigen-binding antibodies and polypeptides in which a plurality of binding sites are synthetically combined to provide for binding to multiple epitopes on the same or different targets. When the targets are different, multispecific constructs are possible that can target and bind to a plurality of different antigens providing the epitopes (eg, to neutralise the antigens). One technique involves the in vitro combination (fusion) of different hybridomas to produce quadromas in which pairings of heavy and light chains from different antibodies are obtained (Milstein & Cuello, Nature, 1983, 305(5934): pp 537-40). This technique disadvantageously leads to mis-match pairings and multiple different combinations of antibody chains, so that the yield of the desired combination of specificities is relatively low. Subsequent techniques have used in vitro antibody engineering in order to synthetically combine epitope binding moieties (eg, antibody varirable domains, dAbs or scFvs) to produce multivalent, multispecific constructs. The Epitope binding moieties are individually selected (usually on the basis of epitope binding affinity) in in vitro techniques such as phage display, ribosome display and yeast display. Once desirable moieties have been identified, these are then combined in vitro by engineering and the performance and characteristics of the resultant multivalent constructs are assessed. While providing for multi-valency and multi-specificity, these techniques are hampered, however, because such engineering in vitro can downgrade the desirable characteristics of the resultant antibody. For example, antigen-binding affinity, antigen specificity, expressability (eg, in cell lines such as CHO or HEK293 cells), half-life and/or biophysical characteristics (eg, melting temperature, solution state, resistance to aggregation etc) can be downgraded, thereby hampering development of the antibody as drugs for human therapeutic or prophylactic use. It would be desirable to have means for producing, maturing and selecting multivalent and multispecific antibodies that addresses these shortcomings in the art. Multivalent and multispecifc formats are disclosed, for example, in Trends Biotechnol. 2010 July; 28(7):355-62. Epub 2010 May 4; "Multivalent antibodies: when design surpasses evolution"; Cuesta A M et al.

Reference is made to the patent applications cited above from Harbour Antibodies and Crescendo Biologics; these relate to the production of heavy chain-only antibodies (H2 antibodies) which lack CH1 and are devoid of light chains. In Proc Natl Acad Sci USA. 2006 Oct. 10; 103(41):15130-5. Epub 2006 Oct. 2; "Generation of heavy-chain-only antibodies in mice"; Janssens et al transgenic mice (MGΔ mice) are disclosed which comprise an antibody heavy chain locus comprising llama VHH exons and a Cμ region upstream of Cγ2 and Cγ3 regions in which CH1 has been deleted. The mice have a μMT background and express light chains. The heavy chain MGΔ loci are introduced by injection of DNA into fertilized mouse eggs follow by random integration of one to five copies of the locus into the mouse genomes. The MGΔ loci did not rescue B-cell development. MGΔ mice contained very few B-cells expressing cell-surface chimaeric Ig; 30% of the bone marrow B220$^+$ cells expressed intracellular IgM, but no IgG. Thus, there is a need for improved transgenic heavy chain loci as well as vertebrates and cells comprising these for the generation of H2 antibodies (eg, class-switched H2 antibodies such as gamma-type H2 antibodies).

SUMMARY OF THE INVENTION

The present invention addresses the need for improved multivalent and multispecific antibodies, chains and polypeptides and means for producing and selecting these. In this respect, the invention provides a solution by providing for the production, maturation and selection of combinations of epitope binding specificities completely in vivo. In this way, the invention enables the skilled person to select antibody variable domains that have been produced, matured and expressed by in vivo systems in the context of one or more predetermined other binding sites or specificities.

Thus, using the present invention it is possible straightforwardly and rapidly to obtain multi-antigen-specific antibodies, chains and polypeptides that comprise an antigen-specific variable domain that has undergone junctional mutation and affinity maturation in vivo in the context of one or more predetermined other binding moieties. Such antibodies, chains and polypeptides are produced and selected totally in vivo in the combination to be used as a final product, and as such the present invention harnesses in vivo filtering for expressability (and provides possibly for aspects of affinity and biophysical characteristics to be factored into in vivo selection) in the context of the desired variable domain and predetermined epitope binding moiety pairings. This avoids problems of down-grading biophysical and affinity characteristics seen in the prior art when separately selecting and then combining epitope binding moieties in vitro. Thus, the present invention allows the skilled person to select multivalent and multispecific antibodies, chains and polypeptides directly in the format that they will be used for subsequent human therapeutic and prophylactic use.

The present invention also addresses the need for improved in vivo production of heavy chain-only antibodies. Using the present invention it is possible to produce and select heavy chain-only antibodies and heavy chains comprising variable domains that have undergone affinity maturation. The invention enables antibody and B-cell compartment development to pass through a favourable 4-chain endogenous IgM stage before proceeding to a subsequent (eg, gamma) stage which selects solely heavy chain-only (H2) antibodies from the good pool of heavy chain VDJ recombinations provided by the earlier 4-chain IgM stage, this subsequent stage essentially eliminating the possibility for 4-chain antibodies. This subsequent stage can incorporate additional epitope specificities in a predetermined way, so that the heavy chain-only antibodies and chains can optionally be multispecific. The invention is expected to provide one or more of the following advantages: good B-cell compartment development (eg, normal bone marrow and/or spleen or secondary lymphoid compartments at or approximating wild-type); normal B-cell ratios in bone marrow and/or splenic compartments; normal serum antibody levels; normal serum gamma-H2 antibody levels; good antigen binding affinities for H2 antibodies; production exclusively of isotype-switched H2 antibodies; and production exclusively of isotype-switched antibodies whose variable domains are antibody single variable domains (ie, dAbs).

Thus, in a First Configuration, the Invention Provides
In a First Aspect:—

A non-human vertebrate (eg, a mouse or a rat), wherein the vertebrate comprises lymphocytic cells, each cell genome comprising (i) an antibody heavy chain locus comprising (in 5' to 3' direction) a rearranged or unrearranged variable region, a first switch, a mu constant region (eg, comprising a CH1 gene segment), a second switch and a non-mu (eg, gamma) constant region; wherein the heavy chain locus of each cell is capable of undergoing IgM to the non-mu (eg, IgG) isotype switching; and wherein (ii) the non-mu constant region comprises (in 5' to 3' direction) a nucleotide sequence encoding an optional linker and a predetermined epitope binding moiety, wherein following isotype switching the vertebrate expresses multivalent polypeptide chains comprising (in N- to C-terminal direction) an antibody variable domain derived from said variable region of the heavy chain locus, an optional linker and an epitope binding moiety, wherein the variable domain and the epitope binding moiety specifically bind respective first and second epitopes.

In a Second Aspect:—

A non-human vertebrate cell (eg, a mouse cell or a rat cell, such as an ES cell or a B-cell), the cell genome comprising (i) an antibody heavy chain locus comprising (in 5' to 3' direction) a rearranged or unrearranged variable region, a first switch, a mu constant region (eg, comprising a CH1 gene segment), a second switch and a non-mu (eg, gamma) constant region; wherein the heavy chain locus of each cell is capable of undergoing IgM to a non-mu (eg, IgG) isotype switching; and wherein (ii) the non-mu constant region comprises (in 5' to 3' direction) a nucleotide sequence encoding an optional linker and a predetermined epitope binding moiety, for expressing a multivalent polypeptide chain comprising (in N- to C-terminal direction) an antibody variable domain derived from said variable region of the heavy chain locus, an optional linker and an epitope binding moiety, wherein the variable domain and the epitope binding moiety specifically bind respective first and second epitopes.

In a Second Configuration, the Invention Provides
In a First Aspect:—

A non-human vertebrate (eg, a mouse or a rat), wherein the vertebrate comprises lymphocytic cells whose genomes comprise an antibody heavy chain locus comprising (in 5' to 3' direction) a rearranged variable region and a non-mu (eg, gamma) constant region;

wherein the non-mu constant region comprises (in 5' to 3' direction) a nucleotide sequence encoding an optional linker and a predetermined epitope binding moiety, wherein the vertebrate expresses multivalent polypeptide chains comprising (in N- to C-terminal direction) an antibody variable domain derived from said variable region of the heavy chain locus, an optional linker and an epitope binding moiety, wherein the variable domain and the epitope binding moiety specifically bind respective first and second epitopes.

In a Second Aspect:—

A non-human vertebrate cell (eg, a mouse cell or a rat cell) or a hybridoma, the cell genome comprising an antibody heavy chain locus comprising (in 5' to 3' direction) a rearranged variable region and a non-mu (eg, gamma) constant region;

wherein
the non-mu constant region comprises (in 5' to 3' direction) a nucleotide sequence encoding an optional linker and a predetermined epitope binding moiety, wherein the cell expresses a multivalent polypeptide chain comprising (in N- to C-terminal direction) an antibody variable domain derived from said variable region of the heavy chain locus, an optional linker and an epitope binding moiety, wherein the variable domain and the epitope binding moiety specifically bind respective first and second epitopes.

In a Third Configuration, the Invention Provides
In a First Aspect:—

A non-human vertebrate (eg, a mouse or a rat), wherein the vertebrate comprises lymphocytic cells, the genome of each cell comprising an antibody light chain locus which comprises (in 5' to 3' direction) a rearranged or unrearranged variable region and a second region;
wherein
the second region comprises (in 5' to 3' direction) a nucleotide sequence encoding an optional linker and a predetermined epitope binding moiety, wherein the vertebrate expresses polypeptide chains comprising (in N- to C-terminal direction) an antibody variable domain derived from said variable region of the light chain locus, an optional linker and an epitope binding moiety, wherein the variable domain and the epitope binding moiety specifically bind respective first and second epitopes.

In a Second Aspect:—

A non-human vertebrate cell (eg, a mouse cell or a rat cell) or a hybridoma, wherein the cell genome comprises an antibody light chain locus comprising (in 5' to 3' direction) a rearranged or unrearranged variable region and a second region;
wherein
the second region comprises (in 5' to 3' direction) a nucleotide sequence encoding an optional linker and a predetermined epitope binding moiety, for expressing a polypeptide chain comprising (in N- to C-terminal direction) an antibody variable domain derived from said variable region of the light chain locus, an optional linker and an epitope binding moiety, wherein the variable domain and the epitope binding moiety specifically bind respective first and second epitopes.

In a Fourth Configuration, the Invention Provides
In a First Aspect:—

A method of producing multivalent polypeptide chains comprising (in N- to C-terminal direction) an antibody variable domain, an optional linker and an epitope binding moiety, wherein the variable domain and the epitope binding moiety specifically bind respective first and second epitopes, the method comprising
(a) expressing in a non-human vertebrate (eg, a mouse or a rat) IgM antibodies in immature B-cells, wherein the antibodies comprise heavy and light chains expressed from heavy and light chain loci respectively, optionally the heavy chains comprising CH1 domains;
(b) immunising the vertebrate with a first predetermined antigen bearing the first epitope and obtaining isotype switching to expression from a non-mu (eg, gamma) constant region in at least some of the heavy chain loci and expression of variable regions that have undergone somatic hypermutation; and
(c) selecting one or more polypeptide chains from said immunised vertebrate by selection for variable regions that bind said first epitope, wherein each selected chain comprises a somatically hypermutated variable region that specifically binds the epitope; and
wherein the method further comprises
(d) providing the nucleotide sequence of the epitope binding moiety in the non-mu constant region of heavy chain loci in the genome of the vertebrate, wherein the polypeptide chains selected in step (c) bind the first and second epitopes.

In a Second Aspect:—

A method of producing in a non-human vertebrate (eg, a mouse or a rat) multivalent polypeptide chains comprising (in N- to C-terminal direction) an antibody variable domain, an optional linker and an epitope binding moiety, wherein the variable domain and the epitope binding moiety specifically bind respective first and second epitopes), the method comprising
(a) immunising the vertebrate with a first predetermined antigen bearing the first epitope, obtaining isotype switching to expression from a non-mu (eg, gamma) constant region in at least some of the heavy chain loci of the vertebrate and expression of variable regions that have undergone somatic hypermutation; and
(b) selecting one or more polypeptide chains from said immunised vertebrate by selection for variable regions that bind said first epitope, wherein each selected chain comprises a somatically hypermutated variable region that specifically binds the epitope; and
wherein the method further comprises
(d) providing the nucleotide sequence of the epitope binding moiety in the non-mu constant region of heavy chain loci in the genome of the vertebrate, wherein the polypeptide chains selected in step (b) bind the first and second epitopes.

In a Fifth Configuration, the Invention Provides
In a First Aspect:—

A multivalent (eg, multispecific or bispecific) polypeptide chain having (in N- to C-terminal direction) the structure V-X-L-E-L-C, where
(i) V is an antibody variable domain that specifically binds a first epitope,
(ii) X is absent, an antibody hinge region or an antibody constant region comprising a constant domain,
(iii) Each L is an optional linker,
(iv) E is an epitope binding moiety that specifically binds a second epitope, and
(v) C is absent or an antibody constant region comprising a constant domain (eg, C is a human gamma Fc),
wherein V is a rearranged antibody variable domain derived from the rearrangement of variable region gene segments in vivo in a non-human vertebrate with somatic hypermutation of the resulting variable region gene in a nucleotide sequence also encoding for the epitope binding moiety; and wherein the rearranged antibody variable domain comprises endogenous AID-pattern somatic hypermutations.

In a Second Aspect:—

A multivalent (eg, multispecific or bispecific) antibody comprising heavy chains associated with light chains, wherein
Each heavy chain is a polypeptide chain as recited in the first aspect of the fifth configuration, wherein E is an antibody variable domain;
Each light chain is a polypeptide chain having (in N- to C-terminal direction) the structure V'-L'-E'-L'-C', where
(i) V' is an antibody variable domain,
(ii) Each L' is an optional linker,
(iv) E' is an epitope binding moiety, and
(v) C' is absent or an antibody constant region comprising a constant domain (eg, C' is a human CL);
wherein
V' is a rearranged antibody variable domain derived from the rearrangement of variable region gene segments in vivo in a non-human vertebrate with somatic hypermutation of the resulting variable region gene in a nucleotide sequence also encoding for E'; and V' comprises endogenous AID-pattern somatic hypermutations;

V and V' form a first binding site that specifically binds a first epitope; and

Optionally E and E' form a second binding site that specifically binds a second epitope when E' is an antibody variable domain (eg, E is a VH and E' is a VL; or E is a VL and E' is a VH).

In a Third Aspect:—

An antigen-binding polypeptide comprising a protein scaffold which is linked to one or more epitope binding moieties wherein the antigen-binding polypeptide comprises at least two epitope binding sites at least one of which is provided by an epitope binding moiety and at least one of which is provided by a first antibody variable domain paired with a second antibody variable domain, wherein each variable domain is a rearranged antibody variable domain derived from the rearrangement of variable region gene segments in vivo in a non-human vertebrate with somatic hypermutation of the resulting variable region gene in a nucleotide sequence also encoding for one or more of the epitope binding moiety(ies); and wherein in that the rearranged antibody variable domains comprise endogenous AID-pattern somatic hypermutations.

In a Fourth Aspect:—

A multispecific antigen binding polypeptide, dimer or antibody according to the first, second or third aspect, which is capable of recruiting the activity of a human immune effector cell by specifically binding to an effector antigen (eg, human CD3) located on the human immune effector cell, a first of the epitope binding sites of the polypeptide, dimer or antibody being capable of specifically binding to said effector antigen, and a second of the epitope binding sites of the polypeptide, dimer or antibody being capable of specifically binding to a target antigen (eg, human EpCAM or human CD19) other than the effector antigen; optionally wherein said target antigen is located on a target cell other than said human immune effector cell.

In a Sixth Configuration, the Invention Provides

In a First Aspect:—

A non-human vertebrate (eg, a mouse or a rat), wherein (a) the vertebrate expresses IgM antibodies comprising heavy and light chains encoded by antibody heavy and light chain loci respectively, optionally wherein each heavy chain comprises a CH1 domain;

(b) the vertebrate is capable of expressing non-mu (eg, IgG) antibodies, each non-mu antibody heavy chain lacking a functional CH1 domain; and (c) the IgM antibodies are expressed by lymphocytic cells, each cell comprising a functional light chain locus for expressing light chains of IgM antibodies expressed by the cell; and wherein (d) the non-mu antibodies are expressed by lymphocytic cells, each cell lacking a functional light chain locus wherein non-mu antibodies are expressed by the cell in the absence of light chain expression.

In a Second Aspect:—

A non-human vertebrate (eg, a mouse or a rat), wherein the vertebrate comprises lymphocytic cells whose genomes comprise (i) an antibody heavy chain locus comprising (in 5' to 3' direction) a rearranged or unrearranged variable region, a first switch, a mu constant region (eg, comprising a CH1 gene segment), a second switch and a non-mu (eg, gamma) constant region lacking a CH1 gene segment;

(ii) a functional antibody light chain locus for expressing light chains;

wherein the cells can express IgM antibodies comprising IgM-type heavy chains and light chains;

wherein the heavy chain locus of each cell is capable of undergoing isotype switching to produce non-mu (eg, IgG) antibodies comprising one or more non-mu-type (eg, IgG-type) heavy chains in the absence of light chains, each heavy chain lacking a CH1 domain; and (iii) means for turning off light chain expression, wherein functional light chains are not expressed after isotype switching to said non-mu-type antibodies.

In a Third Aspect:—

A non-human vertebrate cell (eg, a mouse cell or a rat cell), wherein the cell genome comprises (i) a functional antibody light chain locus for expressing light chains;

(ii) an antibody heavy chain locus comprising (in 5' to 3' direction) a rearranged or unrearranged variable region, a first switch, a mu constant region (eg, comprising a CH1 gene segment), a second switch and a non-mu (eg, gamma) constant region lacking a CH1 gene segment for expressing IgM antibodies comprising IgM-type heavy chains and light chains; and for IgM to non-mu (eg, IgG) isotype switching to produce non-mu (eg, IgG) antibodies comprising one or more non-mu-type heavy chains in the absence of light chains, each heavy chain lacking a CH1 domain; and (iii) means for turning off light chain expression, wherein functional light chains are not expressed after isotype switching to said non-mu-type antibodies.

In a Seventh Configuration, the Invention Provides

A method of producing polypeptide chains comprising somatically hypermutated variable regions in a non-human vertebrate (eg, a mouse or a rat), the method comprising (a) expressing in the vertebrate IgM antibodies in immature B-cells, wherein the antibodies comprise heavy and light chains expressed from heavy and light chain loci respectively;

(b) immunising the vertebrate with a predetermined epitope and obtaining isotype switching in at least some of the heavy chain loci and expression of non-mu (eg, IgG) antibodies that have undergone somatic hypermutation, wherein the antibodies comprise heavy chains that lack a CH1 domain and comprise variable regions that specifically bind the antigen; and (c) selecting one or more polypeptide chains from said immunised vertebrate by selection for variable regions that bind said epitope, wherein each selected chain comprises a somatically hypermutated variable region that specifically binds the epitope; and the method further comprising expressing the non-mu antibodies in step (b) in the absence of light chain expression.

In an Eighth Configuration, the Invention Provides

A non-human vertebrate (eg, a mouse or a rat) whose genome comprises an antibody heavy chain locus and an antibody light chain locus, (a) the light chain locus comprising (in 5' to 3' direction) a light chain variable region and a constant region for expressing light chains in lymphocytic cells expressing IgM antibodies; and (b) means for turning off light chain expression in lymphocytic cells expressing non-mu (eg, IgG) antibodies.

A non-human vertebrate cell (eg, a mouse cell or a rat cell) or hybridoma whose genome comprises an antibody heavy chain locus and an antibody light chain locus, the light chain locus comprising (a) (in 5' to 3' direction) a light chain variable region and a constant region for expressing light chains in lymphocytic cells expressing IgM antibodies; and (b) means for turning off light chain expression in lymphocytic cells expressing non-mu (eg, IgG) antibodies.

The invention also provides:—

A non-human vertebrate (eg, a mouse or a rat) or cell (eg, a mouse cell or a rat cell), wherein an Ig heavy or light chain locus of the genome of the vertebrate or cell comprises (in 5' to 3' orientation) (i) an unrearranged human variable region for encoding a first variable domain, (ii) a sequence encoding an optional linker and (iii) a sequence encoding an epitope binding moiety.

A polypeptide comprising a binding site specific for a target epitope, the binding site having the structure V1-L-E, where V1 is an antibody variable domain, E is an epitope binding moiety and L is an optional peptide linker; and wherein V1 is derived from the rearrangement of human variable region gene segments in vivo in a non-human vertebrate with somatic hypermutation of the resulting variable region gene in a nucleotide sequence also encoding E, wherein V1 comprises endogenous AID-pattern somatic hypermutations and specifically binds the target epitope.

A non-human vertebrate (eg, a mouse or a rat), wherein the vertebrate comprises lymphocytic cells whose genomes comprise an antibody heavy or light chain locus comprising (in 5' to 3' direction) a rearranged variable region and a non-mu constant region;
wherein
the non-mu constant region comprises (in 5' to 3' direction) a nucleotide sequence encoding an optional linker and the rearranged variable region which encodes a first variable domain, wherein following isotype switching the vertebrate expresses polypeptide chains comprising (in N- to C-terminal direction) an epitope binding site comprising second and first antibody variable domains derived respectively from a rearranged second variable domain nucleotide sequence and from the first variable domain nucleotide sequence, wherein the second nucleotide sequence has been rearranged in the vertebrate.

A non-human vertebrate cell (eg, a mouse cell or a rat cell) or a hybridoma, the cell genome comprising (in 5' to 3' direction) a rearranged variable region and a non-mu constant region;
wherein
the non-mu constant region comprises (in 5' to 3' direction) a nucleotide sequence encoding an optional linker and the rearranged variable region which encodes a first variable domain, for expressing polypeptide chains comprising (in N- to C-terminal direction) an epitope binding site comprising second and first antibody variable domains derived respectively from a rearranged second variable domain nucleotide sequence and from the first variable domain nucleotide sequence, wherein the second nucleotide sequence has been rearranged in the cell.

A method of producing a vertebrate of a non-human species, the method comprising breeding two vertebrates of said species together, wherein both of the vertebrates are according to any aspect of the invention.

By turning off light chain expression, isotype switched heavy chains are expressed in the absence of light chain expression and thus there is no possibility for newly-expressed light chains to associate with heavy chains during B-cell proliferation and during somatic mutation and selection of heavy chains following antigen or epitope immunisation. Thus, heavy chain production is essentially exclusively the production of H2 antibody-type heavy chains, wherein the variable regions bind antigen in the absence of a light chain variable region partner. Such H2 antibodies can be a good source for antibody single variable domain sequences (eg, human VH single variable domains when the heavy chain loci comprise human variable regions). Thus, the in vivo antibody production machinery of the non-human vertebrate or cell of the invention can be dedicated to H2 antibody production without any significant 4-chain antibody (H2L2) production hampering the extent of H2 antibody response following immunisation and ultimately the desirable levels of H2 that are obtainable. This advantage enables this isotype-switched, antigen/epitope-specific in vivo response to develop from the desirable recombined VDJ repertoire and B-cell compartments arising from the retention of endogenous IgM stage as further discussed below.

By retaining an endogenous IgM stage, configurations and aspects of the invention retain the ability to harness the endogenous antibody and B-cell development control mechanisms of the non-human vertebrate or cell. This includes the ability to harness endogenous terminal deoxynucleotidyl transferase (TdT) activity and junctional mutation as well as proper B-cell development (including at early stages of development when IgM is expressed) to yield good size B-cell compartments and good size and quality repertoires of recombined VDJ diversity from which to subsequently select and mature isotype-switched heavy chains produced from the antibody heavy or light chain locus of the invention. Thus, for example, a vertebrate of the invention can be immunised with a predetermined therapeutic target antigen (eg, a human, viral or bacterial antigen) and antibodies (eg, gamma-type) or heavy chains (eg, gamma-type heavy chains) can be isolated that (i) have undergone junctional and somatic mutation, and thus affinity maturation in vivo in response to antigen challenge, (ii) have human variable domains, and (iii) have been selected by a totally in vivo system for expression and ability to bind antigen(s) or epitope(s). Thus, the invention employs in vivo systems to direct the skilled person to viable human antibodies (eg, H2 or 4-chain bispecific antibodies) and heavy chains that can be expressed well in vivo and which are specific for a predetermined antigen.

The multivalent configurations of the invention are simply produced by avoiding multi-step combinations of in vivo and in vitro production and engineering to produce multivalent formats as per the prior art methods.

Moreover, having undergone affinity maturation in the vertebrate or cell, the selected antibodies have had their antigen binding affinities tuned by nature—rather than by man. Thus, vertebrates and cells of the invention provide good sources for fully human antigen-specific antibodies and heavy chains with therapeutically-amenable affinities without the need to perform laborious in vitro affinity maturation (or risk downgrading desirable characteristics due to in vitro manipulation). Additionally, the present invention enables the skilled person to design vertebrates and cells to produce multivalent antibodies, chains and polypeptides of a specific, desired isotype in a predictable way. For example, the skilled person is able to design the heavy chain loci in a vertebrate of the invention so that all gamma constant region gene segments comprise the multivalent design described above. In this way, the skilled person will know that all IgG-type antibodies or heavy chains selected from the vertebrate will be multivalent in their H chains and will have been subjected to endogenous antibody development (eg, affinity maturation) and in vivo expression and selection in the context of combinations of binding sites. Going a step further, the skilled person could design a vertebrate in which just the IgG1 isotype gene segments have the multivalent design. Thus, the skilled person will know from the outset that all IgG1 isotype antibodies will be multivalent (eg, bispecific) and matured, expressed and selected in vivo. This is useful for in vivo tailoring antibody sub-types, such as IgG1 or IgG4, to particular target epitope or antigen combinations in a predictable manner.

FIGURES

FIGS. 15A-D show example spleen and lymph nodes obtained from the transgenic vertebrate of the invention, together with the results of PCR analysis of mRNA extracted from such vertebrates. (A) Total RNA extracted from spleen and lymph nodes of transgenic mice KMBS2.1d and KMBS3.1a separated out on a 1% TAE agarose gel (B). First round PCR carried out on cDNA synthesised from RNA extracted from spleen and lymph nodes using an internal semi-nested primer 1. The expected DNA fragment corresponding to the bispecific transcript is ~1.7 kb and is highlighted by the white box. Agarose gel around the expected transcript size was excised and gel extracted and used in a second round PCR (C) using either the same semi-nested reverse primer 1 or an internal semi-nested reverse primer 2. Transcript corresponding to the expected bispecific antibody size was detected in RNA samples extracted from lymph nodes of mouse KMBS2. The ~1.7 kb DNA fragment was excised from the agarose gel and gel extracted and a small portion was used for a third round PCR (D) using a further internal reverse primer 3. The third round PCR yielded a significant amount of products corresponding to a size expected for the novel bispecific transcript. Abbreviations: S, spleen; L, lymph nodes.

Figure 16:
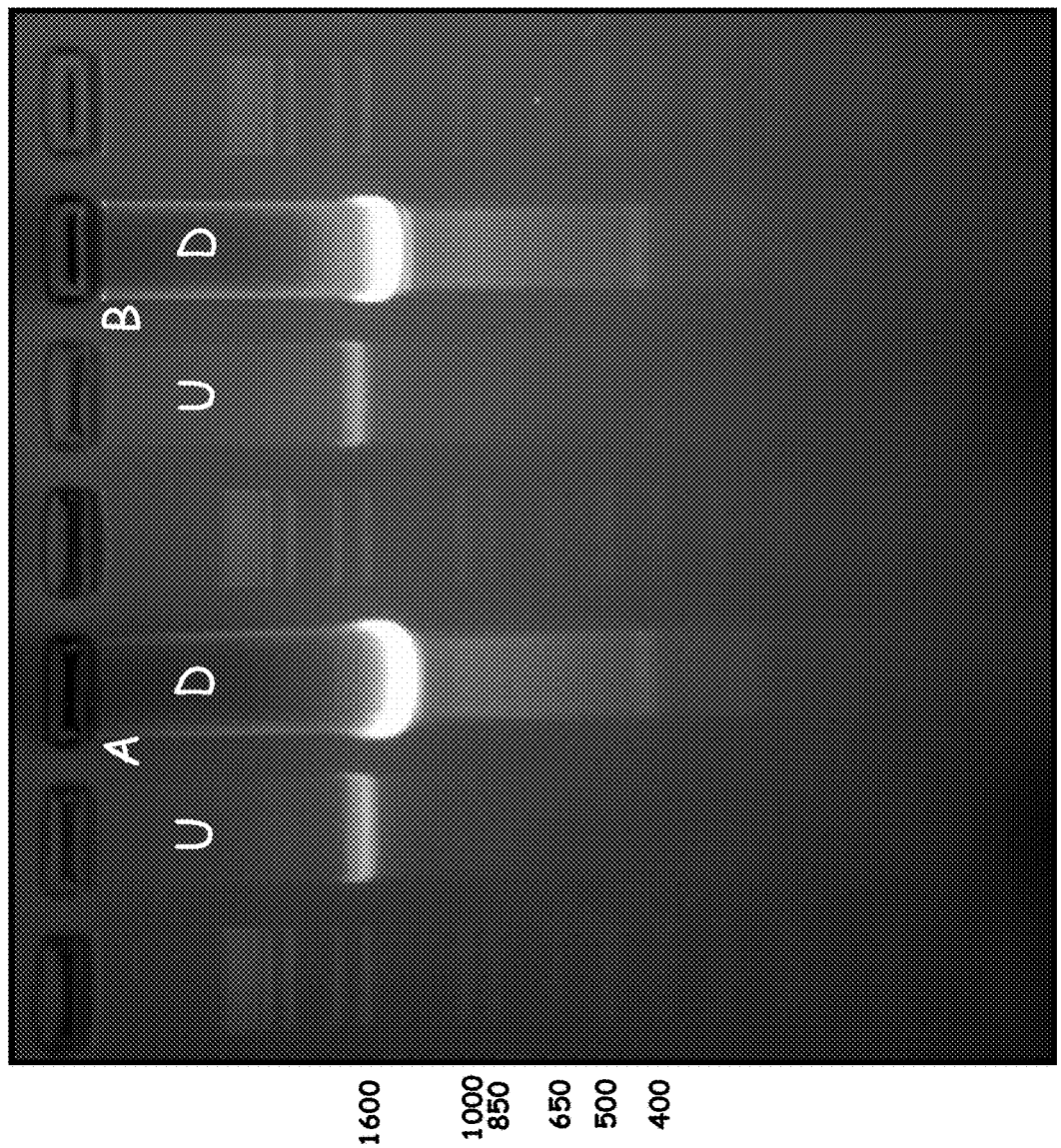

FIG. 16 shows a PCR gel: Analysis of third round PCR products A and B by SalI restriction digestion. The DNA fragment size expected from SalI digestion of transcripts corresponding to bispecific antibody are ~400 bp and 1300 bp. Bands corresponding to the expected bispecific antibody transcripts could be seen following SalI digestion. The SalI digested DNA (D) was run alongside the undigested (U) PCR products.

DETAILED DESCRIPTION OF THE INVENTION

The following definitions apply to any configuration, aspect, provision, clause, attribute, example or embodiment of the invention.

"Derived from" is used in the ordinary sense of the term. Exemplary synonyms include "produced as", "resulting from", "received from", "obtained from", "a product of", "consequence of", and "modified from" For example, a human variable region of a heavy chain can be derived from recombination of human VH, D and JH gene segments and this reflects the in vivo recombination of these gene segments in, for example, a heavy chain locus according to the invention with any accompanying mutation (eg, junctional mutation).

Samples from which B-cells can be obtained include but are not limited to blood, serum, spleen, splenic tissue, bone marrow, lymph, lymph node, thymus, and appendix. Antibodies and immunoglobulin chains can be obtained from each of the previous-mentioned samples and also from the following non-limiting list of B-cells, ascites fluid, hybridomas, and cell cultures.

"Plurality" is used in the ordinary sense of the term and means "at least one" or "more than one".

The term "germline configuration" refers to a germline genomic configuration. For example, human immunoglobulin gene segments of a transgenic immunoglobulin locus are in a germline configuration when the relative order of the gene segments is the same as the order of corresponding gene segments in a human germline genome. For example, when the transgenic locus is a heavy chain locus of the invention comprising hypothetical human immunoglobulin gene segments A, B and C, these would be provided in this order (5' to 3' in the locus) when the corresponding gene segments of a human germline genome comprises the arrangement 5'-A-B-C-3'. In an example, when elements of a human immunoglobulin locus (eg, gene segments, enhancers or other regulatory elements) are provided in a transgenic immunoglobulin locus according to the invention, the human Ig locus elements are in germline configuration when the relative order of the gene segments is the same as the order of corresponding gene segments in a human germline genome and human sequences between the elements are included, these corresponding to such sequences between corresponding elements in the human germline genome. Thus, in a hypothetical example the transgenic locus comprises human elements in the arrangement 5'-A-S1-B-S2-C-S3-3', wherein A, B and C are human immunoglobulin gene segments and S1-S3 are human inter-gene segment sequences, wherein the corresponding arrangement 5'-A-S1-B-S2-C-S3-3' is present in a human germline genome. For example, this can be achieved by providing in a transgenic immunoglobulin locus of the invention a DNA insert corresponding to the DNA sequence from A to C in a human germline genome (or the insert comprising the DNA sequence from A to C). The arrangements in human germline genomes and immunoglobulin loci are known in the art (eg, see the IMGT at the World Wide Web (see above), Kabat and other antibody resources referenced herein).

The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., dAb, Fab, F(ab')2, and Fv). The term "antibody" also includes H2 antibodies that comprise a dimer of a heavy chain (5'-VH-(optional Hinge)-CH2-CH3-3') and are devoid of a light chain (akin to naturally-occurring H2 antibodies; see, eg, Nature. 1993 Jun. 3; 363(6428):446-8; Naturally occurring antibodies devoid of light chains; Hamers-Casterman C, Atarhouch T, Muyldermans S, Robinson G, Hamers C, Songa E B, Bendahman N, Hamers R). Thus, in an embodiment of the present invention, RNA produced from the transgenic heavy chain locus encodes for heavy chains that re devoid of a CH1 gene segment and comprise no functional antibody light chain. In an example, RNA produced from the transgenic heavy chain locus encodes for VH single variable domains (dAbs; domain antibodies). These can optionally comprise a constant region.

The term "immunoglobulin" (Ig) is used interchangeably with "antibody" herein.

Examples of antibodies are classic 4-chain antibodies comprising two heavy chains paired with two light chains (such as, a dimer of 5'-VH-CH1-Hinge-CH2-CH3-3' paired with 5'-VL-CL-3') or H2 antibodies that comprise a dimer of a heavy chain (5'-VH-(optional Hinge)-CH2-CH3-3') and are devoid of a light chain Thus, in an embodiment of the present invention, the heavy chain sequence repertoire encodes for heavy chains that are devoid of a CH1 gene segment and comprise no functional antibody light chain. In an example, the heavy chain sequence repertoire produced by the vertebrate encodes a repertoire of VH single variable domains (dAbs; domain antibodies) with one or more human constant domains.

In an example of any configuration of the invention, a repertoire comprises a plurality of different members (thus, for example, a heavy chain repertoire comprises a plurality of different heavy chain sequences, such as sequences differing in their variable regions and/or human non-mu constant regions). In an example of any configuration of the invention, a repertoire comprises or consists of 2, 3, 4, 5, 6, 7, 8, 9, 10, at least 15, at least 20, at least 30, at least 40, at least 50, at least 60, at least 70, at least 80, at least 90, at least 100, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, or at least $10^{14}$ members. For example, a repertoire of antibody heavy chains or antibodies comprises or consists of at least 100, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, or at least $10^{14}$ antibody chain sequences or antibodies respectively. For example, a repertoire comprises or consists of 2, 3, 4, 5, 6, 7, 8, 9, 10, at least 15, at least 20, at least 30, at least 40, at least 50, at least 60, at least 70, at least 80, at least 90, at least 100, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, or at least $10^{14}$ different members. For example, a repertoire of gene segments comprises or consists of 2, 3, 4, 5, 6, 7, 8, 9, 10, at least 15, at least 20, at least 30, at least 40, at least 50 gene segments.

An "isolated" antibody is one that has been identified, separated and/or recovered from a component of its production environment (eg, naturally or recombinantly). Preferably, the isolated polypeptide is free of association with all other components from its production environment, eg, so that the antibody has been isolated to an FDA-approvable or approved standard. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

An "antibody fragment" comprises a portion of an intact antibody, preferably the antigen binding and/or the variable region of the intact antibody. Examples of antibody fragments include dAb, Fab, Fab', F(ab')2 and Fv fragments; diabodies; linear antibodies; single-chain antibody molecules and multispecific antibodies formed from antibody fragments.

An antibody that "specifically binds to" or is "specific for" a particular polypeptide, antigen, or epitope is one that binds to that particular polypeptide, antigen, or epitope without substantially binding to other polypeptides, antigens or epitopes. For example, binding to the antigen or epitope is specific when the antibody binds with a $K_D$ of 100 µM or less, 10 µM or less, 1 µM or less, 100 nM or less, eg, 10 nM or less, 1 nM or less, 500 pM or less, 100 pM or less, or 10 pM or less. The binding affinity ($K_D$) can be determined using standard procedures as will be known by the skilled person, eg, binding in ELISA and/or affinity determination using surface plasmon resonance (eg, Biacore™, Proteon™ or KinExA™ solution phase affinity measurement which can detect down to fM affinities (Sapidyne Instruments, Idaho)).

In one embodiment, the surface plasmon resonance (SPR) is carried out at 25° C. In another embodiment, the SPR is carried out at 37° C.

In one embodiment, the SPR is carried out at physiological pH, such as about pH7 or at pH7.6 (eg, using Hepes buffered saline at pH7.6 (also referred to as HBS-EP)).

In one embodiment, the SPR is carried out at a physiological salt level, eg, 150 mM NaCl.

In one embodiment, the SPR is carried out at a detergent level of no greater than 0.05% by volume, eg, in the presence of P20 (polysorbate 20; eg, Tween-20™) at 0.05% and EDTA at 3 mM.

In one example, the SPR is carried out at 25° C. or 37° C. in a buffer at pH7.6, 150 mM NaCl, 0.05% detergent (eg, P20) and 3 mM EDTA. The buffer can contain 10 mM Hepes. In one example, the SPR is carried out at 25° C. or 37° C. in HBS-EP. HBS-EP is available from Teknova Inc (California; catalogue number H8022).

In an example, the affinity is determined using SPR by
1. Coupling anti-mouse (or other relevant non-human vertebrate) IgG (eg, Biacore BR-1008-38) to a biosensor chip (eg, GLM chip) such as by primary amine coupling;

2. Exposing the anti-mouse IgG (non-human vertebrate antibody) to a test IgG antibody or heavy chain to capture test antibody on the chip;
3. Passing the test antigen over the chip's capture surface at 1024 nM, 256 nM, 64 nM, 16 nM, 4 nM with a 0 nM (i.e. buffer alone); and
4. And determining the affinity of binding of test antibody/chain to test antigen using surface plasmon resonance, eg, under an SPR condition discussed above (eg, at 25° C. in physiological buffer). SPR can be carried out using any standard SPR apparatus, such as by Biacore™ or using the ProteOn XPR36™ (Bio-Rad®).

Regeneration of the capture surface can be carried out with 10 mM glycine at pH1.7. This removes the captured antibody and allows the surface to be used for another interaction. The binding data can be fitted to 1:1 model inherent using standard techniques, eg, using a model inherent to the ProteOn XPR36™ analysis software.

"Pharmaceutically acceptable" refers to approved or approvable by a regulatory agency of the USA Federal or a state government or listed in the U.S. Pharmacopeia or other generally recognized pharmacopeia for use in animals, including humans. A "pharmaceutically acceptable carrier, excipient, or adjuvant" refers to an carrier, excipient, or adjuvant that can be administered to a subject, together with an agent, e.g., any antibody or antibody chain described herein, and which does not destroy the pharmacological activity thereof and is nontoxic when administered in doses sufficient to deliver a therapeutic amount of the agent.

The term "Fc" as used herein refer to the protein comprising (in N- to C-terminal direction) an immunoglobulin CH2 and CH3 domain. The CH2 and CH3 domains can form at least a part of the constant region of an antibody or heavy chain.

"Constant region" as used herein when referring to an antibody locus of the invention (eg, a heavy chain locus of a genome), is a reference to a stretch of DNA sequence comprising gene segments (constant region gene segments) that combine in vivo with recombined VDJ sequence in the locus. The VDJ yield (optionally following hypermutation), together with the constant region gene segments RNA transcripts in the vertebrate or cell from which can be produced antibody chains (eg, following splicing of RNA), each chain comprising an variable domain and one or more constant domains. When "constant region" is used with reference to an antibody or antibody heavy chain, this is referring to the region C-terminal to the variable domain and comprising one or more constant domains.

"Endogenous" as used herein indicates that the constant region etc is a type of constant region etc that is normally found in the vertebrate or cell (as opposed to an exogenous constant region whose sequence is not normally found in such a vertebrate or cell, eg a human sequence). For example, the endogenous constant region can be those encoded by the wild-type genome of the non-human vertebrate or cell. So, in an example wherein the vertebrate is a mouse, the endogenous constant region would be a mouse constant region. Going further, the endogenous regions are, in an example, strain-matched to the vertebrate or cell. So, in one embodiment, the vertebrate or cell is a mouse 129 ES cell, the endogenous constant region would be mouse 129 constant region. In another embodiment, the vertebrate or cell is a JM8 strain mouse or mouse cell, the endogenous constant region would be mouse JM8 constant region. In another embodiment, the vertebrate or cell is a Black 6 mouse or mouse cell, the endogenous constant region would be mouse Black 6 constant region.

Guided Selection In Vivo

Reference is made to Biotechnology, 1994 September; 12(9):899-903, "Guiding the selection of human antibodies from phage display repertoires to a single epitope of an antigen"; Jespers L S et al. This discloses a route to the guided selection of variable domain pairs in vitro in which a mouse antibody binding site (VH/VL pairing) can be converted into a human VH/VL pairing that retains antigen specificity. This technique does not assess whether or not the resultant product variable domain pairings are well suited to in vivo systems and expression. The following aspect of the invention addresses that problem by providing for in vivo guided selection to effect variable domain combination with another variable domain (or other epitope binding moiety), maturation and expression.

In aspects of the present invention, a non-human vertebrate or cell is provided wherein an Ig heavy or light chain locus of the genome of the vertebrate or cell comprises (in 5' to 3' orientation) (i) an unrearranged human variable region for encoding a first variable domain, (ii) a sequence encoding an optional linker and (iii) an epitope binding moiety (optionally a rearranged sequence of a second variable domain). The epitope binding moiety or second variable domain nucleotide sequence is a predetermined sequence, eg, the sequence encoding a VH or VL domain of the binding site of a known antibody, or a dummy (germline) VH or VL sequence. Sequences (i) and (iii) are close together in the Ig locus (eg, directly adjacent or only separated by a peptide linker-encoding sequence, eg, a linker of no more than 20, 15, 10 or 5 amino acids in the protein product) thereby enabling pairing for combination and selection in vivo. Thus, for example, in the protein product there is no protein domain between the products derived from (i) and (iii). Similarly, in the Ig locus there is, for example, no sequence encoding such a protein domain.

In an embodiment, for (iii) it is desirable to use the VH domain sequence of the binding site of a known antibody, since binding contribution by the VH in a VH/VL pairing is commonly most strong, thereby being useful to guide the selection of the partner variable domain encoded by (i) following rearrangement in vivo. In an example of this embodiment, (i) is an unrearranged human light chain variable region (kappa or lambda human variable region) for pairing with the VH domain derived from (iii). In another example, (i) is an unrearranged human heavy chain variable region or a variable region comprising heavy and light chain variable region gene segments (eg, as disclosed in WO2012018764).

The human variable region of (i) can rearrange in vivo and following immunisation of the vertebrate with a target antigen epitope, affinity maturation and selection occur. Variable regions that successfully rearrange, mature and express a variable domain that can combine with the product encoded by sequence (iii) to provide combinations of V-optional linker-E (eg, V-optional linker-V). The skilled person is able to find antigen binding sites provided by such combinations that can specifically bind a desired antigen (eg, the target antigen or a related antigen). This is useful because this aspect of the invention enables the known sequence of (iii) and its product to guide the selection of suitable partner V domains encoded by the rearranged and matured sequence of (i). The vertebrate is used, therefore, to provide a repertoire of potential matured rearranged sequences whose selection in vivo has been guided by the adjacent epitope binding moiety (eg, V domain) derived from sequence (iii). Successful expression of combinations provides a further selection criterion for potentially useful drugs and drug candidates based on the pairing of the expressed V and E.

Use of a V domain sequence from a known antibody for (iii) is desirable for producing biobetter drugs that bind the same target as the known antibody, but that have modified antigen binding sites based on guided selection using the known V domain as a starting point. The product binding site may have one or more characteristics that are better than those displayed by the binding site of the known, original antibody. For example, the guided selection method can be used to find V pairings that have one or more of a higher affinity binding for the target antigen (eg, better on rate, off rate and/or KD as determined by surface plasmon resonance, eg, Biacore™), a new target specificity (eg, an additional specificity, thereby providing for bispecific binding sites), better pharmacokinetics, better pharmacodynamics, ability to specifically bind a novel epitope on the target antigen (ie, an epitope that is not specifically bound by the original binding site), better in vivo antibody clearance, better in vivo antibody distribution and lower toxicity to an organism (eg, a human patient or a mouse). By finding higher affinity binding sites, it is possible to clone the V domains of the pairing selected by the guided selection method and insert the V domain sequences into standard heavy and light chain vectors for the expression of antibody heavy and light chains that associate to form the binding site. In this way, it is possible to reconstitute biobetter antibodies that specifically bind the target antigen.

In one embodiment, the target antigen used for immunisation is different from the antigen to which the known antibody binding site binds. This provides the possibility of generating bispecific V-optional linker-V pairings using the invention in which the pairing is able to specifically bind the target antigen and the other antigen. In an embodiment, the two antigens are structurally related antigens (see, eg, WO 2002/002773).

In another embodiment, the sequence of (iii) is a germline human variable domain sequence which encodes a dummy V domain. In this case, the dummy may fulfil a scaffolding function, such that the variable domain encoded by rearranged sequence (i) following immunisation is an antibody single variable domain (dAb), ie, it is able to specifically bind the target antigen in the absence of another variable domain. This then provides a useful source of human antibody single variable domains (optionally joined to, and selected in the context of, an Fc or other constant region encoded by the Ig locus 3' of sequence (iii)).

In examples described above, this aspect of the invention is provided in the context of an Ig locus for producing multispecific products based on a further epitope binding moiety (aka, binding module, eg, a known scFv that replaces CH1). In this way, the invention provides combinations of the N-terminal V-optional-linker-E (eg, V-optional linker-V) with the scFv or other binding module.

In other examples of the present aspect of the invention, no such additional epitope binding moiety sequence is provided in the Ig locus, so that the product of the locus is the N-terminal V-optional-linker-E (eg, V-optional linker-V) linked to a constant region (eg, Fc) or without a constant region (eg, where cleavage following the IgM stage is effected using locus construction as described elsewhere herein).

In embodiments, the non-human vertebrate or cell genome comprises sequences (ii) and (iii) 5' of an Ig heavy chain constant region, eg a mouse or human constant region, eg, the heavy chain constant region endogenous to the vertebrate or cell. In an example, the constant region is a gamma (eg, gamma-1) constant region.

In an example, the genome comprises sequences (ii) and (iii) downstream of (3' of) the S-mu, for example downstream of the mu constant region. The sequence (iii) is protected from the action of AID as described above. Thus, this is useful for providing the guided selection based on the known sequence (iii) product. In an example, genome comprises sequence (iii) in place of a gamma CH1 gene (eg, gamma-1 CH1). In this way, the constant region is devoid of a CH1 and heavy chain-only products can be produced. In another embodiment, the sequence (i)-(ii)-(iii) is provided upstream of (5' of) the S-mu so that V-optional linker-E pairings are produced at the IgM stage and then class switching to a gamma (or other non-mu) isotype is obtained after immunisation. This allows for maturation of the V/E pairings by AID, thereby providing a useful repertoire of matured binding sites that are in part related to the input sequence (iii).

In an example of any guided selection aspect of the invention herein, the second variable domain is a Vκ1-39/Jκ or Vκ3-20/Jκ VL domain. These promiscuously pair with VH domains and are thus useful pairing partners in the guided selection method for producing a repertoire of V-V pairings from which to select desired antigen-binding chains. By selecting for two or more VH domains that individually pair with a common VL such as one of these, it is possible to produce mixtures of VH/VL binding sites more simply by expressing the different VHs with a single VL. For example, once suitable VH domains have been selected for pairing with the common VL, it is possible to clone the VH and VL domains into standard heavy and light chain vectors containing heavy and light chains constant regions respectively (eg, heavy chain CH1 to CH3; or Cκ or Cλ respectively) for the production of two or more heavy chains that express different VH domains and for the production of a single light chain containing the VL domain. By mixing or co-expressing such chains together, it is possible to produce mixtures of antibodies all based on a common light chain. Thus, in one embodiment, the invention provides an antibody composition comprising a plurality of different antibodies, wherein the antibodies comprise heavy and light chains, the heavy chains each comprising a VH encoded by a VH-VL pair selected in any guided selection method of the invention, optionally wherein in the method the second variable domain is a Vκ1-39/Jκ or Vκ3-20/Jκ VL domain. In an example, each antibody of the composition comprises a single type of VH/VL pairing. This can be obtained by conventional purification techniques to resolve out the desired mixture. See, eg, EP1523496, WO2004061104, WO2008145133, WO2011097603 and WO2010151792.

In an embodiment, the product of the guided selection vertebrate, cell or method aspect of the invention is an expressed heavy chain comprising the V-optional linker-E (eg, V-optional linker-V) binding site and (3' of that) a heavy chain constant region (eg, Fc, eg, CH2-CH3) devoid of a CH1 domain. In this embodiment, the heavy chains are capable of dimerising to produce $H_2$ antibodies (heavy chain-only antibodies that are devoid of a light chain) that bear paired V-optional linker-V binding sites at their N termini. Thus, in an embodiment, the invention provides such a heavy chain and such a $H_2$ antibody that comprises a V-optional linker-V binding site that specifically binds a target antigen. According to further embodiments of the invention, this aspect can be combined with turning off of light chain expression after isotype switching to non-mu isotype, as described further herein.

Applications of the guided selection aspect are described further below for use in producing multivalent products.

Multivalent Products

The present invention relates to multivalent (eg, multi-specific) antibodies, antibody chains and polypeptides, as well as heavy chain-only antibodies (H2 antibodies) that re devoid of light chains. The invention further relates to the selection, maturation and production of these in vivo in non-human vertebrates and non-human vertebrate cells. To this end the invention also relates to such non-human vertebrates and cells.

Thus, the invention provides

A non-human vertebrate (eg, a mouse or a rat), wherein the vertebrate comprises lymphocytic cells, each cell genome comprising
(i) an antibody heavy chain locus comprising (in 5' to 3' direction) a rearranged or unrearranged variable region, a first switch (eg, an S-mu, eg a human or endogenous S-mu), a mu constant region (eg, comprising a CH1 gene segment), a second switch (eg, an S-gamma, eg a human or endogenous S-gamma), and a non-mu (eg, gamma) constant region; wherein the heavy chain locus of each cell is capable of undergoing IgM to the non-mu (eg, IgG) isotype switching; and optionally the non-mu constant region lacks a CH1 gene segment and/or a hinge nucleotide sequence; and wherein
(ii) the non-mu constant region comprises (in 5' to 3' direction) a nucleotide sequence encoding an optional linker and a predetermined epitope binding moiety, wherein following isotype switching the vertebrate expresses multivalent polypeptide chains comprising (in N- to C-terminal direction) an antibody variable domain derived from said variable region of the heavy chain locus, an optional linker and an epitope binding moiety, wherein the variable domain and the epitope binding moiety specifically bind respective first and second epitopes.

The variable domain is derived from the variable region of the heavy chain locus. Thus, when the variable region of the locus is a rearranged variable region, the variable domain is encoded by the sequence of the variable region (eg, a $V_H DJ_H$ or $V_L J_L$ region) optionally with somatic hypermutation.

When the variable region is an unrearranged variable region, this region comprises one or more V gene segments, one or more J gene segments and optionally one or more D gene segments (eg, wherein all of these segments are human). Following rearrangement of gene segments in the heavy chain locus, a rearranged VDJ or VJ is formed and this encodes the variable domain optionally following somatic hypermutation.

Optionally, the non-mu constant region comprises nucleotide sequences encoding a plurality of epitope binding moieties, eg, two or three epitope binding moieties joined by optional linkers.

Optionally, the non-mu constant region comprises nucleotide sequences encoding one or a plurality of epitope binding moieties (optionally joined by linkers) in place of a CH1 gene segment.

Advantageously, the skilled person is able, in view of the present invention, to choose a desirable, predetermined, epitope binding moiety and purposely include the corresponding nucleotide sequence into the locus for subsequent in vivo mixing-and-matching with a repertoire of variable domains produced by the vertebrate. Successful pairings are those that can be expressed and selected, for example following immunization with a target antigen or epitope. In this sense, selection is firstly performed by the vertebrate's in vivo system, since B-cells that express isotype-switched heavy chains (eg, as part of non-mu antibodies) and wherein the chains (or antibodies) can specifically recognize and bind to the target are selected for proliferation and B-cell expansion by the vertebrate's immune system as per a classic immune response. Thus, those products that are antigen-specific and which can be expressed in the multivalent format are naturally selected. Furthermore, a repertoire of paired binding specificities and valencies is provided, wherein one or more specificities and valencies is provided by a predetermined epitope binding moiety, and one or more other specificities or valencies is provided by a variable domain that has been in vivo selected and matured in the context of the epitope binding moiety(ies). In this way, there is natural selection for combinations that perform well (eg, are expressible to detectable levels and have in vivo-compatible biophysical characteristics, which is useful for subsequent use in drug development). A skilled person is able to perform selection of one or more multivalent heavy chains (or antibodies) from the repertoire (eg, from serum or spleen cells) according to a desirable antibody characteristic, such as affinity for target binding (eg, using surface plasmon resonance as is well known). Thus, the present invention uses a totally in vivo combinatorial process for selection and maturation of variable domains in the context of predetermined further valencies and specificities—and thus in the context of the final drug format for subsequent use in human or animal therapy or prophylaxis. This is a significant advancement over prior art techniques of producing multivalent products that rely on in vitro manipulation, selection and then the need for further in vitro affinity maturation.

Figure 1:
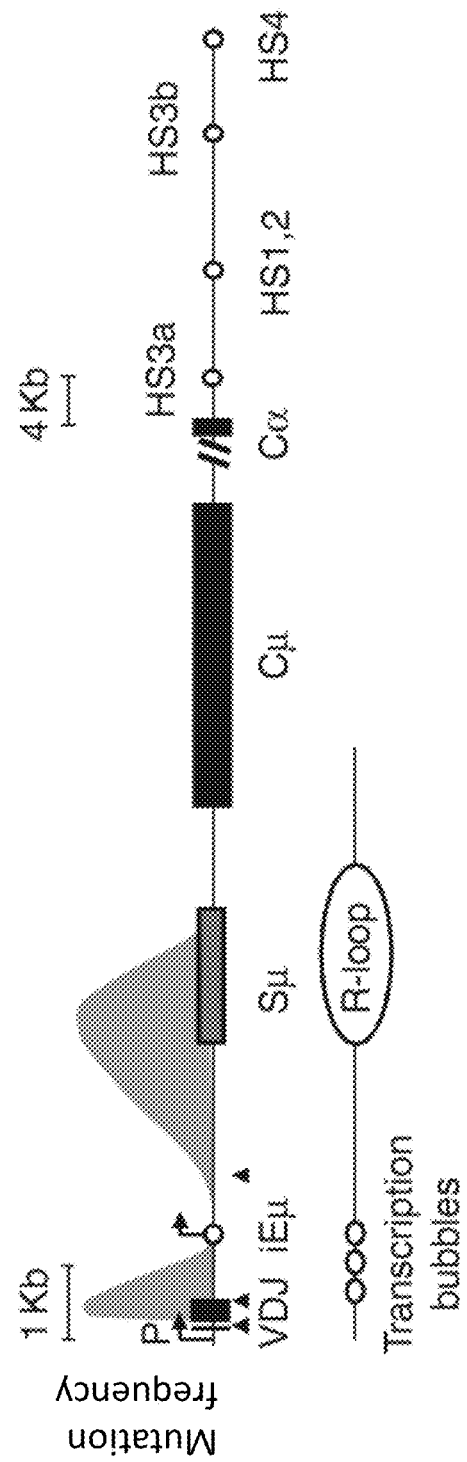
FIG. 1 is a schematic showing the somatic hypermutation pattern of AID in a mouse heavy chain locus.

Furthermore, the present inventors realized that it is advantageous to provide the known epitope binding moiety nucleotide sequence downstream of the S-mu or mu constant region. The inventors considered the desirability of minimizing mutation the epitope binding moiety sequence during the affinity maturation process following target antigen or epitope exposure. This would be useful for retaining the desired epitope-binding characteristics (eg, affinity) and possibly also desirable biophysical characteristics of the moiety. The inventors considered the typical pattern of activity of activation induced cytidine deaminase (AID), the enzyme responsible for introducing sequence mutations during somatic hypermutation. Reference is made to FIG. 1, which is adapted from Mauel, R. W. & Gearhart, P. J.; "AID and somatic hypermutation" *Advances in Immunology* 2010. 105: 159-191", which is incorporated herein by reference. The inventors realised that AID induces somatic hypermutation in the S-mu switch and upstream of (5' of) this in the heavy chain locus. Thus, the inventors decided to cite the nucleotide sequence encoding the epitope binding moiety(ies) downstream of (3' of) the S-mu, for example downstream of the mu constant region. The inventors realised that this would be useful for maximising the chances of retaining the sequence(s) of the epitope binding moiety(ies) intact, and thus providing for better predictability of binding specificity and performance for these elements in the final product. Thus, the skilled person is able to relatively predictably use any epitope binding moiety (comprising an amino acid sequence) generated separately in a prior in vivo or in vitro production and selection process and incorporate this moiety—whose characteristics, such as epitope binding specificity and/or affinity, are already known—into the final multivalent product produced in vivo according to the invention. Thus, the invention extends the utility of known, desirable epitope binding moieties for the production of multivalent and multispecific products (antibodies, chains and polypeptides).

Furthermore, advantageously, the inventors realised that they could selectively situate the coding sequence(s) for the predetermined epitope binding moiety(ies) in a way that enables the production, maturation and selection of isotype (class) switched products (eg, gamma-type antibodies or heavy chains) without compromising the proper functioning of the IgM stage that is so important during early B-cell compartment and primary variable region repertoire development. To this end, the inventors, in certain configurations, decided to provide the epitope binding moiety(ies) coding sequence(s) downstream of (3' of) the mu constant region. Thus, according to an embodiment, the inventors provided these coding sequence(s) in one or more non-mu constant regions 3' of the mu constant region. For example, one (eg, gamma-1) or all gamma constant regions can comprise one or more epitope binding moiety nucleotide sequences. In this way, all gamma heavy chains (and antibodies providing these) will bear a variable domain and one or more epitope binding moieties. Since the coding sequences for the moieties are in this position, the resultant moiety protein sequences will be unmutated (or substantially unmutated) and will be selected for combination and expression together with the upstream variable domain.

In an alternative embodiment, a nucleotide sequence encoding one or more epitope binding moieties is provided in a mu constant region. Thus, these sequences are downstream of the S-mu, which is the extent of the AID activity. In this embodiment, the vertebrate produces multivalent (eg, multispecific) heavy chains (eg, provided by antibodies, eg, H2 antibodies) of mu-isotype comprising one or more epitope binding moieties downstream of an N-terminal antibody variable domain. Following immunization, for example, the variable domain will be matured in the context of the epitope binding moiety(ies). Thus, the invention provides:—

A non-human vertebrate (eg, a mouse or a rat), wherein the vertebrate comprises lymphocytic cells, each cell genome comprising an antibody heavy chain locus comprising (in 5' to 3' direction) a rearranged or unrearranged variable region and a mu constant region comprising a nucleotide sequence encoding an optional linker and a predetermined epitope binding moiety, wherein the vertebrate expresses multivalent polypeptide chains comprising (in N- to C-terminal direction) an antibody variable domain derived from said variable region of the heavy chain locus, an optional linker and an epitope binding moiety, wherein the variable domain and the epitope binding moiety specifically bind respective first and second epitopes. Optionally the mu constant region lacks a CH1 gene segment; this example is useful for producing multivalent H2 antibodies that bind the first and second epitopes. In another example, the mu constant region comprises a CH1; this is useful for producing 4-chain (H2L2) multivalent antibodies that bind the first and second epitopes. Optionally, the mu constant region lacks a hinge nucleotide sequence.

B-cells are an example of lymphocytic cells. Samples from which B-cells can be obtained include but are not limited to blood, serum, spleen, splenic tissue, bone marrow, lymph, lymph node, thymus, and appendix. For example, the B-cells are immature B-cells and/or mature B-cells.

The non-mu constant region is, in one embodiment, a gamma constant region (eg, gamma-1). Alternatively, the non-mu constant region is a delta, alpha or epsilon constant region. In an embodiment, each non-mu constant region of the heavy chain locus (or all the heavy chain loci) of the genome is according to (ii) above. In an embodiment, each gamma constant region of the heavy chain locus (or all the heavy chain loci) of the genome is according to (ii) above. For example, the heavy chain locus (or loci) of the genome comprises gamma-1, gamma-2a, gamma-2b and optionally a gamma-4 constant regions, wherein each of these constant regions is according to (ii) above.

In an embodiment, the genome is homozygous for said heavy chain locus.

Optionally, in an alternative the mu constant region does not comprise a CH1 gene segment. By including a CH1 gene segment in the mu constant region, however, it is possible to express heavy chains during antibody repertoire and B-cell compartment development that are 4-chain (H2L2) IgM antibodies. Surface-expression of such constructs can be advantageous during early B-cell development to provide good spleen and bone marrow B-cell compartments. Thus, a useful primary antibody repertoire can be provided from which to subsequently select isotype-switched chains (with our without CH1) in response to antigen.

Omission of a CH1 gene segment in a non-mu constant region is useful for producing and selecting heavy chains without light chain pairing, eg, as seen when H2 antibodies are produced. In the absence of light chain pairing the variable domains of the non-mu-type heavy chains expressed by the locus recited above are selected and matured without a variable domain partner (eg, where the variable domains of the heavy chains are VH, these are produced, affinity matured and selected in the absence of a VH/VL pair, and thus the VH are antibody single variable domains (aka dAbs or domain antibodies). The utility and advantages of H2 antibodies and dAbs are well known in the art, as described, for example, in the Harbour Antibodies and Crescendo Biologics patent applications mentioned herein and as described in patent applications filed in the name of Domantis Limited and Ablynx. Optionally, light chain expression does not occur when the non-mu-type chains are expressed. This provides the advantages described above for the production of H2 antibodies and heavy chains.

The variable region can be unrearranged, ie, the variable region of the heavy chain locus comprises one or more VH gene segments, one or more D gene segments and one or more JH gene segments (eg, a plurality of human VH gene segments, one or more human D gene segments and one or more human JH gene segments). The gene segments are capable of rearranging to form a rearranged variable region (a VDJ, eg, a human VDJ) which can combine with a constant region sequence. Thus, following rearrangement of the variable region, the heavy chain can encode RNA comprising a nucleotide sequence encoding an antibody heavy chain variable domain and constant region.

Alternatively, the variable region of the heavy chain locus is rearranged (ie, a VDJ nucleotide sequence).

In order to obtain switching from the mu to non-mu isotype, the locus comprises a switch 5' of the mu constant region (eg, the endogenous S-mu is retained) and a second switch 5' of the (or each) non-mu constant region. The second switch can be the switch usually present with the constant region (eg, when the constant region is a gamma-1 constant region, the gamma-1 switch is retained). Switch sequences are known in the art, for example, see Nikaido et al, Nature 292: 845-848 (1981) and also WO2011004192, U.S. Pat. Nos. 7,501,552, 6,673,986, 6,130,364, WO2009/076464 and U.S. Pat. No. 6,586,251, eg, SEQ ID NOs: 9-24 disclosed in U.S. Pat. No. 7,501,552. Commercial human and mouse BAC libraries (eg, the RPC-11 and Caltech A, B, C and D libraries) are sources of suitable immunoglobulin locus sequences, eg, sequences of switches or constant regions. Alternatively, human DNA samples can be obtained de novo from consenting donors (eg, using cheek swabs) and DNA sequences obtained from the samples.

In any configuration of the invention, there is provided a multivalent antibody, antibody chain or polypeptide. By "multivalent" in the context of an antibody chain is meant that the chain comprises two or more valencies (ie, epitope or antigen binding sites). For example, a heavy chain according to the invention can comprise first and second epitope binding sites (an no other epitope binding sites), and as such the chain is bivalent. This contrasts with antibody chains produced in vivo in the state of the art, which are monovalent by virtue of an N-terminal variable domain (eg, which pairs with a V domain on a partner light chain to form a VH/VL epitope binding site). By "multivalent" in the context of an antibody is meant that the antibody comprises two or more valencies (ie, epitope or antigen binding sites) when the antibody is a H2 antibody, or three or more valencies when the antibody is a 4-chain (H2L2) antibody. Corresponding epitope-binding fragments of such antibodies (eg, a Fab) comprises more epitope binding sites than equivalent antibody fragments in the art. For example, a Fab-like structure according to the invention may have two epitope binding sites, whereas a conventional Fab would have one binding site (provided by a VH/VL pair). A polypeptide according to the invention is multivalent when it comprises two or more epitope or antigen binding sites.

In addition to being multivalent, the antibody, chain or polypeptide of the invention is optionally multispecific (eg, bispecific). This means that the antibody, chain or polypeptide specifically binds to two or more different epitopes or antigens (simultanteously or non-simultaneously). The epitopes can, for example, be provided by different antigens or the same antigenic species (which is advantageous for providing an avidity of binding to target antigen). Binding can be assessed using standard in vitro techniques, eg, competition surface plasmon resonance (eg, Biacore™ or Proteon) or competition ELISA. Binding to different epitopes in a patient administered with a drug (eg, an antibody, chain or polypeptide or derivative thereof of the invention) is useful for addressing many diseases or conditions in humans or animals.

Alternatively, the antibody, chain or polypeptide is multivalent and monospecific, ie comprises a plurality of epitope binding sites that specifically bind to the same epitopic species (eg, bind simultaneously to copies of the same epitope, eg on a single antigen, which may be useful of providing avidity of binding).

The antigen is, for example, any of the antigens disclosed in EP1697421 (Micromet AG), WO2007024715 (Abbott Laboratories) or WO2010136485 (Glaxo Group Limited), the disclosures of which are incorporated herein by reference. For example, the present invention can related to one or more antigens and antigen classes specifically discussed in WO2007024715 at page 6, line 14-page 8, line 23; page 16, line 15-page 18, line 26; page 24, lines 9-26; page 52, lines 5-22; and page 55, line 10-page 66, line 23, with or without use in one or more of the medical indications cited. These examples of antigens are specifically incorporated herein as though specifically and explicitly disclosed herein as possible antigens with respect to the present invention and for possible inclusion in one or more claims herein. For example, the present invention can related to one or more antigens and antigen classes specifically discussed in WO2010136485, including but not limited to VEGF, TNFα, EGFR, VEGFR2, IL-13 and HER2, with or without use in one or more of the medical indications cited. These examples of antigens are specifically incorporated herein as though specifically and explicitly disclosed herein as possible antigens with respect to the present invention and for possible inclusion in one or more claims herein. Examples of suitable epitopes for use in the present invention are epitopes provided by one or more of these antigens.

For example in any configuration of the invention, the or each antigen is selected from the group consisting of ABCF1; ACVR1; ACVR1B; ACVR2; ACVR2B; ACVRL1; ADORA2A; Aggrecan; AGR2; AICDA; AWI; AIG1; AKAP1; AKAP2; AIYIH; AMHR2; ANGPT1; ANGPT2; ANGPTL3; ANGPTL4; ANPEP; APC; APOC1; AR; AZGP1 (zinc-a-glycoprotein); B7.1; B7.2; BAD; BAFF; BAG1; BAI1; BCL2; BCL6; BDNF; BLNK; BLR1 (MDR15); B1yS; BMP1; BMP2; BMP3B (GDF1O); BMP4; BMP6; BMP8; BMPR1A; BMPR1B; BMPR2; BPAG1 (plectin); BRCA1; Cl9orflO (IL27w); C3; C4A; C5; C5R1; CANT1; CASP1; CASP4; CAV1; CCBP2 (D6/JAB61); CCL1 (I-309); CCL11 (eotaxin); CCL13 (MCP-4); CCL15 (MIP-id); CCL16 (HCC-4); CCL17 (TARC); CCL18 (PARC); CCL19 (MIP-3b); CCL2 (MCP-1); MCAF; CCL2O (MIP-3a); CCL21 (MIP-2); SLC; exodus-2; CCL22 (MDC/STC-1); CCL23 (MPIF-1); CCL24 (MPIF-2 I eotaxin-2); CCL25 (TECK); CCL26 (eotaxin-3); CCL27 (CTACK/ILC); CCL28; CCL3 (MIP-1a); CCL4 (MIP-1b); CCL5 (RANTES); CCL7 (MCP-3); CCL8 (mcp-2); CCNA1; CCNA2; CCND1; CCNE1; CCNE2; CCR1 (CKR1/HM145); CCR2 (mcp-1RB/RA); CCR3 (CKR3/CMKBR3); CCR4; CCR5 (CMKBR5/ChemR13); CCR6 (CMKBR6/CKR-L3/STRL22/DRY6); CCR7 (CKR7/EBI1); CCR8 (CMKBR8/TER1/CKR-L1); CCR9 (GPR-9-6); CCRL1 (VSHK1); CCRL2 (L-CCR); CD164; CD19; CD1C; CD2O; CD200; CD-22; CD24; CD28; CD3; CD37; CD38; CD3E; CD3G; CD3Z; CD4; CD4O; CD4OL; CD44; CD45RB; CD52; CD69; CD72; CD74; CD79A; CD79B; CD8; CD8O; CD81; CD83; CD86; CDH1 (E-cadherin); CDH10; CDH12; CDH13; CDH18; CDH19; CDH2O; CDH5; CDH7; CDH8; CDH9; CDK2; CDK3; CDK4; CDK5; CDK6; CDK7; CDK9; CDKN1A (p2lWap1/Cip1); CDKN1B (p27Kip1); CDKNIC; CDKN2A (p16lNK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CLU (clusterin); CMKLR1; CMKOR1 (RDC1); CNR1; COL18A1; COL1A1; COL4A3; COL6A1; CR2; CRP; CSF1 (M-CSF); CSF2 (GM-CSF); CSF3 (GCSF); CTLA4; CTNNB1 (b-catenin); CTSB (cathepsin B); CX3CL1 (SCYDi); CX3CR1 (V28); CXCL1 (GRO1); CXCL1O (IP-10); CXCL11 (I-TAC/IP-9); CXCL12 (SDF1); CXCL13; CXCL14; CXCL16; CXCL2 (GRO2); CXCL3 (GRO3); CXCL5 (ENA-78 I LIX); CXCL6 (GCP-2); CXCL9 (MIG); CXCR3 (GPR9/CKR-L2); CXCR4; CXCR6 (TYMSTR ISTRL33 I Bonzo); CYB5; CYC1; CYSLTR1; DAB2IP; DES; DKFZp451J0118; DNCL1; DPP4; E2F1; ECGF1; EDG1; EFNAI; EFNA3; EFNB2; EGF; EGFR; ELAC2; ENG; ENO1; ENO2; ENO3; EPHB4; EPO; ERBB2 (Her-2); EREG; ERK8; ESR1; ESR2; F3 (TF); FADD; FasL; FASN; FCER1A; FCER2; FCGR3A; FGF; FGF1 (aFGF); FGF1O; FGF11; FGF12; FGF12B; FGF13; FGF14; FGF16; FGF17; FGF18; FGF19; FGF2 (bFGF); FGF2O; FGF21; FGF22; FGF23; FGF3 (int-2); FGF4 (HST); FGF5; FGF6 (HST-2); FGF7 (KGF); FGF8; FGF9; FGFR3; FIGF (VEGFD); FIL1 (EPSILON); FIL1 (ZETA); FLJ12584; FLJ25530; FLRT1 (fibronectin); FLT1; FOS; FOSL1 (FRA-I); FY (DARC); GABRP (GABAa); GAGEB1; GAGEC1;

GALNAC4S-65T; GATA3; GDF5; GFI1; GGT1; GM-CSF; GNAS1; GNRH1; GPR2 (CCR1O); GPR31; GPR44; GPR81 (FKSG8O); GRCC10 (C10); GRP; GSN (Gelsolin); GSTP1; HAVCR2; HDAC4; EDAC5; HDAC7A; HDAC9; HGF; HIF1A; HIP1; histamine and histamine receptors; HLA-A; HLA-DRA; HM74; HMOX1; HUMCYT2A; ICE-BERG; ICOSL; 1D2; IFN-a; IFNA1; IFNA2; IFNA4; IFNA5; IFNA6; IFNA7; IFNB1; IFNgamma; TFNW1; IGBP1; IGF1; IGF1R; IGF2; IGFBP2; IGFBP3; IGFBP6; IL-1; IL10; IL10RA; IL10RB; IL11; IL11RA; IL-12; IL12A; IL12B; IL12RB1; IL12RB2; 1L13; IL13RA1; IL13RA2; 1L14; IL15; IL15RA; 1L16; 1L17; IL17B; IL17C; IL17R; 1L18; IL18BP; IL18R1; IL18RAP; 1L19; IL1A; IL1B; IL1F1O; IL1F5; IL1F6; IL1F7; IL1F8; IL1F9; IL1HY1; IL1R1; IL1R2; IL1RAP; IL1RAPL1; IL1RAPL2; IL1RL1; IL1RL2 IL1RN; 1L2; 1L20; IL2ORA; IL21R; 1L22; IL22R; 1L22RA2; 1L23; 1L24; 1L25; 1L26; 1L27; 1L28A; IL28B; 1L29; IL2RA; IL2RB; IL2RG; 1L3; 1L30; IL3RA; 1L4; IL4R; 1L5; IL5RA; 1L6; IL6R; IL6ST (glycoprotein 130); 1L7; TL7R; 1L8; IL8RA; IL8RB; IL8RB; 1L9; IL9R; ILK; INHA; INHBA; INSL3; INSL4; IRAK1; IRAK2; ITGA1; ITGA2; 1TGA3; ITGA6 (a6 integrin); ITGAV; ITGB3; ITGB4 (b 4 integrin); JAG1; JAK1; JAK3; JUN; K6HF; KAI1; KDR; MTLG; KLF5 (GC Box BP); KLF6; KLK10; KLK12; KLK13; KLK14; KLK15; KLK3; KLK4; KLK5; KLK6; KLK9; KRT1; KRT19 (Keratin 19); KRT2A; KRTHB6 (hair-specific type II keratin); LAMAS; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDK; MIB1; midkine; MIF; MIP-2; MK167 (Ki-67); MMP2; MMP9; MS4A1; MSMB; MT3 (metallothionectin-ifi); MISS 1; MUC 1 (mucin); MYC; MYD88; NCK2; neurocan; NFKB 1; NFKB2; NGFB (NGF); NGFR; NgR-Lingo; NgR-Nogo66 (Nogo); NgR-p75; NgR-Troy; NME1 (NM23A); NOX5; NPPB; NROB1; NROB2; NR1D1; NR1D2; NR1H2; NR1H3; NR1H4; NR1I2; NR1I3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPRD1; P2RX7; PAP; PART1; PATE; PAWR; PCA3; PCNA; PDGFA; PDGFB; PECAM1; PF4 (CXCL4); PGF; PGR; phosphacan; PIAS2; PIK3CG; PLAU (uPA); PLG; PLXDC1; PPBP (CXCL7); PPID; PR1; PRKCQ; PRKD1; PRL; PROC; PROK2; PSAP; PSCA; PTAFR; PTEN; PTGS2 (COX-2); PTN; RAC2 (p2IRac2); RARB; RGS1; RGS13; RGS3; RNF11O (ZNF144); ROBO2; S100A2; SCGB1D2 (lipophilin B); SCGB2A1 (mammaglobin 2); SCGB2A2 (mammaglobin 1); SCYE1 (endothelial Monocyte-activating cytokine); SDF2; SER-PINA1; SERPINIA3; SERPINB5 (maspin); SERPINE1 (PAT-i); SERPINF1; SHBG; SLA2; SLC2A2; SLC33A1; SLC43A1; SLIT2; SPP1; SPRR1B (Spri); ST6GAL1; STAB1; STATE; STEAP; STEAP2; TB4R2; TBX21; TCP1O; TDGF1; TEK; TGFA; TGFB1; TGFB1l1; TGFB2; TGFB3; TGFB1; TGFBR1; TGFBR2; TGFBR3; TH1L; THBS1 (thrombospondin-1); THBS2; THBS4; THPO; TIE (Tie-i); T]MP3; tissue factor; TLR1O; TLR2; TLR3; TLR4; TLR5; TLR6; TLR7; TLR8; TLR9; TNF; TNF-a; TNFAIP2 (B94); TNFAIP3; TNFRSF1 1A; TNFRSF1A; TNFRSF1B; TNFRSF21; TNFRSF5; TNFRSF6 (Fas); TNFRSF7; TNFRSF8; TNFRSF9; TNFSF1O (TRAIL); TNFSF1 1 (TRANCE); TNFSF12 (APO3L); TNFSF13 (April); TNFSF13B; TNFSF14 (HVEM-L); TNFSF1 5 (VEGI); TNFSF1 8; TNFSF4 (0X40 ligand); TNFSF5 (CD4O ligand); TNFSF6 (FasL); TNFSF7 (CD27 ligand); TNFSF8 (CD3O ligand); TNFSF9 (4-1BB ligand); TOLLIP; Toll-like receptors; TOP2A (topoisomerase lia); TP53; TPM1; TPM2; TRADD; TRAF1; TRAF2; TRAF3; TRAF4; TRAF5; TRAF6; TREM1; TREM2; TRPC6; TSLP; TWEAK; VEGF; VEGFB; VEGFC; versican; VHL C5; VLA-4; XCL1 (lymphotactin); XCL2 (SCM-Ib); XCR1 (GPR5/CCXCR1); YY1; and ZFPM2. Examples of suitable epitopes for use in the present invention are epitopes provided by one or more of these antigens.

For example in any configuration of the invention, the first and second epitope or antigen are selected from the group consisting of EpCAM and CD3; CD19 and CD3; VEGF and VEGFR2; VEGF and EGFR; CD138 and CD2O; CD138 and CD4O; CD2O and CD3; CD38 and CD138; CD38 and CD2O; CD38 and CD4O; CD4O and CD2O; CD19 and CD2O; CD-8 and IL-6; PDL-1 and CTLA-4; CTLA-4 and BTNO2; CSPGs and RGM A; IGF1 and IGF2; IGF1 and/or 2 and Erb2B; IL-12 and IL-18; IL-12 and TWEAK; IL-13 and ADAMS; IL-13 and CL25; IL-13 and IL-1beta; IL-13 and IL-25; IL-13 and IL-4; IL-13 and IL-5; IL-13 and IL-9; IL-13 and LHR agonist; IL-13 and MDC; IL-13 and MIF; IL-13 and PED2; IL-13 and SPRR2a; IL-13 and SPRR2b; IL-13 and TARC; IL-13 and TGF-beta; IL-1 alpha and IL-1 beta; MAG and RGM A; NgR and RGM A; NogoA and RGM A; OMGp and RGM A; RGM A and RGM B; Te38 and TNF alpha; TNF alpha and IL-12; TNF alpha and IL-12p40; TNF alpha and IL-13; TNF alpha and IL-15; TNF alpha and IL-17; TNF alpha and IL-18; TNF alpha and IL-1 beta; TNF alpha and IL-23; TNF alpha and MIF; TNF alpha and PEG2; TNF alpha and PGE4; TNF alpha and VEGF; and VEGFR and EGFR; TNF alpha and RANK ligand; TNF alpha and Blys; TNF alpha and GP130; TNF alpha and CD-22; and TNF alpha and CTLA-4.

For example in any configuration of the invention, the first epitope or antigen is selected from the group consisting of CD3; CD16; CD32; CD64; and CD89; and the second epitope or antigen is selected from the group consisting of EGFR; VEGF; IGF-1R; Her2; c-Met (aka HGF); HER3; CEA; CD33; CD79a; CD19; PSA; EpCAM; CD66; CD30; HAS; PSMA; GD2; ANG2; IL-4; IL-13; VEGFR2; and VEGFR3.

It is contemplated that the use of an antibody, chain or polypeptide of the invention is any use disclosed in EP1697421 (Micromet AG), WO2007024715 (Abbott Laboratories) or WO2010136485 (Glaxo Group Limited), the disclosures of which are incorporated herein by reference. For example, the present invention can related to one or more uses specifically discussed in WO2007024715 at page 11, line 24-page 15, line 14; page 51, line 6-page 66, line 23; page 76, line 1-page 79, line 29; and page 84, line 1-page 90, line 2. These examples of uses are specifically incorporated herein as though specifically and explicitly disclosed herein as possible uses with respect to the present invention and for possible inclusion in one or more claims herein. For example, the present invention can related to one or more uses specifically discussed in WO2010136485, including but not limited to those uses disclosed at page 12, line 33-page 13, line 7; and page 15, lines 16-32. These examples of uses are specifically incorporated herein as though specifically and explicitly disclosed herein as possible antigens with respect to the present invention and for possible inclusion in one or more claims herein. For example, the present invention can related to one or more uses specifically discussed in EP1697421, including but not limited to those uses disclosed at page 6, lines 31-33. These examples of uses are specifically incorporated herein as though specifically and explicitly disclosed herein as possible antigens with respect to the present invention and for possible inclusion in one or more claims herein.

It is contemplated that the use of, or composition comprising, an antibody, chain or polypeptide of the invention is any use or composition in combination with a second agent as disclosed in EP1697421 (Micromet AG), WO2007024715 (Abbott Laboratories) or WO2010136485 (Glaxo Group Limited), the disclosures of which are incorporated herein by reference. For example, the present invention can related to an antibody, chain or polypeptide of the invention with one or more additional pharmaceutically-acceptable agents specifically discussed in WO2007024715 at page 11, lines 7-23; page 15, lines 15-32; and page 79, line 30-page 90, line 2. These examples of uses, combinations and compositions are specifically incorporated herein as though specifically and explicitly disclosed herein as possible uses, combinations and compositions with respect to the present invention and for possible inclusion in one or more claims herein, with the exception that an antibody, chain or polypeptide of the invention is used instead of an antibody, chain or polypeptide disclosed in these prior art disclosures.

It is contemplated that the composition comprising, an antibody, chain or polypeptide of the invention has the general mixture of ingredients of any composition disclosed in EP1697421 (Micromet AG), WO2007024715 (Abbott Laboratories) or WO2010136485 (Glaxo Group Limited), the disclosures of which are incorporated herein by reference, with the exception that an antibody, chain or polypeptide of the invention is used instead of an antibody, chain or polypeptide disclosed in these prior art documents. For example, the present invention can relate to an antibody, chain or polypeptide of the invention in a pharmaceutical composition specifically discussed in WO2007024715 at page 66, line 25-page 75, line 23; and page 90, lines 2-26. These examples of compositions are specifically incorporated herein as though specifically and explicitly disclosed herein as possible compositions with respect to the present invention and for possible inclusion in one or more claims herein, with the exception that an antibody, chain or polypeptide of the invention is used instead of an antibody, chain or polypeptide disclosed in these prior art disclosures.

It is contemplated that an composition, antibody, chain or polypeptide of the invention is administered or administrable as disclosed in EP1697421 (Micromet AG), WO2007024715 (Abbott Laboratories) or WO2010136485 (Glaxo Group Limited), the disclosures of which are incorporated herein by reference, with the exception that an antibody, chain or polypeptide of the invention is used instead of an antibody, chain or polypeptide disclosed in these prior art documents. For example, the present invention can related to the administration of an antibody, chain or polypeptide of the invention (or a pharmaceutical composition for this purpose) as per administration specifically discussed in WO2007024715 at page 69, line 29-page 75, line 23; and page 90, lines 3-33. These examples of compositions are specifically incorporated herein as though specifically and explicitly disclosed herein as possible compositions, and administration routes and regimes with respect to the present invention and for possible inclusion in one or more claims herein, with the exception that an antibody, chain or polypeptide of the invention is used instead of an antibody, chain or polypeptide disclosed in these prior art disclosures.

Each linker (when present) is an amino acid sequence in the antibody, chain or polypeptide of the invention. In the locus of the genome, the locus comprises a corresponding nucleotide sequence to encode each linker.

For use in the present invention, it is contemplated that one, more or each linker is as disclosed in EP1697421 (Micromet AG), WO2007024715 (Abbott Laboratories) or WO2010136485 (Glaxo Group Limited), the disclosures of which are incorporated herein by reference. For example, the present invention can use a linker as specifically discussed in WO2007024715 at page 4, line 25-page 6, line 13; page 24, line 27-page 25, line 2; page 44, line 11-page 45, line 3. These examples of linkers are specifically incorporated herein as though specifically and explicitly disclosed herein as possible linkers for use with respect to the present invention and for possible inclusion in one or more claims herein. For example, the present invention can use a linker as specifically discussed in WO2010136485 at page 10, line 27-page 12, line 28; and page 14, lines 6-14; or a linker set out in SEQ ID NO: 10-38 of WO2010136485. These examples of linkers are specifically incorporated herein as though specifically and explicitly disclosed herein as possible linkers for use with respect to the present invention and for possible inclusion in one or more claims herein.

For example in any configuration of the invention, one, more or each linker is a $(GGGGS)_n$ linker, where n=1, 2, 3, 4, 5, 6, 7, 8, 9 or 10.

For example in any configuration of the invention, one, more or each linker is a linker selected from the group consisting of AKTTPKLEEGEFSEAR; AKTTPKLBEGEFSEARV; AKTTPKLGG; SAKTTPKLGG; AKTTPKLEEGEFSEARV; SAKTTP; SAKTTPKLGG; RADAAP; RADAAPTVS; RADAAAAGGPGS; RADAAAA($G_4$S)$_4$; SAKTTP; SAKTTPKLGG; SAKTTPKLEBGEFSEARV; ADAAP; ADAAPTVSIFPP; TVAAP; TVAAPSVFIFPP; QPKAAP; QPKAAPSVTLFPP; AKTTPP; AKTTPPSVTPLAP; AKTTAP; AKTTAPSVYPLAP; ASTKGP; ASTKGPSVFPLAP; GGGGSGGGGSGGGGS; GBNKVEYAPALMALS; GPAKELTPLKEAKVS; and GHEAAAVMQVQYPAS.

For example in any configuration of the invention, one, more or each linker is an amino acid sequence from 1 amino acid to 150 amino acids in length, or from 1 amino acid to 140 amino acids, for example, from 1 amino acid to 130 amino acids, or from 1 to 120 amino acids, or from 1 to 80 amino acids, or from 1 to 50 amino acids, or from 1 to 20 amino acids, or from 1 to 10 amino acids, or from 5 to 18 amino acids. Such sequences may have their own tertiary structure, for example, a linker of the present invention may be or comprise a domain, eg, an antibody single variable domain. The size of a linker in one embodiment is equivalent to a single variable domain. Suitable linkers may be of a size from 1 to 20 angstroms, for example less than 15 angstroms, or less than 10 angstroms, or less than 5 angstroms.

In one embodiment of the present invention a linker comprises from 1 to 150 amino acids, for example 1 to 50 amino acids, for example 1 to 20 amino acids, for example 1 to 10 amino acids. Such linkers may be selected from any one of those set out in SEQ ID NO: 10-38 or SEQ ID NO: 42-44 as disclosed in WO2010136485 (which disclosure is explicitly incorporated herein by reference as though specifically and explicitly disclosed herein as possible linkers for use with respect to the present invention and for possible inclusion in one or more claims herein), or multiples of such linkers.

Linkers may comprise alone or in addition to other linkers, one or more sets of GS residues, for example GSTVAAPS or TVAAPSGS or GSTVAAPSGS.

An example of a linker is $(PAS)n(GS)m$. In another embodiment, a linker is $(GGGGS)n(GS)m$. In another embodiment a linker is $(TVAAPS)n(GS)m$. In another embodiment a linker is (GS)m(TVAAPSGS)n. In another embodiment a linker is (PAVPPP)n(GS)m. In another embodiment a linker is (TVSDVP)n(GS)m. In another embodiment a linker is (TGLDSP)n(GS)m. In all such embodiments, n=1, 2, 3, 4, 5, 6, 7, 8, 9 or 10, and m=0, 1, 2, 3 or 4.

Examples of such linkers include (PAS)n(GS)m, wherein n=1 and m=1, (PAS)n(GS)m, wherein n=2 and m=1, (PAS)n(GS)m, wherein n=3 and m=1, (PAS)n(GS)m wherein n=4 and m=1, (PAS)n(GS)m wherein n=2 and m=0, (PAS)n(GS)m wherein n=3 and m=0, (PAS)n(GS)m wherein n=4 and m=0.

Examples of such linkers include (GGGGS)n(GS)m wherein n=1 and m=1, (GGGGS)n(GS)m wherein n=2 and m=1, (GGGGS)n(GS)m wherein n=3 and m=1, (GGGGS)n(GS)m wherein n=4 and m=1, (GGGGS)n(GS)m wherein n=2 and m=0, (GGGGS)n(GS)m wherein n=3 and m=0, (GGGGS)n(GS)m wherein n=4 and m=0.

Examples of such linkers include (TVAAPS)n(GS)m wherein n=1 and m=1, (TVAAPS)n(GS)m wherein n=2 and m=1, (TVAAPS)n(GS)m wherein n=3 and m=1, (TVAAPS)n(GS)m wherein n=4 and m=1, (TVAAPS)n(GS)m wherein n=2 and m=0, (TVAAPS)n(GS)m wherein n=3 and m=0, (TVAAPS)n(GS)m wherein n=4 and m=0.

Examples of such linkers include (GS)m(TVAAPSGS)n wherein n=1 and m=1, (GS)m(TVAAPSGS)n wherein n=2 and m=1, (GS)m(TVAAPSGS)n wherein n=3 and m=1, (GS)m(TVAAPSGS)n wherein n=4 and m=1, (GS)m(TVAAPSGS)n wherein n=5 and m=1, (GS)m(TVAAPSGS)n wherein n=6 and m=1, (GS)m(TVAAPSGS)n wherein n=1 and m=0, (GS)m(TVAAPSGS)n wherein n=2 and m=10, (GS)m(TVAAPSGS)n wherein n=3 and m=0, or (GS)m wherein m=0, 1, 2, 3, 4, 5, 6, 7, 8, 9 or 10.

Examples of such linkers include (PAVPPP)n(GS)m wherein n=1 and m=1, (PAVPPP)n(GS)m wherein n=2 and m=1, (PAVPPP)n(GS)m wherein n=3 and m=1, (PAVPPP)n(GS)m wherein n=4 and m=1, (PAVPPP)n(GS)m wherein n=2 and m=0, (PAVPPP)n(GS)m wherein n=3 and m=0, or (PAVPPP)n(GS)m wherein n=4 and m=0.

Examples of such linkers include (TVSDVP)n(GS)m wherein n=1 and m=1, (TVSDVP)n(GS)m wherein n=2 and m=1, (TVSDVP)n(GS)m wherein n=3 and m=1, (TVSDVP)n(GS)m wherein n=4 and m=1, (TVSDVP)n(GS)m wherein n=2 and m=0, (TVSDVP)n(GS)m wherein n=3 and m=0, (TVSDVP)n(GS)m wherein n=4 and m=0.

Examples of such linkers include (TGLDSP)n(GS)m wherein n=1 and m=1, (TGLDSP)n(GS)m wherein n=2 and m=1, (TGLDSP)n(GS)m wherein n=3 and m=1, (TGLDSP)n(GS)m wherein n=4 and m=1, (TGLDSP)n(GS)m wherein n=2 and m=0, (TGLDSP)n(GS)m wherein n=3 and m=0, or (TGLDSP)n(GS)m wherein n=4 and m=0.

In another embodiment there is no linker between the epitope binding moiety and the variable domain (and thus the locus does not comprise a corresponding linker-encoding nucleotide sequence). In another embodiment the epitope binding moiety is linked to the variable domain by the linker TVAAPS. In another embodiment the epitope binding moiety, is linked to the variable domain by the linker TVAAPSGS. In another embodiment the epitope binding moiety is linked to the variable domain by the linker GS. In another embodiment the epitope binding moiety is linked to the variable domain by the linker ASTKGPT.

In an embodiment, the vertebrate or cell of the invention comprises an antibody heavy chain locus that comprises (in 5' to 3' direction) a rearranged or unrearranged variable region, a first switch (eg, an S-mu switch, eg an endogenous S-mu), an endogenous mu constant region, a second switch (an S-gamma switch; eg, endogenous S-gamma) and a human constant region of said non-mu isotype; wherein the heavy chain locus is capable of undergoing switching from IgM to the non-mu isotype. Thus, for example, this can be provided by inserting one or more human non-mu constant region sequences downstream (3') of an endogenous mu region in the genome of a non-human vertebrate or cell (eg, ES cell). In this way, the human sequences are provided within the location of the endogenous heavy chain locus and expression from the human sequence can be effectively controlled using endogenous antibody and B-cell mechanisms.

In the present invention, the variable region of the or each locus is optionally a human variable region. For example, the variable region is a human rearranged VDJ or VJ. For example, the variable region is unrearranged and comprises a plurality of human V gene segments, one or more human J gene segments and optionally one or more human D gene segments (eg, a plurality of human VH gene segments, one or more human JH gene segments and one or more human D gene segments). It is contemplated that the variable region can encode heavy or light chain variable domains (VH, VHH or VL). The variable region can be any variable region disclosed in any of the Kymab Limited, Regeneron, Harbour Antibodies, Crescendo Biologics or Ablexis patent applications cited herein, and the disclosures of the composition of these variable region (such as the repertoire of gene segments contained therein) is incorporated herein by reference as though explicitly written herein, and for possible inclusion in one or more claims herein.

In the present invention, the mu constant region of the or each locus is optionally a non-human vertebrate mu constant region, eg of the same species or strain as the vertebrate per se. For example, the mu constant region is a mouse constant region.

In the present invention, the mu constant region of the or each locus is optionally an endogenous host mu constant region. In this way, the constant region (and the IgM stage) is host-matched for good B-cell compartment and primary repertoire development.

In the present invention, the or each non-mu constant region of the or each locus is optionally a non-human vertebrate constant region, eg of the same species or strain as the vertebrate per se. For example, the or each non-mu constant region is a mouse constant region.

In the present invention, the or each non-mu constant region of the or each locus is optionally an endogenous host constant region. In this way, the constant region is host-matched for good B-cell compartment and antibody/chain development.

In an embodiment, the vertebrate species is selected from human, mouse, rat, rabbit, guinea pig, chicken, a fish, a bird, a reptile, a *Camelid*, bovine, chimpanzee, a non-human primate and a primate.

In an embodiment, the vertebrate is a mouse. In an embodiment, the vertebrate is a rat.

The invention also provides a non-human vertebrate cell (eg, a mouse cell or a rat cell), the cell genome comprising (i) an antibody heavy chain locus comprising (in 5' to 3' direction) a rearranged or unrearranged variable region, a first switch (eg, an S-mu switch, eg, an endogenous S-mu), a mu constant region (eg, comprising a CH1 gene segment), a second switch (eg, an S-gamma switch, eg, an endogenous S-gamma) and a non-mu (eg, gamma) constant region; wherein the heavy chain locus of each cell is capable of undergoing IgM to a non-mu (eg, IgG) isotype switching; and wherein
(ii) the non-mu constant region comprises (in 5' to 3' direction) a nucleotide sequence encoding an optional linker and a predetermined epitope binding moiety, for expressing a multivalent (eg, multispecific, eg, bispecific) polypeptide chain comprising (in N- to C-terminal direction) an antibody variable domain derived from said variable region of the heavy chain locus, an optional linker and an epitope binding moiety, wherein the variable domain and the epitope binding moiety specifically bind respective first and second epitopes (eg, wherein the epitopes are different).

Optionally the gamma constant region lacks a CH1 gene segment, as described above.

Optional features described herein with reference to a vertebrate are also applicable to cells of the invention.

In one example, the cell is a B-cell, hybridoma, ES cell or iPS cell. ES cells and iPS cells (induced pluripotent stem cells) can be used to develop corresponding non-human vertebrates (vertebrates of the invention).

In an embodiment of the vertebrate or cell of the invention, the genome comprises a functional antibody light chain locus for expressing light chains; wherein the cells can express IgM antibodies comprising IgM-type heavy chains and light chains, each heavy chain comprising a CH1 domain. Optionally, the light chain locus comprises a human rearranged or unrearranged variable region.

Optionally, the light chain locus comprises means for turning off light chain expression, wherein functional light chains are not expressed after IgM to non-mu isotype switching. Examples of suitable means are described below. Optionally, also the non-mu gamma constant region does not comprise a CH1 gene segment. Thus, non-mu heavy chains lacking a CH1 domain are expressible by the vertebrate or cell in the absence of light chains; this is useful for producing H2 multivalent antibodies.

In an embodiment, the vertebrate expresses polypeptide chains comprising (in N- to C-terminal direction) (a) an antibody variable domain derived from said variable region of the heavy chain locus (optionally following somatic hypermutation), an optional linker, an epitope binding moiety and a non-mu (eg, gamma) constant domain (eg, gamma Fc) or (b) an antibody variable domain derived from said variable region of the heavy chain locus (optionally following somatic hypermutation), a non-mu (eg, gamma) constant domain (eg, gamma Fc), an optional linker and an epitope binding moiety, wherein the variable domain and the epitope binding moiety specifically bind the respective first and second epitopes. In an example, the polypeptide chains have the structure V-L-E or V-L-E-L, where V is an antibody variable domain (VH, VHH or VL) derived from said variable region of the heavy chain locus, L is an optional linker and E is an epitope binding domain. Possible structures are V-L-E-Fc or V-L-E-L-Fc, where Fc is an antibody Fc region (eg a gamma Fc).

In an embodiment, the or each epitope binding moiety is an epitope binding domain.

In an embodiment of the vertebrate or cell of the invention, the non-mu constant region is a gamma constant region and the heavy chain locus is capable of undergoing isotype switching to produce IgG antibodies comprising one or more IgG heavy chains in the absence of light chains, each heavy chain lacking a CH1 domain.

In an embodiment of the vertebrate or cell of the invention, there is provided a non-human (eg, rat or mouse) vertebrate or cell that expresses multivalent heavy chains (or dimers thereof) comprising the structure V-L-E or V-L-E-L (eg, V-L-E-Fc or V-L-E-L-Fc), where V is an antibody variable domain (VH, VHH or VL), L is an optional linker and E is an epitope binding moiety, wherein V and E specifically bind respective first and second antigens, wherein the antigens are different.

Rearranged Non-Mu (eg, Gamma) Locus

The invention also relates to non-human vertebrates and cells that have a non-mu isotype, such as a gamma isotype constant region without a mu constant region—for production of non-mu heavy chains (optionally provided by non-mu antibodies). The invention also relates to non-human vertebrates and cells that have undergone isotype switching to a non-mu isotype, such as a gamma isotype for production of non-mu heavy chains (optionally provided by non-mu antibodies). To this end, the invention provides:—

A non-human vertebrate (eg, a mouse or a rat), wherein the vertebrate comprises lymphocytic cells whose genomes comprise an antibody heavy chain locus comprising (in 5' to 3' direction) a rearranged variable region and a non-mu (eg, gamma) constant region;
wherein
the non-mu constant region comprises (in 5' to 3' direction) a nucleotide sequence encoding an optional linker and a predetermined epitope binding moiety, wherein the vertebrate expresses multivalent (eg, bivalent, eg, bispecific) polypeptide chains comprising (in N- to C-terminal direction) an antibody variable domain derived from said variable region of the heavy chain locus, an optional linker and an epitope binding moiety, wherein the variable domain and the epitope binding moiety specifically bind respective first and second epitopes (eg, wherein the epitopes are different).

Also, the invention provides a non-human vertebrate cell (eg, a mouse cell or a rat cell) or a hybridoma, the cell genome comprising an antibody heavy chain locus comprising (in 5' to 3' direction) a rearranged variable region and a non-mu (eg, gamma) constant region;
wherein
the non-mu constant region comprises (in 5' to 3' direction) a nucleotide sequence encoding an optional linker and a predetermined epitope binding moiety, wherein the cell expresses a multivalent polypeptide chain comprising (in N- to C-terminal direction) an antibody variable domain derived from said variable region of the heavy chain locus, an optional linker and an epitope binding moiety, wherein the variable domain and the epitope binding moiety specifically bind respective first and second epitopes.

Optional features described above in the context of vertebrates and cells comprising mu constant regions are also applicable to these isotype-switched embodiments of vertebrates and cells.

In an embodiment of the vertebrate or cell, the heavy chain locus has undergone IgM to non-mu (eg, IgG) isotype switching.

In an embodiment of the vertebrate or cell, the linker and/or epitope binding moiety nucleotide sequence is provided in place of a CH1 domain gene segment in the non-mu (eg, gamma) constant region. Thus, the product comprises or consists of the structure V-L-E (eg, V-L-E-CH2-CH3, where the constant domains are gamma-type constant domains).

L Chain Locus for Multivalent Products

The invention similarly provides light chain loci for expression of multivalent (eg, multispecific, eg, bispecific) light chains. To this end, the invention provides:—

A non-human vertebrate (eg, a mouse or a rat), wherein the vertebrate comprises lymphocytic cells, the genome of each cell comprising an antibody light chain locus (eg, a kappa or lambda locus) which comprises (in 5' to 3' direction) a rearranged or unrearranged variable region and a second region;
wherein
the second region comprises (in 5' to 3' direction) a nucleotide sequence encoding an optional linker and a predetermined epitope binding moiety, wherein the vertebrate expresses polypeptide chains comprising (in N- to C-terminal direction) an antibody variable domain derived from said variable region of the light chain locus (optionally following mutation, eg, somatic hypermutation), an optional linker and an epitope binding moiety, wherein the variable domain and the epitope binding moiety specifically bind respective first and second epitopes (eg, wherein the epitopes are different).

The variable domain is derived from the variable region of the light chain locus. Thus, when the variable region of the locus is a rearranged variable region, the variable domain is encoded by the sequence of the variable region (eg, a $V_H DJ_H$ or $V_L J_L$ region) optionally with somatic hypermutation. When the variable region is an unrearranged variable region, this region comprises one or more V gene segments, one or more J gene segments and optionally one or more D gene segments (eg, wherein all of these segments are human). Following rearrangement of gene segments in the light chain locus, a rearranged VDJ or VJ is formed and this encodes the variable domain optionally following somatic hypermutation.

Optionally, the second region comprises nucleotide sequences encoding a plurality of epitope binding moieties, eg, two or three epitope binding moieties joined by optional linkers.

Optionally, the second region comprises nucleotide sequences encoding one or a plurality of epitope binding moieties (optionally joined by linkers) in place of a CL gene segment or in addition thereto. For example, the second region comprises (in 5' to 3' direction) a nucleotide sequence encoding an optional linker, a predetermined epitope binding moiety and a CL; or CL, an optional linker and a predetermined epitope binding moiety; or an optional linker and a predetermined epitope binding moiety (in the absence of a CL).

For example, the polypeptide chains each comprise an antibody variable domain derived from said variable region of the light chain locus, an optional linker, an epitope binding moiety and a CL domain; or an antibody variable domain derived from said variable region of the light chain locus, a CL domain, an optional linker and an epitope binding moiety; or an antibody variable domain derived from said variable region of the light chain locus, an optional linker and an epitope binding moiety.

Features described herein that relate to a non-human vertebrate comprising the light chain locus of the invention also apply to a cell that comprises a light chain locus of the invention. The invention, thus also provides:—

A non-human vertebrate cell (eg, a mouse cell or a rat cell) or a hybridoma, wherein the cell genome comprises an antibody light chain locus comprising (in 5' to 3' direction) a rearranged or unrearranged variable region and a second region;
wherein
the second region comprises (in 5' to 3' direction) a nucleotide sequence encoding an optional linker and a predetermined epitope binding moiety, for expressing a polypeptide chain comprising (in N- to C-terminal direction) an antibody variable domain derived from said variable region of the light chain locus, an optional linker and an epitope binding moiety, wherein the variable domain and the epitope binding moiety specifically bind respective first and second epitopes.

In an example, there is provided a non-human vertebrate or cell comprising a heavy chain and light chain of the invention as herein described. Thus, the vertebrate is capable of expressing multivalent heavy chains and multivalent light chains, eg, as provided by multivalent antibodies. For example, the antibodies can be bispecific, trispecific, tetraspecific, pentaspecific, hexaspecific or heptaspecific or have more than 7 specificities. For example, the antibodies can have 3, 4, 5, 6, 7, 8 or more valencies. Valencies and specificities refer to specific epitope or antigen binding.

In an example, there is provided a non-human vertebrate or cell comprising a heavy chain and light chain of the invention as described. Optionally, the vertebrate or cell genome comprises said heavy and light chain loci, wherein said polypeptide chain variable domains derived from the heavy chain locus form binding sites with the polypeptide chain variable domains derived from the light chain locus, wherein the binding sites specifically bind the first epitope. For example, the epitope binding moieties of the polypeptide chains derived from the heavy and light chain loci are antibody variable domains, wherein the epitope binding domains of the chains derived from the heavy chain locus associate with the epitope binding domains of the chains derived from the light chain locus to form binding sites that specifically bind the second epitope. In one embodiment, the epitope binding moieties in chains derived from the heavy chain locus are VH domains; and the epitope binding moieties in chains derived from the light chain locus are VL domains. In another embodiment, the epitope binding moieties in chains derived from the heavy chain locus are VL domains; and the epitope binding moieties in chains derived from the light chain locus are VH domains. The VH and VL domains between heavy and light chains optionally form VH/VL pairs, each VH/VL providing an epitope binding site. Chains are derived from a locus when, for example following rearrangement and somatic hypermutation the loci encode RNA, the RNA in turn encoding for the chains. This may take place, for example, following immunisation of the vertebrate to the first epitope (ie, the epitope that is specifically bound by the N-terminal variable domain in the product chain).

In an example, the vertebrate or cell of the invention is homozygous for a heavy chain as described herein and/or a light chain as described herein.

Methods

The invention also provides methods for the in vivo production, maturation and selection of multivalent antibodies, antibody chains and polypeptides that specifically bind first and second epitopes. To this end, the invention provides:—

A method of producing multivalent (eg, bivalent, eg, bispecific) polypeptide chains comprising (in N- to C-terminal direction) an antibody variable domain, an optional linker and an epitope binding moiety, wherein the variable domain and the epitope binding moiety specifically bind respective first and second epitopes (eg, wherein the epitopes are different or the same), the method comprising
(a) expressing in a non-human vertebrate (eg, a mouse or a rat) IgM antibodies in immature B-cells (eg, T1 and T2 B-cells, eg, splenic B-cells), wherein the antibodies comprise heavy and light chains expressed from heavy and light chain loci respectively;
(b) immunising the vertebrate with a first predetermined antigen bearing the first epitope and obtaining isotype switching to expression from a non-mu (eg, gamma) constant region in at least some of the heavy chain loci and expression of variable regions that have undergone somatic hypermutation (eg, variable regions provided by IgG antibody heavy chains); and (c) selecting one or more polypeptide chains from said immunised vertebrate by selection for variable regions that bind said first epitope (eg, by selection of heavy chains of said non-mu isotype), wherein each selected chain comprises a somatically hypermutated variable region that specifically binds the epitope; and wherein the method comprises (d) providing the nucleotide sequence of the epitope binding moiety (or a predetermined parent thereof that specifically binds the second epitope) in the non-mu constant region of heavy chain loci in the genome of the vertebrate, wherein the polypeptide chains selected in step (c) bind the first and second epitopes.

Optionally in (a) the heavy chains comprise CH1 domains.

Optional features described herein with reference to vertebrates and cells also apply mutatis mutandis to methods of the invention.

For example in any method of the invention, the epitopes are provided by first and second antigens that are different, so the product is multispecific (eg, bispecific where the product is bivalent).

Figure 2:
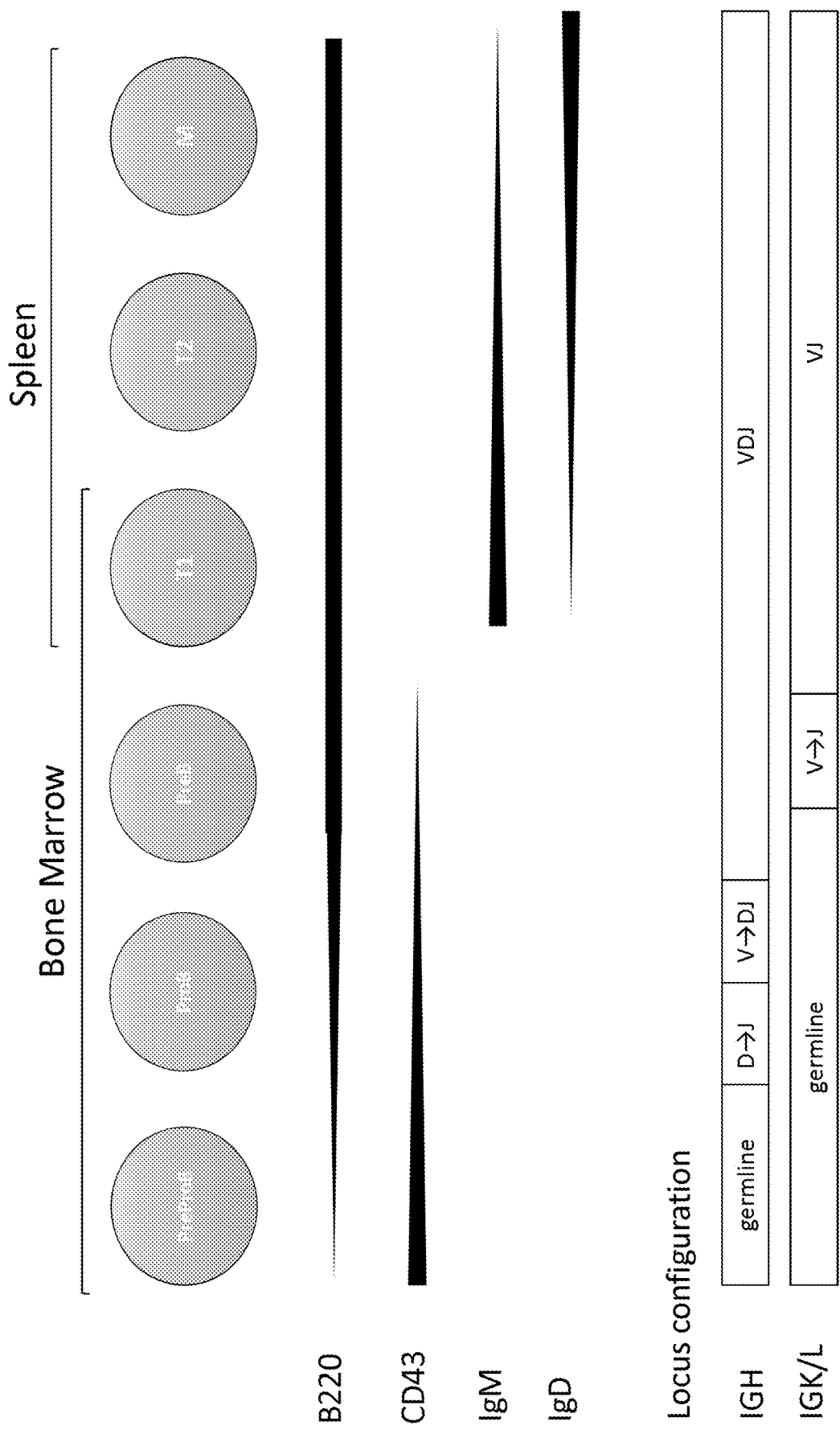
FIG. 2 is a schematic showing B-cell development and markers in the bone marrow and splenic compartments.

In spleen, B cells are characterized as immature (T1 and T2) and mature (M) based on the levels of cell surface markers, IgM and IgD. T1 cells have high IgM and low IgD. T2 cells have medium levels of both them. M cells have low IgM but high IgD (FIG. 2). See also J Exp Med. 1991 May 1; 173(5):1213-25; "Resolution and characterization of pro-B and pre-pro-B cell stages in normal mouse bone marrow"; Hardy R R et al and J Exp Med. 1999 Jul. 5; 190(1):75-89; "B cell development in the spleen takes place in discrete steps and is determined by the quality of B cell receptor-derived signals"; Loder F et al.

For example, in step (c) selection of the chains is from serum, blood, spleen tissue, lymph node tissue, or secondary lymphoid organ tissue. For example, the chains are B-cell secreted chains.

Optionally in any method of the invention the polypeptide chains comprise one or more heavy chain constant domains and in this sense, the chains can be regarded as heavy chains. In another embodiment, the chains are chains comprising no constant domains, eg, wherein the chain consists of a V-L-E polypeptide as described herein.

Step (d) can be performed by any standard genome manipulation technology, as will be readily apparent to the skilled person. For example, using ES cell technology with subsequent generation of progeny organism(s).

In an example, each somatically mutated variable region in step (b) is provided by an non-mu-type (eg, IgG-type) heavy chain that lacks a CH1 domain. This is useful for producing heavy chain-only (H2) antibodies, particularly when light chain expression is inactive. Thus, for example, step (b) comprises expressing the somatically mutated variable regions in the absence of light chain expression.

The invention further provides a method of producing in a non-human vertebrate (eg, a mouse or a rat) multivalent (eg, bivalent, eg, bispecific) polypeptide chains comprising (in N- to C-terminal direction) an antibody variable domain, an optional linker and an epitope binding moiety, wherein the variable domain and the epitope binding moiety specifically bind respective first and second epitopes (eg, wherein the epitopes are different or the same), the method comprising (a) immunising the vertebrate with a first predetermined antigen bearing the first epitope, obtaining isotype switching to expression from a non-mu (eg, gamma) constant region in at least some of the heavy chain loci of the vertebrate and expression of variable regions (eg, as provided by IgG antibody heavy chains) that have undergone somatic hypermutation; and (b) selecting one or more polypeptide chains from said immunised vertebrate by selection for variable regions that bind said first epitope, wherein each selected chain comprises a somatically hypermutated variable region that specifically binds the epitope; and wherein (d) providing the nucleotide sequence of the epitope binding moiety (or a predetermined parent thereof that specifically binds the second epitope) in the non-mu constant region of heavy chain loci in the genome of the vertebrate (eg, done using ES cell technology), wherein the polypeptide chains selected in step (b) bind the first and second epitopes.

In an example, each somatically mutated variable region in step (a) is provided by a non-mu-type (eg, IgG-type) heavy chain that lacks a CH1 domain. Optionally, step (a) comprises expressing the somatically mutated variable regions in the absence of light chain expression.

Optionally in any method of the invention, the vertebrate is according to any configuration, aspect, embodiment or example of the invention herein.

Optionally a method of the invention further comprises isolating or synthesizing a nucleic acid comprising a nucleotide sequence encoding a polypeptide chain selected in the method; and optionally humanising the sequence (eg, replacing non-human antibody constant domains with one or more (or corresponding) human antibody constant domains).

The invention also provides a multivalent (eg, multispecific, eg, bispecific) polypeptide chain obtained by the method of the invention or a derivative thereof that specifically binds the first and second epitopes. Examples of derivatives (eg, conjugates or crystals or glycosylated forms) are disclosed at page 9, line 22 to page 10, line 4; page 10, line 25 to page 11, line 6; and page 47, line 26 to page 50, line 23 of WO2007024715. These examples are specifically incorporated herein as though specifically and explicitly disclosed herein as possible derivatives with respect to the present invention and for possible inclusion in one or more claims herein, with the exception that an antibody, chain or polypeptide of the invention is used instead of an antibody, chain or polypeptide disclosed in these prior art disclosures.

Products

The invention provides multivalent products as follows:—

A multivalent (eg, multispecific, eg, bispecific) polypeptide chain having or consisting of (in N- to C-terminal direction) the structure V-X-L-E-L-C, where (i) V is an antibody variable domain that specifically binds a first epitope, (ii) X is absent, an antibody hinge region or an antibody constant region comprising a constant domain (eg, gamma-type CH1, a human gamma constant domain, an antibody hinge region-CH domain; or a CH domain-antibody hinge region), (iii) Each L is an optional linker, (iv) E is an epitope binding moiety that specifically binds a second epitope, and (v) C is absent or an antibody constant region comprising one or more (eg, 1, 2, 3 or 4) constant domains (eg, C is a human gamma Fc or gamma CH1-hinge-CH2-CH3), wherein V is a rearranged antibody variable domain derived from the rearrangement of variable region gene segments in vivo in a non-human vertebrate with somatic hypermutation of the resulting variable region gene in a nucleotide sequence also encoding for the epitope binding moiety (or a parent thereof sharing the same epitope binding specificity); and wherein the rearranged antibody variable domain comprises endogenous AID-pattern somatic hypermutations.

This means that the B-cell has carried out somatic hypermutation and selection of the rearranged variable domain in the context of the predetermined epitope binding domain. This is superior to current methods in which binding moieties are separately selected (eg, in separate phage display experiments in vitro) and then combined to form a bispecific polypeptide. In this prior art case, consideration is given to bispecificity, but not to construction for well-behaved polypeptides that have good biophysical characteristics and expression compatible with in vivo animal systems.

Thus, where a variable domain was produced in a mouse, each rearranged variable domain will comprise somatic hypermutations caused by mouse AID. Mutation hotspots for AID are known (see Mauel, R. W. & Gearhart, P. J.; "AID and somatic hypermutation" *Advances in Immunology* 2010. 105: 159-191"), and thus the skilled person will readily be able to identify one or more mutations that are at such hotspots for the endogenous AID (eg, by comparing against the predicted amino acid sequence that would be produced in the absence of any mutation).

In an example, V is a rearranged antibody variable domain derived from the rearrangement of human VH with a DH and JH. In another example, V is a VL domain derived from the rearrangement of human VL and a JL (eg, Vκ and a Jκ or a Vλ and a Jλ).

In one embodiment, in addition to E, a plurality (eg, 1, 2 or 3) further epitope binding moieties is provided between V and C, each further moiety having binding specificity for a respective epitope. In an example, the epitope binding moieties have different epitope specificities. In another example, they share specificity for the second epitope. For example, the chain has or consists of the structure (in N- to C-terminal direction) the structure V-X-L-E-L-E"L-C, where E" is a further epitope binding domain, eg, having binding specificity for a third epitope that is different from the first and second epitopes.

The antibody hinge can be from any species, eg, a mouse hinge, a rat hinge, a human hinge or a Camelid hinge.

Examples of polypeptides according to the invention are the following N- to C-terminally:—
(i) V-dAb-human Fc (optionally as a dimer), wherein V is a VH, VHH or VL and the dAb is a VH, VHH or VL;
(ii) V-dAb (optionally as a dimer), wherein V is a VH, VHH or VL and the dAb is a VH, VHH or VL;
(iii) V-scFv-human Fc (optionally as a dimer), wherein V is a VH, VHH or VL
(iv) V-scFv (optionally as a dimer), wherein V is a VH, VHH or VL and the dAb is a VH, VHH or VL;
(v) mAb-dAb (ie, a mAb covalently attached to or comprising one or more dAbs, eg in the heavy chains of the mAb), wherein the heavy chain variable domains of the mAb are V domains as recited, wherein V represents a VH, VHH or VL;
(vi) Fab-dAb (ie, a Fab covalently attached to or comprising one or more dAbs, eg in the heavy chains of the Fab), wherein the heavy chain variable domain of the Fab is V as recited, wherein V represents a VH, VHH or VL;
(vii) $Fab_2$-dAb (ie, a $Fab_2$ covalently attached to or comprising one or more dAbs, eg in the heavy chains of the $Fab_2$), wherein the heavy chain variable domains of the Fabs are V domains as recited, wherein V represents a VH, VHH or VL.

VHH denotes a Camelid heavy chain single variable domain or a camelised human VH single variable domain, as is known in the art.

There is provided a method of producing a polypeptide chain of the invention, the method comprising immunising a non-human vertebrate (eg, a mouse or a rat) with the first epitope and causing somatic hypermutation of a variable region gene in a nucleotide sequence also encoding for the epitope binding moiety (E), the variable region gene encoding V; and isolating said polypeptide chain comprising V and E. The method optionally further comprises producing a derivative polypeptide chain (eg, a humanised version thereof) which retains specificity for the first and second epitopes.

According to an embodiment of the method of polypeptide chain, the epitope binding moiety lacks endogenous AID-pattern somatic hypermutations. Thus, when a mouse according to the invention is used to generate the chain, the epitope binding moiety of the chain does not comprise endogenous (mouse) AID mutations and neither does its nucleotide sequence. Advantageously, this may result from positioning of the moiety nucleotide sequence downstream of S-mu or the mu constant region in a heavy chain locus of the invention. Thus, the desired characteristics (eg, binding characteristics) of the epitope binding moiety are not downgraded by AID mutations.

In an alternative, the epitope binding moiety comprises endogenous AID-pattern somatic hypermutations. This may be useful for providing in vivo-selected variants of the predetermined epitope binding domain, which variants can be combined with the repertoire of N-terminal variable domains and which can be expressed by in vivo systems in this format. Variants can be selected (in this multivalent product format) for one or more desirable characteristics, such as an improvement in epitope binding affinity versus the parent epitope binding moiety.

There is further provided a dimer of polypeptides according to the invention, wherein the dimer lacks antibody light chains. Thus, for example, when the polypeptides are heavy chains lacking CH1 domains, the dimer may provide a multivalent (eg, multispecific) heavy chain-only (H2) antibody that is produced, matured and selected in vivo in this format.

There is further provided a polypeptide, dimer or method according to the invention, wherein the polypeptide has (in N- to C-terminal direction) the structure V-N-E; V-CH1-M-CH2-CH3-L-E; or V-M-CH2-CH3-L-E, wherein N is L together with an optional antibody hinge region; and M is an optional antibody hinge region. Optionally the constant domains are human gamma constant domains. Thus, M can be L alone; hinge-L; L-hinge; or hinge.

There is further provided a polypeptide, dimer or method according to the invention, wherein V is peptide bonded to a second antibody variable domain (V2) to form a binding site comprising first and second variable domains that specifically binds the first epitope; optionally wherein V and V2 are provided as an scFv. For example, V is a VH (eg, human VH) selected as a multivalent polypeptide chain from a heavy chain locus of the invention, wherein the VH pairs with a VL to form a binding site for the first epitope (eg, wherein the VL is a human VL encoded by a light chain locus of the vertebrate or cell). Following selection of the heavy chain or a nucleotide encoding this, using recombinant DNA technology or protein engineering the VL or a nucleotide sequence encoding this can be combined with the VL (or VL nucleotide sequence) to produce a heavy chain comprising an N-terminal scFv and also an epitope binding moiety. The scFv provides a binding site for the first epitope and the epitope binding moiety provides a binding site for the second epitope.

In one embodiment of the polypeptide, dimer or method of the invention, the polypeptide lacks a CH1 domain.

In one embodiment of the polypeptide, dimer or method of the invention, the polypeptide comprises a CH1 domain and the polypeptide is present in first and second copies in antibody, the first polypeptide being associated with a first antibody light chain, and the second copy being associated with a second antibody light chain. Optionally, the light chains are identical. Thus, the product can have a 4-chain mAb-like structure.

The invention provides an antibody comprising the dimer, polypeptide chain or a humanised version thereof as recited herein.

The invention provides a bivalent (eg, bispecific) antibody comprising or consisting of a dimer of a heavy chain, wherein each heavy chain is a polypeptide as recited herein and has in N- to C-terminal direction) the structure
V-CH1-M-CH2-CH3-L-E,
V-M-CH2-CH3-L-E,
V-L-E-L-CH1-M-CH2-CH3,
V-L-E-L-M-CH2-CH3,
V-CH1-N-E,
V-L-E-N-CH1, or
V-N-E-L-CH1,
wherein N is L together with an optional antibody hinge region; M is an optional antibody hinge region (thus, M can be L alone; hinge-L; L-hinge; or hinge);
optionally wherein the constant domains are human constant domains (eg, human gamma constant domains).

Optionally the human and constant regions of the antibody or polypeptide of the invention are human.

Somatically Hypermutated VH/VL Pairs with Fixed Epitope Binding Domain(s)

Optionally, the antibody comprises two copies of a light chain, each heavy chain being associated with a respective light chain, wherein V in each heavy chain forms an antigen binding site with the variable domain of its respective light chain and the variable domain of each light chain comprises endogenous AID-pattern somatic hypermutations. Thus, the variable domain of each heavy chain can be selected as a V pair (eg, VH/VL) with a V from a light chain partner, the V pair being affinity matured and selected in vivo following immunisation with target antigen. For example, the antibody is a mAb-dAb (ie, a mAb structure comprising one or more dAbs on the heavy chains, eg at the C-termini thereof).

Optionally the human and constant regions of the antibody of the invention are human.

The invention provides a multivalent (eg, multispecific, eg, bispecific) antibody comprising heavy chains associated with light chains, wherein Each heavy chain is a polypeptide chain as recited above having or consisting of the structure V-X-L-E-L-C, wherein E is an antibody variable domain;

Each light chain is a polypeptide chain having or consisting of (in N- to C-terminal direction) the structure V'-L'-E'-L'-C', where
(i) V' is an antibody variable domain,
(ii) Each L' is an optional linker,
(iv) E' is an epitope binding moiety, and (v) C' is absent or an antibody constant region comprising a constant domain (eg, one, two, three or four constant domains, eg, C' is a human CL);
wherein
V' is a rearranged antibody variable domain derived from the rearrangement of variable region gene segments in vivo in a non-human vertebrate with somatic hypermutation of the resulting variable region gene in a nucleotide sequence also encoding for E' (or a parent thereof that specifically binds the epitope that is specifically bound by E'); and
V' comprises endogenous AID-pattern somatic hypermutations;
V and V' form a first binding site that specifically binds a first epitope; and
Optionally E and E' form a second binding site that specifically binds a second epitope when E' is an antibody variable domain (eg, E is a VH and E' is a VL).

In an example, V' is derived from the rearrangement of human VH with a DH and JH. In another example, V' is a VL domain derived from the rearrangement of human VL and a JL (eg, Vκ and a Jκ or a Vλ and a Jλ).

The invention also provides an antigen-binding polypeptide comprising a protein scaffold which is linked to one or more epitope binding moieties wherein the antigen-binding polypeptide comprises at least two epitope binding sites at least one of which is provided by an epitope binding moiety and at least one of which is provided by a first antibody variable domain paired with a second antibody variable domain, wherein each variable domain is a rearranged antibody variable domain derived from the rearrangement of variable region gene segments in vivo in a non-human vertebrate with somatic hypermutation of the resulting variable region gene in a nucleotide sequence also encoding for one or more of the epitope binding moiety(ies) (or a respective parent thereof having the same epitope binding specificity); and wherein the rearranged antibody variable domains comprise endogenous AID-pattern somatic hypermutations.

Thus, where the variable domain was produced in a mouse, each rearranged variable domain will comprise somatic hypermutations caused by mouse AID. Mutation hotspots for AID are known (see Mauel, R. W. & Gearhart, P. J.; "AID and somatic hypermutation" *Advances in Immunology* 2010. 105: 159-191"), and thus the skilled person will readily be able to identify one or more mutations that are at such hotspots for the endogenous AID (eg, by comparing against the predicted amino acid sequence that would be produced in the absence of any mutation).

The invention also provides an antigen-binding polypeptide that is a copy of the antigen binding polypeptide comprising the protein scaffold. Thus, the variable domain(s) of the copies need not themselves have been produced in a vertebrate, but could for example be expressed in vitro from a vector comprising nucleotide sequence encoding the polypeptide.

In an example, each variable domain is a rearranged antibody variable domain derived from the rearrangement of human VH with a DH and JH. In another example, each variable domain is a VL domain derived from the rearrangement of human VL and a JL (eg, Vκ and a Jκ or a Vλ and a Jλ).

In an example, the protein scaffold is an antibody scaffold, ie, a scaffold comprising a heavy chain (or dimer thereof, eg, H2 antibody); a heavy chain and a paired light chain (or a dimer thereof, eg, a H2L2 antibody).

In an example, the protein scaffold is an Ig scaffold, eg, an IgG scaffold. For example, the IgG scaffold is selected from IgGI, IgG2, IgG3 and IgG4. For example, an epitope binding domain is attached to the Ig scaffold at the N-terminus of the light chain thereof. For example, an epitope binding domain is attached to the Ig scaffold at the N-terminus of the heavy chain. For example, an epitope binding domain is attached to the Ig scaffold at the C-terminus of the light chain. For example, an epitope binding domain is attached to the Ig scaffold at the C-terminus of the heavy chain.

In an example, the protein scaffold comprises or consists of a monovalent or bivalent antibody (eg, bivalent monospecific antibody).

In an example, at least one of said epitope binding moieties linked to the protein scaffold by a peptide linker which comprises at least 10 amino acids (eg, between 10 and 50 amino acids). In one example, a (or each) epitope binding moiety (eg, domain) is linked to the protein scaffold by a linker selected from those set out in SEQ ID NO: 53 to 60, SEQ ID NO:62-72, SEQ ID NO:74, SEQ ID NO:76-78 and SEQ ID NO:112-114 and combinations or multiples of such linkers (wherein the sequences are those disclosed in WO2010136483, the disclosure of which is incorporated herein by reference for use with the present invention and for possible inclusion in claims herein). In an example, the linker is selected from (PAS)n(GS)m, (GGGGS)p(GS)m, (TVAAPS)p(GS)m, (GS)m(TVAAPSGS)p, (PAVPPP)n (GS)m, (TVSDVP)n(GS)m, and (TGLDSP)n(GS)m, wherein n=an integer from 1-10, and m=0 or a integer from 1-4, and p=an integer from 2-10.

In an example, the linker is selected from (PAS)n(GS)m wherein n=an integer from 1-10, and m=0 or an integer from 1-4.

In an example, the linker is selected from (TVAAPS)p (GS)m and (GS)m wherein m=0 or an integer from 1-10, and p=or an integer from 2-10.

The invention provides a polynucleotide sequence encoding a heavy chain of an antigen binding polypeptide recited above. The invention provides a polynucleotide sequence encoding a light chain of an antigen binding polypeptide recited above.

The invention also relates to multispecific polypeptides that are useful for recruiting immune effector cells in patients. Thus, the invention provides a multispecific antigen binding polypeptide, dimer or antibody according to the description above, which is capable of recruiting the activity of a human immune effector cell by specifically binding to an effector antigen (eg, human CD3) located on a human immune effector cell, a first of the epitope binding sites of the polypeptide, dimer or antibody being capable of specifically binding to said effector antigen, and a second of the epitope binding sites of the polypeptide, dimer or antibody being capable of specifically binding to a target antigen (eg, human EpCAM or human CD19) other than the effector antigen; optionally wherein said target antigen is located on a target cell other than said human immune effector cell.

For example, the effector antigen is selected from the group consisting of CD3, CD16, CD32, CD64 and CD89.

For example, the target antigen is selected from the group consisting of EGFR; VEGF; IGF-1R; Her2; c-Met (aka HGF); HER3; CEA; CD33; CD79a; CD19; PSA; EpCAM; CD66; CD30; HAS; PSMA; GD2; ANG2; IL-4; IL-13; VEGFR2; and VEGFR3.

In an embodiment, there is provided the vertebrate, cell polypeptide, dimer or antibody of the invention, wherein the second epitope is provided by human immune effector cell antigen (eg, human CD3).

In an embodiment, there is provided the vertebrate, cell polypeptide, dimer or antibody of the invention, wherein the first epitope is provided by a target antigen (eg, human EpCAM or human CD19) other than the effector antigen; optionally wherein said target antigen is an antigen of a target cell other than said human immune effector cell.

The invention also provides light chains and light chain dimers. To this end, the invention provides a multivalent (eg, multispecific) light chain having (in N- to C-terminal direction) the structure V-X-L-E-L-C, where (i) V is an antibody variable domain (eg, a VL) that specifically binds a first epitope,
(ii) X is absent, or an antibody constant region comprising a constant domain (eg, a CL),
(iii) Each L is an optional linker,
(iv) E is an epitope binding moiety that specifically binds a second epitope, and
(v) C is absent or an antibody constant region comprising a constant domain (eg, C is a CL),
wherein V is a rearranged antibody variable domain derived from the rearrangement of variable region gene segments in vivo in a non-human vertebrate with somatic hypermutation of the resulting variable region gene in a nucleotide sequence also encoding for the epitope binding moiety; and wherein the rearranged antibody variable domain comprises endogenous AID-pattern somatic hypermutations.

The invention also provides a dimer of such a light chain.

A corresponding vertebrate is provided which comprises a light chain locus for producing such a construct. To this end, the invention provides A non-human vertebrate (eg, a mouse or a rat), wherein the vertebrate comprises lymphocytic cells, each cell genome comprising (i) an antibody light chain locus comprising (in 5' to 3' direction) a rearranged or unrearranged variable region, a nucleotide sequence encoding an optional linker and a predetermined epitope binding moiety, and a CL gene segment, wherein the vertebrate expresses multivalent light chains comprising (in N- to C-terminal direction) an antibody variable domain derived from said variable region of the light chain locus, an optional linker, an epitope binding moiety and a CL domain, wherein the variable domain and the epitope binding moiety specifically bind respective first and second epitopes (which can be any epitopes as defined herein); or (ii) an antibody light chain locus comprising (in 5' to 3' direction) a rearranged or unrearranged variable region, a CL gene segment, a nucleotide sequence encoding an optional linker and a predetermined epitope binding moiety, wherein the vertebrate expresses multivalent light chains comprising (in N- to C-terminal direction) an antibody variable domain derived from said variable region of the light chain locus, a CL domain, an optional linker and an epitope binding moiety, wherein the variable domain and the epitope binding moiety specifically bind respective first and second epitopes (which can be any epitopes as defined herein).

A non-human vertebrate cell (eg, a mouse cell or a rat cell), the cell genome comprising (i) an antibody light chain locus comprising (in 5' to 3' direction) a rearranged or unrearranged variable region, a nucleotide sequence encoding an optional linker and a predetermined epitope binding moiety, and a CL gene segment, wherein the cell expresses multivalent light chains comprising (in N- to C-terminal direction) an antibody variable domain derived from said variable region of the light chain locus, an optional linker, an epitope binding moiety and a CL domain, wherein the variable domain and the epitope binding moiety specifically bind respective first and second epitopes (which can be any epitopes as defined herein); or (ii) an antibody light chain locus comprising (in 5' to 3' direction) a rearranged or unrearranged variable region, a CL gene segment, a nucleotide sequence encoding an optional linker and a predetermined epitope binding moiety, wherein the cell expresses multivalent light chains comprising (in N- to C-terminal direction) an antibody variable domain derived from said variable region of the light chain locus, a CL domain, an optional linker and an epitope binding moiety, wherein the variable domain and the epitope binding moiety specifically bind respective first and second epitopes (which can be any epitopes as defined herein).

Examples of Epitope Binding Domains

In an example, the or each epitope binding moiety or domain is selected from the group consisting of an antibody variable domain (eg, a VL or a VH, an antibody single variable domain (domain antibody or dAb), a camelid VHH antibody single variable domain, a shark immunoglobulin single variable domain (NARV), a Nanobody™ or a camelised VH single variable domain); a T-cell receptor binding domain; an immunoglobulin superfamily domain; an agnathan variable lymphocyte receptor (J Immunol; 2010 Aug. 1; 185(3):1367-74; "Alternative adaptive immunity in jawless vertebrates; Herrin B R & Cooper M D.); a fibronectin domain (eg, an Adnectin™); an antibody constant domain (eg, a CH3 domain, eg, a CH2 and/or CH3 of an Fcab™) wherein the constant domain is not a functional CH1 domain (defined as a CH1 domain that can associate with a light chain); an scFv; an (scFv)$_2$; an sc-diabody; an scFab; a centyrin and an epitope binding domain derived from a scaffold selected from CTLA-4 (Evibody™); a lipocalin domain; Protein A such as Z-domain of Protein A (eg, an Affibody™ or SpA); an A-domain (eg, an Avimer™ or Maxibody™); a heat shock protein (such as and epitope binding domain derived from GroEI and GroES); a transferrin domain (eg, a trans-body); ankyrin repeat protein (eg, a DARPin™); peptide aptamer; C-type lectin domain (eg, Tetranectin™); human γ-crystallin or human ubiquitin (an affilin); a PDZ domain; scorpion toxin; and a kunitz type domain of a human protease inhibitor.

Further sources of epitope binding moieties are variable domains and VH/VL pairs of antibodies disclosed in WO2007024715 at page 40, line 23 to page 43, line 23. This specific disclosure is incorporated herein by reference as though explicitly written herein to provide basis for epitope binding moieties for use in the present invention and for possible inclusion in claims herein.

A "domain" is a folded protein structure which has tertiary structure independent of the rest of the protein. Generally, domains are responsible for discrete functional properties of proteins and in many cases may be added, removed or transferred to other proteins without loss of function of the remainder of the protein and/or of the domain. A "single antibody variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

The phrase "immunoglobulin single variable domain" refers to an antibody variable domain (VH, VHH, VL) that specifically binds an antigen or epitope independently of a different V region or domain. An immunoglobulin single variable domain can be present in a format (e.g., homo- or hetero-multimer) with other, different variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" which is capable of binding to an antigen as the term is used herein. An immunoglobulin single variable domain may be a human antibody variable domain, but also includes single antibody variable domains from other species such as rodent (for example, as disclosed in WO 00/29004), nurse shark and Camelid VHH immunoglobulin single variable domains. Camelid VHH sre immunoglobulin single variable domain polypeptides that are derived from species including camel, llama, alpaca, dromedary, and guanaco, which produce heavy chain antibodies naturally devoid of light chains. Such VHH domains may be humanised according to standard techniques available in the art, and such domains are still considered to be "domain antibodies" according to the invention. As used herein "VH includes camelid VHH domains. NARV are another type of immunoglobulin single variable domain which were identified in cartilaginous fish including the nurse shark. These domains are also known as Novel Antigen Receptor variable region (commonly abbreviated to V(NAR) or NARV). For further details see Mol. Immunol. 44, 656-665 (2006) and US20050043519A.

CTLA-4 (Cytotoxic T Lymphocyte-associated Antigen 4) is a CD28-family receptor expressed on mainly CD4+ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies. For further details see Journal of Immunological Methods 248 (1-2), 31-45 (2001)

Lipocalins are a family of extracellular proteins which transport small hydrophobic molecules such as steroids, bilins, retinoids and lipids. They have a rigid β-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633 An affibody is a scaffold derived from Protein A of *Staphylococcus aureus* which can be engineered to bind to antigen. The domain consists of a three-helical bundle of approximately 58 amino acids. Libraries have been generated by randomisation of surface residues. For further details see Protein Eng. Des. Sel. 17, 455-462 (2004) and EP1641818A1.

Avimers™ are multidomain proteins derived from the A-domain scaffold family. The native domains of approximately 35 amino acids adopt a defined disulphide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007).

A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem 274, 24066-24073 (1999).

Designed Ankyrin Repeat Proteins (DARPins™) are derived from ankyrin which is a family of proteins that mediate attachment of integral membrane proteins to the cytoskeleton. A single ankyrin repeat is a33 residue motif consisting of two α-helices and a β-turn. They can be engineered to bind different target antigens by randomising residues in the first α-helix and a β-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1.

Fibronectin is a scaffold which can be engineered to bind to antigen. Adnectins™ consist of a backbone of the natural amino acid sequence of the 10th domain of the 15 repeating units of human fibronectin type III (FN3). Three loops at one end of the β-sandwich can be engineered to enable an Adnectin to specifically recognize a therapeutic target of interest. For further details see Protein Eng. Des. Sel. 18, 435-444 (2005), US20080139791, WO2005056764 and US6818418B1.

Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005).

Microbodies are derived from naturally occurring microproteins of 25-50 amino acids in length which contain 3-4 cysteine bridges—examples of microproteins include KalataBI and conotoxin and knottins. The microproteins have a loop which can be engineered to include upto 25 amino acids without affecting the overall fold of the microprotein. For further details of engineered knottin domains, see WO2008098796.

Other epitope binding moieties and domains include proteins which have been used as a scaffold to engineer different target antigen binding properties include human γ-crystallin and human ubiquitin (affilins), kunitz type domains of human protease inhibitors, PDZ-domains of the Ras-binding protein AF-6, scorpion toxins (charybdotoxin), C-type lectin domain (tetranectins) are reviewed in Chapter 7—Non-Antibody Scaffolds from Handbook of Therapeutic Antibodies (2007, edited by Stefan Dubel) and Protein Science 15:14-27 (2006). Epitope binding moieties and domains of the present invention could be derived from any of these alternative protein domains.

In one embodiment of the invention a or each Epitope binding moiety, domain or antigen-binding site binds to antigen or second epitope with a KD of 1 mM, for example a KD of 10 nM, 1 nM, 500 pM, 200 pM, 100 pM or 10 pM or less (ie, better affinity) to each antigen as measured by Biacore™ or Proteon™, such as the Biacore™ method as described in method 4 or 5 of WO2010136485 or as described elsewhere herein.

In one embodiment of the invention a or each variable domain, variable domain pair or antigen-binding site at the N-terminus of a polypeptide, chain or antibody of the invention binds to antigen or first epitope with a KD of 1 mM, for example a KD of 10 nM, 1 nM, 500 pM, 200 pM, 100 pM or 10 pM or less (ie, better affinity) to each antigen as measured by Biacore™ or Proteon™, such as the Biacore™ method as described in method 4 or 5 of WO2010136485 or as described elsewhere herein.

In an example of the vertebrate, cell polypeptide, dimer or antibody of the present invention, the or each N-terminal variable domain or 5'-terminal variable region is a human variable domain or region.

In an example of the vertebrate, cell polypeptide, dimer or antibody of the invention, each constant region or domain is an endogenous non-human vertebrate constant region or domain.

The invention provides a non-human vertebrate (eg, a mouse or a rat), wherein the vertebrate comprises lymphocytic cells, each cell genome comprising an antibody heavy chain locus comprising (in 5' to 3' direction) a rearranged or unrearranged variable region and a mu constant region comprising a nucleotide sequence encoding an optional linker and a predetermined epitope binding moiety, wherein the vertebrate expresses multivalent polypeptide chains comprising (in N- to C-terminal direction) an antibody variable domain derived from said variable region of the heavy chain locus, an optional linker and an epitope binding moiety, wherein the variable domain and the epitope binding moiety specifically bind respective first and second epitopes. This is useful for producing mu-type multivalent (eg, multispecific, eg, bispecific) heavy chains and antibodies.

The invention provides a non-human vertebrate cell (eg, a mouse cell or a rat cell), wherein the cell genome comprises an antibody heavy chain locus comprising (in 5' to 3' direction) a rearranged or unrearranged variable region and a mu constant region comprising a nucleotide sequence encoding an optional linker and a predetermined epitope binding moiety, wherein the cell expresses multivalent polypeptide chains comprising (in N- to C-terminal direction) an antibody variable domain derived from said variable region of the heavy chain locus, an optional linker and an epitope binding moiety, wherein the variable domain and the epitope binding moiety specifically bind respective first and second epitopes. This is useful for producing mu-type multivalent (eg, multispecific, eg, bispecific) heavy chains and antibodies.

The invention provides a non-human (eg, rat or mouse) vertebrate or cell that expresses multivalent, multispecifc heavy chains (or dimers thereof) comprising the structure V-L-E or V-L-E-L (eg, V-L-E-Fc or V-L-E-L-Fc), where V is an N-terminal antibody variable domain, L is an optional linker and E is an epitope binding moiety, wherein V and E specifically bind respective first and second antigens, wherein the antigens are different. Optionally, V is a human variable domain.

Heavy Chain-Only Antibodies & Loci

As explained above and as exemplified below, the invention relates also to the improved production of heavy chain antibodies (H2 antibodies) in vivo.

Thus, the invention provides a non-human vertebrate (eg, a mouse or a rat), wherein (a) the vertebrate expresses IgM antibodies comprising heavy and light chains encoded by antibody heavy and light chain loci respectively;

(b) the vertebrate is capable of expressing non-mu (eg, IgG) antibodies, each non-mu antibody heavy chain lacking a functional CH1 domain; and (c) the IgM antibodies are expressed by lymphocytic cells (eg, immature B-cells), each cell comprising a functional light chain locus for expressing light chains of IgM antibodies expressed by the cell; and wherein (d) the non-mu antibodies are expressed by lymphocytic cells (eg, mature B-cells, plasmablasts or plasma cells), each cell lacking a functional light chain locus wherein non-mu antibodies are expressed by the cell substantially in the absence of light chain expression.

Optionally in (a) each heavy chain comprises a CH1 domain.

In an example, in (b) expression of the non-mu antibodies is following immunisation with a predetermined antigen and isotype switching.

The invention also provides a non-human vertebrate (eg, a mouse or a rat), eg, a vertebrate according to the embodiment immediately above, wherein the vertebrate comprises lymphocytic cells whose genomes comprise
(i) an antibody heavy chain locus comprising (in 5' to 3' direction) a rearranged or unrearranged variable region, a first switch (eg, a S-mu, eg, an endogenous S-mu), a mu constant region (eg, comprising a CH1 gene segment), a second switch (eg, a S-gamma, eg, an endogenous S-gamma) and a non-mu (eg, gamma) constant region lacking a CH1 gene segment;
(ii) a functional antibody light chain locus for expressing light chains (following VJ rearrangement);
wherein the cells can express IgM antibodies comprising IgM-type heavy chains and light chains, (optionally each heavy chain comprising a CH1 domain);
wherein the heavy chain locus of each cell is capable of undergoing isotype switching to produce non-mu (eg, IgG) antibodies comprising one or more non-mu-type (eg, IgG-type) heavy chains in the absence of light chains, each heavy chain lacking a CH1 domain; and
(iii) means for turning off light chain expression, wherein functional light chains are not expressed after isotype switching to said non-mu-type antibodies.

Similarly, the invention relates to cells. Thus, there is provided a non-human vertebrate cell (eg, a mouse cell or a rat cell, eg, a lymphocytic cell or other cell defined herein), wherein the cell genome comprises
(i) a functional antibody light chain locus for expressing light chains;
(ii) an antibody heavy chain locus comprising (in 5' to 3' direction) a rearranged or unrearranged variable region, a first switch (eg, a S-mu, eg, an endogenous S-mu), a mu constant region (eg, comprising a CH1 gene segment), a second switch (eg, a S-gamma, eg, an endogenous S-gamma) and a non-mu (eg, gamma) constant region lacking a CH1 gene segment for expressing IgM antibodies comprising IgM-type heavy chains and light chains, (optionally each heavy chain comprising a CH1 domain); and for IgM to non-mu (eg, IgG) isotype switching to produce non-mu (eg, IgG) antibodies comprising one or more non-mu-type heavy chains in the absence of light chains, each heavy chain lacking a CH1 domain; and
(iii) means for turning off light chain expression, wherein functional light chains are not expressed after isotype switching to said non-mu-type antibodies.

In an example, of the vertebrate or cell, the means for turning off light chain expression comprises a nucleotide sequence (eg, a light chain variable region, J region and/or a CL region of the light chain locus) that is essential for functional light chain expression from said light chain locus, wherein the nucleotide sequence is functional in immature B-cells expressing IgM, but the nucleotide sequence is absent or substantially non-functional in mature B-cells expressing said non-mu-type antibodies.

For example, all or substantially all of each light chain locus is deleted in the vertebrate. For example, the kappa (or kappa and lambda) light chain loci are rendered non-functional by deleting the light chain constant gene segments and/or the J region of each locus. Deletion can be performed using stage-specific recombinase, for example, as described in the examples below. For example, the kappa (or kappa and lambda) light chain loci are rendered non-functional by deleting the light chain variable region (rearranged or unrearranged V-J) gene segments. In another example, the kappa (or kappa and lambda) light chain loci are rendered non-functional by insertion of an interfering sequence such as a neomycin resistance nucleotide sequence into the or each said light chain locus or by recombinase or transposase-mediated inversion of light chain loci gene segments (eg, constant region and/or J region segments). Inversion can inactivate loci, as discussed further in the Kymab Limited PCT application mentioned herein.

In one example, the nucleotide sequence is the light chain locus or a portion thereof, the sequence being flanked by first and second site-specific recombination elements (SSRE) and wherein the genome comprises one or more gene(s) that encodes a corresponding site-specific recombinase(s), wherein the gene is inactive in immature B-cells expressing IgM, but active to cut at the first and second SSREs and delete the light chain locus or portion from the genome or inactivate the locus in mature B-cells expressing said IgG-type antibodies.

Required genetic manipulations can be made in an ES cell, so that conditional light chain inactivation can be effected in subsequent differentiation states of progeny B-cells and corresponding vertebrates as exemplified below.

In an embodiment, kappa chain expression is turned off using this means. In an embodiment, lambda chain expression is turned off using this means. In an embodiment, kappa and lambda chain expression is turned off using this means. Where a mouse system is used, lambda chain expression is normally low (around 5%), so it may not be necessary to turn off lambda chain expression as long as kappa chain expression is turned off when isotype-switched chains are being expressed.

In an embodiment of the vertebrate or cell the means for turning off light chain expression comprises a nucleotide sequence comprising a regulatory element (eg, a promoter) for driving light chain expression from said light chain locus in immature B-cells expressing IgM, and wherein the regulatory element is substantially inactive or absent in mature B-cells expressing said non-mu-type antibodies.

In an embodiment of the vertebrate or cell the nucleotide sequence or regulatory element is flanked by (eg, 5' and 3' immediately upstream and downstream) first and second combination elements (eg, site-specific recombination elements or transposase elements, such as piggyBac LTRs) and wherein the genome comprises a gene(s) that encodes a corresponding recombinase(s) or transposase(s), wherein the gene is inactive in immature B-cells expressing IgM, but active to cut at the first and second recombination elements and inactivate the nucleotide sequence or regulatory element in mature B-cells expressing said non-mu-type antibodies. The cutting can lead to deletion, translocation and/or inversion of the nucleotide sequence or regulatory element to inactivate it.

Examples of site-specific recombination elements and recombinases are frt/flp, dre/rox and cre/lox or combinations of these. The first and second recombination elements can be different.

In an embodiment of the vertebrate or cell the regulatory element is induced in immature B-cells expressing IgM and/or repressed in mature B-cells expressing said non-mu-type antibodies.

In an embodiment of the vertebrate or cell the means for turning off light chain expression is another locus in the genome for expressing a polypeptide chain comprising a rearranged light chain variable domain, eg, a predetermined VL of known epitope binding specificity. This uses light chain allelic exclusion to switch off light chain expression. Similarly, in an alternative example, said another locus is a heavy chain locus as defined above, wherein following said isotype switching the heavy chain locus encodes an antibody chain comprising said rearranged light chain variable domain. Optionally, the antibody chain further comprises a second antibody variable domain; optionally wherein the light chain variable domain and said second antibody variable domain specifically bind respective first and second epitopes that are different.

In an embodiment of the vertebrate or cell the rearranged light chain variable domain is derived from said unrearranged variable region of the heavy chain locus as defined above (eg, a VL-Fc is produced), wherein the unrearranged variable region of the heavy chain locus comprises one or more light chain V gene segments 5' of one or more light chain J gene segments.

In an embodiment of the vertebrate or cell the antibody chain comprises (in 5' to 3' direction) a variable domain derived from said variable region of the heavy chain locus as defined above (eg, a VL-Fc is produced), an optional linker (eg, any linker defined herein) and said rearranged light chain variable domain.

In an embodiment of the vertebrate or cell the non-mu constant region comprises (in 5' to 3' direction) a nucleotide sequence encoding an optional linker and a predetermined epitope binding moiety (or a plurality of epitope binding domains, eg, two or three with optional linkers; eg, in place of a CH1 domain), wherein following isotype switching the vertebrate expresses multivalent (eg, bivalent, eg, bispecific) polypeptide chains comprising (in N- to C-terminal direction) an antibody variable domain derived from said variable region of the heavy chain locus, an optional linker and an epitope binding moiety, wherein the variable domain and the epitope binding moiety specifically bind respective first and second epitopes (eg, wherein the epitopes are different or the same).

For example, the polypeptide chains have the structure V-L-E, where V is antibody variable domain derived from said rearranged variable region of the heavy chain locus, L is the optional linker and E is the epitope binding domain), such as defined above.

In an embodiment of the vertebrate, the non-mu constant region comprises one or more non-mu constant region gene segments (eg, CH2 and CH3 gene segments) 3' of said epitope binding moiety, wherein following isotype switching the vertebrate expresses multivalent polypeptide chains each comprising (in N- to C-terminal direction) an antibody variable domain derived from said variable region of the heavy chain locus, an optional linker, an epitope binding moiety and said one or more non-mu constant region gene segments.

In an embodiment of the vertebrate or cell, a poly(A) site is 3' (eg, immediately 3') of the nucleotide sequence encoding the epitope binding moiety, wherein following isotype switching the vertebrate expresses multivalent polypeptide chains having or consisting of (in N- to C-terminal direction) the structure V-X-L-E, where V is an antibody variable domain derived from said variable region of the heavy chain locus, X is absent an antibody hinge region or a polypeptide encoded by the gamma constant region, L is the optional linker and E is the epitope binding moiety; optionally wherein the vertebrate expresses V-X-L-E or V-L-E dimers.

For example, the poly(A) site is provided together with a stop codon to terminate transcription.

For example, the non-mu constant region is a gamma-type CH2-CH3. Thus, in one example a bispecific chain is expressed having the structure V-CH2-CH3-L-E, and this may for example be produced as a dimer (in this case, the mutual affinity of the CH2-CH3 of the chains may aid dimerisation). Dimers provide multiple binding sites for each epitope specificity, which is useful for providing avidity of binding. The provision of gamma CH2 and CH3 in embodiments of the invention also is useful for providing Fc activity, such as half-life extension, recirculation, ADCC or cell killing activity, in vivo. ADCC and cell killing may be useful for treating indications in the cancer, inflammatory disease, autoimmune disease and infectious disease fields.

"Antibody-dependent cell-mediated cytotoxicity" or ADCC" refers to a form of cytotoxicity in which secreted Ig bound onto Fc receptors (FcRs) present on certain cytotoxic cells (e.g., Natural Killer (NK) cells, neutrophils, and macrophages) that enables these cytotoxic effector cells to bind specifically to an antigen-bearing target cell and subsequently kill the target cell with cytotoxins. Ligand specific high-affinity IgG antibodies directed to the surface of target cells stimulate the cytotoxic cells and are required for such killing. Lysis of the target cell is extracellular, requires direct cell-to-cell contact, and does not involve complement.

The ability of any particular antibody to mediate lysis of the target cell by ADCC can be assayed. To assess ADCC activity, an antibody of interest is added to target cells displaying the target ligand in combination with immune effector cells, which may be activated by the antigen antibody complexes resulting in cytolysis of the target cell. Cytolysis is generally detected by the release of label (e.g., radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al, 1985, 19:21 1; Bruggemann et al, 1987, J Exp Med 166: 1351; Wilkinson et al, 2001, J Immunol Methods 258: 183; Patel et al, 1995 J Immunol Methods 184:29 (each of which is incorporated by reference). Alternatively, or additionally, ADCC activity of the antibody of interest may be assessed in vivo, e.g., in an animal model, such as that disclosed in Clynes et al, 1998, PNAS USA 95:652, the contents of which are incorporated by reference in its entirety.

"Complement-directed cytotoxicity" or CDC refers to the form of cytotoxicity in which the complement cascade is activated by the complement component C1q binding to antibody Fc.

The term "Fc" as used herein refer to the protein comprising (in N- to C-terminal direction) an immunoglobulin CH2 and CH3 domain. The CH2 and CH3 domains can form at least a part of the constant region of an antibody or heavy chain.

In an example, a poly(A) site is 3' of the nucleotide sequence encoding the one or more non-mu constant region gene segments, wherein following isotype switching the vertebrate expresses multivalent polypeptide chains having or consisting of (in N- to C-terminal direction) the structure V-X-L-E-L-C, where V is an antibody variable domain derived from said variable region of the heavy chain locus, X is absent an antibody hinge region or a polypeptide encoded by the non-mu constant region, L is the optional linker, E is the epitope binding moiety and $C_n$ is the one or more non-mu constant region gene segments (eg, gamma Fc); optionally wherein the vertebrate expresses V-X-L-E-L-C or V-L-E-L-C dimers.

In an example, the non-mu constant region is a gamma-type CH2, CH3 or CH2-CH3. Thus, in one example a bispecific chain is expressed having the structure V-CH2-L-E-CH3, and this may for example be produced as a dimer (in this case, the mutual affinity of the CH2 and CH3 between the chains may aid dimerisation). Dimers provide multiple binding sites for each antigen specificity, which is useful for providing avidity of binding.

In an example of the vertebrate or cell, the or each epitope binding moiety is any such moiety disclosed herein, for example it is selected from the group consisting of an antibody variable domain (eg, a VL or a VH, an antibody single variable domain (domain antibody or dAb), a camelid VHH antibody single variable domain, a shark immunoglobulin single variable domain (NARV), a Nanobody™ or a camelised VH single variable domain); a T-cell receptor binding domain; an immunoglobulin superfamily domain; an agnathan variable lymphocyte receptor; a fibronectin domain (eg, an Adnectin™); an antibody constant domain (eg, a CH3 domain, eg, a CH2 and/or CH3 of an Fcab™) wherein the constant domain is not a functional CH1 domain; an scFv; an (scFv)$_2$; an sc-diabody; an scFab; a centyrin and an epitope binding domain derived from a scaffold selected from CTLA-4 (Evibody™); a lipocalin domain; Protein A such as Z-domain of Protein A (eg, an Affibody™ or SpA); an A-domain (eg, an Avimer™ or Maxibody™); a heat shock protein (such as and epitope binding domain derived from GroEI and GroES); a transferrin domain (eg, a trans-body); ankyrin repeat protein (eg, a DARPin™); peptide aptamer; C-type lectin domain (eg, Tetranectin™); human γ-crystallin or human ubiquitin (an affilin); a PDZ domain; scorpion toxin; and a kunitz type domain of a human protease inhibitor.

In an example of the vertebrate or cell, the vertebrate comprises lymphocytic cells that have undergone isotype switching to produce said non-mu-type (eg, IgG-type) antibodies; or the cell has undergone isotype switching to produce said non-mu-type (eg, IgG-type) antibodies.

In an example of the vertebrate or cell, the vertebrate has been immunised with a predetermined antigen, the vertebrate expressing non-mu-type (eg, IgG-type) antibodies lacking a CH1 domain and comprising a variable domain that specifically binds the predetermined antigen; or the cell is isolated from such a vertebrate.

In an example of the vertebrate or cell, the or each N-terminal variable domain or 5'-terminal variable region is a human variable domain or region. Human variable domains are variable domains that are encoded by RNA that is derived from a rearranged variable region DNA sequence, wherein the rearrangement is a rearrangement of a human V gene segment with a human J gene segment (and also optionally with a human D gene segment if the rearranged variable region is a VH region). Thus, for example, the RNA is derived from a rearranged variable region DNA sequence when it is encoded by such a DNA sequence, optionally with mutation naturally seen in vivo during antibody production.

In an example of the vertebrate or cell, the or each N-terminal variable domain or 5'-terminal variable region is a Camelid, camelised human; mouse; rat; rodent; rabbit; chicken; or bovine variable domain or region.

In an example of the polypeptide, chain, antibody, vertebrate or cell, each constant region or domain is an endogenous non-human vertebrate constant region or domain. In an example of the polypeptide, chain, antibody, vertebrate or cell, each non-mu constant region or domain is a human non-human vertebrate constant region or domain.

In an example of the vertebrate or cell, the lymphocytic cells comprise B-cells expressing said non-mu antibodies or bivalent polypeptide chains, wherein the non-mu antibodies or multivalent chains are specific for an antigen that is foreign to said non-human vertebrate (eg, a human antigen or an antigen of an infectious disease pathogen); or wherein said non-human vertebrate cell is such a B-cell.
The Invention Also Provides B-Cells, Hybridomas and Products as Follows.

An immortalised B-cell or hybridoma produced from a B-cell recited above.

A non-mu-type (eg, IgG-type) antibody or multivalent chain isolated from a B-cell or hybridoma recited above; or a humanised version thereof wherein non-human constant domains have been replaced with human constant domains. For example, all of the non-human constant domains have been deleted and optionally replaced with one or more human constant domains (eg, corresponding to the deleted non-human domains). Thus, in one embodiment, a non-human (eg, mouse) Fc is replaced with a human Fc.
Methods The invention provides improved methods for the in vivo production of isotype-switched non-mu H2 antibodies and heavy chains as follows.

Thus, the invention provides a method of producing polypeptide chains comprising somatically hypermutated variable regions in a non-human vertebrate (eg, a mouse or a rat), the method comprising
(a) expressing in the vertebrate IgM antibodies in immature B-cells, wherein the antibodies comprise heavy and light chains expressed from heavy and light chain loci respectively, (optionally the heavy chains comprising CH1 domains);
(b) immunising the vertebrate with a predetermined epitope and obtaining isotype switching in at least some of the heavy chain loci and expression of non-mu (eg, IgG) antibodies that have undergone somatic hypermutation, wherein the antibodies comprise heavy chains that lack a CH1 domain and comprise variable regions that specifically bind the antigen; and
(c) selecting one or more polypeptide chains from said immunised vertebrate by selection for variable regions that bind said epitope, wherein each selected chain comprises a somatically hypermutated variable region that specifically binds the epitope; and
the method further comprising expressing the non-mu antibodies in step (b) in the absence of light chain expression.

For example, in step (c) the chains are selected from serum, blood, spleen cells or tissue, lymph node cells or tissue or secondary lymphoid organ cells or tissue.

Optionally the polypeptide chains comprise one or more heavy chain constant domains and in this sense, the chains can be regarded as heavy chains. In another embodiment, the chains are chains comprising no constant domains, eg, wherein the chain is a V-L-E polypeptide as described herein.

The method optionally comprises isolating from the immunised vertebrate a B-cell that expresses a polypeptide chain comprising a somatically hypermutated variable region that binds the epitope; and optionally immortalising the cell or producing a hybridoma therefrom.

The method optionally comprises obtaining a nucleotide sequence that encodes a selected polypeptide chain comprising a somatically hypermutated variable region that binds the epitope, and introducing the nucleotide sequence into a expression vector for expression of the polypeptide chain or a humanised version thereof; optionally wherein vector is in a host cell (eg, an E. coli, yeast, Picchia, Saccharomyces, CHO or HEK293 cell).

In an embodiment of the method, the vertebrate is according to any aspect of the invention herein.

The invention provides a multispecific polypeptide chain obtained by the method or a derivative thereof that specifically binds the epitope.

Stage-Switchable Light Chain Locus

As explained herein and in the examples below, it is desirable to provide conditional, or stage-specific, light chain expression in the vertebrates and cells of the invention. This is useful, for example, when expressing non-mu heavy chains or antibodies that specifically bind a predetermined epitope or antigen.

Thus, the invention provides a non-human vertebrate (eg, a mouse or a rat), optionally according to any other aspect of the invention, whose genome comprises an antibody heavy chain locus and an antibody light chain locus,
(a) the light chain locus comprising (in 5' to 3' direction) a light chain variable region and a constant region (eg, a Cκ or Cλ) for expressing light chains in lymphocytic cells expressing IgM antibodies (eg, in immature B-cells); and
(b) means for turning off light chain expression in lymphocytic cells expressing non-mu (eg, IgG) antibodies.

For example, the light chain variable region comprises one or more human Vκ gene segments and one or more human Jκ gene segments; or one or more human Vλ gene segments and one or more human Jλ gene segments.

A non-human vertebrate cell (eg, a mouse cell or a rat cell) or hybridoma, optionally according to any other aspect of the invention, whose genome comprises an antibody heavy chain locus and an antibody light chain locus, the light chain locus comprising
(a) (in 5' to 3' direction) a light chain variable region and a constant region (eg, a Cκ or Cλ) for expressing light chains in lymphocytic cells expressing IgM antibodies (eg, in immature B-cells); and
(b) means for turning off light chain expression in lymphocytic cells expressing non-mu (eg, IgG) antibodies.

For example, the light chain variable region comprises one or more human Vκ gene segments and one or more human Jκ gene segments; or one or more human Vλ gene segments and one or more human Jλ gene segments.

Examples of means for turning off light chain expression are provided above and in the examples.

Each heavy and light chain locus is, in a preferred embodiment, a heavy chain or light chain locus of the endogenous non-human vertebrate genome, ie, it is in the germline location of a heavy or light chain locus of said type of vertebrate or cell. In this example, therefore, a locus of the invention can be constructed by inserting exogenous DNA into the endogenous (ie, non-human vertebrate) heavy or light chain locus. In another embodiment, a locus of the invention is synthetically constructed elsewhere in the genome (ie, not in the endogenous heavy chain locus location) and may be on a different chromosome to that chromosome harbouring the heavy chain locus in a wild-type vertebrate or cell. For example, the locus of the invention is constructed at the Rosa26 locus.

Stretches of human DNA can be inserted in one piece or in serial insertions into the genome of a non-human vertebrate or cell (eg, ES cell) genome. For example, a plurality of bacterial artificial chromosomes (BACs) can be constructed using standard recombineering techniques which between them comprise the entire sequence of human constant region DNA to be inserted, each BAC containing a portion of that stretch of DNA. By using serial insertions from serial BACs (eg, using standard homologous recombination (eg, see the Regeneron and Ablexis PCTs disclosed herein) or serial recombinase mediated cassette exchange—sRMCE—(eg, see the Kymab Limited PCTs disclosed herein) the skilled person can build up transgenic loci in the genome. When an ES cell is manipulated in this way, the ES cell can be used, as is standard, to implant in a donor blastocyst, which is then implanted into a foster mother. With germline transmission and any necessary subsequent breeding and crossing (again as is conventional), the skilled person can arrive at progeny vertebrates and cells bearing a gene locus of the invention. The gene locus may be present in a homozygous state (eg, a gene locus of the invention at each heavy chain allele) or heterozygous state (eg, with the second allele being an inactivated endogenous heavy chain so that only heavy chain expression from the first allele—bearing the gene locus of the invention—provides expression of heavy chains). In an alternative, different gene loci of the invention are provided at the first and second alleles of the heavy chain locus in the genome, so that different combinations of human isotype switched heavy chains can be expressed by the combination of loci.

In an embodiment, the genome also comprises transgenic light chain loci that express human light chain variable regions and endogenous light chain expression is substantially inactive; also endogenous heavy chain expression is substantially inactive. This embodiment advantageously provides a genome for predictable expression of only fully human heavy chain and light chain N-terminal variable regions, from which pool of antibodies the skilled person can select (eg, after immunisation with target antigen) non-mu type antibodies (eg, gamma type) that have undergone mutation and maturation and selection by the in vivo machinery of the vertebrate or cell.

By accommodating VH, D and JH recombination and initial expression in the context of an endogenous IgM, this advantageously enables endogenous RAG-1 and RAG-2 to be efficiently employed, as well as harnessing endogenous control, mutation and signalling involved in antibody and B-cell development. The invention subsequently enables switching to a human non-mu C region, which enables one to produce product heavy chains which have been affinity matured by somatic hypermutation effected by endogenous activation induced cytidine deaminase (AID). Those rearranged variable regions that still work well (eg, good expression, affinity, biophysical characteristics) (eg, in the context of the epitope binding moiety) are selected in vivo by the mouse and amplified following immunisation with a predetermined antigen. This retains the advantage of harnessing endogenous antibody and B-cell production and control, together with affinity maturation and in vivo amplification of selected B-cells expressing desirable antibodies/heavy chains in a way that harnesses the mouse (or other non-vertebrate) system to select for good, fully-human antibodies and heavy chains. This is superior to the prior art method of engineering in vitro, where selection for good biophysical characteristics, expression, affinity etc is not factored in (thus often resulting in a down-grading of these in the prior art) and which adds multi-step procedures following initial production in vivo.

In one embodiment, the vertebrate or cell of the invention does not express endogenous antibody heavy chains of said non-mu isotype. For example, this is effected using standard methods to delete or inactivate endogenous heavy chain variable regions. Thus, the skilled person will know that heavy chains (and antibodies comprising these) of the predetermined human non-mu isotype (eg, IgG antibodies) produced by the vertebrate or cell will always comprise human variable regions when human V, D and J gene segments (or a human rearranged VDJ) are included in the heavy chain locus.

In one embodiment, in the vertebrate or cell of the invention the human non-mu constant region is a gamma constant region (eg, gamma-1, -2, 3 or -4). Instead of a gamma constant region, the constant region can be a delta, alpha (eg, alpha-1 or -2) or epsilon constant region. Thus, the invention allows the skilled person to tailor the genome of the vertebrate or cell according to desired constant region functionality of resultant antibodies and heavy chains.

In one embodiment, in the vertebrate or cell of the invention the gamma constant region comprises CH2 and CH3 gene segments for encoding an antibody Fc region. In an example, the constant region also comprises a CH1 gene segment. This is useful for producing heavy chains that are to form part of 4-chain antibodies (classic H2L2 antibodies). In another example, the constant region lacks a CH1 gene segment. This is useful for producing heavy chains that are to form part of heavy-chain only antibodies (H2 antibodies) which are devoid of light chains.

In one embodiment, in the vertebrate or cell of the invention the genome comprises a light chain locus comprising human VL and JL gene segments upstream of a constant region for expression of light chains comprising human variable regions; optionally wherein the constant region is a human light chain constant region. For example, the genome comprises a light chain locus comprising human Vκ and Jκ gene segments upstream of an endogenous or human kappa constant region in the endogenous kappa locus for expression of kappa light chains comprising human variable regions. In this example, where the vertebrate is a mouse, it may not be necessary to humanise the lambda locus, since lambda chain expression in mice is relatively low. Optionally, the lambda locus is inactive and/or comprises human Vλ and Jλ upstream of an endogenous or human lambda constant region. Optionally, endogenous kappa chain expression is inactive.

For example, the vertebrate or cell does not substantially express endogenous light chains following isotype switching.

Inactivation of endogenous antibody, antibody chain or gene segment usage is, for example, substantially complete inactivation or prevention (substantially 100%, ie, essentially none (eg, less than 10, 5, 4, 3, 2, 1 or 0.5%) of the endogenous antibody chain etc (eg, no endogenous heavy chains etc) is expressed). This can be determined, for example, at the antibody chain (protein) level by assessing the antibody repertoire produced by the non-human vertebrate or cell or at the nucleotide level by assessing mRNA transcripts of antibody gene loci, eg, using RACE. In an embodiment, inactivation is more than 50% (ie, 50% or less of the antibodies or transcripts are of an endogenous antibody chain), 60%, 70%, 80%, 85%, 90%, 95%, 96%, 97%, 98% or 99%. For example, in an embodiment, endogenous heavy chain expression is substantially inactivated such that no more than 85%, 90%, 95%, 96%, 97%, 98% or 99% of the heavy chain repertoire of the vertebrate is provided by endogenous heavy chains. For example, endogenous heavy chain expression is substantially inactivated such that substantially none of the heavy chain repertoire of the vertebrate is provided by endogenous heavy chains. For example, in an embodiment, endogenous kappa chain expression is substantially inactivated such that no more than 85%, 90%, 95%, 96%, 97%, 98% or 99% of the kappa chain repertoire of the vertebrate is provided by endogenous kappa chains. For example, endogenous kappa chain expression is substantially inactivated such that substantially none of the kappa chain repertoire of the vertebrate is provided by endogenous kappa chains. For example, in an embodiment, endogenous lambda chain expression is substantially inactivated such that no more than 85%, 90%, 95%, 96%, 97%, 98% or 99% of the lambda chain repertoire of the vertebrate is provided by endogenous lambda chains. For example, endogenous lambda chain expression is substantially inactivated such that substantially none of the lambda chain repertoire of the vertebrate is provided by endogenous lambda chains.

In one embodiment, in the vertebrate or cell of the invention the gamma constant region does not comprise a CH1 gene segment. In this embodiment, in an example, light chain expression is inactive when the non-mu heavy chains are expressed. This is useful for producing heavy-chain only antibodies of the non-mu isotype.

In an example, the variable region and/or mu constant region are in human and endogenous germline configurations respectively. The term "germline configuration" refers to a germline genomic configuration. For example, human immunoglobulin gene segments present in the gene locus of the invention are in a germline configuration when the relative order of the human gene segments is the same as the order of corresponding gene segments in a human germline genome. For example, when the gene locus of the invention comprises hypothetical human immunoglobulin constant region gene segments A, B and C, these would be provided in this order (5' to 3' in the locus) when the corresponding gene segments of a human germline genome comprises the arrangement 5'-A-B-C-3'; and optionally the inter-gene segments too are in germline configuration (ie, the nucleotide sequence from A to C corresponds to a stretch of contiguous nucleotide sequence from A to C in a human germline genome). Available databases and sources of human germline sequence are discussed below. Thus, in an example, when elements of a human immunoglobulin locus (eg, gene segments, enhancers or other regulatory elements) are provided in a gene locus according to the invention, the human Ig locus elements are in germline configuration when the relative order of the elements is the same as the order of corresponding elements in a human germline genome and human sequences between the elements are included, these corresponding to such sequences between corresponding elements in the human germline genome. Thus, in a hypothetical example the transgenic locus comprises human elements in the arrangement 5'-A-S1-B-S2-C-S3-3', wherein A, B and C are human immunoglobulin gene segments and S1-S3 are human inter-gene segment sequences, wherein the corresponding arrangement 5'-A-S1-B-S2-C-S3-3' is present in a human germline genome. For example, this can be achieved by providing in a transgenic immunoglobulin locus of the invention a DNA insert corresponding to the DNA sequence from A to C in a human germline genome (or the insert comprising the DNA sequence from A to C). The arrangements in human germline genomes and immunoglobulin loci are known in the art (eg, see the IMGT, Kabat and other antibody resources).

In an embodiment, VH gene segment repertoire of the heavy chain locus (or each heavy chain locus) is a substantially complete repertoire of functional human VH gene segments; optionally providing at least 6 different human JH gene segments, 27 different human D segments and at least 40 different human VH gene segments.

In an embodiment, VH gene segment repertoire of the heavy chain locus (or each heavy chain locus) is at least 20, 25, 30, 35 or 40 different human VH gene segments.

In an embodiment, the method of the invention comprises the step of selecting one or more heavy chains or antibodies on the basis of a desired antibody or heavy chain characteristic (eg, binding affinity for target antigen), wherein the selected antibodies comprise non-mu heavy chains, or the selected heavy chains are non-mu chains.

Methods of Antibody/Chain Selection

An aspect provides a method of isolating an antibody, heavy chain or nucleotide sequence encoding said antibody, the method comprising (a) immunising (see e.g. Harlow, E. & Lane, D. 1998, 5$^{th}$ edition, Antibodies: A Laboratory Manual, Cold Spring Harbor Lab. Press, Plainview, N.Y.; and Pasqualini and Arap, Proceedings of the National Academy of Sciences (2004) 101:257-259) a vertebrate according to the invention with an antigen such that the vertebrate produces antibodies; and (b) isolating from the immunised vertebrate an antibody or heavy chain that specifically binds to said antigen and/or a nucleotide sequence encoding at least the heavy chain variable region of said antibody.

Suitably an immunogenic amount of the antigen is delivered in the method of the invention. The invention also relates to a method for detecting a target antigen comprising detecting an antibody or heavy chain produced as above or a derivative thereof with a secondary detection agent which recognises a portion of that antibody/chain.

Isolation of the antibody in step (b) can be carried out using conventional antibody selection techniques, eg, panning for antibodies against antigen that has been immobilised on a solid support, optionally with iterative rounds at increasing stringency, as will be readily apparent to the skilled person.

As a further optional step, after step (b) the amino acid sequence of the heavy chain variable region is mutated to improve affinity for binding to said antigen. Mutation can be generated by conventional techniques as will be readily apparent to the skilled person, eg, by error-prone PCR. Affinity can be determined by conventional techniques as will be readily apparent to the skilled person, eg, by surface plasmon resonance, eg, using Biacore™ or Proteon™.

Additionally or alternatively, as a further optional step, after step (b) the amino acid sequence of the heavy chain variable region is mutated to further improve one or more biophysical characteristics of the antibody, eg, one or more of melting temperature, solution state (monomer or dimer), stability and expression (eg, in CHO or *E coli*).

An aspect provides an antibody, chain or polypeptide of the invention, optionally for use in human medicine, eg, for treating and/or preventing a medical condition or disease in a human patient.

The invention provides a pharmaceutical composition comprising an antibody, chain or polypeptide of the invention or a copy or derivative thereof.

Optionally, the method comprises the step of isolating a B-cell from said immunised vertebrate, wherein the B-cell expresses said isolated antibody or heavy chain; and optionally immortalising the B-cell.

Optionally, the method comprises the step of isolating a nucleotide sequence from said immunised vertebrate or B-cell, wherein the nucleotide sequence encodes said isolated antibody or a heavy chain thereof.

The method provides a vector (optionally in a host cell) comprising the nucleotide sequence of the invention or a copy thereof, or a derivative thereof; optionally comprising up to 15, 10, 9, 8, 7, 6, 5, 4, 3, or 1 mutations. The derivative specifically binds target antigen.

The method provides a method of treating or preventing a medical condition or disease in a human associated or caused by one or more of said antigens eptiopes, the method comprising administering to the human the antigen-specific antibody or heavy chain obtained in the method or isolated from a vertebrate or cell of the invention.

The method provides the antigen-specific antibody or heavy chain obtained in the method or isolated from a vertebrate or cell of the invention for use in the treatment or prophylaxis of a medical condition or disease in a human associated or caused by said antigen.

The method provides the use of the antigen-specific antibody or heavy chain obtained in the method or isolated from a vertebrate or cell of the invention in the manufacture of a medicament for use in the treatment or prophylaxis of a medical condition or disease in a human associated or caused by said antigen.

As will be readily apparent to the skilled person, the operable connection of a human gene segment (eg, a V or J gene segment) upstream of a constant region in an Ig locus in any configuration of the invention enables the gene segment to be recombined and expressed in an immunoglobulin chain comprising sequence encoded by the constant region of the locus.

In one embodiment in any configuration of the invention, each vertebrate is a non-human mammal. In one embodiment in any configuration of the invention, the vertebrate is a mouse, rat, rabbit, Camelid (eg, a llama, alpaca or camel), chicken, lamprey or shark. For example, all vertebrates are of the same vertebrate species, eg, all mice or all rats.

In any configuration of the invention, the human gene regions or segments may be derived from the same individual or different individuals, or be synthetic (synthetically mutated human gene segments) or represent human consensus sequences.

Techniques for constructing non-human vertebrates and vertebrate cells whose genomes comprise a human immunoglobulin gene segments are well known in the art. For example, reference is made to WO2011004192, U.S. Pat. Nos. 7,501,552, 6,673,986, 6,130,364, WO2009076464 and U.S. Pat. No. 6,586,251, the disclosures of which are incorporated herein by reference in their entirety.

In one example, a non-human vertebrate of any configuration of the invention is able to generate a diversity of at least $1 \times 10^6$ different functional non-mu immunoglobulin sequence combinations.

Human variable regions are suitably inserted upstream of a non-human vertebrate mu constant region, the latter together with downstream human constant region(s) comprising all of the DNA required to encode the full constant region or a sufficient portion of the constant region to allow the formation of an effective non-mu antibody/heavy chain capable of specifically recognising a target antigen.

The endogenous mu non-human vertebrate constant region herein is optionally the endogenous host wild-type constant region located at the wild type locus, as appropriate for the heavy chain.

In one optional aspect where the vertebrate is a mouse, the insertion of human variable region DNA (V, D and J gene segments) is targeted to the region between the J4 exon and the endogenous Sμ locus in the mouse genome IgH locus, and in one aspect is inserted between coordinates 114,667,090 and 114,665,190, suitably at coordinate 114,667,091, after 114,667,090.

All nucleotide co-ordinates for the mouse are those corresponding to NCBI m37 for the mouse C57BL/6J strain, e.g. April 2007 ENSEMBL Release 55.37h, e.g. NCBI37 July 2007 (NCBI build 37) (e.g. UCSC version mm9 see www.genome.ucsc.edu and http://genome.ucsc.edu/FAQ/FAQreleases.html) unless otherwise specified. Human nucleotides coordinates are those corresponding to GRCh37 (e.g. UCSC version hg 19, http://genome.ucsc.edu/FAQ/FAQreleases.html), February 2009 ENSEMBL Release 55. or are those corresponding to NCBI36, Ensemble release 54 unless otherwise specified. Rat nucleotides are those corresponding to RGSC 3.4 Dec. 2004 ENSEMBL release 55.34w, or Baylor College of Medicine HGSC v3.4 Nov. 2004 (e.g., UCSC rn4, see www.genome.ucsc.edu and http://genome.ucsc.edu/FAQ/FAQreleases.html) unless otherwise specified.

Reference to location of a human variable region, constant region or a gene segment upstream or downstream of an endogenous mu constant region means that there is a suitable relative location of the antibody nucleotide elements to enable formation of mu and then non-mu heavy chains in vivo in the vertebrate. Thus, the inserted human DNA and endogenous constant region and any other endogenous sequences are in operable connection with one another for antibody or antibody chain production.

As a source of human and non-human antibody gene segment sequences, the skilled person will also be aware of the following available databases and resources (including updates thereof) the contents of which are incorporated herein by reference:

The Kabat Database (G. Johnson and T. T. Wu, 2002; World Wide Web (www) kabatdatabase.com). Created by E. A. Kabat and T. T. Wu in 1966, the Kabat database publishes aligned sequences of antibodies, T-cell receptors, major histocompatibility complex (MHC) class I and II molecules, and other proteins of immunological interest. A searchable interface is provided by the SeqhuntII tool, and a range of utilities is available for sequence alignment, sequence subgroup classification, and the generation of variability plots. See also Kabat, E. A., Wu, T. T., Perry, H., Gottesman, K., and Foeller, C. (1991) *Sequences of Proteins of Immunological Interest*, 5th ed., NIH Publication No. 91-3242, Bethesda, Md., which is incorporated herein by reference, in particular with reference to human gene segments for use in the present invention.

KabatMan (A. C. R. Martin, 2002; World Wide Web (www) bioinf.org.uk/abs/simkab.html). This is a web interface to make simple queries to the Kabat sequence database.

IMGT (the International ImMunoGeneTics Information System®; M.-P. Lefranc, 2002; World Wide Web (www) imgt.cines.fr). IMGT is an integrated information system that specializes in antibodies, T cell receptors, and MHC molecules of all vertebrate species. It provides a common portal to standardized data that include nucleotide and protein sequences, oligonucleotide primers, gene maps, genetic polymorphisms, specificities, and two-dimensional (2D) and three-dimensional (3D) structures. IMGT includes three sequence databases (IMGT/LIGM-DB, IMGT/MHC-DB, IMGT/PRIMERDB), one genome database (IMGT/GENE-DB), one 3D structure database (IMGT/3Dstructure-DB), and a range of web resources ("IMGT Marie-Paule page") and interactive tools.

V-BASE (I. M. Tomlinson, 2002; World Wide Web (www) mrc-cpe.cam.ac.uk/vbase). V-BASE is a comprehensive directory of all human antibody germline variable region sequences compiled from more than one thousand published sequences. It includes a version of the alignment software DNAPLOT (developed by Hans-Helmar Althaus and Werner Müller) that allows the assignment of rearranged antibody V genes to their closest germline gene segments.

Antibodies—Structure and Sequence (A. C. R. Martin, 2002; World Wide Web (www) bioinf.org.uk/abs). This page summarizes useful information on antibody structure and sequence. It provides a query interface to the Kabat antibody sequence data, general information on antibodies, crystal structures, and links to other antibody-related information. It also distributes an automated summary of all antibody structures deposited in the Protein Databank (PDB). Of particular interest is a thorough description and comparison of the various numbering schemes for antibody variable regions.

AAAAA (A Ho's Amazing Atlas of Antibody Anatomy; A. Honegger, 2001; World Wide Web (www) unizh.ch/~antibody). This resource includes tools for structural analysis, modeling, and engineering. It adopts a unifying scheme for comprehensive structural alignment of antibody and T-cell-receptor sequences, and includes Excel macros for antibody analysis and graphical representation.

WAM (Web Antibody Modeling; N. Whitelegg and A. R. Rees, 2001; World Wide Web (www) antibody.bath.ac.uk). Hosted by the Centre for Protein Analysis and Design at the University of Bath, United Kingdom. Based on the AbM package (formerly marketed by Oxford Molecular) to construct 3D models of antibody Fv sequences using a combination of established theoretical methods, this site also includes the latest antibody structural information.

Mike's Immunoglobulin Structure/Function Page (M. R. Clark, 2001; World Wide Web (www) path.cam.ac.uk/~mrc7/mikeimages.html) These pages provide educational materials on immunoglobulin structure and function, and are illustrated by many colour images, models, and animations. Additional information is available on antibody humanization and Mike Clark's Therapeutic Antibody Human Homology Project, which aims to correlate clinical efficacy and anti-immunoglobulin responses with variable region sequences of therapeutic antibodies.

The Antibody Resource Page (The Antibody Resource Page, 2000; World Wide Web (www) antibodyresource.com). This site describes itself as the "complete guide to antibody research and suppliers." Links to amino acid sequencing tools, nucleotide antibody sequencing tools, and hybridoma/cell-culture databases are provided.

Humanization bY Design (J. Saldanha, 2000; World Wide Web (www) people.cryst.bbk.ac.uk/~ubcg07s). This resource provides an overview on antibody humanization technology. The most useful feature is a searchable database (by sequence and text) of more than 40 published humanized antibodies including information on design issues, framework choice, framework back-mutations, and binding affinity of the humanized constructs.

See also Antibody Engineering Methods and Protocols, Ed. Benny K C Lo, *Methods in Molecular Biology*™, Human Press. Also at World Wide Web (www) blogsua.com/pdf/antibody-engineering-methods-and-protocolsantibody-engineering-methods-and-protocols.pdf Samples from which B-cells can be obtained include but are not limited to blood, serum, spleen, splenic tissue, bone marrow, lymph, lymph node, thymus, and appendix. Antibodies and immunoglobulin chains can be obtained from each of the previous-mentioned samples and also from the following non-limiting list of B-cells, ascites fluid, hybridomas, and cell cultures.

In one embodiment in any configuration of the invention, the genome of the vertebrate or cell has been modified to prevent or reduce the expression of fully-endogenous antibody or heavy chains. Examples of suitable techniques for doing this can be found in WO2011004192, U.S. Pat. Nos. 7,501,552, 6,673,986, 6,130,364, WO2009/076464, EP1399559 and U.S. Pat. No. 6,586,251, the disclosures of which are incorporated herein by reference. In one embodiment, the non-human vertebrate VDJ region of the endogenous heavy chain immunoglobulin locus, and optionally VJ region of the endogenous light chain immunoglobulin loci (lambda and/or kappa loci), have been inactivated. For example, all or part of the non-human vertebrate VDJ region is inactivated by inversion in the endogenous heavy chain immunoglobulin locus of the mammal, optionally with the inverted region being moved upstream or downstream of the endogenous Ig locus. For example, all or part of the non-human vertebrate VJ region is inactivated by inversion in the endogenous kappa chain immunoglobulin locus of the mammal, optionally with the inverted region being moved upstream or downstream of the endogenous Ig locus. For example, all or part of the non-human vertebrate VJ region is inactivated by inversion in the endogenous lambda chain immunoglobulin locus of the mammal, optionally with the inverted region being moved upstream or downstream of the endogenous Ig locus. In one embodiment the endogenous heavy chain locus is inactivated in this way as is one or both of the endogenous kappa and lambda loci.

Additionally or alternatively, the vertebrate has been generated in a genetic background which prevents the production of mature host B and T lymphocytes, optionally a RAG-1-deficient and/or RAG-2 deficient background. See U.S. Pat. No. 5,859,301 for techniques of generating RAG-1 deficient animals.

In one embodiment of any configuration of the vertebrate or cell of the invention the genome comprises an antibody light chain locus which comprises all or part of the human Igλ locus including at least one human Jλ region and at least one human Cλ region, optionally $C_\lambda 6$ and/or $C_\lambda 7$. Optionally, the light chain locus comprises a plurality of human Jλ regions, optionally two or more of $J_\lambda 1$, $J_\lambda 2$, $J_\lambda 6$ and $J_\lambda 7$, optionally all of $J_\lambda 1$, $J_\lambda 2$, $J_\lambda 6$ and $J_\lambda 7$. The human lambda immunoglobulin locus comprises a unique gene architecture composed of serial J-C clusters. In order to take advantage of this feature, the invention in optional aspects employs one or more such human J-C clusters. Thus, optionally the light chain locus comprises at least one human $J_\lambda$-$C_\lambda$ cluster, optionally at least $J_\lambda 7$-$C_\lambda 7$. The construction of such transgenes is facilitated by being able to use all or part of the human lambda locus such that the transgene comprises one or more J-C clusters in germline configuration, advantageously also including intervening sequences between clusters and/or between adjacent J and C regions in the human locus. This preserves any regulatory elements within the intervening sequences which may be involved in VJ and/or JC recombination and which may be recognised by endogenous AID (activation-induced deaminase).

An aspect provides a nucleotide sequence encoding the polypeptide, antibody, chain or derivative of the invention, optionally wherein the nucleotide sequence is part of a vector. Suitable vectors will be readily apparent to the skilled person, eg, a conventional antibody expression vector comprising the nucleotide sequence together in operable linkage with one or more expression control elements.

An aspect provides a pharmaceutical composition comprising the polypeptide, antibody, chain or derivative of the invention and a diluent, excipient or carrier, optionally wherein the composition is contained in an IV container (eg, and IV bag) or a container connected to an IV syringe.

An aspect provides the use of the polypeptide, antibody, chain or derivative of the invention in the manufacture of a medicament for the treatment and/or prophylaxis of a disease or condition in a human patient.

The skilled person will generally be familiar with standard cloning techniques and recombinant DNA technology—see e.g. Sambrook, J and Russell, D. (2001, 3'd edition) Molecular Cloning: A Laboratory Manual (Cold Spring Harbor Lab. Press, Plainview, N.Y.).

In a further aspect the invention relates to humanised antibodies and antibody heavy chains produced according to the present invention, and use of said antibodies in human medicine. The invention also relates to a pharmaceutical composition comprising such an antibody or heavy chain and a pharmaceutically acceptable carrier or other excipient.

Methods for the generation of both monoclonal and polyclonal antibodies are well known in the art, and the present invention relates to both polyclonal and monoclonal antibodies of fully humanised antibodies and heavy chains produced in response to antigen challenge in a vertebrate or cel according to the present invention.

In a further aspect, the invention relates to use of a non-human vertebrate of the present invention in the analysis of the likely effects of drugs and vaccines in the context of an antibody chain repertoire.

The invention also relates to a method for identification or validation of a drug or vaccine, the method comprising delivering the vaccine or drug to a vertebrate of the invention and monitoring one or more of: the immune response, the safety profile; the effect on disease.

The invention also relates to a kit comprising an antibody, polypeptide, chain or derivative as disclosed herein and either instructions for use of such optionally with a suitable laboratory reagent, such as a buffer, antibody detection reagent.

The invention also relates to a method for making an antibody, or part thereof, the method comprising providing:
(i) a nucleic acid encoding an polypeptide, antibody or chain, obtained using the vertebrate or cell of the present invention; or
(ii) sequence information from which a nucleic acid encoding an antibody, polypeptide or chain, obtained using the vertebrate or cell of the present invention can be expressed to allow an antibody, chain or polypeptide to be produced.

In an embodiment, each vertebrate is a non-human vertebrate, mouse or rat, whose genome comprises
(a) a heavy chain locus as defined above; and
(b) an antibody kappa light chain locus and/or an antibody lambda chain locus;
wherein all of the V, D and J in said loci are human V, D and J;
wherein endogenous antibody heavy and light chain expression has been inactivated; and optionally wherein said genome is homozygous for said heavy and light chain loci. This is useful for generating, predictably, only human N-terminal variable domains in antibodies and chains in the vertebrate.

In an embodiment, each kappa chain locus comprises a substantially complete human functional Vκ and Jκ repertoire; and each lambda chain locus comprises a substantially complete human functional Vλ and Jλ repertoire. "Functional" here acknowledges that Ig gene segment pseudogenes and non-functional human Ig gene segments can be excluded.

In one example the gene locus of the invention is a heavy chain locus which comprises a S-mu switch (eg, endogenous S-mu) as said first switch and a S-gamma switch (eg, endogenous S-gamma) as said second switch. For example, the C-mu region and switches are mouse 129 C-mu region and switches; or the C-mu region and switches are mouse Black 6 C-mu region and switches. In another embodiment (where the non-human vertebrate species is mouse or rat), S-mu is a rat Smu and the C-mu region is mouse and optionally there is a mouse S-gamma 3' of the non-mu C region.

In one aspect each vertebrate is a mouse whose genetic background is selected from mouse strains C57BL/6, M129 such as 129/SV, BALB/c, and any hybrid of C57BL/6, M129 such as 129/SV, or BALB/c.

In an embodiment, the J segments of each gene locus of the invention are human JH gene segments; optionally wherein each heavy chain locus comprises a substantially complete functional repertoire of human JH gene segments.

In an embodiment, each gene locus of the invention comprises at least 2, 3, 4, 5 or 6 different human JH gene segments.

In an embodiment, the D segments of each gene locus of the invention are human D gene segments; optionally wherein each heavy chain locus comprises a substantially complete functional repertoire of human D gene segments.

In an embodiment, each gene locus of the invention comprises at least 5, 10, 15, 20, 25, 26 or 27 different human D gene segments.

In an embodiment, each heavy chain locus comprises at least two human JH gene segments selected from the group consisting of J1, J2, J3, J4, J5 and J6; optionally all of the gene segments of the group.

In an embodiment, each heavy chain locus comprises human VH gene segments selected from the group consisting of V6-1, V1-2, V1-3, V4-4, V7-41, V2-5, V3-7, V1-8, V3-9, V3-11, V3-15, V1-18, V3-20, V3-21, V3-23, V1-24, V2-26, V4-28, V3-30, V4-31, V3-33, V4-34, V4-39, V3-43, V1-45, V1-46, V3-48, V3-49, V5-51, V3-53, V1-58, V4-59, V4-61, V3-64, V3-66, V1-69, V2-70, V3-72, V3-73 and V3-74; wherein the VH gene repertoire comprises a substantially complete human functional VH gene repertoire.

In an embodiment, endogenous antibody heavy chain expression has been inactivated in the vertebrate or cell of the invention. For example, less than 10, 5, 4, 3, 2, 1 or 0.5% (or 0) of heavy chains are provided by endogenous heavy chains (ie, heavy chains whose variable regions are derived from recombination of non-human vertebrate V, D and J gene segments).

The VL gene segments of a repertoire can, in one embodiment, be recombined VL, ie, provided as part of a variable region sequence derived from the recombination of human VL with JL (eg, where the VL and JL are human).

In an embodiment, the J segments of each light chain locus are human JL gene segments; optionally wherein each light chain locus comprises a substantially complete functional repertoire of human Jκ or Jλ gene segments (eg, each locus comprises human Vλ gene segments and Jλ gene segments, optionally a substantially complete functional repertoire of human Jλ gene segments; or each locus comprises human Vκ gene segments and Jκ gene segments, optionally a substantially complete functional repertoire of human Jκ gene segments).

In an embodiment, the kappa chain repertoire of the vertebrate or cell genome comprises a substantially complete repertoire of functional human Vκ gene segments; optionally providing at least 5 different human Jκ gene segments and at least at least 40 different human Vκ gene segments.

In an embodiment, the kappa chain repertoire comprises at least 20, 25, 30, 35 or 40 different human Vκ gene segments.

In an embodiment, the lambda chain repertoire of the vertebrate or cell genome comprises a substantially complete repertoire of functional human Vλ gene segments; optionally providing at least 5 different human Jλ gene segments and at least 40 different human Vλ gene segments.

In an embodiment, the lambda chain repertoire comprises at least 20, 25, 30, 35 or 40 different human Vλ gene segments.

In an embodiment, each light chain locus of the vertebrate or cell comprises at least 2, 3, 4, 5 or 6 different human Jκ or Jλ gene segments.

In an embodiment, endogenous antibody kappa and/or lambda light chain expression has been inactivated in the vertebrate or cell.

For selection of antibodies, chains or polypeptides in the methods of the invention, examples of a desirable antibody/chain/polypeptide characteristic are affinity for binding a predetermined antigen or epitope (eg, as determined by surface plasmon resonance), completion with a known antibody for binding to a predetermined antigen or epitope, epitopic specificity (eg, as determined by X-ray crystallography, competition with a known antibody for antigen binding wherein the known antibody specifically binds to the antigen (eg, as determined by surface plasmon resonance, eg, Biacore™ or Proteon™), performance in ELISA or another immunoassay, a desirable biophysical characteristic (eg, melting temperature, pI, solution state, degree of aggregation, storage profile etc). In an embodiment, affinity is determined by surface plasmon resonance.

Methods of immunisation for use in the invention are well known to the skilled person and may involve a classic prime-boost regime, RIMMS or any other protocol. An adjuvant may be administered with the antigen, as is known in the art.

Examples of derivative antibodies/chains/polypeptides (according to any aspect herein) are antibodies/chains/polypeptides that have one or more mutations compared to the isolated antibody or chain or polypeptide (eg, to improve antigen-binding affinity and/or to enhance or inactivate Fc function). Such mutants specifically bind the antigen. Mutation or adaptation to produce a derivative includes, eg, mutation to produce Fc enhancement or inactivation. A derivative can be an a antibody or chain or polypeptide following conjugation to a toxic payload or reporter or label or other active moiety.

In an embodiment, the vertebrate is naïve (ie, not immunised with a predetermined antigen, as the term is understood in the art; for example, such a vertebrate that has been kept in a relatively sterile environment as provided by an animal house used for R&D). In another example, the vertebrate has been immunised with a predetermined antigen, eg, an antigen bearing a human epitope.

In an embodiment, the method comprises comprising selecting one or more antibody heavy chains (eg, as part of an antibodies) from said population or repertoire according to a desired characteristic (eg, affinity for biding an antigen).

It is expected for example that, by using the present invention, this does not substantially change the ratio of B-cells in the splenic compartment and/or bone marrow B progenitor compartment and the immunoglobulin levels in serum are normal and the correct Ig subtypes are expressed. This would demonstrate that loci according to the invention (eg, heavy chain loci comprising an insertion of at least human $V_H$ gene segments $V_H$2-5, 7-4-1, 4-4, 1-3, 1-2, 6-1, and all the human D and $J_H$ gene segments D1-1, 2-2, 3-3, 4-4, 5-5, 6-6, 1-7, 2-8, 3-9, 5-12, 6-13, 2-15, 3-16, 4-17, 6-19, 1-20, 2-21, 3-22, 6-25, 1-26 and 7-27; and J1, J2, J3, J4, J5 and J6) are fully functional for VDJ gene segment rearrangement from the transgenic heavy chain locus, B-cell receptor (BCR) signalling and proper B-cell maturation Thus, in one aspect it is expected that mice according to the invention can for example express a normal relative proportion of serum IgG1, IgG2a, IgG2b and IgM antibodies.

By "normal" is meant comparable to expression in a mouse (eg, a naïve mouse) expressing only mouse antibody chains, eg, a mouse whose genome comprises only wild-type functional Ig heavy and light chain loci, eg, a wild-type mouse.

Thus, in one aspect it is expected that mice according to the invention can for example express
(i) serum IgG1 at a concentration of about 25-350 µg/ml;
(ii) serum IgG2a at a concentration of about 0-200 µg/ml;
(iii) serum IgG2b at a concentration of about 30-800 µg/ml; and
(iv) serum IgM at a concentration of about 50-300 µg/ml;
or
(i) serum IgG1 at a concentration of about 10-600 µg/ml;
(ii) serum IgG2a at a concentration of about 0-500 µg/ml;
(iii) serum IgG2b at a concentration of about 20-700 µg/ml; and
(iv) serum IgM at a concentration of about 50-700 µg/ml;
as determined by Ig capture on a plate followed by incubation (eg, for one hour at RT, eg, for one hour at 20° C.) with anti-mouse isotype-specific labelled antibodies and quantification of Ig using the label (eg, using anti-mouse Ig isotype specific antibodies each conjugated to horseradish peroxidase conjugated at a ratio of 1/10000 in PBS with 0.1% Tween™, followed by development of the label with tetramethylbenzidine substrate (TMB) for 4-5 minutes in the dark at room temperature (eg, 20° C.), adding sulfuric acid to stop development of the label and reading of the label at 450 nm).

Thus, in one aspect it is expected that mice according to the invention can for example express
(i) serum IgG1 at a concentration of about 25-150 µg/ml;
(ii) serum IgG2a at a concentration of about 0-200 µg/ml;
(iii) serum IgG2b at a concentration of about 30-300 µg/ml; and
(iv) serum IgM at a concentration of about 50-200 µg/ml;
or
(i) serum IgG1 at a concentration of about 10-200 µg/ml;
(ii) serum IgG2a at a concentration of about 0-500 µg/ml;
(iii) serum IgG2b at a concentration of about 20-400 µg/ml; and
(iv) serum IgM at a concentration of about 50-700 µg/ml;
as determined by Ig capture on a plate followed by incubation (eg, for one hour at RT, eg, for one hour at 20° C.) with anti-mouse isotype-specific labelled antibodies and quantification of Ig using the label (eg, using anti-mouse Ig isotype specific antibodies each conjugated to horseradish peroxidase conjugated at a ratio of 1/10000 in PBS with 0.1% Tween™, followed by development of the label with tetramethylbenzidine substrate (TMB) for 4-5 minutes in the dark at room temperature (eg, 20° C.), adding sulfuric acid to stop development of the label and reading of the label at 450 nm).

Thus, in one aspect it is expected that mice according to the invention can for example express Ig in the relative proportions of
(i) serum IgG1 at a concentration of about 25-150 µg/ml;
(ii) serum IgG2a at a concentration of about 0-200 µg/ml;
(iii) serum IgG2b at a concentration of about 30-300 µg/ml; and
(iv) serum IgM at a concentration of about 50-200 µg/ml;
or
(i) serum IgG1 at a concentration of about 10-200 µg/ml;
(ii) serum IgG2a at a concentration of about 0-500 µg/ml;
(iii) serum IgG2b at a concentration of about 20-400 µg/ml; and
(iv) serum IgM at a concentration of about 50-700 µg/ml;
as determined by Ig capture on a plate followed by incubation (eg, for one hour at RT, eg, for one hour at 20° C.) with anti-mouse isotype-specific labelled antibodies and quantification of Ig using the label (eg, using anti-mouse Ig isotype specific antibodies each conjugated to horseradish peroxidase conjugated at a ratio of 1/10000 in PBS with 0.1% Tween™, followed by development of the label with tetramethylbenzidine substrate (TMB) for 4-5 minutes in the dark at room temperature (eg, 20° C.), adding sulfuric acid to stop development of the label and reading of the label at 450 nm).

Thus, in one aspect it is expected that mice according to the invention can for example express heavy chains from splenic B-cells in a mouse that produces a normal proportion or percentage of mature splenic B-cells, eg as determined by FACS.

By "normal" is meant comparable to mature splenic B-cell production in a mouse (eg, a naïve mouse) expressing only mouse antibody chains, eg, a mouse whose genome comprises only wild-type functional Ig heavy and light chain loci, eg, a wild-type mouse.

For example, at least 40, 50, 60 or 70% of total splenic B-cells produced by the mouse of the invention are mature B-cells. Splenic B-cells are $B220^+$ and express B220 at relatively high levels as the skilled person will know. Mature splenic B-cells express B220 and IgD, both at relatively high levels as will be known by the skilled person. IgM expression is relatively low in mature splenic B-cells, again as is known in the art. For example, see J Exp Med. 1999 Jul. 5; 190(1):75-89; "B cell development in the spleen takes place in discrete steps and is determined by the quality of B cell receptor-derived signals"; Loder F et al.

Optionally the mouse produces a normal ratio of T1, T2 and mature splenic B-cells, eg, as determined by FACS. For example, the mouse of the invention produces about 40-70% mature splenic B-cells, 15-35% splenic T1 cells; and 5-10% splenic T2 cells (percentage with reference to the total splenic B220-positive (high) population). For example, about 40-60% mature splenic B-cells, 15-30% splenic T1 cells; and 5-10% splenic T2 cells. By "normal" is meant comparable to a T1/T2/mature splenic B-cell proportion in a mouse (eg, a naïve mouse) expressing only mouse antibody chains, eg, a mouse whose genome comprises only wild-type functional Ig heavy and light chain loci, eg, a wild-type mouse.

Thus, in one aspect it is expected that mice according to the invention can for example express heavy chains in a mouse that produces a normal proportion or percentage of bone marrow B-cell progenitor cells (eg as determined by FACS).

In one embodiment, the mouse is for expressing said heavy chains in a mouse that produces a normal proportion or percentage of bone marrow pre-, pro and prepro-B-cells (eg as determined by FACS). See J Exp Med. 1991 May 1; 173(5):1213-25; "Resolution and characterization of pro-B and pre-pro-B cell stages in normal mouse bone marrow"; Hardy R R et al for more discussion on progenitor cells.

By "normal" is meant comparable to bone marrow B-cell production in a mouse (eg, a naïve mouse) expressing only mouse antibody chains, eg, a mouse whose genome comprises only wild-type functional Ig heavy and light chain loci, eg, a wild-type mouse.

In one example of such a mouse, at least 90% of the heavy chains are heavy chains comprising human variable regions. For example, at least 90, 95, 96, 97, 98, 99 or 99.5% or 100% of the heavy chains comprise human variable regions, ie, variable regions derived from the recombination of human VH with human D and JH gene segments.

In one embodiment, the genome of the vertebrate, mouse or cell comprises human kappa gene segments (i) Vκ1-5, Vκ1-6, Vκ1-8 and Vκ1-9 (and optionally Vκ5-2 and Vκ4-1); or (ii) Vκ1-5, Vκ1-6, Vκ1-8, Vκ1-9, Vκ3-11, Vκ1-12, Vκ3-15, Vκ1-16, Vκ1-17, Vκ3-20 (and optionally Vκ 2-24 and/or Vκ1-13); or (iii) Vκ1-5, Vκ1-6, Vκ1-8, Vκ1-9, Vκ3-11, Vκ1-12, Vκ3-15, Vκ1-16, Vκ1-17, Vκ3-20, Vκ 2-24, Vκ1-27, Vκ2-28, Vκ2-30 and Vκ1-33 (and optionally Vκ 2-29 and/or Vκ2-40 and/or Vκ1-39);

and optionally (iv) Jκ1, Jκ2, Jκ3, Jκ4 and Jκ5.

In one embodiment, the genome also comprises (i) at least human $V_H$ gene segments $V_H$2-5, 7-4-1, 4-4, 1-3, 1-2, 6-1, and all the human D and $J_H$ gene segments D1-1, 2-2, 3-3, 4-4, 5-5, 6-6, 1-7, 2-8, 3-9, 5-12, 6-13, 2-15, 3-16, 4-17, 6-19, 1-20, 2-21, 3-22, 6-25, 1-26 and 7-27; and J1, J2, J3, J4, J5 and J6 and (ii) at least human gene segments Vκ2-24, Vκ3-20, Vκ1-17, Vκ1-16, Vκ3-15, Vκ1-13, Vκ1-12, Vκ3-11, Vκ1-9, Vκ1-8, Vκ1-6, Vκ1-5, Vκ5-2, Vκ4-1, Jκ1, Jκ2, Jκ3, Jκ4 and Jκ5.

Lox Sites

Novel Lox variants are described in the examples below (lox2272/66 and lox2272/71). These are useful for site-specific recombination (eg, in ES cells or other nucleic acid sources). Furthermore, since these sites are not compatible, they can be used for RMCE (recombinase-mediated cassette exchange). Thus, the invention comprises A site specific recombination site which is lox2272/66. The sequence is given below.

A site specific recombination site which is lox2272/71. The sequence is given below.

```
lox2272/66:
5'-ATAACTTCGTATA-AaGTATcC-TATACGAAcggta-3' lox2272/71:
5'-taccgTTCGTATA-AaGTATcC-TATACGAAGTTAT-3'
```

A DNA vector or DNA sequence comprising lox2272/66 and/or lox2272/71. For example, the vector or sequence comprises a nucleotide sequence (eg, a gene or gene segment sequence) flanked by lox2272/66 and lox2272/71; optionally wherein the lox sites are inverse to each other (which is useful for locking in sequences inserted into genomes, as explained in the examples). In this sense, lox2272/66 is 5' (eg, immediately 5') of the nucleotide sequence and lox2272/71 is 3' (eg, immediately 3') of the sequence. In another example, lox2272/71 is 5' (eg, immediately 5') of the nucleotide sequence and lox2272/66 is 3' (eg, immediately 3') of the sequence. In an example, the DNA sequence is part of a cell genome, eg, an ES cell genome or a B-cell genome or a hybridoma genome or an iPS cell genome.

STATEMENTS OF INVENTION

Aspects of the Invention are Set Out in the Following Clauses

1.

Multivalent

A non-human vertebrate (eg, a mouse or a rat), wherein the vertebrate comprises lymphocytic cells, each cell genome comprising (i) an antibody heavy chain locus comprising (in 5' to 3' direction) a rearranged or unrearranged variable region, a first switch, a mu constant region, a second switch and a non-mu (eg, gamma) constant region; wherein the heavy chain locus of each cell is capable of undergoing IgM to the non-mu (eg, IgG) isotype switching; and wherein (ii) the non-mu constant region comprises (in 5' to 3' direction) a nucleotide sequence encoding an optional linker and a predetermined epitope binding moiety, wherein following isotype switching the vertebrate expresses multivalent polypeptide chains comprising (in N- to C-terminal direction) an antibody variable domain derived from said variable region of the heavy chain locus, an optional linker and an epitope binding moiety, wherein the variable domain and the epitope binding moiety specifically bind respective first and second epitopes.

or

In Vivo Guided Selection

A non-human vertebrate (eg, a mouse or a rat) whose genome comprises an Ig locus comprising (in 5' to 3' orientation) (i) an unrearranged human variable region (eg, a heavy chain variable region) for encoding a first variable domain, (ii) a sequence encoding an optional linker and (iii) a rearranged sequence of a second variable domain (eg, a VL domain), wherein sequence (i) is capable of undergoing rearrangement so that the vertebrate produces antibody chains each having an epitope binding site that comprises first and second variable domains derived from sequences (i) and (iii), wherein there is no further antibody domain between the first and second variable domains.

Optionally, (i), (ii) and (iii) are 5' of S-mu when the locus is a heavy chain locus. Optionally, Optionally, (i) is 5' of S-mu when the locus is a heavy chain locus and (ii) and (iii) are downstream of S-mu.

or

A non-human vertebrate (eg, a mouse or a rat), wherein the vertebrate comprises lymphocytic cells, each cell genome comprising (i) an antibody heavy chain locus comprising (in 5' to 3' direction) a rearranged or unrearranged variable region (eg, a heavy chain variable region), a first switch, a mu constant region, a second switch and a non-mu (eg, gamma) constant region; wherein the heavy chain locus of each cell is capable of undergoing IgM to the non-mu (eg, IgG) isotype switching; and wherein (ii) the non-mu constant region comprises (in 5' to 3' direction) a nucleotide sequence encoding an optional linker and a first variable domain (eg, a VL domain), wherein following isotype switching the vertebrate expresses polypeptide chains comprising (in N- to C-terminal direction) an epitope binding site comprising first and second antibody variable domains derived respectively from the first variable domain nucleotide sequence said from said variable region of the heavy chain locus.

2.

Multivalent

A non-human vertebrate cell (eg, a mouse cell or a rat cell), the cell genome comprising (i) an antibody heavy chain locus comprising (in 5' to 3' direction) a rearranged or unrearranged variable region, a first switch, a mu constant region, a second switch and a non-mu (eg, gamma) constant region; wherein the heavy chain locus of each cell is capable of undergoing IgM to a non-mu (eg, IgG) isotype switching; and wherein (ii) the non-mu constant region comprises (in 5' to 3' direction) a nucleotide sequence encoding an optional linker and a predetermined epitope binding moiety, for expressing a multivalent polypeptide chain comprising (in N- to C-terminal direction) an antibody variable domain derived from said variable region of the heavy chain locus, an optional linker and an epitope binding moiety, wherein the variable domain and the epitope binding moiety specifically bind respective first and second epitopes.

or

In Vivo Guided Selection

A non-human vertebrate cell (eg, a mouse cell or a rat cell) whose genome comprises an Ig locus comprising (in 5' to 3' orientation) (i) an unrearranged human variable region (eg, a heavy chain variable region) for encoding a first variable domain, (ii) a sequence encoding an optional linker and (iii) a rearranged sequence of a second variable domain (eg, a VL domain), wherein sequence (i) is capable of undergoing rearrangement so that the cell produces antibody chains each having an epitope binding site that comprises first and second variable domains derived from sequences (i) and (iii), wherein there is no further antibody domain between the first and second variable domains.

or

A non-human vertebrate cell (eg, a mouse cell or a rat cell), the cell genome comprising (i) an antibody heavy chain locus comprising (in 5' to 3' direction) a rearranged or unrearranged variable region (eg, a heavy chain variable region), a first switch, a mu constant region, a second switch and a non-mu (eg, gamma) constant region; wherein the heavy chain locus of each cell is capable of undergoing IgM to the non-mu (eg, IgG) isotype switching; and wherein (ii) the non-mu constant region comprises (in 5' to 3' direction) a nucleotide sequence encoding an optional linker and a first variable domain (eg, a VL domain), for expressing polypeptide chains comprising (in N- to C-terminal direction) an epitope binding site comprising first and second antibody variable domains derived respectively from the first variable domain nucleotide sequence said from said variable region of the heavy chain locus.

3. The vertebrate of clause 1 or the cell of clause 2, wherein the genome comprises a functional antibody light chain locus for expressing light chains; wherein the cells can express IgM antibodies comprising IgM-type heavy chains and light chains.

4. The vertebrate or cell of clause 3, wherein the light chain locus comprises means for turning off light chain expression, wherein functional light chains are not expressed after IgM to non-mu isotype switching.

5. The vertebrate or cell of any preceding clause, wherein the vertebrate expresses polypeptide chains comprising (in N- to C-terminal direction) (a) an antibody variable domain derived from said variable region of the heavy chain locus, an optional linker, an epitope binding moiety and a non-mu (eg, gamma) constant domain (eg, gamma Fc) or (b) an antibody variable domain derived from said variable region of the heavy chain locus, a non-mu (eg, gamma) constant domain (eg, gamma Fc), an optional linker and an epitope binding moiety, wherein the variable domain and the epitope binding moiety specifically bind the respective first and second epitopes.

6. The vertebrate or cell of any preceding clause, wherein the non-mu constant region is a gamma constant region and the heavy chain locus is capable of undergoing isotype switching to produce IgG antibodies comprising one or more IgG heavy chains in the absence of light chains, each heavy chain lacking a CH1 domain.

7.

Multivalent

A non-human vertebrate (eg, a mouse or a rat), wherein the vertebrate comprises lymphocytic cells whose genomes comprise an antibody heavy chain locus comprising (in 5' to 3' direction) a rearranged variable region and a non-mu (eg, gamma) constant region; wherein the non-mu constant region comprises (in 5' to 3' direction) a nucleotide sequence encoding an optional linker and a predetermined epitope binding moiety, wherein the vertebrate expresses multivalent polypeptide chains comprising (in N- to C-terminal direction) an antibody variable domain derived from said variable region of the heavy chain locus, an optional linker and an epitope binding moiety, wherein the variable domain and the epitope binding moiety specifically bind respective first and second epitopes.

In an embodiment, there is no mu constant region between the rearranged variable region and the non-mu constant region.

or

In Vivo Guided Selection

A non-human vertebrate (eg, a mouse or a rat), wherein the vertebrate comprises lymphocytic cells whose genomes comprise an antibody heavy or light chain locus comprising (in 5' to 3' direction) a rearranged variable region and a non-mu constant region; wherein the non-mu constant region comprises (in 5' to 3' direction) a nucleotide sequence encoding an optional linker and the rearranged variable region which encodes a first variable domain, wherein following isotype switching the vertebrate expresses polypeptide chains comprising (in N- to C-terminal direction) an epitope binding site comprising second and first antibody variable domains derived respectively from a rearranged second variable domain nucleotide sequence and from the first variable domain nucleotide sequence, wherein the second nucleotide sequence has been rearranged in the vertebrate.

8. A non-human vertebrate cell (eg, a mouse cell or a rat cell) or a hybridoma, the cell genome comprising (in 5' to 3' direction) a rearranged variable region and a non-mu constant region;

wherein the non-mu constant region comprises (in 5' to 3' direction) a nucleotide sequence encoding an optional linker and the rearranged variable region which encodes a first variable domain, for expressing polypeptide chains comprising (in N- to C-terminal direction) an epitope binding site comprising second and first antibody variable domains derived respectively from a rearranged second variable domain nucleotide sequence and from the first variable domain nucleotide sequence, wherein the second nucleotide sequence has been rearranged in the cell.

In an embodiment of the vertebrate or cell, there is no mu constant region between the rearranged variable region encoding the first variable domain and the non-mu constant region.

9. The vertebrate of clause 7 or the cell of clause 8, wherein the heavy chain locus has undergone IgM to non-mu (eg, IgG) isotype switching.
10. The vertebrate or cell of any preceding clause, wherein the linker and/or epitope binding moiety nucleotide sequence is provided in place of a CH1 domain gene segment in the non-mu constant region.

or

The vertebrate or cell of any preceding clause, wherein said linker or first variable domain nucleotide sequence is provided in place of a CH1 domain gene segment in the non-mu constant region.

11.

Multivalent

A non-human vertebrate (eg, a mouse or a rat), wherein the vertebrate comprises lymphocytic cells, the genome of each cell comprising an antibody light chain locus which comprises (in 5' to 3' direction) a rearranged or unrearranged variable region and a second region;

wherein the second region comprises (in 5' to 3' direction) a nucleotide sequence encoding an optional linker and a predetermined epitope binding moiety, wherein following immunisation the vertebrate expresses polypeptide chains comprising (in N- to C-terminal direction) an antibody variable domain derived from said variable region of the light chain locus, an optional linker and an epitope binding moiety, wherein the variable domain and the epitope binding moiety specifically bind respective first and second epitopes.

or

In Vivo Guided Selection

A non-human vertebrate (eg, a mouse or a rat), wherein the vertebrate comprises lymphocytic cells, the genome of each cell comprising an antibody light chain locus which comprises (in 5' to 3' direction) an unrearranged variable region (eg, a heavy chain variable region) and a second region (which is a non-mu constant region);

wherein the second region comprises (in 5' to 3' direction) a nucleotide sequence encoding an optional linker and a first variable domain (eg, a VL domain), wherein following immunisation the vertebrate expresses polypeptide chains comprising (in N- to C-terminal direction) an epitope binding site comprising first and second antibody variable domains derived respectively from the first variable domain nucleotide sequence said from said variable region of the light chain locus.

12.

Multivalent

A non-human vertebrate cell (eg, a mouse cell or a rat cell) or a hybridoma, wherein the cell genome comprises an antibody light chain locus comprising (in 5' to 3' direction) a rearranged or unrearranged variable region and a second region;

wherein the second region comprises (in 5' to 3' direction) a nucleotide sequence encoding an optional linker and a predetermined epitope binding moiety, for expressing a polypeptide chain comprising (in N- to C-terminal direction) an antibody variable domain derived from said variable region of the light chain locus, an optional linker and an epitope binding moiety, wherein the variable domain and the epitope binding moiety specifically bind respective first and second epitopes.

or

In Vivo Guided Selection

A non-human vertebrate cell (eg, a mouse cell or a rat cell) or a hybridoma, wherein the cell genome comprises an antibody light chain locus comprising (in 5' to 3' direction) an unrearranged or rearranged variable region (eg, a heavy chain variable region) and a second region;

wherein the second region comprises (in 5' to 3' direction) a nucleotide sequence encoding an optional linker and a first variable domain (eg, a VL domain), for expressing polypeptide chains comprising (in N- to C-terminal direction) an epitope binding site comprising first and second antibody variable domains derived respectively from the first variable domain nucleotide sequence said from said variable region of the light chain locus.

13. The vertebrate of clause 11 or the cell of clause 12, which is according to the vertebrate or cell of any one of clauses 1 to 10.
14. A non-human vertebrate or cell according to clause 13, wherein the genome comprises said heavy and light chain loci, wherein said polypeptide chain variable domains derived from the heavy chain locus form binding sites with the polypeptide chain variable domains derived from the light chain locus, wherein the binding sites specifically bind the first epitope.
15. The vertebrate or cell of clause 14, wherein the epitope binding moieties of the polypeptide chains derived from the heavy and light chain loci are antibody variable domains, wherein the epitope binding domains of the chains derived from the heavy chain locus associate with the epitope binding domains of the chains derived from the light chain locus to form binding sites that specifically bind the second epitope.
16. A method of producing multivalent polypeptide chains comprising (in N- to C-terminal direction) an antibody variable domain, an optional linker and an epitope binding moiety, wherein the variable domain and the epitope binding moiety specifically bind respective first and second epitopes, the method comprising
(a) expressing in a non-human vertebrate (eg, a mouse or a rat) IgM antibodies in immature B-cells, wherein the antibodies comprise heavy and light chains expressed from heavy and light chain loci respectively;
(b) immunising the vertebrate with a first predetermined antigen bearing the first epitope and obtaining isotype switching to expression from a non-mu (eg, gamma) constant region in at least some of the heavy chain loci and expression of variable regions that have undergone somatic hypermutation; and
(c) selecting one or more polypeptide chains from said immunised vertebrate by selection for variable regions that bind said first epitope, wherein each selected chain comprises a somatically hypermutated variable region that specifically binds the epitope; and
wherein the method comprises
(d) providing the nucleotide sequence of the epitope binding moiety in the non-mu constant region of heavy chain loci in the genome of the vertebrate, wherein the polypeptide chains selected in step (c) bind the first and second epitopes.

17. The method of clause 16, wherein each somatically mutated variable region in step (b) is provided by an non-mu-type (eg, IgG-type) heavy chain that lacks a CH1 domain.

18. The method of clause 16 or 17, wherein step (b) comprises expressing the somatically mutated variable regions in the absence of light chain expression.

19. A method of producing in a non-human vertebrate (eg, a mouse or a rat) multivalent polypeptide chains comprising (in N- to C-terminal direction) an antibody variable domain, an optional linker and an epitope binding moiety, wherein the variable domain and the epitope binding moiety specifically bind respective first and second epitopes), the method comprising
(a) immunising the vertebrate with a first predetermined antigen bearing the first epitope, obtaining isotype switching to expression from a non-mu (eg, gamma) constant region in at least some of the heavy chain loci of the vertebrate and expression of variable regions that have undergone somatic hypermutation; and
(b) selecting one or more polypeptide chains from said immunised vertebrate by selection for variable regions that bind said first epitope, wherein each selected chain comprises a somatically hypermutated variable region that specifically binds the epitope; and
wherein
(d) providing the nucleotide sequence of the epitope binding moiety in the non-mu constant region of heavy chain loci in the genome of the vertebrate, wherein the polypeptide chains selected in step (b) bind the first and second epitopes.

20. The method of clause 19, wherein each somatically mutated variable region in step (a) is provided by a non-mu-type (eg, IgG-type) heavy chain that lacks a CH1 domain.

21. The method of clause 19 or 20, wherein step (a) comprises expressing the somatically mutated variable regions in the absence of light chain expression.

22. The method of any one of clauses 19 to 21, wherein the vertebrate is according to any one of clauses 1 to 15.

23. The method of any one of clauses 19 to 22, further comprising isolating or synthesizing a nucleic acid comprising a nucleotide sequence encoding a polypeptide chain selected in the method; and optionally humanising the sequence.

24. A multispecific polypeptide chain obtained by the method of any one of clauses 19 to 23 or a derivative thereof that specifically binds the first and second epitopes.

25. A multivalent (eg, multispecific) polypeptide chain having (in N- to C-terminal direction) the structure V-X-L-E-L-C, where (i) V is an antibody variable domain that specifically binds a first epitope,
(ii) X is absent, an antibody hinge region or an antibody constant region comprising a constant domain,
(iii) Each L is an optional linker,
(iv) E is an epitope binding moiety that specifically binds a second epitope, and
(v) C is absent or an antibody constant region comprising a constant domain (eg, C is a human gamma Fc),
wherein V is a rearranged antibody variable domain derived from the rearrangement of variable region gene segments in vivo in a non-human vertebrate with somatic hypermutation of the resulting variable region gene in a nucleotide sequence also encoding for the epitope binding moiety; and
wherein the rearranged antibody variable domain comprises endogenous AID-pattern somatic hypermutations.

26. A method of producing a polypeptide chain of clause 25, the method comprising immunising a non-human vertebrate (eg, a mouse or a rat) with the first epitope and causing somatic hypermutation of a variable region gene in a nucleotide sequence also encoding for the epitope binding moiety (E), the variable region gene encoding V; and isolating said polypeptide chain comprising V and E.

27. The polypeptide of clause 25 or the method of clause 26, wherein the epitope binding moiety lacks endogenous AID-pattern somatic hypermutations.

28. The polypeptide of clause 25 or the method of clause 26, wherein the epitope binding moiety comprises endogenous AID-pattern somatic hypermutations.

29. A dimer of polypeptides according to any one of clauses 25 to 28, wherein the dimer lacks antibody light chains.

30. A polypeptide, dimer or method according to any one of clauses 25 to 29, wherein the polypeptide has (in N- to C-terminal direction) the structure V-N-E; V-CH1-M-CH2-CH3-L-E; or V-M-CH2-CH3-L-E, wherein N is L together with an optional antibody hinge region; and M is an optional antibody hinge region.

31. A polypeptide, dimer or method according to any one of clauses 25 to 30, wherein V is peptide bonded to a second antibody variable domain (V2) to form a binding site comprising first and second variable domains that specifically binds the first epitope; optionally wherein V and V2 are provided as an scFv.

32. The polypeptide, dimer or method of any one of clauses 25 to 31, wherein the polypeptide lacks a CH1 domain.

33. A polypeptide, dimer or method according to any one of clauses 25 to 31, wherein the polypeptide comprises a CH1 domain and the polypeptide is present in first and second copies in antibody, the first polypeptide being associated with a first antibody light chain, and the second copy being associated with a second antibody light chain.

34. An antibody comprising the dimer, polypeptide chain or a humanised version thereof as recited in any one of clauses 25 to 33.

35. A bivalent (eg, bispecific) antibody comprising a dimer of a heavy chain, wherein each heavy chain is a polypeptide according to any one of clauses 25, 27, 28 and 30 to 33 and has in N- to C-terminal direction) the structure
V-CH1-M-CH2-CH3-L-E,
V-M-CH2-CH3-L-E,
V-L-E-L-CH1-M-CH2-CH3,
V-L-E-L-M-CH2-CH3,
V-CH1-N-E,
V-L-E-N-CH1, or
V-N-E-L-CH1, wherein N is L together with an optional antibody hinge region; M is an optional antibody hinge region;

optionally wherein the constant domains are human constant domains.

36. The antibody of clause 35, wherein the antibody comprises two copies of a light chain, each heavy chain being associated with a respective light chain, wherein V in each heavy chain forms an antigen binding site with the variable domain of its respective light chain and the variable domain of each light chain comprises endogenous AID-pattern somatic hypermutations.

37. A multivalent (eg, multispecific) antibody comprising heavy chains associated with light chains, wherein Each heavy chain is a polypeptide chain as recited in any one of clauses 25 and 27 to 35, wherein E is an antibody variable domain;

Each light chain is a polypeptide chain having (in N- to C-terminal direction) the structure V'-L'-E'-L'-C', where (i) V' is an antibody variable domain,
(ii) Each L' is an optional linker,
(iv) E' is an epitope binding moiety, and
(v) C' is absent or an antibody constant region comprising a constant domain (eg, C' is a human CL);

wherein

V' is a rearranged antibody variable domain derived from the rearrangement of variable region gene segments in vivo in a non-human vertebrate with somatic hypermutation of the resulting variable region gene in a nucleotide sequence also encoding for E'; and V' comprises endogenous AID-pattern somatic hypermutations;

V and V' form a first binding site that specifically binds a first epitope; and

Optionally E and E' form a second binding site that specifically binds a second epitope when E' is an antibody variable domain.

38. An antigen-binding polypeptide comprising a protein scaffold which is linked to one or more epitope binding moieties wherein the antigen-binding polypeptide comprises at least two epitope binding sites at least one of which is provided by an epitope binding moiety and at least one of which is provided by a first antibody variable domain paired with a second antibody variable domain, wherein each variable domain is a rearranged antibody variable domain derived from the rearrangement of variable region gene segments in vivo in a non-human vertebrate with somatic hypermutation of the resulting variable region gene in a nucleotide sequence also encoding for one or more of the epitope binding moiety(ies); and wherein the rearranged antibody variable domains comprise endogenous AID-pattern somatic hypermutations.

or

An antigen-binding polypeptide comprising a protein scaffold which is linked to one or more epitope binding moieties wherein the antigen-binding polypeptide comprises at least two epitope binding sites at least one of which is provided by an epitope binding moiety and at least one of which is provided by a first antibody variable domain paired with a second antibody variable domain, wherein the first variable domain is a rearranged antibody variable domain derived from the rearrangement of variable region gene segments in vivo in a non-human vertebrate with somatic hypermutation of the resulting variable region gene in a nucleotide sequence also encoding for the second variable domain and the one or more of the epitope binding moiety(ies); and wherein the rearranged first antibody variable domain comprises endogenous AID-pattern somatic hypermutations.

39. The polypeptide of clause 38, comprising at least one of said epitope binding moiety linked to the protein scaffold by a peptide linker which comprises at least 10 amino acids (eg, between 10 and 50 amino acids).

40. A multispecific antigen binding polypeptide, dimer or antibody according to any one of clauses 25 and 27 to 39, which is capable of recruiting the activity of a human immune effector cell by specifically binding to an effector antigen (eg, human CD3) located on the human immune effector cell, a first of the epitope binding sites of the polypeptide, dimer or antibody being capable of specifically binding to said effector antigen, and a second of the epitope binding sites of the polypeptide, dimer or antibody being capable of specifically binding to a target antigen (eg, human EpCAM or human CD19) other than the effector antigen; optionally wherein said target antigen is located on a target cell other than said human immune effector cell.

41. The vertebrate, cell polypeptide, dimer or antibody of any preceding clause, wherein the second epitope is provided by human immune effector cell antigen (eg, human CD3).

42. The vertebrate, cell polypeptide, dimer or antibody of any preceding clause, wherein the first epitope is provided by a target antigen (eg, human EpCAM or human CD19) other than the effector antigen; optionally wherein said target antigen is an antigen of a target cell other than said human immune effector cell.

43. The vertebrate, cell polypeptide, dimer or antibody of any preceding clause, wherein the epitope binding moiety is selected from the group consisting of an antibody variable domain (eg, a VL or a VH, an antibody single variable domain (domain antibody or dAb), a camelid VHH antibody single variable domain, a shark immunoglobulin single variable domain (NARV), a Nanobody™ or a camelised VH single variable domain); a T-cell receptor binding domain; an immunoglobulin superfamily domain; an agnathan variable lymphocyte receptor; a fibronectin domain (eg, an Adnectin™); an antibody constant domain (eg, a CH3 domain, eg, a CH2 and/or CH3 of an Fcab™) wherein the constant domain is not a functional CH1 domain; an scFv; an (scFv)₂; an sc-diabody; an scFab; a centyrin and an epitope binding domain derived from a scaffold selected from CTLA-4 (Evibody™); a lipocalin domain; Protein A such as Z-domain of Protein A (eg, an Affibody™ or SpA); an A-domain (eg, an Avimer™ or Maxibody™); a heat shock protein (such as and epitope binding domain derived from GroEI and GroES); a transferrin domain (eg, a transbody); ankyrin repeat protein (eg, a DARPin™); peptide aptamer; C-type lectin domain (eg, Tetranectin™); human γ-crystallin or human ubiquitin (an affilin); a PDZ domain; scorpion toxin; and a kunitz type domain of a human protease inhibitor.

44. The vertebrate, cell polypeptide, dimer or antibody of any preceding clause, wherein the or each N-terminal variable domain or 5'-terminal variable region is a human variable domain or region.

45. The vertebrate, cell polypeptide, dimer or antibody of any preceding clause, wherein each constant region or domain is an endogenous non-human vertebrate constant region or domain.

46. A non-human vertebrate (eg, a mouse or a rat), wherein
   (a) the vertebrate expresses IgM antibodies comprising heavy and light chains encoded by antibody heavy and light chain loci respectively;
   (b) the vertebrate is capable of expressing non-mu (eg, IgG) antibodies, each non-mu antibody heavy chain lacking a functional CH1 domain; and
   (c) the IgM antibodies are expressed by lymphocytic cells, each cell comprising a functional light chain locus for expressing light chains of IgM antibodies expressed by the cell; and
   wherein
   (d) the non-mu antibodies are expressed by lymphocytic cells, each cell lacking a functional light chain locus wherein non-mu antibodies are expressed by the cell in the absence of light chain expression.

47. A non-human vertebrate (eg, a mouse or a rat), wherein the vertebrate comprises lymphocytic cells whose genomes comprise
   (i) an antibody heavy chain locus comprising (in 5' to 3' direction) a rearranged or unrearranged variable region, a first switch, a mu constant region, a second switch and a non-mu (eg, gamma) constant region lacking a CH1 gene segment;
   (ii) a functional antibody light chain locus for expressing light chains;
   wherein the cells can express IgM antibodies comprising IgM-type heavy chains and light chains;
   wherein the heavy chain locus of each cell is capable of undergoing isotype switching to produce non-mu (eg, IgG) antibodies comprising one or more non-mu-type (eg, IgG-type) heavy chains in the absence of light chains, each heavy chain lacking a CH1 domain; and
   (iii) means for turning off light chain expression, wherein functional light chains are not expressed after isotype switching to said non-mu-type antibodies.

48. A non-human vertebrate cell (eg, a mouse cell or a rat cell), wherein the cell genome comprises
   (i) a functional antibody light chain locus for expressing light chains;
   (ii) an antibody heavy chain locus comprising (in 5' to 3' direction) a rearranged or unrearranged variable region, a first switch, a mu constant region, a second switch and a non-mu (eg, gamma) constant region lacking a CH1 gene segment for expressing IgM antibodies comprising IgM-type heavy chains and light chains; and for IgM to non-mu (eg, IgG) isotype switching to produce non-mu (eg, IgG) antibodies comprising one or more non-mu-type heavy chains in the absence of light chains, each heavy chain lacking a CH1 domain; and
   (iii) means for turning off light chain expression, wherein functional light chains are not expressed after isotype switching to said non-mu-type antibodies.

49. The vertebrate or cell of any one of clauses 46 to 48, wherein the means for turning off light chain expression comprises a nucleotide sequence (eg, a light chain variable region or a CL region of the light chain locus) that is essential for functional light chain expression from said light chain locus, wherein the nucleotide sequence is functional in immature B-cells expressing IgM, but the nucleotide sequence is absent or substantially non-functional in mature B-cells expressing said non-mu-type antibodies.

50. The vertebrate or cell of any one of clauses 46 to 49, wherein the means for turning off light chain expression comprises a nucleotide sequence comprising a regulatory element (eg, a promoter) for driving light chain expression from said light chain locus in immature B-cells expressing IgM, and wherein the regulatory element is substantially inactive or absent in mature B-cells expressing said non-mu-type antibodies.

51. The vertebrate or cell of clause 49 or 50, wherein the nucleotide sequence or regulatory element is flanked by first and second combination elements (eg, site-specific recombination elements) and wherein the genome comprises a gene(s) that encodes a corresponding recombinase(s) or transposase(s), wherein the gene is inactive in immature B-cells expressing IgM, but active to cut at the first and second recombination elements and inactivate the nucleotide sequence or regulatory element in mature B-cells expressing said non-mu-type antibodies.

52. The vertebrate or cell of clause 50, wherein the regulatory element is induced in immature B-cells expressing IgM and/or repressed in mature B-cells expressing said non-mu-type antibodies.

53. The vertebrate or cell of any one of clauses 46 to 48, wherein the means for turning off light chain expression is another locus in the genome for expressing a polypeptide chain comprising a rearranged light chain variable domain.

54. The vertebrate or cell of clause 53, wherein said another locus is a heavy chain locus as defined in clause 47 or 48, wherein following said isotype switching the heavy chain locus encodes an antibody chain comprising said rearranged light chain variable domain.

55. The vertebrate or cell of clause 54, wherein the antibody chain further comprises a second antibody variable domain; optionally wherein the light chain variable domain and said second antibody variable domain specifically bind respective first and second epitopes that are different.

56. The vertebrate or cell of any one of clauses 53 to 55, wherein the rearranged light chain variable domain is derived from said unrearranged variable region of the heavy chain locus as defined in clause 47 or 48, wherein the unrearranged variable region of the heavy chain locus comprises one or more light chain V gene segments 5' of one or more light chain J gene segments.

57. The vertebrate or cell of clause 54 or 55, wherein the antibody chain comprises (in 5' to 3' direction) a variable domain derived from said variable region of the heavy chain locus as defined in clause 47 or 48, an optional linker and said rearranged light chain variable domain.

58. The vertebrate or cell of any one of clauses 47, 48 and 49 to 57 when dependent from clause 47 or 48, wherein the non-mu constant region comprises (in 5' to 3' direction) a nucleotide sequence encoding an optional linker and a predetermined epitope binding moiety, wherein following isotype switching the vertebrate expresses multivalent polypeptide chains comprising (in N- to C-terminal direction) an antibody variable domain derived from said variable region of the heavy chain locus, an optional linker and an epitope binding moiety, wherein the variable domain and the epitope binding moiety specifically bind respective first and second epitopes.

59. The vertebrate of clause 58, wherein non-mu constant region comprises one or more non-mu constant region gene segments (eg, CH2 and CH3 gene segments) 3' of said epitope binding moiety, wherein following isotype switching the vertebrate expresses multivalent polypeptide chains each comprising (in N- to C-terminal direction) an antibody variable domain derived from said variable region of the heavy chain locus, an optional linker, an epitope binding moiety and said one or more non-mu constant region gene segments.

60. The vertebrate or cell of clause 58 or 59, wherein a poly(A) site is 3' of the nucleotide sequence encoding the epitope binding moiety, wherein following isotype switching the vertebrate expresses multivalent polypeptide chains having or consisting of (in N- to C-terminal direction) the structure V-X-L-E, where V is an antibody variable domain derived from said variable region of the heavy chain locus, X is absent an antibody hinge region or a polypeptide encoded by the gamma constant region, L is the optional linker and E is the epitope binding moiety; optionally wherein the vertebrate expresses V-X-L-E or V-L-E dimers.

61. The vertebrate or cell of clause 58 or 59, wherein a poly(A) site is 3' of the nucleotide sequence encoding the one or more non-mu constant region gene segments, wherein following isotype switching the vertebrate expresses multivalent polypeptide chains having or consisting of (in N- to C-terminal direction) the structure V-X-L-E-L-C, where V is an antibody variable domain derived from said variable region of the heavy chain locus, X is absent an antibody hinge region or a polypeptide encoded by the non-mu constant region, L is the optional linker, E is the epitope binding moiety and $C_n$ is the one or more non-mu constant region gene segments (eg, gamma Fc); optionally wherein the vertebrate expresses V-X-L-E-L-C or V-L-E-L-C dimers.

62. The vertebrate or cell of any one of clauses 46 to 61, wherein the epitope binding moiety is selected from the group consisting of an antibody variable domain (eg, a VL or a VH, an antibody single variable domain (domain antibody or dAb), a camelid VHH antibody single variable domain, a shark immunoglobulin single variable domain (NARV), a Nanobody™ or a camelised VH single variable domain); a T-cell receptor binding domain; an immunoglobulin superfamily domain; an agnathan variable lymphocyte receptor; a fibronectin domain (eg, an Adnectin™); an antibody constant domain (eg, a CH3 domain, eg, a CH2 and/or CH3 of an Fcab™) wherein the constant domain is not a functional CH1 domain; an scFv; an (scFv)$_2$; an sc-diabody; an scFab; a centyrin and an epitope binding domain derived from a scaffold selected from CTLA-4 (Evibody™); a lipocalin domain; Protein A such as Z-domain of Protein A (eg, an Affibody™ or SpA); an A-domain (eg, an Avimer™ or Maxibody™); a heat shock protein (such as and epitope binding domain derived from GroEI and GroES); a transferrin domain (eg, a trans-body); ankyrin repeat protein (eg, a DARPin™); peptide aptamer; C-type lectin domain (eg, Tetranectin™); human γ-crystallin or human ubiquitin (an affilin); a PDZ domain; scorpion toxin; and a kunitz type domain of a human protease inhibitor.

63. The vertebrate or cell of any one of clauses 46 to 62, wherein the vertebrate comprises lymphocytic cells that have undergone isotype switching to produce said non-mu-type (eg, IgG-type) antibodies; or the cell has undergone isotype switching to produce said non-mu-type (eg, IgG-type) antibodies.

64. The vertebrate or cell of any one of clauses 46 to 63, wherein the vertebrate has been immunised with a predetermined antigen, the vertebrate expressing non-mu-type (eg, IgG-type) antibodies lacking a CH1 domain and comprising a variable domain that specifically binds the predetermined antigen; or the cell is isolated from such a vertebrate.

65. The vertebrate or cell of any one of clauses 46 to 64, wherein the or each N-terminal variable domain or 5'-terminal variable region is a human variable domain or region.

66. The vertebrate or cell of any one of clauses 46 to 65, wherein each constant region or domain is an endogenous non-human vertebrate constant region or domain.

67. The vertebrate or cell of any one of clauses 46 to 66, wherein the lymphocytic cells comprise B-cells expressing said non-mu antibodies or bivalent polypeptide chains, wherein the non-mu antibodies or multivalent chains are specific for an antigen that is foreign to said non-human vertebrate; or wherein said non-human vertebrate cell is such a B-cell.

68. An immortalised B-cell or hybridoma produced from a B-cell recited in clause 67.

69. A non-mu-type (eg, IgG-type) antibody or multivalent chain isolated from a B-cell or hybridoma of clause 67 or 68; or a humanised version thereof wherein non-human constant domains have been replaced with human constant domains.

70. A method of producing polypeptide chains comprising somatically hypermutated variable regions in a non-human vertebrate (eg, a mouse or a rat), the method comprising
  (a) expressing in the vertebrate IgM antibodies in immature B-cells, wherein the antibodies comprise heavy and light chains expressed from heavy and light chain loci respectively;
  (b) immunising the vertebrate with a predetermined epitope and obtaining isotype switching in at least some of the heavy chain loci and expression of non-mu (eg, IgG) antibodies that have undergone somatic hypermutation, wherein the antibodies comprise heavy chains that lack a CH1 domain and comprise variable regions that specifically bind the antigen; and
  (c) selecting one or more polypeptide chains from said immunised vertebrate by selection for variable regions that bind said epitope, wherein each selected chain comprises a somatically hypermutated variable region that specifically binds the epitope; and the method further comprising expressing the non-mu antibodies in step (b) in the absence of light chain expression.

71. The method of clause 70, comprising isolating from the immunised vertebrate a B-cell that expresses a polypeptide chain comprising a somatically hypermutated variable region that binds the epitope; and optionally immortalising the cell or producing a hybridoma therefrom.

72. The method of clause 70 or 71, comprising obtaining a nucleotide sequence that encodes a selected polypeptide chain comprising a somatically hypermutated variable region that binds the epitope, and introducing the nucleotide sequence into a expression vector for expression of the polypeptide chain or a humanised version thereof; optionally wherein vector is in a host cell.

73. The method of any one of clauses 70 to 72, wherein the vertebrate is according to any one of clauses 46 to 69.

74. A multispecific polypeptide chain obtained by the method of any one of clauses 70 to 73 or a derivative thereof that specifically binds the epitope.

75. A non-human vertebrate (eg, a mouse or a rat) whose genome comprises an antibody heavy chain locus and an antibody light chain locus,
  (a) the light chain locus comprising (in 5' to 3' direction) a light chain variable region and a constant region for expressing light chains in lymphocytic cells expressing IgM antibodies; and (b) means for turning off light chain expression in lymphocytic cells expressing non-mu (eg, IgG) antibodies.

76. A non-human vertebrate cell (eg, a mouse cell or a rat cell) or hybridoma whose genome comprises an antibody heavy chain locus and an antibody light chain locus, the light chain locus comprising
    (a) (in 5' to 3' direction) a light chain variable region and a constant region for expressing light chains in lymphocytic cells expressing IgM antibodies; and
    (b) means for turning off light chain expression in lymphocytic cells expressing non-mu (eg, IgG) antibodies.

77. The vertebrate of clause 73 or cell of clause 74, wherein the means for turning off light chain expression is as recited in any one of clauses 49 to 56.

78. A non-human vertebrate (eg, a mouse or a rat), wherein the vertebrate comprises lymphocytic cells, each cell genome comprising an antibody heavy chain locus comprising (in 5' to 3' direction) a rearranged or unrearranged variable region and a mu constant region comprising a nucleotide sequence encoding an optional linker and a predetermined epitope binding moiety, wherein the vertebrate expresses multivalent polypeptide chains comprising (in N- to C-terminal direction) an antibody variable domain derived from said variable region of the heavy chain locus, an optional linker and an epitope binding moiety, wherein the variable domain and the epitope binding moiety specifically bind respective first and second epitopes.

79. A non-human vertebrate cell (eg, a mouse cell or a rat cell), wherein the cell genome comprises an antibody heavy chain locus comprising (in 5' to 3' direction) a rearranged or unrearranged variable region and a mu constant region comprising a nucleotide sequence encoding an optional linker and a predetermined epitope binding moiety, wherein the cell expresses multivalent polypeptide chains comprising (in N- to C-terminal direction) an antibody variable domain derived from said variable region of the heavy chain locus, an optional linker and an epitope binding moiety, wherein the variable domain and the epitope binding moiety specifically bind respective first and second epitopes.

80. A non-human (eg, rat or mouse) vertebrate or cell that expresses multivalent, multispecifc heavy chains (or dimers thereof) comprising the structure V-L-E or V-L-E-L (eg, V-L-E-Fc or V-L-E-L-Fc), where V is an N-terminal antibody variable domain, L is an optional linker and E is an epitope binding moiety, wherein V and E specifically bind respective first and second antigens, wherein the antigens are different.

81. The vertebrate or cell of clause 80, wherein V is a human variable domain.

82. A multivalent (eg, multispecific) light chain having (in N- to C-terminal direction) the structure V-X-L-E-L-C, where
    (i) V is an antibody variable domain (eg, a VL) that specifically binds a first epitope,
    (ii) X is absent, or an antibody constant region comprising a constant domain (eg, a CL),
    (iii) Each L is an optional linker,
    (iv) E is an epitope binding moiety that specifically binds a second epitope, and
    (v) C is absent or an antibody constant region comprising a constant domain (eg, C is a CL),
    wherein V is a rearranged antibody variable domain derived from the rearrangement of variable region gene segments in vivo in a non-human vertebrate with somatic hypermutation of the resulting variable region gene in a nucleotide sequence also encoding for the epitope binding moiety; and
    wherein the rearranged antibody variable domain comprises endogenous AID-pattern somatic hypermutations.

83. A dimer of light chains according to clause 82.

84. A non-human vertebrate (eg, a mouse or a rat), wherein the vertebrate comprises lymphocytic cells, each cell genome comprising
    (i) an antibody light chain locus comprising (in 5' to 3' direction) a rearranged or unrearranged variable region, a nucleotide sequence encoding an optional linker and a predetermined epitope binding moiety, and a CL gene segment, wherein the vertebrate expresses multivalent light chains comprising (in N- to C-terminal direction) an antibody variable domain derived from said variable region of the light chain locus, an optional linker, an epitope binding moiety and a CL domain, wherein the variable domain and the epitope binding moiety specifically bind respective first and second epitopes (which can be any epitopes as defined herein); or
    (ii) an antibody light chain locus comprising (in 5' to 3' direction) a rearranged or unrearranged variable region, a CL gene segment, a nucleotide sequence encoding an optional linker and a predetermined epitope binding moiety, wherein the vertebrate expresses multivalent light chains comprising (in N- to C-terminal direction) an antibody variable domain derived from said variable region of the light chain locus, a CL domain, an optional linker and an epitope binding moiety, wherein the variable domain and the epitope binding moiety specifically bind respective first and second epitopes (which can be any epitopes as defined herein).

85. A non-human vertebrate cell (eg, a mouse cell or a rat cell), the cell genome comprising
    (i) an antibody light chain locus comprising (in 5' to 3' direction) a rearranged or unrearranged variable region, a nucleotide sequence encoding an optional linker and a predetermined epitope binding moiety, and a CL gene segment, wherein the cell expresses multivalent light chains comprising (in N- to C-terminal direction) an antibody variable domain derived from said variable region of the light chain locus, an optional linker, an epitope binding moiety and a CL domain, wherein the variable domain and the epitope binding moiety specifically bind respective first and second epitopes (which can be any epitopes as defined herein); or
    (ii) an antibody light chain locus comprising (in 5' to 3' direction) a rearranged or unrearranged variable region, a CL gene segment, a nucleotide sequence encoding an optional linker and a predetermined epitope binding moiety, wherein the cell expresses multivalent light chains comprising (in N- to C-terminal direction) an antibody variable domain derived from said variable region of the light chain locus, a CL domain, an optional linker and an epitope binding moiety, wherein the variable domain and the epitope binding moiety specifically bind respective first and second epitopes (which can be any epitopes as defined herein).

86. A polypeptide comprising a binding site specific for an epitope, the binding site having the structure V1-L-E (optionally V1-L-V2), where V1 and V2 are antibody variable domains (eg, VH and VL respectively or each a VH), E is an epitope binding moiety and L is an optional peptide linker (eg, of 20, 15 or 10 or less amino acids); and wherein V1 is derived from the rearrangement of human variable region gene segments in vivo in a nonhuman vertebrate with somatic hypermutation of the resulting variable region gene in a nucleotide sequence also encoding E, wherein V1 comprises endogenous AID-pattern somatic hypermutations. Here "endogenous" refers to a pattern caused by AID that is endogenous to the vertebrate (eg, caused by mouse AID where the vertebrate is a mouse).

87. A method of producing a polypeptide according to clause 86, the method comprising immunising a non-human vertebrate with said epitope and obtaining somatic hypermutation by endogenous AID of an Ig locus to produce a mutated Ig locus encoding Viand E; and isolating the polypeptide and/or a nucleic acid encoding the polypeptide.

88. A non-human vertebrate (eg, a mouse or a rat) or cell (eg, a mouse cell or a rat cell), wherein an Ig heavy or light chain locus of the genome of the vertebrate or cell comprises (in 5' to 3' orientation) (i) an unrearranged human variable region for encoding a first variable domain, (ii) a sequence encoding an optional linker and (iii) a sequence encoding an epitope binding moiety (optionally a rearranged sequence of a second variable domain).

In an example, the vertebrate is according to clause 1, 7 or 11. In an embodiment, the polypeptide or nucleic acid is modified or mutated after isolation to produce (or encode) a polypeptide derivative that specifically binds the epitope.

89. Use of first and second rearranged antibody variable domains in the manufacture of an antigen-binding polypeptide comprising a protein scaffold which is linked to one or more epitope binding moieties wherein the antigen-binding polypeptide comprises at least two epitope binding sites at least one of which is provided by an epitope binding moiety and at least one of which is provided by a first antibody variable domain paired with a second antibody variable domain, wherein the use comprises (i) obtaining the sequence of the first variable domain by rearrangement of variable region gene segments in vivo in a non-human vertebrate with somatic hypermutation of the resulting variable region gene in a nucleotide sequence also encoding for the second variable domain and the one or more of the epitope binding moiety(ies); and isolating the variable domain sequences wherein the rearranged first antibody variable domain sequence comprises endogenous AID-pattern somatic hypermutations; (ii) expressing and combining the variable domains with the protein scaffold and one or more epitope binding moieties to produce said antigen-binding polypeptide; and (iii) isolating said polypeptide.

Optionally, the second variable domain used in step (ii) comprises endogenous AID-pattern somatic hypermutations.

90. A method of producing a vertebrate of a non-human species, the method comprising breeding two vertebrates of said species together, wherein both of the vertebrates are according to any one of the clauses above.

91. The vertebrate, cell or method of any preceding clause, wherein a common light chain is expressed at the IgM stage.

92. The vertebrate or cell of any preceding clause, whose genome comprises means for expressing a common light chain at the IgM stage.

The common light chain comprises, for example, a human Vκ1-39Jκ or Vκ3-20Jκ (eg, Vκ1-39Jκ 5 or Vκ3-20Jκ 1) or VpreB (such as human VpreB). These variable domains pair promiscuously with VH, so are useful for producing a repertoire of binding sites during antibody development in the vertebrate or cell.

In an embodiment of any of the multivalent aspects of the invention, the first epitope is a human CD19 epitope and the second epitope is a human CD3 or CD16 epitope.

It will be understood that particular embodiments described herein are shown by way of illustration and not as limitations of the invention and (unless the context states otherwise) embodiments can be applied to any of the configurations of the invention described herein. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word "a" or an when used in conjunction with the term "comprising" in the claims and/or the specification may mean "one," but it is also consistent with the meaning of "one or more," "at least one," and "one or more than one." The use of the term or in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Any part of this disclosure may be read in combination with any other part of the disclosure, unless otherwise apparent from the context.

All of the compositions, populations, vertebrates, antibodies, repertoires and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention is described in more detail in the following non limiting prophetic Examples.

EXAMPLES

Example 1: Improved Production of Heavy Chain-Only Antibodies

Figure 3:
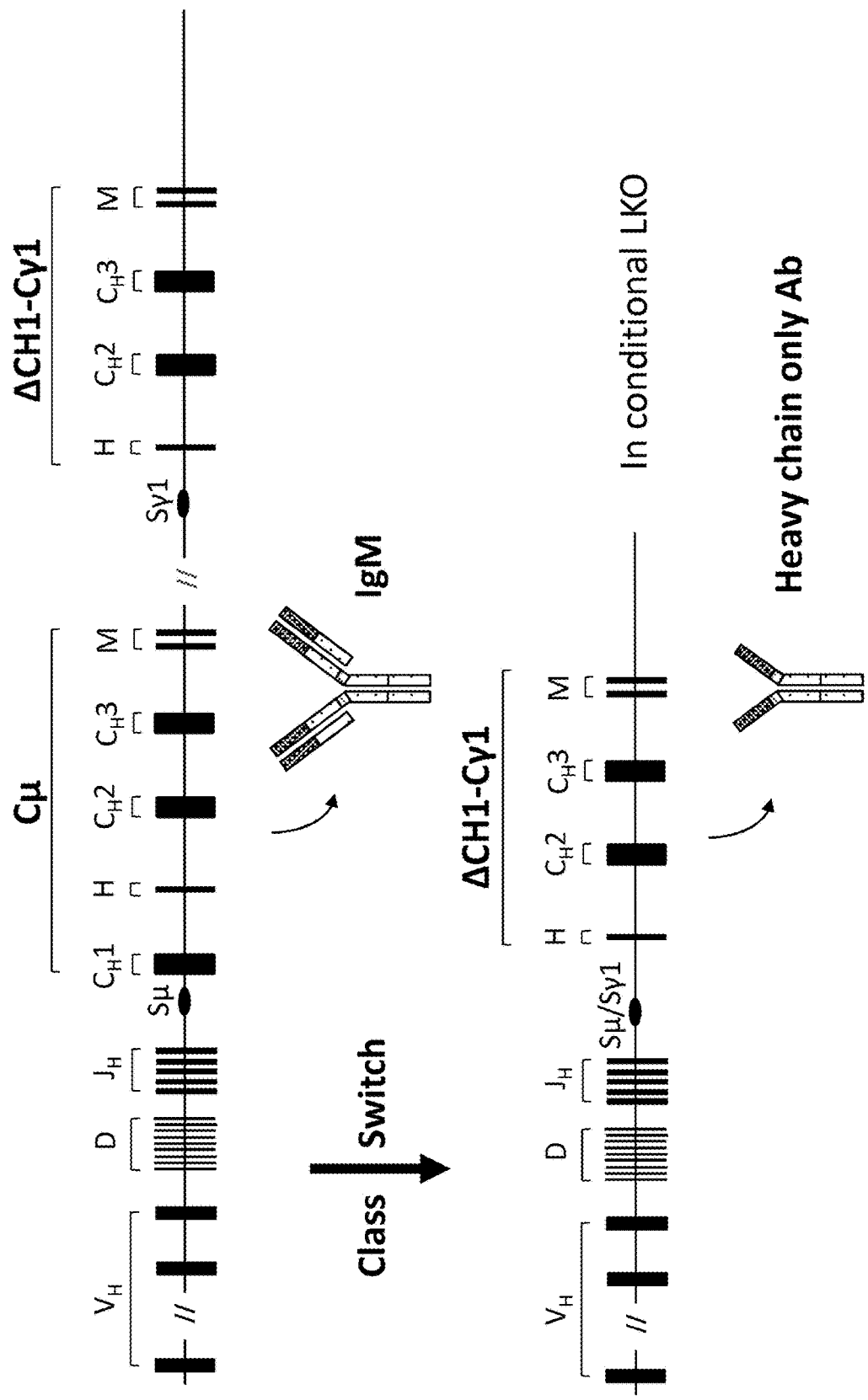
FIG. 3 is a schematic representation of an improved route to in vivo production of heavy chain-only antibodies in non-human vertebrates according to the invention.

FIG. 3 is a schematic representation of an improved route to in vivo production of heavy chain-only antibodies in non-human vertebrates according to the invention. The figure shows the architecture of heavy chain loci in a transgenic vertebrate. Each heavy chain locus comprises a variable region comprising human VH, D and JH gene segments upstream of an endogenous (eg, mouse or rat) S-mu switch and an endogenous C-mu region comprising constant region gene segments (CH1, CH2, CH3, H (hinge) and M (membrane regions)). Downstream of this is a S-gamma switch (eg, an endogenous switch) and a gamma-1 constant region (eg, an endogenous gamma-1 constant region). The gamma constant region does not comprise a CH1 gene segment. Methods are known in the art for deleting gene segments, and specifically deleting CH1 (see, eg, Janssens 2006 mentioned above). For example, deletion by homologous recombination or RMCE can be effected in ES cell ancestors of the non-human vertebrates. Further exemplification is provided below in an embodiment where a binding module is used to replace gamma CH1 in the heavy chain loci.

Four-chain IgM antibodies (H2L2) can be produced by the combination of heavy chains from the heavy chain loci with light chains expressed from light chain loci in the vertebrates, such as during B-cell development (eg, for surface expression on immature splenic B-cells). By enabling a normal IgM stage, the invention provides for the development of normal B-cell compartments and primary variable region repertoires.

According to the invention, during the subsequent isotype (class) switching stage, such as following immunisation with target antigen, light chain expression is switched off by means of a conditional light chain knock-out (as further exemplified below). Thus, heavy chains expressed from the isotype-switched heavy chain locus can form heavy chain dimers lacking CH1 and light chains (ie, H2 antibodies). Thus, heavy chain-only expression and maturation during these later stages are performed by the vertebrate in vivo without being hampered by light chain expression (and avoiding the risk of heavy chain use being directed to undesirable 4-chain H2L2 antibody production and thus reduction of useful H2 yield and repertoire). This is, therefore, advantageous for maximising the production and repertoire of isotype-switched and matured heavy chain-only antibodies produced following immunisation of the vertebrate. In this way, the variable domains of the H2 antibodies are matured and selected without the influence of any light chain variable domain pairing, and thus the H2 variable domains are selected for performance in the H2 format. This is useful for selection of H2 antibodies for desirable antigen-binding affinity and also H2 solubility and expression in vivo. Thus, these H2 antibodies can provide a good source of antibody single variable domains (dAbs).

Furthermore, by accommodating a normal IgM early stage, the chances of maximising the heavy chain variable region repertoire (primary repertoire) are retained, and this provides a good repertoire from which H2 antibody V domains can subsequently be selected.

Example 2: Conditional Light Chain Expression

Conditional, or stage-specific, expression can be performed according to the invention during early stages of B-cell compartment and V repertoire development. As explained in Example 1, the invention provides for light chain expression to be switched off when isotype-switched (non-mu) heavy chains are being expressed.

Figure 4:
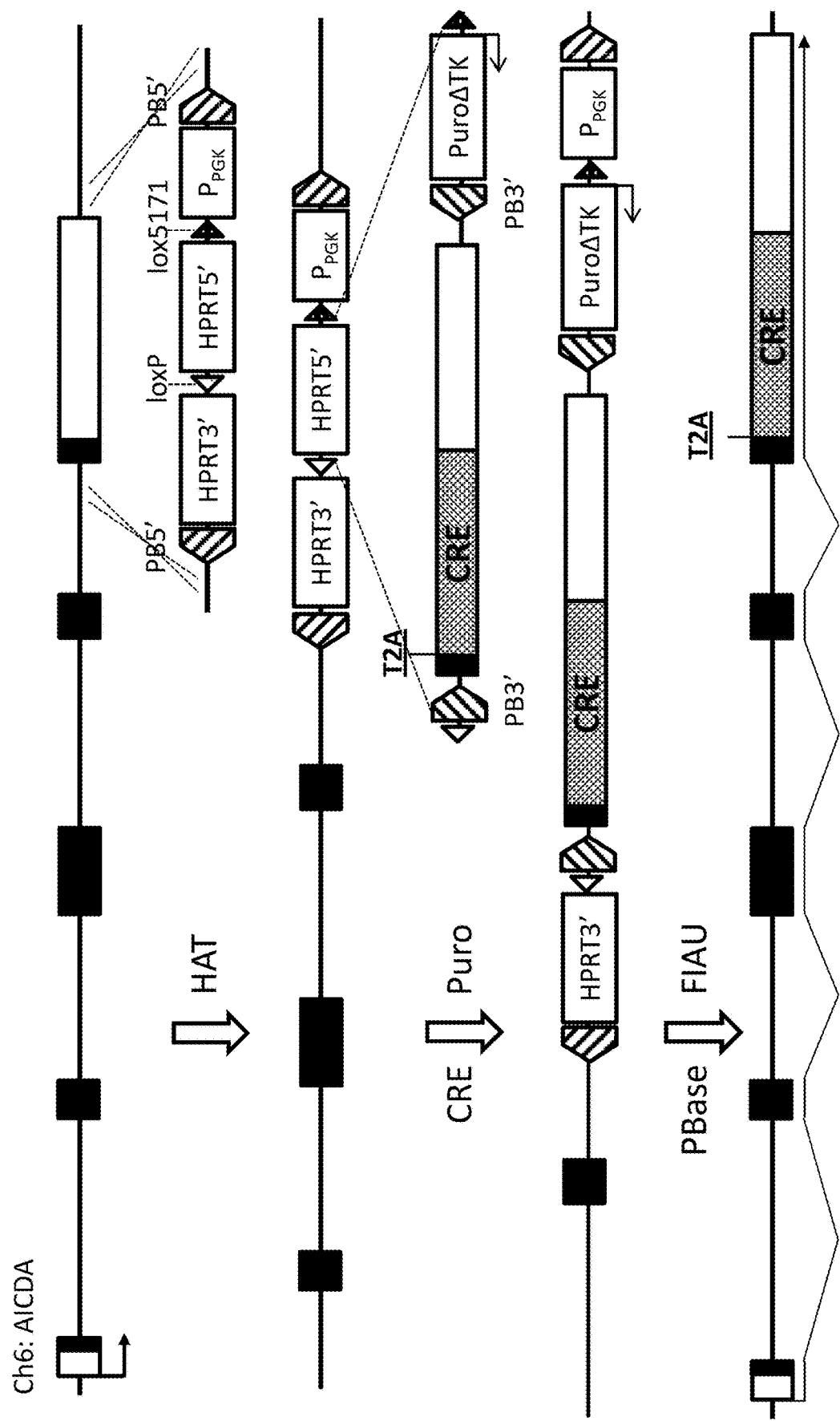
FIGS. 4 and 5 show an example of how to engineer the genome of non-human vertebrates to provide for conditional light chain expression.
Figure 5:
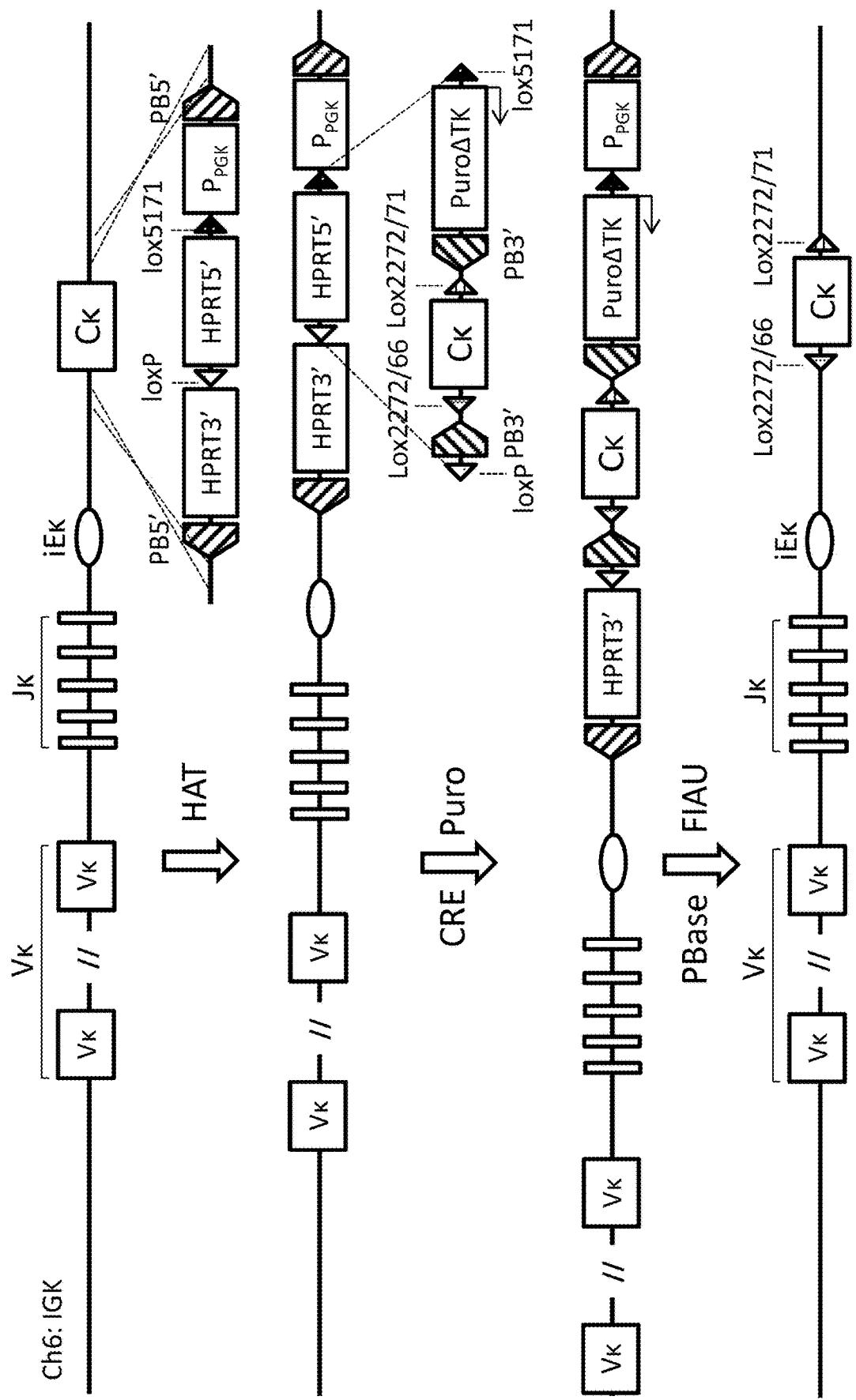

FIGS. 4 and 5 show an example of how to engineer the genome of non-human vertebrates (mice in this example) to provide for such conditional light chain expression. Mouse chromosome 6 contains the activation induced cytidine deaminase (AICDA or AID) gene. This comprises 5 exons as shown by the solid boxes in the locus shown at the top of FIG. 4. UTRs are shown in open boxes at the 5' and 3' ends. AID is stage-specifically expressed in B-cells, and indeed is active when isotype-switched non-mu (eg, gamma) heavy chains are being expressed. The inventors have realised that this profile of expression can advantageously be harnessed to express recombinase (in this case cre recombinase) in this stage-specific manner. Genomic manipulations are made using ES cell technology as will be known by the skilled person (eg, using RMCE, landing pads, markers and transposase activity as described in WO2011004192, the disclosure of which is incorporated herein by reference). Suitable ES cells are also known by the skilled person, eg, mouse AB2.1 cells (obtainable from Baylor College of Medicine, Texas, USA).

(a) Generation of Cre Expression by AID Regulatory Elements

A landing pad identical to the one used for engineering the IGγ1 locus (see below) is targeted to the AID locus to replace a sequence comprising the $5^{th}$ exon of the AID gene, a stop codon and 3' UTR (mouse chromosome 6: coordinates 12256576-122564230) (FIG. 4). The correctly-targeted clones are selected by HAT and confirmed by genotyping. An insertion vector with a structure of "loxP-PB3'LTR-a sequence corresponding to the AID $5^{th}$ exon and stop codon—followed by T2A coding sequence (5'-GGAAGCG-GAGAGGGCAGAGGAAGTCTGCTAACATGCGGT-GACGTCGAGGAGAATC CTGGACCT-3') and the cre gene-3'UTR-PB3'LTR-PuroΔTK-lox5171" is inserted to inactivate the HPRT gene and place PuroΔTK next to the PGK promoter as shown in FIG. 4. The correctly-targeted clones are selected by puromycin and confirmed by junction PCRs. The insertion results in two inverted transposon structures (FIG. 4) in the locus. To delete them, a PiggyBac transposase is transiently expressed in those clones, as is known in the art. Clones with correct deletion are selected by FIAU and confirmed by junction PCRs.

T2A is a self-cleaving peptide identified from Thosea asigna virus. T2A-mediated cleavage is a universal phenomenon in eukaryotic cells. Insertion of a T2A sequence between proteins allows stoichiometric expression of multiple proteins (Szymczak A L et al; "Development of 2A peptide-based strategies in the design of multicistronic vectors"; Expert Opin Biol Ther. 5: 627-638.).

The resulting genomic structure is shown at the foot of FIG. 4 and provides for the co-expression of both AID and cre activity in a stage-specific manner as regulated by AID regulatory elements in the genome.

(b) Generation of a Conditional IGκ Allele

A landing pad is targeted to the IGκ locus downstream of the intronic IGκ enhancer (iEκ) to replace the exon encoding the Cκ region (mouse chromosome 6: coordinates 70724743-70727043) in a mouse ES cell (FIG. 5). The correctly-targeted clones are selected by HAT and confirmed by genotyping. A targeting vector with a structure of "loxP-PB3'LTR-lox2272/66-Cκ exon-lox2272/71-PB3'LTR-PuroΔTK-lox5171" (FIG. 5) is used to replace the sequence between loxP and lox5171 in the landing pad. The insertion results in two inverted transposon structures (FIG. 5) in the locus. To delete them, a PiggyBac hypertransposae is transiently expressed in those clones. Clones with correct deletions are selected by FIAU and confirmed by junction PCRs. The lox2272/66 (5'-ATAACTTCGTATA-AaGTATcC-TATACGAAcggta-3') and lox2272/71 (5'-taccgTTCG-TATA-AaGTATcC-TATACGAAGTTAT-3') are flanking the Cκ exon and inverse to each other. Progeny mice are generated from such genomically-engineered ES cells, the mice also bearing an AID-cre gene for stage-specific expression of cre as described in Example 2(a). In mouse, with cre expression from the AID-cre gene, the Cκ exon is deleted, thereby inactivating light chain expression when isotype-switched heavy chains are being expressed.

In an alternative design, other or additional portions of the kappa locus are flanked by lox sites so that they are deleted on expression of cre. For example, the scheme in FIG. 5 can be changed so that the lox2272/66 is immediately 5' of the first Jk gene segment so that the stretch from the first Jk to the Cκ is deleted upon cre expression. Alternatively, the lox2272/66 and lox2272/71 can immediately flank the 5' and 3' of the first and last Jk gene segments respectively so that the entire J region is deleted upon cre expression.

In one embodiment, only kappa chain expression is inactivated during the isotype-switched stage. In mice lambda chain expression is relatively low (on the order of only 5% of light chains normally), so it may be acceptable to provide conditional kappa chain expression only. In another embodiment, both kappa and lambda chain expression are conditional (eg, the genome also comprises Cλ flanked by lox sites), in that they occur in a stage-specific manner during the early IgM stage but not during expression of isotype-switched non-mu heavy chains.

Example 3: Genetic Engineering of the IGγ1 Locus & Multivalent Heavy Chains and Antibodies Reference is made to FIG. 6 which shows a schematic method for producing bi-specific heavy chains and antibodies as well as heavy chain loci in non-human vertebrate (eg, mouse or rat) genomes for producing these in vivo.

Figure 6:
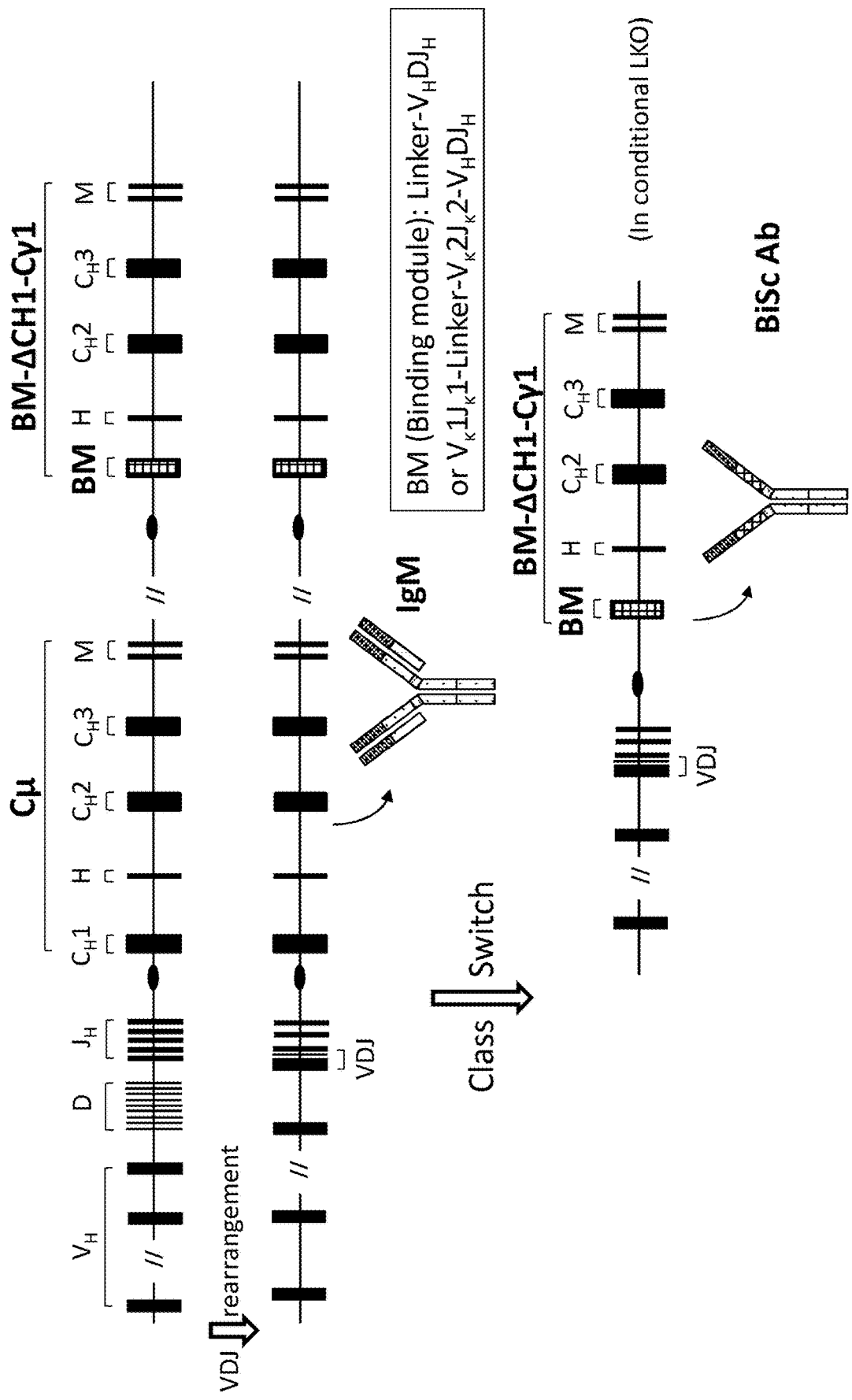
FIG. 6 shows a schematic method for producing bi-specific heavy chains and antibodies.

At the top of FIG. 6 is shown a heavy chain locus of the invention comprising (in 5' to 3' direction) an unrearranged variable region (comprising human VH, D and JH gene segments), endogenous S-mu, a mu constant region (comprising CH1, H, CH2, CH3 and M gene segments), an endogenous S-gamma-1 and a gamma-1 constant region. The latter comprises a nucleotide sequence (referred to as binding module, or BM) comprising linker and variable region binding domain nucleotide sequences, as well as gamma-1H, CH2, CH3 and M gene segments. In this example, the BM encodes Linker (eg, (GGGGS)$_3$)-VH, where VH is an antibody single variable domain (dAb) of known antigen-binding specificity; or an scFv (VH-Linker-VL or VL-Linker-VH) of known antigen-binding specificity; or dAb-Linker-scFv.

Thus the binding moiety(ies) of BM are functional without need for light chain pairing.

Following VDJ rearrangement, IgM are expressed as 4-chain (H2L2) antibodies. Subsequently, following isotype (class) switching (eg, following immunisation with a target antigen) in a stage-specific light chain knock-out background (see Example 2), H2 antibodies of gamma-1 type are produced as dimers of multispecific heavy chains. Each heavy chain bears an affinity matured N-terminal VH domain which specifically binds the target antigen. Furthermore, each heavy chain comprises one or other antigen binding sites with the predetermined specificities chosen for BM. In this example, each BM is immediately N-terminal to a hinge-gamma1 Fc. Thus, the multispecific antibody usefully retains Fc function (such as FcRn binding and recycling and ADCC and/or CDC function).

In an alternative embodiment (where there is not stage-specific light chain knock-out), the isotype-switched heavy chains are expressed together with light chains as part of 4-chain (H2L2) antibodies. CH1 is present in the non-mu (eg, gamma) constant region of the heavy chain locus. In these antibodies, the N-terminal VH/VL pairs are matured and selected against target antigen that has been used for immunisation. In embodiments, it is desirable to position BM downstream of the non-mu CH1 gene segment or hinge so that the CH1 is free to pair with CL in light chains, the BM being present on a part of the constant region that does not require pairing with light chain domains. For example, the BM nucleotide sequence can be positioned immediately 5' of the CH2 gene segment in the non-mu constant region (and thus immediately N-terminal of the CH2 or Fc in the product heavy chain and antibodies), or it can replace CH2 or CH3, or it can be 3' of CH3 (ie, at the C-terminus of the Fc in a resulting product). For the latter, for example, the BM can encode optional linker-dAb (where the dAb is of known antigen binding specificity); the resulting 4-chain product is a mAb with a dAb at the C-terminus of each heavy chain.

Similar arrangements can be made for light chain loci, so that multivalent (eg, bispecific) light chains can be produced according to the invention.

Example 4: Producing Secreted Isotype-Switched & Matured Multivalent, Multispecific Antibodies & Chains The inventors have devised a method of enabling normal cell surface expression of membrane-bound 4-chain IgM during early stages of B-cell compartment and V repertoire development, and then followed by secretion of specifically designed multivalent heavy chains and antibodies of the invention that are class switched and matured (eg, following immunisation).

Figure 7:
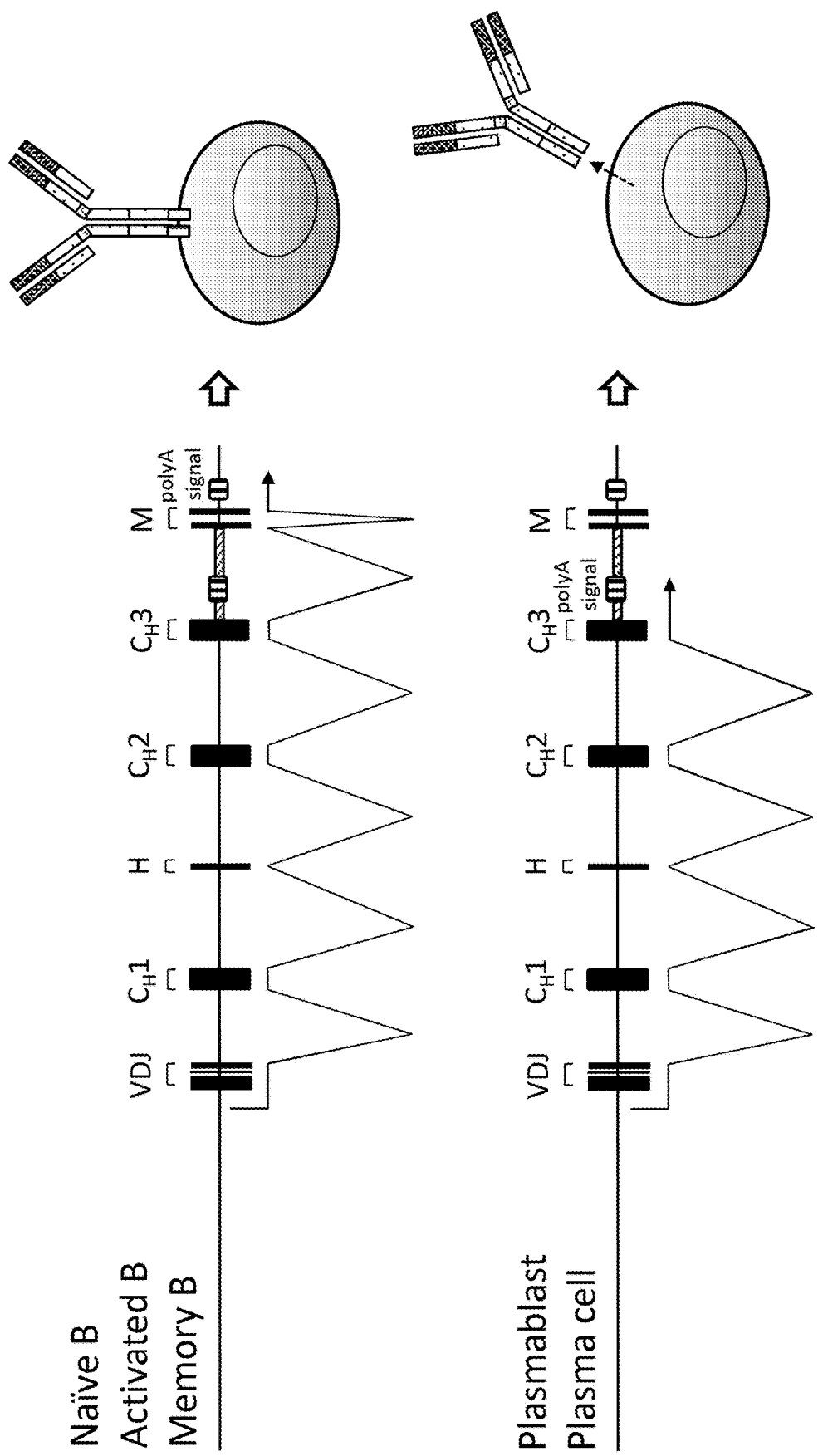
FIG. 7 illustrates the competition between splicing and polyadenylation for membrane-bound or secreted antibodies in a wild-type vertebrate (eg, a mouse or rat).

Reference is made to FIG. 7 which illustrates the competition between splicing and polyadenylation for membrane-bound or secreted antibodies in a wild-type vertebrate (eg, a mouse or rat).

Early during B-cell development, IgM is surface-expressed by virtue of heavy chains comprising membrane-anchor domains (encoded by M in the heavy chain loci).

Later, during the plasmablast and plasma cell stages, antibodies are secreted instead. This arises due to the stopping of transcription short of M and the activity of a polyA signal between CH3 and M (which is different to the polyA 3' of M, as shown in FIG. 7).

Figure 8:
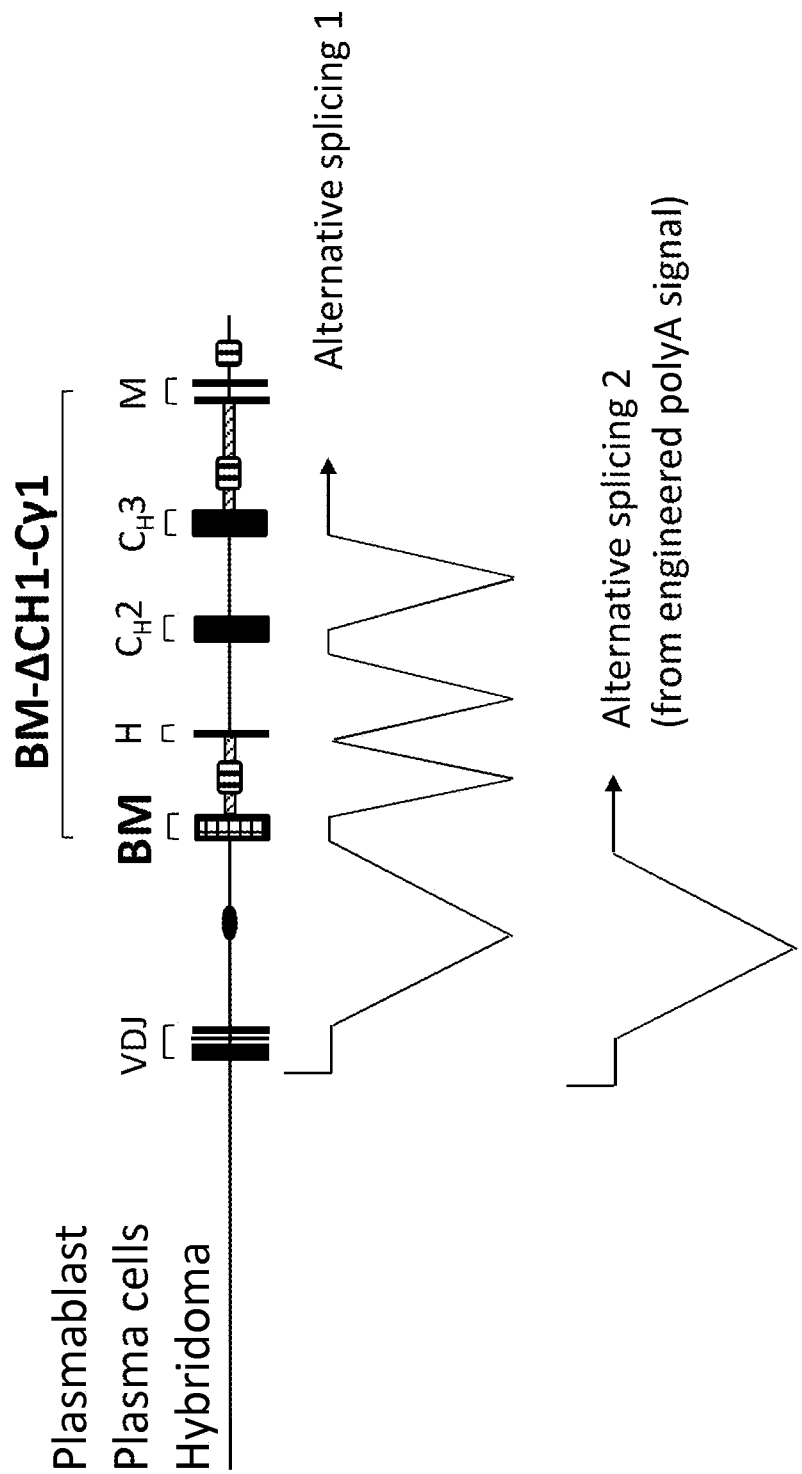
FIGS. 8 and 9 are schematic illustrating alternative splicing to produce multivalent products of the invention.
Figure 9:
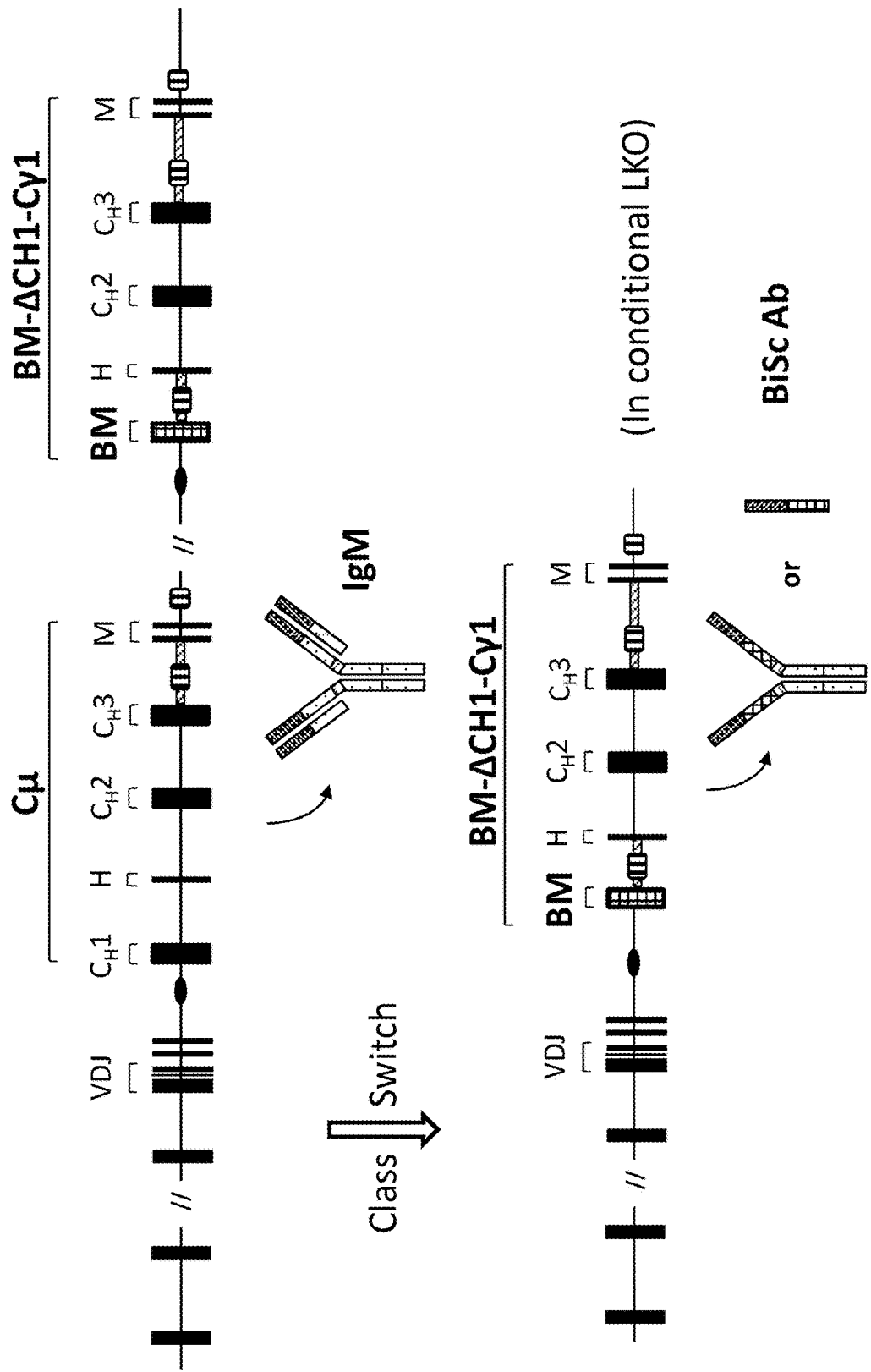

According to the present example of the invention, a stop codon (transcription termination site) and polyA can be inserted immediately 3' of the sequence encoding the epitope binding moiety (or the 3'-most moiety). In FIG. 8, this is shown between BM and H. For example, this can be performed by including polyA and flanking intron sequence (including a stop codon) corresponding to a stretch of DNA between CH3 and M in a vertebrate genome (eg, a human genome, mouse genome, rat genome or non-human genome). Suitable DNA sequences are sequences corresponding to mouse chromosome 12: coordinates 113324868-113328978; and human chromosome 14: coordinates 106206531-106207817. As shown in FIGS. 8 and 9 (optionally in a conditional kappa light chain knock out), alternative splicing in cells of a resulting vertebrate or cell can produce the following secreted products (i) V-BM-H-gamma 1Fc (which can, for example, dimerise to produce bispecific H2 antibodies comprising Fc); or (ii) V-BM (as monomer or dimers). It is possible to favour, for example, the latter product by engineering in a polyA signal between BM and H that is stronger than the polyA between CH3 and M. Use of a stronger polyA signal between CH3 and M would favour product (i). Alternatively, it is possible to omit the polyA between CH3 and M so that only secreted V-BM (as monomer or dimers) is produced.

Figure 10A:
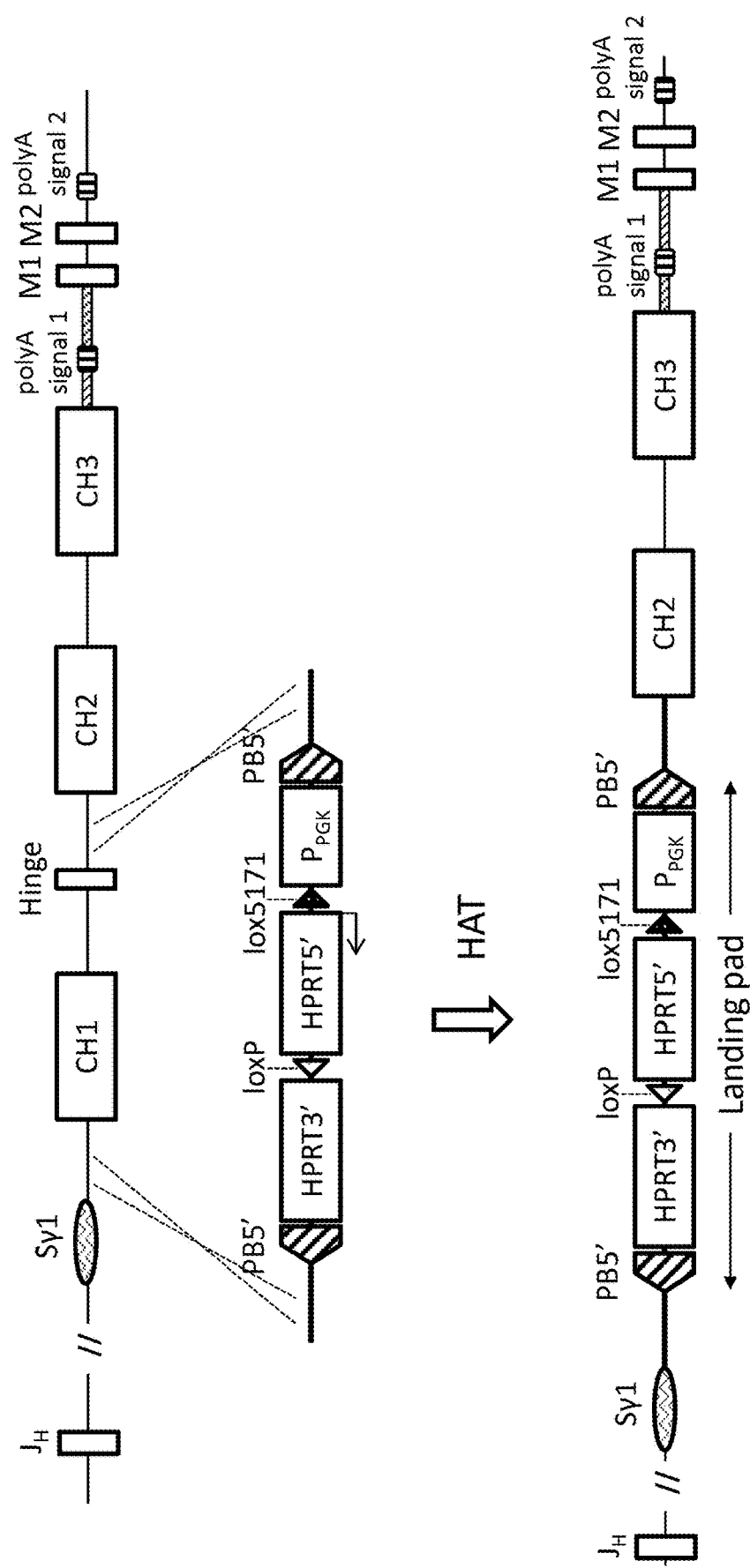
FIGS. 10A and 10B show detailed schematics of a method for constructing a relevant bivalent heavy chain locus of the invention.
Figure 10B:
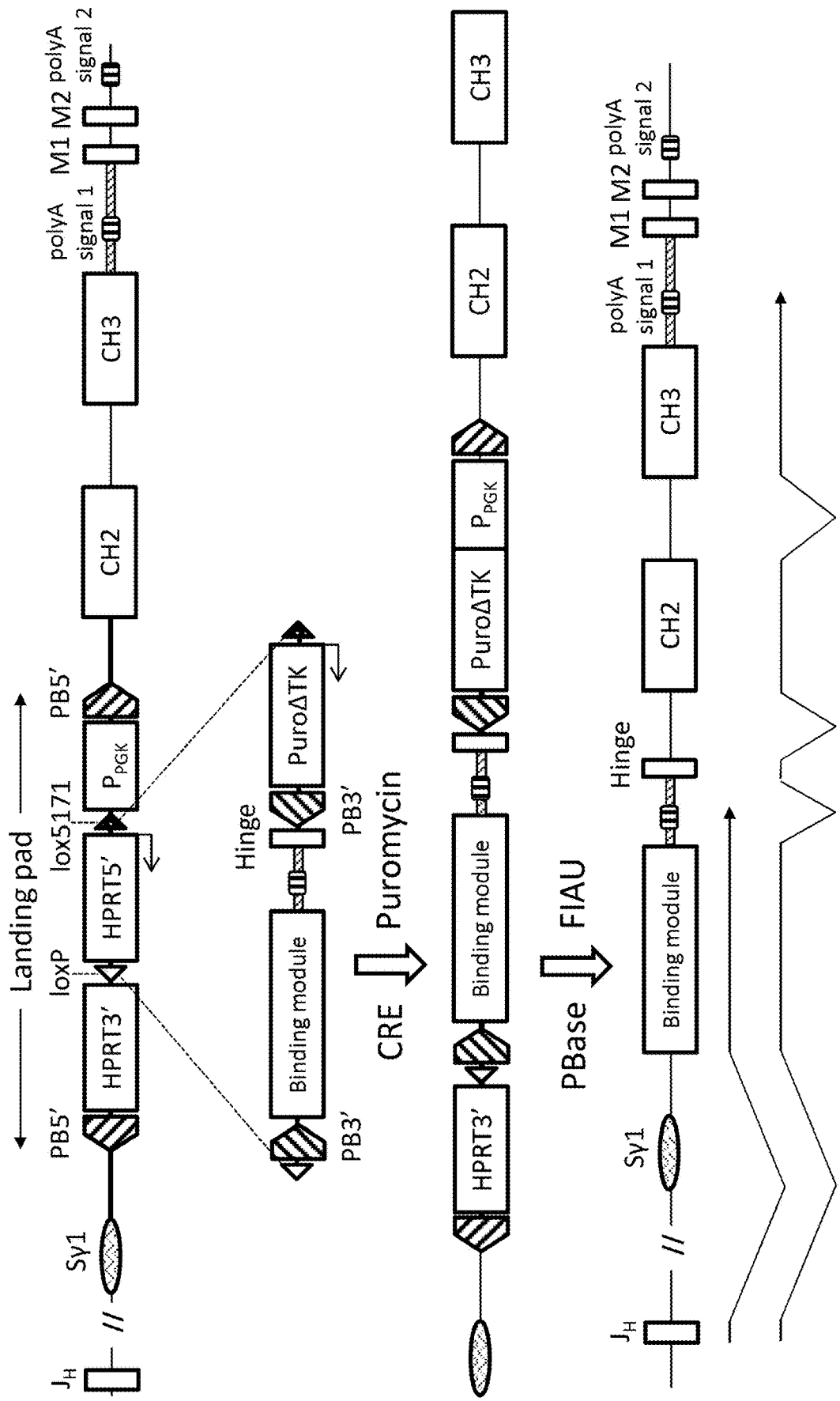

FIGS. 10A and 10B show detailed schematics of a method for constructing a relevant heavy chain locus of the invention. A landing pad with the structure of "PiggyBac (PB) 5'LTR-HPRT3' portion-loxP-HPRT5'portion-lox5171-PGK promoter-PB5'LTR" (FIG. 10A) is targeted into mouse Cγ1 locus of ES cells to replace exons encoding CH1 and hinge and the intron between them (mouse chromosome 12: coordinates 113329794-113330598). The correctly-targeted clones are selected by HAT and confirmed by genotyping. Following the landing pad targeting, an insertion vector containing the structure of "loxP-PB3'LTR-a sequence encoding BM—an intron with similar sequence to the intron between CH3 and M1 exons—an exon to encode a hinge region-PB3'LTR-a gene to encoding Puromycin-delta-thymidine kinase (PuroΔTK)-lox5171" (FIG. 10B) is inserted to replace the sequence between loxP and lox5171 in the landing pad through cre recombinase-mediated cassette exchange (RMCE). In this example, the hinge sequence in the insertion vector is identical to the hinge sequence that was deleted in the first step, but it is possible to construct the insertion vector with no hinge or different hinges, eg, hinges from human or Camelid or a different mouse or rat strain when the ES cell is a mouse or rat ES cell. The correctly-inserted clones are selected by puromycin and confirmed by junction PCRs. The insertion results in two inverted transposon structures (FIG. 10B) in the locus. To excise these two transposons, a PiggyBac hypertransposase (Yusa, K et al. PNAS. 2010. 108: 1531-1536) is transiently expressed in those clones. Clones with correct deletion are selected by thymidine analogue 5-iodo-2'-fluoro-2'-deoxy-1-β-D-arabino-furonosyluracil (FIAU) and confirmed by junction PCRs.

As shown in FIG. 10B, products (i) and (ii) described above are possible.

Example 5: Generation of a Conditional Common Light Chain Allele

Figure 11A:
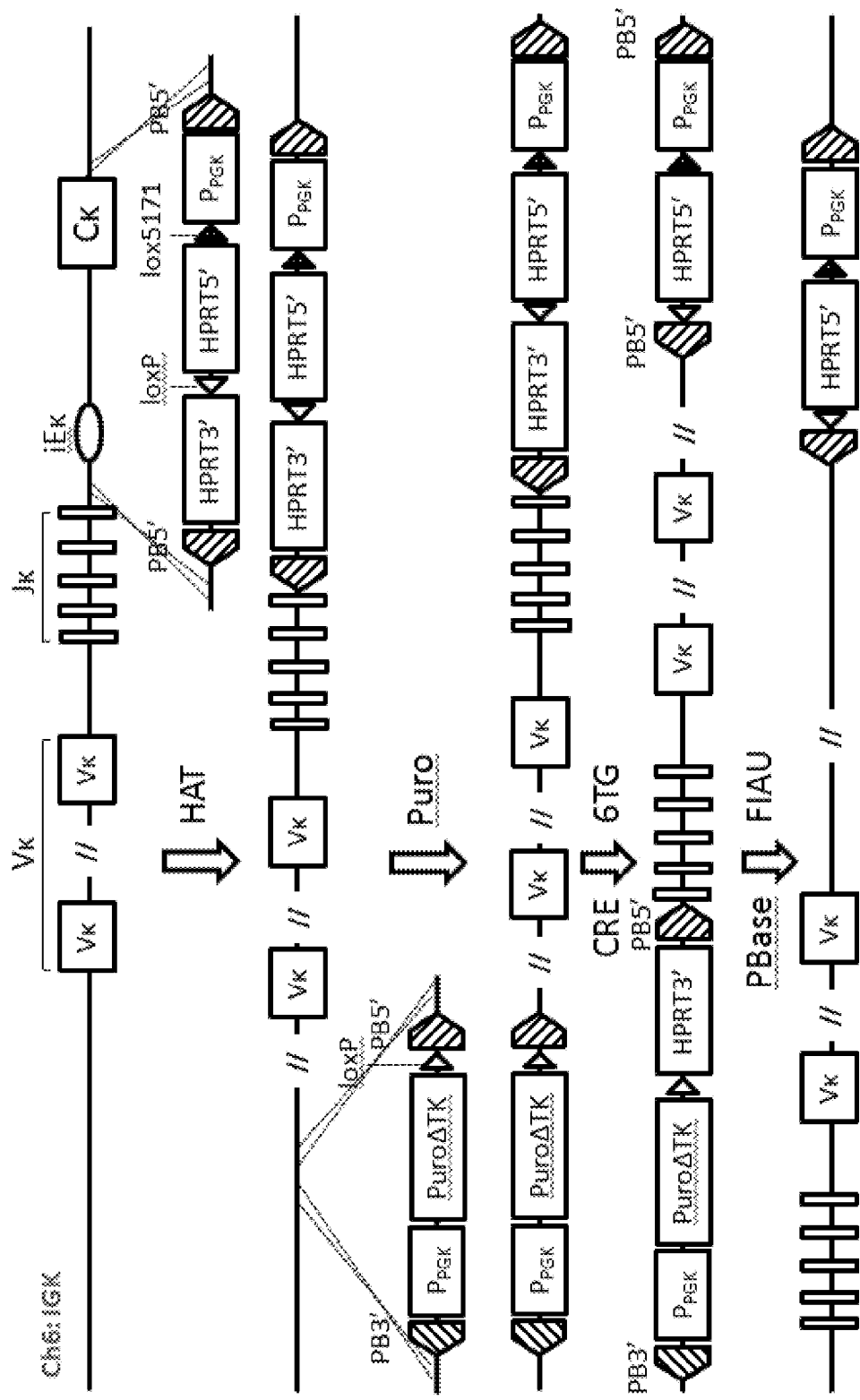
FIGS. 11A and 11B show detailed schematics of a method for constructing a locus expressing a common light chain.
Figure 11B:
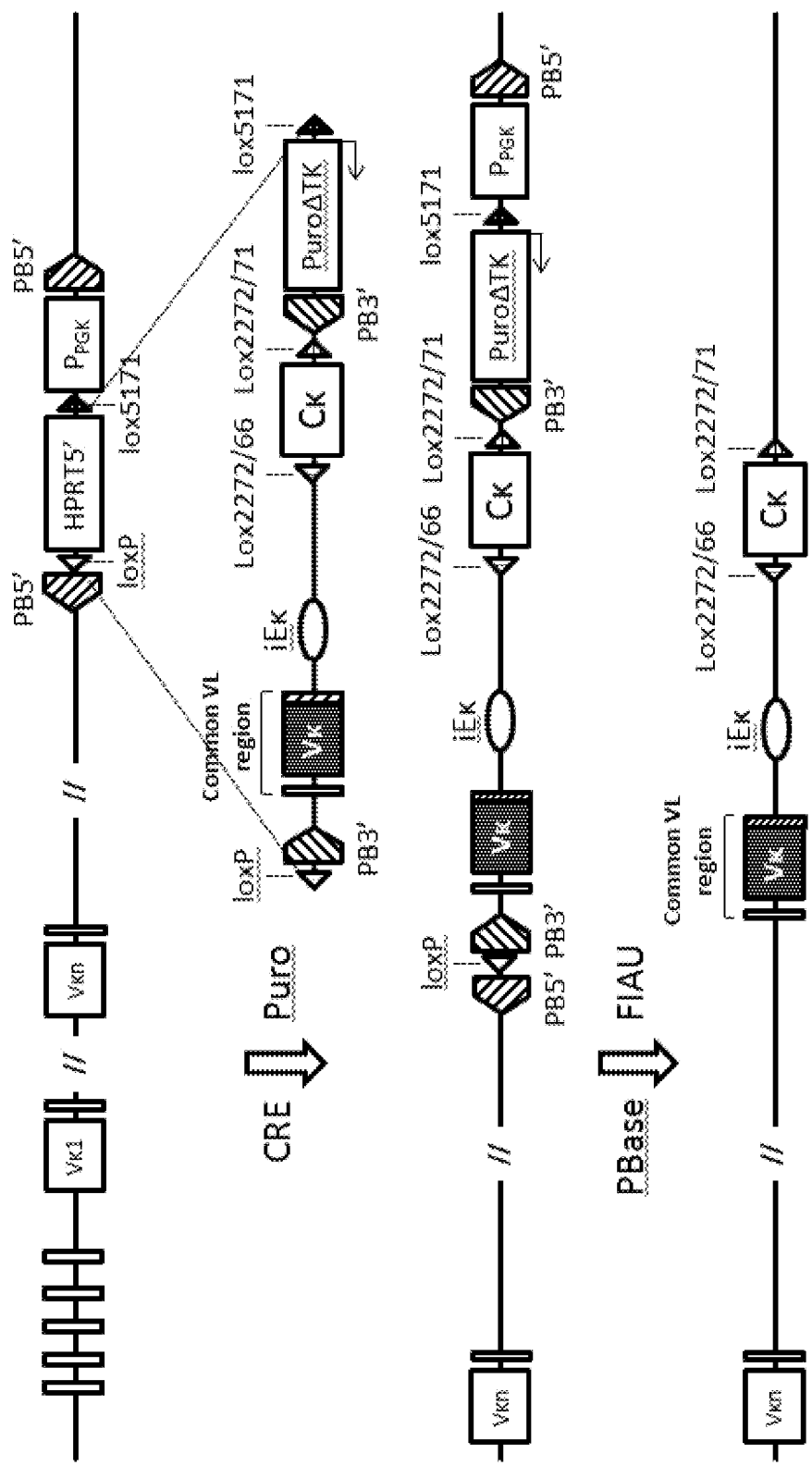

Reference is made to FIGS. 11A and 11B. Although useful for engineering any non-human vertebrate genome, the present example is applied to the engineering of mice genomes.

Inactivation of Endogenous Variable Region

Inversion of the endogenous mouse Vκ-Jκ gene segments inactivates endogenous kappa variable region expression. FIG. 11A shows a method for doing this using recombinase-mediated cassette exchange. In the presence of Cre recombinase, recombination at the inserted loxP sites leads to inversion of endogenous mouse kappa variable region DNA, which inactivates expression of endogenous Vκ. A final step uses piggyBac transposase to remove the 5' cassette, leaving just the 3' cassette in place in the kappa locus for use in the method shown in FIG. 11B.

Insertion of Conditional Vκ

Reference is made to FIG. 11B. DNA fragments including a synthetic common light chain genomic sequence (a promoter, a leader exon, a intron and an exon encoding the common light chain), a mouse genomic intronic Eκ region, and a lox2272/66 and lox2272/71-floxed mouse Cκ region are ligated together to generate the insertion sequence (see sequence below). The insertion sequence is further subcloned into a vector, pBR322 with loxP-PB3'LTR and PB3'LTR-promoter-less PuroΔTK gene-lox5171 to form an insertion vector. Following the inversion of the endogenous mouse Vκ-Jκ gene segments, the insertion vector is inserted into the inverted endogenous IGκ locus using RMCE with transient expression of Cre. Following the insertion, the modifying cassettes in the 5' and 3' ends with transposon structure are excised out by transient expression of piggyBac transposase. The resulting lox-flanked Cκ sequence can be deleted upon stage-specific cre expression as described above such as at a class switch stage by using AID regulatory elements to drive Cre expression.

Use of a common light chain variable region human Vκ1-39Jκ or Vκ3-20Jκ (eg, Vκ1-39Jκ5 or Vκ3-20Jκ1) or VpreB (such as human VpreB) is, the inventors believe, useful since such variable regions promiscuously pair with human VH regions, and thus may have a scaffolding ability that is advantageous to the selection (in the 4-chain IgM stage) of human VH domain sequences that can provide a useful primary repertoire for subsequent selection of VH domains that perform in H2 antibodies following class switching, wherein the VH domains are not paired with VL domains.

Common Light Chain Insertion Sequence (5' to 3'):

```
atctttcagggacaatgatgcccatgcaggcagcatatttataatgcaca gtaaacactaggaggaaacaaggcagtgagagaggaaagagagcagcgat accgaaaatgtcctcagcgagaagctaccacagaggatgaatggagatca agcccacgtggaaacatgggaaatgtctcagtattttccacctaagaa gggagggagatggggtatgtatacacctccctgtcctcactgattgaggg ctttccgagaggatgctcattccaggtgctgtgataggccatgtgtacag gcagggctgccttctccagcttcagatagagcagtgaggaaaagatatgg ccatgggggtcagcagaagtacagcaaagggaaaagggaaagggtagca agagtgacaactatattcaccccccacacacacacacacacacgaa attgtgtattgcaatccagaactgcttctctctgaacctaaatcttagca agcagtttaccagtaactgcccttgaaattcaggccctggaaaggagca gggggttgtgtacaggctataccacagcagtctgcccacccttagtgatg catgagtaatgctccctggactccccaggttctagtcttctcatgtcgat
```

-continued

```
gtagttgattccacttcccttgctgcacaaccaggctgggatgcctgggc
agaggcagacatgtgaggtatagggggttcaaatctgtttccaagtttat
ccagcttcaaagcatttctccgtgtacatgagcggtggcttgacaggaga
tggagactctctttcctggatgtgaggcaaggaggcaggcgtctgagtca
ggatgatgtccctactcactgctaaagagaaaagtggctttgatggtgca
gggcagggaaatgcactgagtggtcgccaccctcacagaagagaaagtgt
tcactgacctggccttcccccagggcctctccctcccattgctttccaga
aagccatgattttgagagccacacctgaacactcacaaacattatggtg
ggaaaagcagatcagagcattaggcaagttgcattaccttggccttcttc
ctttggagacaattgatgtggggttctagattgacccagagtttcaagtt
tatcctgattcaggcttcaacagctggaggaagaaacagagatgttttt
gaagtaaacagatctagcattactaatcaaccttcatactgatgaccta
tgggaaataatacccaaggcagaaaaatgggcagaataaggggagcccc
aaaccaagacgaagctgctgcccattgagaccctgggtattacagagacc
tatagctctggataatggaagatctatgagtggcacaggcgctgaggaat
cacagcatcattatcgtgcatctgcagggaattgcttgtaaatatactgg
taattacaaatgtttaaggtcactacaaatactttggagtgtattaaata
tgcttctgataaagactgtttttctcacatgaaacaatgggaaccatgtg
acaatcacagaggtgttgttactatagcaaaagggattgttactctccac
atcccttaagtaacttgaaggcctgatagacccacctctaagacttca
ttagacattccctacgaatggttatactctcctgtatactcccaatacaa
ctctaaaatatattattccatatagtccttaggtttgtattaaagtttga
cttttttccttcaaaatatctcttgtcacaacagcggctctagagagaaa
tacattccctccaggcaaatctatgctgcgctggtctgacctgggaccct
ggggacattgccccgtgctgagttactaagatgagccagccctgcagct
gtgctcagcctgccccatgcctgctgattgatttgcatgttccagagca
cagcccctgccctgaagactttttttatgggctggtcgcaccctgtgcag
gagtcagtctcagtcaggacacagcATGGACATGAGGGTCCCCGCTCAGC
TCCTGGGGCTCCTGCTACTCTGGCTCCGAGgtaaggatggagaacactag
gaatttactcagccagtgtgctcagtactgactggaacttcagggaagtt
ctctgataacatgattaatagtaagaatatttgtttttatgtttccaatc
tcagGTGCCAGATGTGACATCCAGATGACCCAGTCTCCATCCTCCCTGTC
TGCATCTGTAGGAGACAGAGTCACCATCACTTGCCGGGCAAGTCAGAGCA
TTAGCAGCTATTTAAATTGGTATCAGCAGAAACCAGGGAAAGCCCCTAAG
CTCCTGATCTATGCTGCATCCAGTTTGCAAAGTGGGGTCCCATCAAGGTT
CAGTGGCAGTGGATCTGGGACAGATTTCACTCTCACCATCAGCAGTCTGC
AACCTGAAGATTTTGCAACTTACTACTGTCAACAGAGTTACAGTACCCCG
ATCACCTTCGGCCAAGGGACACGACTGGAGATTAAACgtaagtacacttt
tctcatcttttttatgtgtaagcacaggttttcatgttaggagttaaa
gtcagttcagaaaatcttgagaaaatggagagggctcattatcagttgac
gtggcatacagtgtcagattttctgtttatcaagctagtgagattagggg
```

-continued

```
caaaaagaggctttagttgagaggaaagtaattaatactatggtcaccat
ccaagagattggatcggagaataagcatgagtagttattgagatctgggt
ctgactgcaggtagcgtggtcttctagacgttaagtgggagatttggag
gggatgaggaatgaaggaacttcaggatagaaaagggctgaagtcaagtt
cagctcctaaaatggatgtgggagcaaactttgaagataaactgaatgac
ccagaggatgaaacagcgcagatcaaagaggggcctggagctctgagaag
agaaggagactcatccgtgttgagtttccacaagtactgtcttgagtttt
gcaataaaagtgggatagcagagttgagtgagccgtaggctgagttctct
cttttgtctcctaagttttttatgactacaaaaatcagtagtatgtcctga
aataatcattaagctgtttgaaagtatgactgcttgccatgtagatacca
tggcttgctgaataatcagaagaggtgtgactcttattctaaaatttgtc
acaaaatgtcaaaatgagagactctgtaggaacgagtccttgacagacag
ctcaaggggttttttcctttgtctcatttctacatgaaagtaaatttga
aatgatcttttttattataagagtagaaatacagttgggtttgaactata
tgttttaatggccacggttttgtaagacatttggtcctttgttttcccag
ttattactcgattgtaattttatatcgccagcaatggactgaaacggtcc
gcaacctcttctttacaactgggtgacctcgcggctgtgccagccatttg
gcgttcaccctgccgctaagggccatgtgaaccccgcggtagcatccct
tgctccgcgtggaccactttcctgaggcacagtgataggaacagagccac
taatctgaagagaacagagatgtgacagactacactaatgtgagaaaaac
aaggaaagggtgacttattggagatttcagaaataaaatgcatttattat
tatattccctttattttaattttctattagggaattagaaagggcataaac
tgctttatccagtgttatattaaaagcttaatgtatataatcttttagag
gtaaaatctacagccagcaaaagtcatggtaaatattctttgactgaact
ctcactaaaactcctctaaattatatgtcatattaactggttaaattaata
taaatttgtgacatgaccttaactggttaggtaggatatttttcttcatg
caaaaatatgactaataataatttagcacaaaaatatttcccaatacttt
aattctgtgatagaaaatgtttaactcagctactataatcccataatttt
tgaaaactatttattagcttttgtgtttgaccctccctagccaaaggca
actatttaaggaccctttaaaactcttgaaactactttagagtcattaag
ttatttaaccacttttaattacttaaatgatgtcaattccctttaac
tattaatttatttaagggggaaaggctgctcataattctattgttttt
cttggtaaagaactctcagttttcgttttactacctctgtcacccaaga
gttggcatctcaacagaggggactttccgagaggccatctggcagttgct
taagatcagaagtgaagtctgccagttcctcccaggcaggtggcccagat
tacagttgacctgttctggtgtggctaaaaattgtcccatgtggttacaa
accattagaccagggtctgatgaattgctcagaatatttctggacaccca
aatacagaccctggcttaaggccctgtccatacagtaggtttagcttggc
tacaccaaaggaagccatacagaggctaatatcagagtattcttggaaga
gacaggagaaaatgaaagccagtttctgctcttaccttatgtgcttgtgt
```

-continued
tcagactcccaaacatcaggagtgtcagataaactggtctgaatctctgt ctgaagcatggaactgaaaagaatgtagtttcagggaagaaaggcaatag aaggaagcctgagaatatcttcaaagggtcagactcaatttactttctaa agaagtagctaggaactagggaataacttagaaacaacaagATAACTTCG TATAAAGTATCCTATACGAACGGTAattgtatatatgtgcatcctggccc cattgttccttatctgtagggataagcgtgcttttttgtgtgtctgtata taacataactgtttacacataatacactgaaatggagcccttccttgtta cttcataccatcctctgtgcttccttcctcagGGGCTGATGCTGCACCAA

CTGTATCCATCTTCCCACCATCCAGTGAGCAGTTAACATCTGGAGGTGCC

TCAGTCGTGTGCTTCTTGAACAACTTCTACCCCAAAGACATCAATGTCAA

GTGGAAGATTGATGGCAGTGAACGACAAAATGGCGTCCTGAACAGTTGGA

CTGATCAGGACAGCAAAGACAGCACCTACAGCATGAGCAGCACCCTCACG

TTGACCAAGGACGAGTATGAACGACATAACAGCTATACCTGTGAGGCCAC

TCACAAGACATCAACTTCACCCATTGTCAAGAGCTTCAACAGGAATGAGT

GTtagagacaaaggtcctgagacgATAACTTCGTATAGGATACTTTATAC

GAACGGTA

The sequence comprises the following components (numbers relate to positions in the sequence):—
1. Human Vκ1-39 promoter: 1894-2000
2. Rearranged human Vκ1-39/Jκ 5: 2026-2537
   a. Leader exon: 2026-2080
   b. Vκ1-39/Jκ5 exon: 2205-2537
3. Mouse intronic sequence: 2538-4891
4. Lox2272/66: 4892-4925
5. Mouse Cκ exon: 5083-5402
6. Lox2272/71: 5425-5458

In another embodiment, the initial step of inverting the mouse variable region DNA is not carried out, but instead mouse Vκ expression is substantially inactivated by insertion of the common Vκ as described above.

Example 6: Common VL Domain Multispecifics: Generation of a Tandem ScFv Allele within the Cγ1 Locus Reference is made to FIGS. 12A and 12B. Although useful for engineering any non-human vertebrate genome, the present example is applied to the engineering of mice genomes. The method replaces endogenous CH1 of the endogenous gamma constant region with a common Vκ. The method can also be used to insert a binding module 3' of the common Vκ.

Figure 12A:
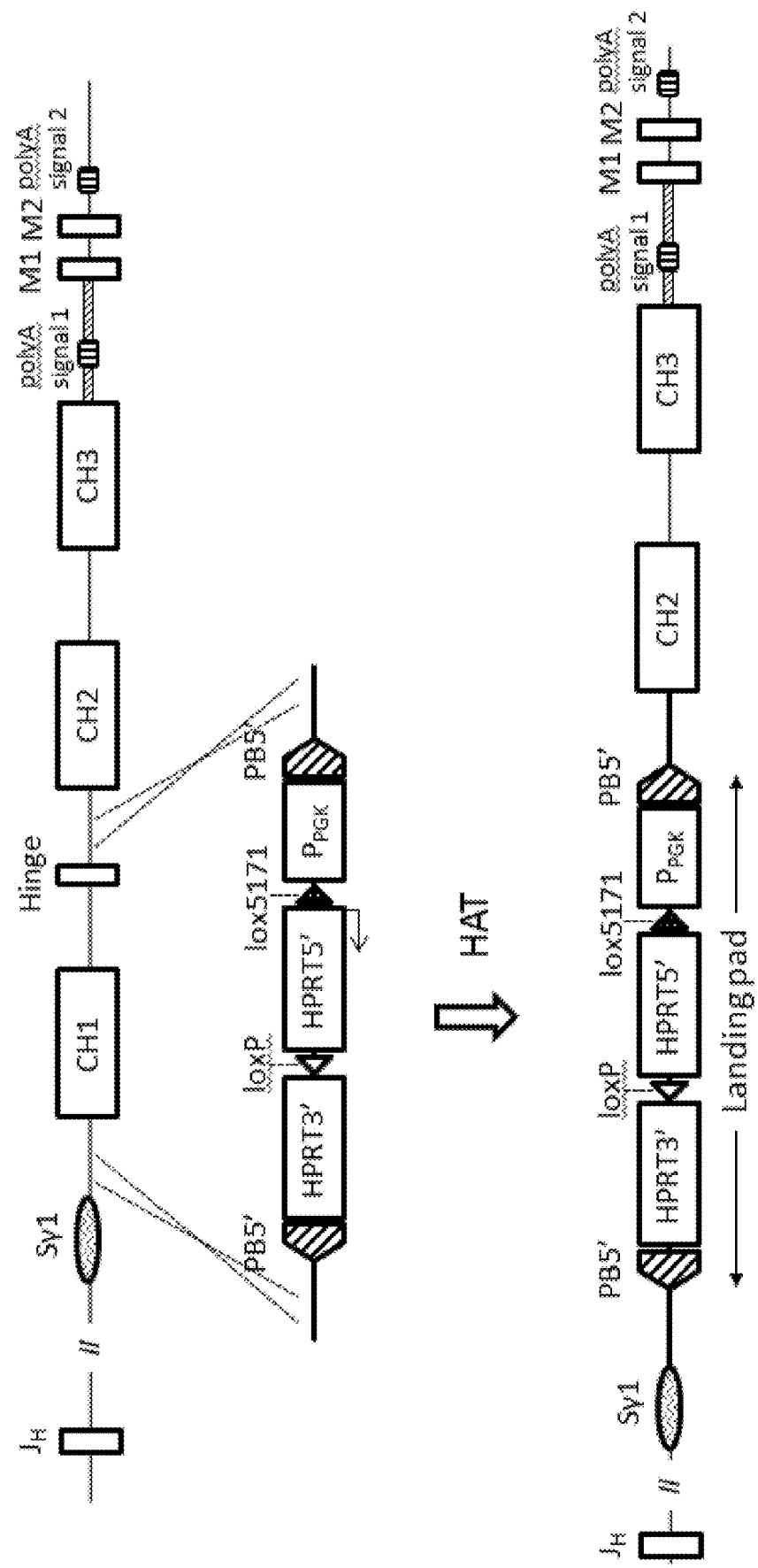
FIGS. 12A-12B and 13A-13E show detailed schematics of a method for constructing loci for expressing multivalent polypeptides in vivo, as well as example products.
Figure 12B:
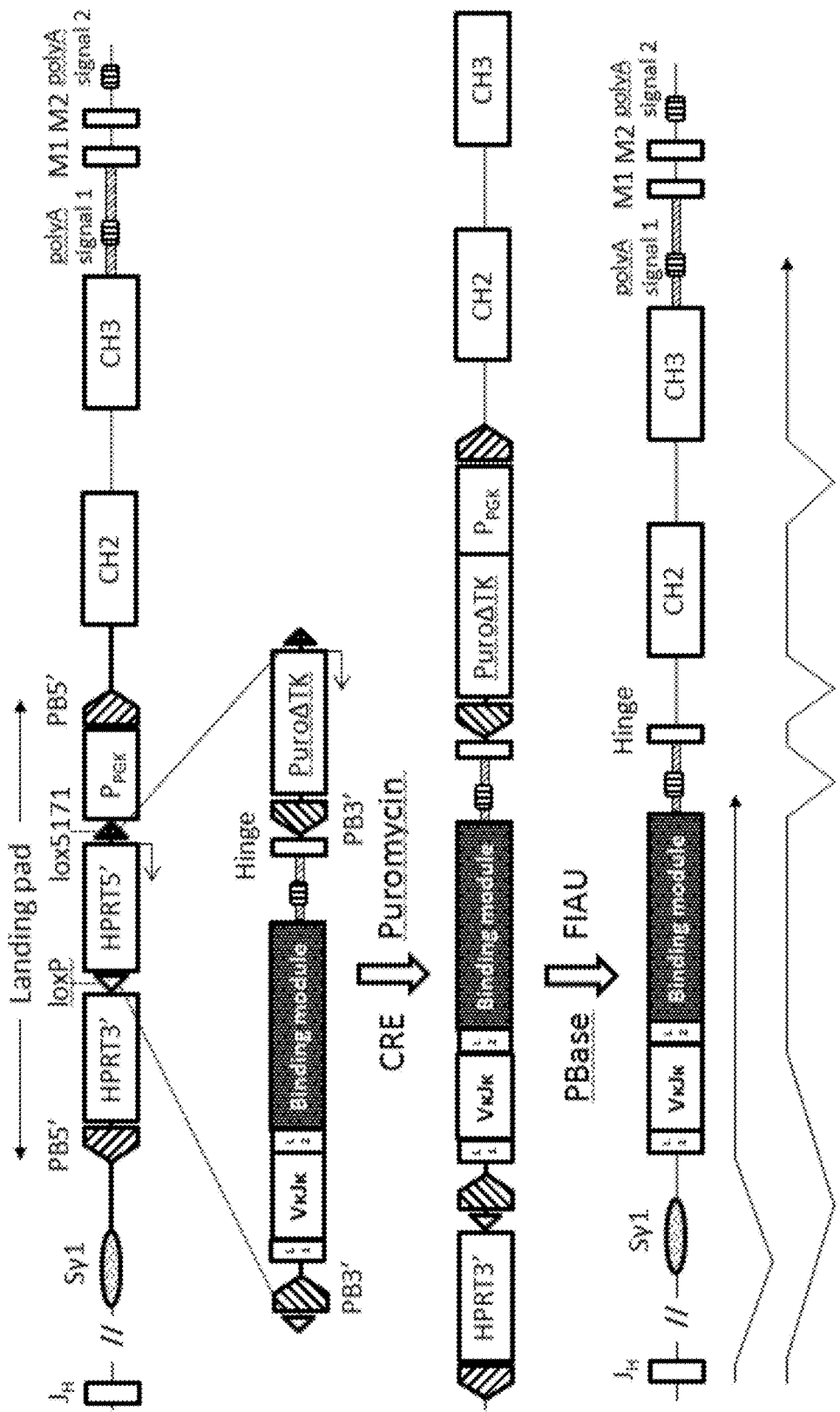

A DNA fragment including an exon encoding the structure "linker (L1)-common human light chain VκJκ-linker (L2)-binding module" and a intron containing "alternative splicing site-polyadenylation site" is synthesized and inserted between loxP-PB3'LTR and PB3'LTR-promoterless PuroΔTK gene-lox5171 cassettes to generate the insertion vector (FIG. 12B; the alternative splicing site-polyadenylation site is denoted by the small box with vertical hatching and which is shown between Binding Module and Hinge). The linker can be a sequence encoding one to four "Gly-Gly-Gly-Gly-Ser". The common light chain region can be a human sequence, eg, a sequence encoding human Vκ1-39Jκ5 or Vκ3-20Jκ1 or human VpreB (see sequences below) or a rearranged or germline VλJλ. The binding module can be a sequence encoding a single chain Fv (ScFv) or a rearranged $V_H DJ_H$ or any other form of epitope binding moiety or domain to bind to a first human target antigen (eg, the antigen is human CD3 or human CD16 or another cell surface antigen to engage effector cell killing of targeted cells). The alternative splicing site-polyadenylation site can be provided by a sequence similar or identical to the intron sequence between the Cγ1H3 and the M1 exons (eg, of a mouse genome), which comprises a structure of "alternative splicing site—the sequence encoding the carboxyl terminal end of the secreted form of IgG1-stop codon-polyadenylation site". The insertion vector is targeted into the Cγ1H1 in mouse ES cells, replacing the landing pad that has been previously inserted through RMCE with transient expression of Cre as shown in FIG. 12A.

Following the insertion, the modifying cassettes in the 5' and 3' ends with transposon structure are excised out by transient expression of piggyBac transposase. Progeny mice are generated using standard procedures from the ES cells.

By placing the epitope binding moiety sequence (binding module) downstream of the mu switch and mu constant region (in this case in a gamma-1 region), this sequence is shielded away from the AID mutation hotspots in the locus.

During the naïve B-cell stage, the resulting locus can produce a membrane-bound heavy chain (eg, as part of a H2 antibody) consisting of the following structure in N- to C-terminal direction:—
VH-L1-Common VL-L2-Binding Module-Hinge-Fc-Membrane Anchoring Region In the present example, the Binding Module is an scFv that specifically binds human CD3 or human CD16A (eg, as further described below).

Following immunisation of a mouse with a target antigen (eg, human CD19 or human EpCAM), plasmablasts and plasma B-cells express secreted heavy chains (eg, as part of secreted H2 antibodies) of the structure shown by the penultimate line at the bottom of FIG. 12B, as follows in N- to C-terminal direction:—
scFv1-L2-Binding Module Here, scFv1 is provided by "VH-L1-VL" where the VL is based on the common VL and scFv1 specifically binds the target antigen (eg, CD19 or EpCAM) used for immunisation. In the present example, a second scFv (Binding Module) specifically binds CD3 or CD16A.

Alternatively, there is secreted (see bottom line of FIG. 12B) in N- to C-terminal direction:—
scFv1-L2-Binding Module-hinge-Fc It is possible to delete the polyA site between CH3 and M1, in order to eliminate production of this product, and thus favouring production of secreted scFv1-L2-Binding Module.

Advantageously, the binding domains have been combined and selected completely in vivo which avoids problems in the art that rely on one or more in vitro steps for such combination and selection.

Biobetters

In an example, a biobetter version of an existing antibody is produced, where the antibody is specific for an antigen. In this embodiment, the Binding Module comprises an scFv (or other binding format) that specifically binds the antigen and comprises the VH and VL pairing found in a binding site of the antibody. The common VL is the VL found in that pairing. The locus comprises human V, D and J gene segments 5' of the common VL sequence. After production of non-human vertebrate from the resulting ES cell, the vertebrate is immunised with the antigen, and VDJ recombination and maturation is effected in vivo. Thus, matured VH is combined with the common VL and the Binding Module scFv to produce a product scFv-linker-scFv where each scFv is specific for the antigen. Using this method, products can be obtained that bind the antigen and a product can be chosen that has higher binding affinity to the target and/or binds a different epitope than the original starting antibody, or has more desirable therapeutic efficacy, expression or biophysical characteristics.

Thus, in an aspect of the invention, the epitopes bound by the product of the invention are epitopes found on the same antigen species.

In another example, the 3' scFv Binding Module is omitted, so that a single scFv binding site at the N-terminus is produced, this being a binding site that has undergone guided selection in the presence of the VL from the pre-existing (original) antibody. As discussed above, the selected VH/VL pairing can be used for cloning into heavy and light chain expression vectors for producing an antibody that is a biobetter version of the original antibody.

Example 7: Common VL Domain Multispecifics: Anti-CD19/Anti-CD3/Anti-CD16 Bispecific Constructs The invention relates to multispecific polypeptides that are useful for recruiting immune effector cells in patients. Thus, the invention provides a multispecific antigen binding polypeptide, dimer or antibody which is capable of recruiting the activity of a human immune effector cell by specifically binding to (i) an effector antigen (eg, human CD3) located on a human immune effector cell and (ii) a target antigen (eg, human EpCAM or human CD19) other than the effector antigen; optionally wherein said target antigen is located on a target cell other than said human immune effector cell. An anti-CD19/anti-CD3 product is useful, for example, for treating cancer in a patient, such as leukaemia or non-Hodgkin's lymphoma. To this end, the present example provides for such a product. Examples are shown in Table 1.

In alternative embodiments, each of L2 and L3 is separately selected from
VEGGSGGSGGSGGSGGVD; or
(GGGGS); or
(GGGGS)$_2$; or
(GGGGS)$_3$; or
(GGS)$_3$; or
AKTTP; or
AKTTPRLGG; or
EEGEFSEA.

Other alternatives are provided below.

See FIG. 13 for schematics showing the methods of locus construction and some example products. In FIGS. 13D and E, BM1 comprises the sequences arising from rearrangement of the variable region at the 5' part of the locus; BM2 is derived from the sequence of the known Binding Module that was inserted.

The common VL and L1 (linker that is 5' of the common VL as shown in FIG. 12B) can be omitted in an alternative embodiment, so that the final product contains an N-terminal dAb (single variable domain that specifically binds the antigen used for immunisation, eg, CD19). Optionally, instead of using an scFv, the Binding Module can be a dAb that specifically binds the second antigen (eg, CD3 or CD16). Thus, the product would comprise (N- to C-terminally) dAb1-linker-dAb2, where the dAbs bind different antigens (or different epitopes on the same antigen species, eg, to produce a biobetter product that is improved).

Figure 13A:
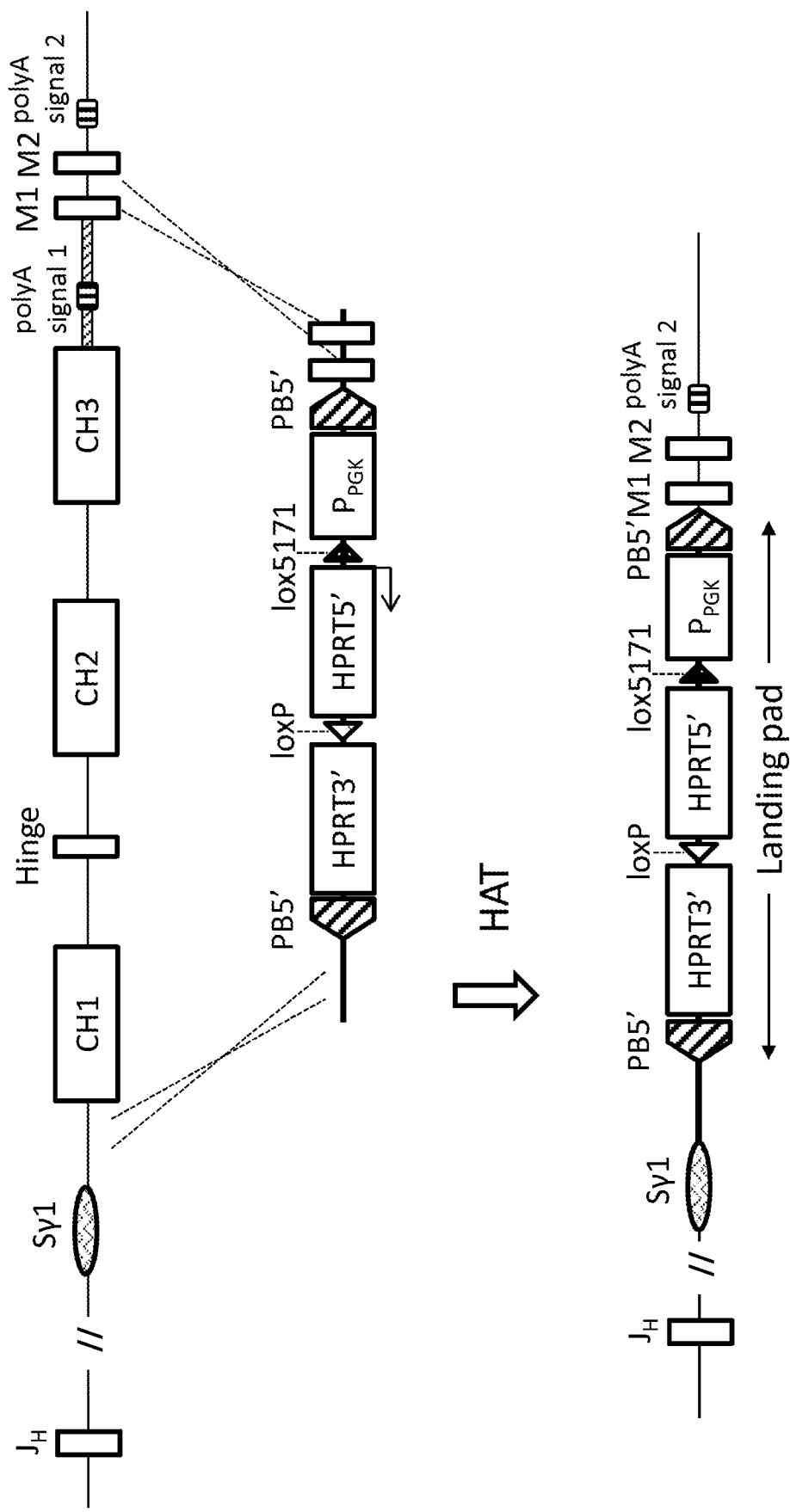
Figure 13B:
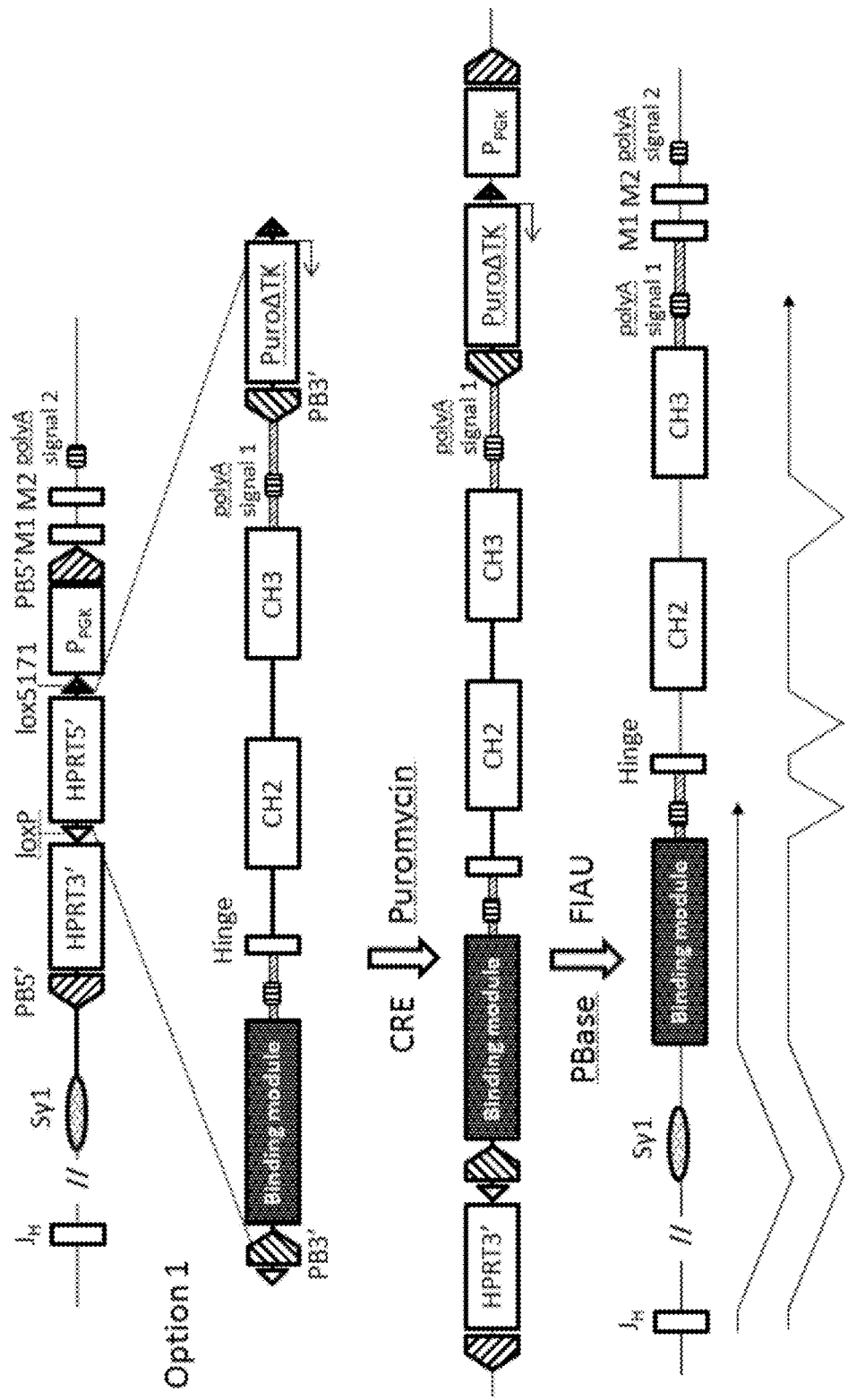
Figure 13C:
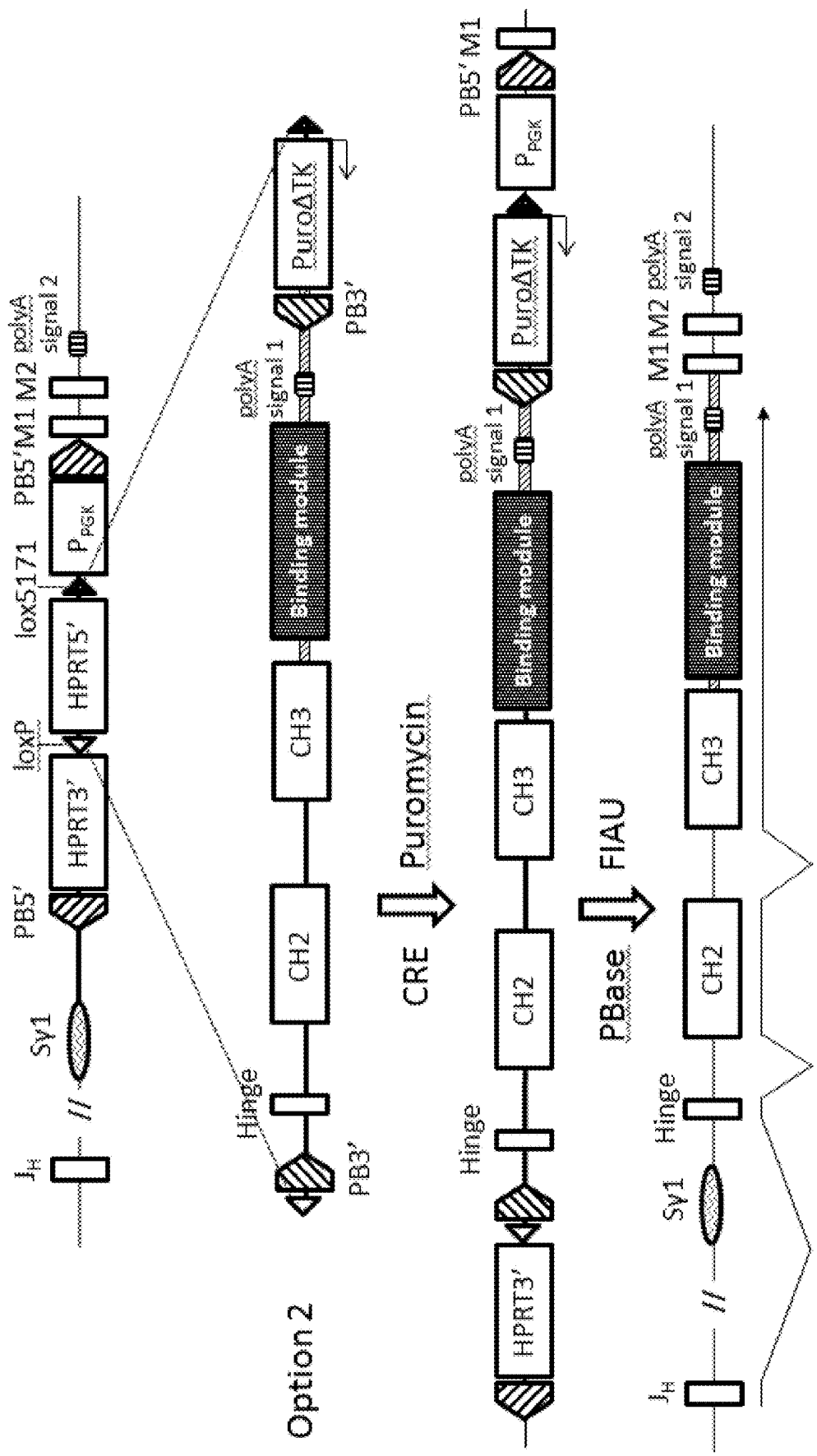
Figure 13D:
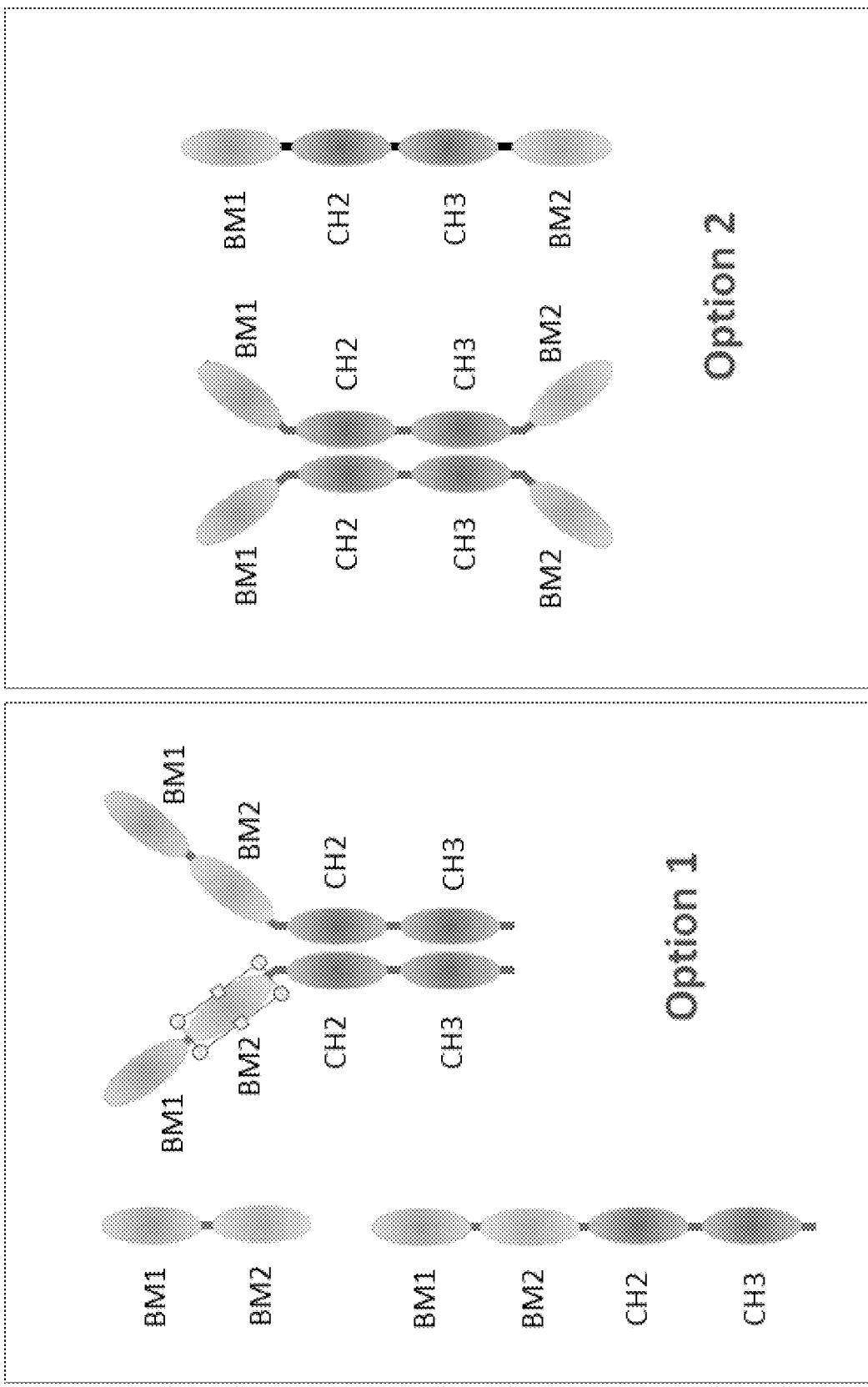
Figure 13E:
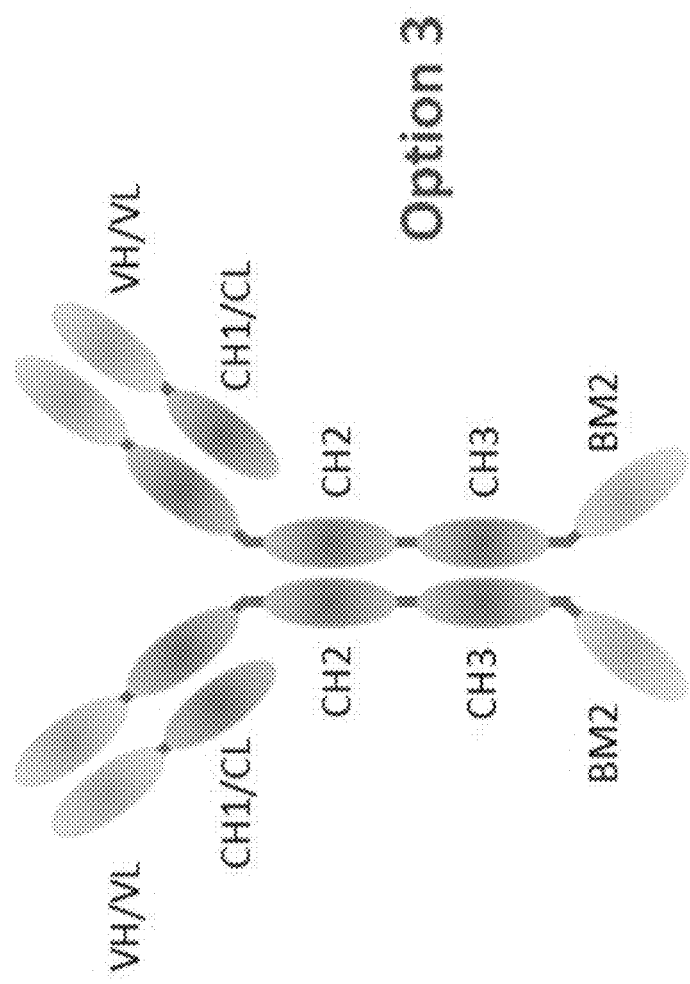

In another example, the Binding Module sequence is inserted 3' of CH3 (FIG. 13C).

In an example, all Binding Module variable regions are human. Additionally or alternatively, the common VL is human. Thus, where human V, D and J gene segments are present in the IgH locus 5' of the common VL sequence, following immunisation with the antigen, there are produced bispecific products whose binding domains are all human (the product would have a 5' scFv specific for the antigen used for immunisation and a 3' scFv specific for the other antigen). The 5' binding domains would be selected and matured in vivo in response to immunisation. The 3' binding domains would retain specificity for the antigen (eg, CD3 or CD16) against which they originally bound.

TABLE 1

Examples bispecific products specific for CD19 and CD3 or CD16

| Common VL specific for target* | L2 linker connecting to target specific Binding Module (BM) | First V-region of BM | L3 linker connecting the two V-regions of BM | Second V-region of BM |
|---|---|---|---|---|
| Anti-CD19 VL | (GGS)$_3$ | Anti-CD3 VH | VEGGSGGSGGSGGSGGVD | Anti-CD3 VL |
| | (GGGGS)$_3$ | Anti-CD3 VL | (GGGGS)$_3$ | Anti-CD3 VH |
| | (GGGGS)$_2$ | Anti-CD16 VH | (GGGGS)$_2$ | Anti-CD16 VL |
| | (GGGGS) | Anti-CD16 VL | (GGGGS); or AKTTP; or AKTTPRLGG; or EEGEFSEA | Anti-CD16VH |
| | VEGGSGGSGGSGGSGGVD | | (GGGGS); or AKTTP; or AKTTPRLGG; or EEGEFSEA | |

*or a dummy (germline) VL sequence can be used.

The general concept of linking V-regions with suitable linkers and connecting such created scFv or binding units with other binding modules to generate mono- or bispecific binding entities and the optimization of such linkers is described extensively in the literature (for example, see Neri D, Momo M, Prospero T, Winter G. J Mol Biol. 1995 Feb. 24; 246(3):367-73); Wright M J, Deonarain M P. Mol Immunol. 2007 April; 44(11):2860-9). The linker length can influence the molecular format that is preferentially produced. For example, monomeric bispecific tandem scFvs or so-called diabody formats where V regions form a VH-VL binding module are provided by two independent polypeptide chains.

Examples for L3 sequences are:

VEGGSGGSGGSGGSGGVD encoded by
GTCGAAGGTGGAAGTGGAGGTTCTGGTGGAAGTGGAGGTTCAGGTGGAGT
CGAC

GGGGSGGGGSGGGGS (aka (G4S)3) encoded by
GGTGGTGGTGGTTCTGGCGGCGGCGGCTCCGGTGGTGGTGGTTCT

GGGGSGGGGSGGGGS (aka (G4S)2) encoded by
GGCGGCGGCGGCTCCGGTGGTGGTGGTTCT

GGGGS Encoded by GGAGGTGGTGGATCC

AKTTP Encoded by gccaaaacaacaccc
(see WO2004024771)

AKTTPRLGG (see WO2004024771)

EEGEFSEA encoded by
gaagaaggtgaatttcagaagca
(see US20090214574)

Examples for L2 sequences are:

GGSGGSGGS (aka (G2S)3) encoded by
GGTGGTTCTGGTGGTTCTGGTGGTTCT

GGGGSGGGGSGGGGS (aka (G4S)3) encoded by
GGTGGTGGTGGTTCTGGCGGCGGCGGCTCCGGTGGTGGTGGTTCT

GGGGSGGGGSGGGGS (aka (G4S)2) encoded by
GGCGGCGGCGGCTCCGGTGGTGGTGGTTCT

GGGGS Encoded by GGAGGTGGTGGATCC

VEGGSGGSGGSGGSGGVD encoded by
GTCGAAGGTGGAAGTGGAGGTTCTGGTGGAAGTGGAGGTTCAGGTGGAGT
CGAC

Examples of human anti-CD3 variable regions that can be employed in such bispecific therapeutics are: (see WO2010132872, the sequences of which are incorporated herein by reference for use in the present invention)
VH (which is SEQ ID NO: 2 in WO2010132872)

QVQLVESGGGVVQPGRSLRLSCAASGFKFSGYGMHWVRQAPGKGLEWVAV
IWYDGSKKYYVDSVKGRFTISRDNSKNTLYLQMNSLRAEDTAVYYCARQM
GYWHFDLWGRGTLVTVSS

Encoded by

```
caggtgcagc tggtggagtc cgggggaggc gtggtccagc
ctgggaggtc cctgagactc tcctgtgcag cgtctggatt
caagttcagt ggctatggca tgcactgggt ccgccaggct
ccaggcaagg gctgagtg ggtggcagtt atatggtatg
```

```
atggaagtaa gaaatactat gtagactccg tgaagggccg
cttcaccatc tccagagaca attccaagaa cacgctgtat
ctgcaaatga acagcctgag agccgaggac acggctgtgt
attactgtgc gagacaaatg ggctactggc acttcgatct
ctggggccgt ggcaccctgg tcactgtctc ctca
```

VL (which is SEQ ID NO: 4 in WO2010132872)

EIVLTQSPATLSLSPGERATLSCRASQSVSSYLAWYQQKPGQAPRLLIYD
ASNRATGIPARFSGSGSGTDFTLTISSLEPEDFAVYYCQQRSNWPPLTFG
GGTKVEIK

Encoded by

```
gaaattgtgt tgacacagtc tccagccacc ctgtctttgt
ctccagggga aagagccacc ctctcctgca gggccagtca
gagtgttagc agctacttag cctggtacca acagaaacct
ggccaggctc ccaggctcct catctatgat gcatccaaca
gggccactgg catcccagcc aggttcagtg gcagtgggtc
tgggacagac ttcactctca ccatcagcag cctagagcct
gaagattttg cagtttatta ctgtcagcag cgtagcaact
ggcctccgct cactttcggc ggagggacca aggtggagat
caaa
```

Human Anti CD3VH

QVQLVESGGGVVQPGRSLRLSCAASGFKFSpYGMHIWVRQAPGKGLEWVA
IVIWYDGSKKYYVDSVKGIRFTISRDNSKNTLYLQMNSLRAEDTAVYYCA
R^GYWHFDLIWGRGTLVTVSS encoded by GAAATTGTGTTGACACAGTCTCCAGCCACCCTGTCTTTGTCTCCAGGGGA
AAGAGCCACCCTCTCCTGCAGGGCCAGTCAGAGTGTTAGCAGCTACTTAG
CCTGGTACCAACAGAAACCTGGCCAGGCTCCCAGGCTCCTCATCTATGAT
GCATCCAACAGGGCCACTGGCATCCCAGCCAGGTTCAGTGGCAGTGGGTC
TGGGACAGACTTCACTCTCACCATCAGCAGCCTAGAGCCTGAAGATTTTG
CAGTTTATTACTGTCAGCAGCGTAGCAACTGGCCTCCGCTCACTTTCGGC
GGAGGGACCAAGGTGGAGATCAAA Human Anti-CD3 VL EIVLTQS PATLSLS PGERATLSCIRASQSVS
SYLAJWYQQKPGQAPRLLIYIDASNRATIGI PAR
FSGSGSGTDFTLT I S SLEPEDFAVYYCQQRSNWPPLT
FGGGTKVEIK encoded by

GAAATTGTGTTGACACAGTCTCCAGCCACCCTGTCTTTGTCTCCAGGGGA

AAGAGCCACCCTCTCCTGCAGGGCCAGTCAGAGTGTTAGCAGCTACTTAG

CCTGGTACCAACAGAAACCTGGCCAGGCTCCCAGGCTCCTCATCTATGAT

GCATCCAACAGGGCCACTGGCATCCCAGCCAGGTTCAGTGGCAGTGGGTC

TGGGACAGACTTCACTCTCACCATCAGCAGCCTAGAGCCTGAAGATTTTG

CAGTTTATTACTGTCAGCAGCGTAGCAACTGGCCTCCGCTCACTTTCGGC

GGAGGGACCAAGGTGGAGATCAAA

Further examples of CD3 binding VH and VLs are shown below

Anti CD3 VH

DIKLQQSGAELARPGASVKMSCKTSGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSS

Encoded by

GATATCAAACTGCAGCAGTCAGGGGCTGAACTGGCAAGACCTGGGGCCTC

AGTGAAGATGTCCTGCAAGACTTCTGGCTACACCTTTACTAGGTACACGA

TGCACTGGGTAAAACAGAGGCCTGGACAGGGTCTGGAATGGATTGGATAC

ATTAATCCTAGCCGTGGTTATACTAATTACAATCAGAAGTTCAAGGACAA

GGCCACATTGACTACAGACAAATCCTCCAGCACAGCCTACATGCAACTGA

GCAGCCTGACATCTGAGGACTCTGCAGTCTATTACTGTGCAAGATATTAT

GATGATCATTACTGCCTTGACTACTGGGGCCAAGGCACCACTCTCACAGT

CTCCTCA

Anti CD3 VH

QVQLQQSGAELARPGASVKMSCKASGYTFTRYTMHWVKQRPGQGLEWIGY

INPSRGYTNYNQKFKDKATLTTDKSSSTAYMQLSSLTSEDSAVYYCARYY

DDHYSLDYWGQGTTLTVSS

Encoded by

Caggtgcagctgcagcagtctggggctgaactggcaagacctggggcctc agtgaagatgtcctgcaaggcttctggctacacctttactaggtacacga tgcactgggtaaaacagaggcctggacagggtctggaatggattggatac attaatcctagccgtggttatactaattacaatcagaagttcaaggacaa ggccacattgactacagacaaatcctccagcacagcctacatgcaactga gcagcctgacatctgaggactctgcagtctattactgtgcaagatattat gatgatcattacagccttgactactggggccaaggcaccactctcacagt ctcctca Anti CD3 VL

DIQLTQSPAIMSASPGEKVTMTCRASSSVSYMNWYQQKSGTSPKRWIYDT

SKVASGVPYRFSGSGSGTSYSLTISSMEAEDAATYYCQQWSSNPLTFGAG

TKLELK

Encoded by

GACATTCAGCTGACCCAGTCTCCAGCAATCATGTCTGCATCTCCAGGGGA

GAAGGTCACCATGACCTGCAGAGCCAGTTCAAGTGTAAGTTACATGAACT

GGTACCAGCAGAAGTCAGGCACCTCCCCCAAAAGATGGATTTATGACACA

TCCAAAGTGGCTTCTGGAGTCCCTTATCGCTTCAGTGGCAGTGGGTCTGG

GACCTCATACTCTCTCACAATCAGCAGCATGGAGGCTGAAGATGCTGCCA

CTTATTACTGCCAACAGTGGAGTAGTAACCCGCTCACGTTCGGTGCTGGG

ACCAAGCTGGAGCTGAA

Anti CD3 VL

DIVLTQSPAIMSASPGEKVTMTCSASSSVSYMNWYQQKSGTSPKRWIYDT

SKLASGVPAHFRGSGSGTSYSLTISGMEAEDAATYYCQQWSSNPFTFGSG

TKLEIN

Encoded by

Gatatcgtgctcactcagtctccagcaatcatgtctgcatctccagggga gaaggtcaccatgacctgcagtgccagctcaagtgtaagttacatgaact ggtaccagcagaagtcaggcacctcccccaaaagatggatttatgacaca tccaaactggcttctggagtccctgctcacttcaggggcagtgggtctgg gacctcttactctctcacaatcagcggcatggaggctgaagatgctgcca cttattactgccagcagtggagtagtaacccattcacgttcggctcgggg acaaagttggaaataaac A suitable scFv binding module to CD3 could therefore be encoded by:

GATATCAAACTGCAGCAGTCAGGGGCTGAACTGGCAAGACCTGGGGCCTC

AGTGAAGATGTCCTGCAAGACTTCTGGCTACACCTTTACTAGGTACACGA

TGCACTGGGTAAAACAGAGGCCTGGACAGGGTCTGGAATGGATTGGATAC

ATTAATCCTAGCCGTGGTTATACTAATTACAATCAGAAGTTCAAGGACAA

GGCCACATTGACTACAGACAAATCCTCCAGCACAGCCTACATGCAACTGA

GCAGCCTGACATCTGAGGACTCTGCAGTCTATTACTGTGCAAGATATTAT

GATGATCATTACTGCCTTGACTACTGGGGCCAAGGCACCACTCTCACAGT

CTCCTCAGTCGAAGGTGGAAGTGGAGGTTCTGGTGGAAGTGGAGGTTCAG

GTGGAGTCGACGACATTCAGCTGACCCAGTCTCCAGCAATCATGTCTGCA

TCTCCAGGGGAGAAGGTCACCATGACCTGCAGAGCCAGTTCAAGTGTAAG

TTACATGAACTGGTACCAGCAGAAGTCAGGCACCTCCCCCAAAAGATGGA

TTTATGACACATCCAAAGTGGCTTCTGGAGTCCCTTATCGCTTCAGTGGC

AGTGGGTCTGGGACCTCATACTCTCTCACAATCAGCAGCATGGAGGCTGA

AGATGCTGCCACTTATTACTGCCAACAGTGGAGTAGTAACCCGCTCACGT

TCGGTGCTGGGACCAAGCTGGAGCTGAA

Translating into a polypeptide sequence of

DIKLQQSGAELARPGASVKMSCKTSGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSSVEGGSGGSGGSGGSGGVDDIQLTQSPAIMSA

SPGEKVTMTCRASSSVSYMNWYQQKSGTSPKRWIYDTSKVASGVPYRFSG

SGSGTSYSLTISSMEAEDAATYYCQQWSSNPLTFGAGTKLEL

Alternatively, VH and VL sequences that constitute binding moieties for CD16 effector cell recruitment could be used, which favours the recruitment of NK-cells rather than T-cells. Examples of human anti-CD16 variable regions are described in US2009021474.

Human Anti-CD16A VH

EVQLVQSGAEVKKPGESLKVSCKASGYTFTSYYMHWVRQAPGQGLEWMGI

INPSGGSTSYAQKFQGRVTMTRDTSTSTVYMELSSLRSEDTAVYYCARGS

AYYYDFADYWGQGTLVTVSS

Encoded by

GAGGTCCAGCTGGTACAGTCTGGAGCAGAGGTGAAAAAGCCCGGGGAGTC

TCTGAAGGTTTCCTGCAAGGCATCTGGATACACCTTCACCAGCTACTATA

TGCACTGGGTGCGACAGGCCCCTGGACAAGGGCTTGAGTGGATGGGAATA

ATCAACCCTAGTGGTGGTAGCACAAGCTACGCACAGAAGTTCCAGGGCAG

AGTCACCATGACCCGGGACACGTCCACGAGCACAGTCTACATGGAGCTTA

GCAGCCTGAGATCTGAGGACACGGCCGTGTATTACTGTGCTAGAGGTAGT

GCTTATTACTACGATTTTGCTGACTACGGGGCCAGGGAACCCTGGTCAC

CGTCTCCTCA

Human Anti-CD16A VL

QPVLTQPSSVSVAPGQTATISCGGHNIGSKNVHWYQQRPGQSPVLVIYQD

NKRPSGIPERFSGSNSGNTATLTISGTQAMDEADYYCQVWDNYSVLFGGG

TKLTVL

Encoded by

CAGCCTGTGCTGACTCAGCCATCCTCGGTGTCAGTGGCCCCAGGACAGAC

GGCCACGATCTCCTGTGGGGGACACAACATTGGGAGTAAAAATGTGCACT

GGTACCAGCAGAGGCCAGGCCAGTCCCCTGTGTTGGTCATTTATCAGGAT

AATAAGCGGCCCTCAGGGATCCCTGAGCGATTCTCTGGCTCCAACTCTGG

GAACACAGCCACTCTGACCATCAGCGGGACCCAGGCGATGGATGAGGCTG

ACTACTATTGTCAGGTGTGGGACAATTACAGTGTGCTATTCGGCGGAGGG

ACCAAGCTGACCGTCCTA

Further examples of CD16 binding V-regions are described in EP1314741, the sequences of which are incorporated herein by reference for use in the present invention.

Anti-CD16 Binding VL

DIQAVVTQESALTTSPGETVTLTCRSNTGTVTTSNYANWVQEKPDHLFTG

LIGHTNNRAPGVPARFSGSLIGDKAALTITGAQTEDEAIYFCALWYNNHW

VFGGGTKLTVL

Encoded by

GATATCCAGCTGACCCAGTCTCCAGCTTCTTTGGCTGTGTCTCTAGGGCA

GAGGGCCACCATCTCCTGCAAGGCCAGCCAAAGTGTTGATTATGATGGTG

ATAGTTATTTGAACTGGTACCAACAGATTCCAGGACAGCCACCCAAACTC

CTCATCTATGATGCATCCAATCTAGTTTCTGGGATCCCACCCAGGTTTAG

TGGCAGTGGGTCTGGGACAGACTTCACCCTCAACATCCATCCTGTGGAGA

AGGTGGATGCTGCAACCTATCACTGTCAGCAAAGTACTGAGGATCCGTGG

ACGTTCGGTGGAGGGACCAAGCTCGAGATCAAA

Anti-CD16 Binding VH

QVQLQQSGAELVRPGTSVKISCKASGYTFTNYWLGWVKQRPGHGLEWIGD

IYPGGGYTNYNEKFKGKATVTADTSSRTAYVQVRSLTSEDSAVYFCARSA

SWYFDVWGARTTVTVSS

Encoded by

CAGGTGCAGCTGCAGCAGTCTGGGGCTGAGCTGGTGAGGCCTGGGTCCTC

AGTGAAGATTTCCTGCAAGGCTTCTGGCTATGCATTCAGTAGCTACTGGA

TGAACTGGGTGAAGCAGAGGCCTGGACAGGGTCTTGAGTGGATTGGACAG

ATTTGGCCTGGAGATGGTGATACTAACTACAATGGAAAGTTCAAGGGTAA

AGCCACTCTGACTGCAGACGAATCCTCCAGCACAGCCTACATGCAACTCA

GCAGCCTAGCATCTGAGGACTCTGCGGTCTATTTCTGTGCAAGACGGGAG

ACTACGACGGTAGGCCGTTATTACTATGCTATGGACTACTGGGGCCAAGG

GACCACGGTCACCGTCTCCTCCG

An example of a CD19 binding scFv VL-VH including a linker coding for GGGGSGGGGSGGGGS (G4S)3 (highlighted in bold)

DIQLTQSPASLAVSLGQRATISCKASQSVDYDGDSYLNWYQQIPGQPPKL

LIYDASNLVSGIPPRFSGSGSGTDFTLNIHPVEKVDAATYHCQQSTEDPW

TFGGGTKLEIKGGGGSGGGGSGGGGSQVQLQQSGAELVRPGSSVKISCKA

SGYAFSSYWMNWVKQRPGQGLEWIGQIWPGDGDTNYNGKFKGKATLTADE

SSSTAYMQLSSLASEDSAVYFCARRETTTVGRYYYAMDYWGQGTTVTVSS

Encoded by

```
GATATCCAGCTGACCCAGTCTCCAGCTTCTTTGGCTGTGTCTCTAGGGCA
GAGGGCCACCATCTCCTGCAAGGCCAGCCAAAGTGTTGATTATGATGGTG
ATAGTTATTTGAACTGGTACCAACAGATTCCAGGACAGCCACCCAAACTC
CTCATCTATGATGCATCCAATCTAGTTTCTGGGATCCCACCCAGGTTTAG
TGGCAGTGGGTCTGGGACAGACTTCACCCTCAACATCCATCCTGTGGAGA
AGGTGGATGCTGCAACCTATCACTGTCAGCAAAGTACTGAGGATCCGTGG
ACGTTCGGTGGAGGGACCAAGCTCGAGATCAAAGGTGGTGGTGGTTCTGG
CGGCGGCGGCTCCGGTGGTGGTGGTTCTCAGGTGCAGCTGCAGCAGTCTG
GGGCTGAGCTGGTGAGGCCTGGGTCCTCAGTGAAGATTTCCTGCAAGGCT
TCTGGCTATGCATTCAGTAGCTACTGGATGAACTGGGTGAAGCAGAGGCC
TGGACAGGGTCTTGAGTGGATTGGACAGATTTGGCCTGGAGATGGTGATA
CTAACTACAATGGAAAGTTCAAGGGTAAAGCCACTCTGACTGCAGACGAA
TCCTCCAGCACAGCCTACATGCAACTCAGCAGCCTAGCATCTGAGGACTC
TGCGGTCTATTTCTGTGCAAGACGGGAGACTACGACGGTAGGCCGTTATT
ACTATGCTATGGACTACTGGGGCCAAGGGACCACGGTCACCGTCTCCTCC
```

An example of a CD19 binding scFv VH-VL including a linker coding for GGGGSGGGGSGGGGS (G4S)3 (highlighted in bold)

QVQLQQSGAELVRPGSSVKISCKASGYAFSSYWMNWVKQRPGQGLEWIGQ

IWPGDGDTNYNGKFKGKATLTADESSSTAYMQLSSLASEDSAVYFCARRE

TTTVGRYYYAMDYWGQGTIVIVSSGGGGSGGGGSGGGGSDIQLTQSPASL

AVSLGQRATISCKASQSVDYDGDSYLNWYQQIPGQPPKLLIYDASNLVSG

IPPRFSGSGSGTDFTLNIHPVEKVDAATYHCQQSTEDPWTFGGGTKLEIK

Encoded by

```
CAGGTGCAGCTGCAGCAGTCTGGGGCTGAGCTGGTGAGGCCTGGGTCCTC
AGTGAAGATTTCCTGCAAGGCTTCTGGCTATGCATTCAGTAGCTACTGGA
TGAACTGGGTGAAGCAGAGGCCTGGACAGGGTCTTGAGTGGATTGGACAG
ATTTGGCCTGGAGATGGTGATACTAACTACAATGGAAAGTTCAAGGGTAA
AGCCACTCTGACTGCAGACGAATCCTCCAGCACAGCCTACATGCAACTCA
GCAGCCTAGCATCTGAGGACTCTGCGGTCTATTTCTGTGCAAGACGGGAG
ACTACGACGGTAGGCCGTTATTACTATGCTATGGACTACTGGGGCCAAGG
GACCACGGTCACCGTCTCCTCC GGTGGTGGTGGTTCTGGCGGCGGCGGC
TCCGGTGGTGGTGGTTCTGATATCCAGCTGACCCAGTCTCCAGCTTCTTT
GGCTGTGTCTCTAGGGCAGAGGGCCACCATCTCCTGCAAGGCCAGCCAAA
GTGTTGATTATGATGGTGATAGTTATTTGAACTGGTACCAACAGATTCCA
GGACAGCCACCCAAACTCCTCATCTATGATGCATCCAATCTAGTTTCTGG
GATCCCACCCAGGTTTAGTGGCAGTGGGTCTGGGACAGACTTCACCCTCA
ACATCCATCCTGTGGAGAAGGTGGATGCTGCAACCTATCACTGTCAGCAA
AGTACTGAGGATCCGTGGACGTTCGGTGGAGGGACCAAGCTCGAGATCAA
A
```

An example module as described in Table x with a fixed VL from a CD19 binding antibody and a scFv specific for human CD3 is encoded as:

```
GGTGGTGGTGGTTCTGGCGGCGGCGGCTCCGGTGGTGGTGGTTCTGATAT
CCAGCTGACCCAGTCTCCAGCTTCTTTGGCTGTGTCTCTAGGGCAGAGGG
CCACCATCTCCTGCAAGGCCAGCCAAAGTGTTGATTATGATGGTGATAGT
TATTTGAACTGGTACCAACAGATTCCAGGACAGCCACCCAAACTCCTCAT
CTATGATGCATCCAATCTAGTTTCTGGGATCCCACCCAGGTTTAGTGGCA
GTGGGTCTGGGACAGACTTCACCCTCAACATCCATCCTGTGGAGAAGGTG
GATGCTGCAACCTATCACTGTCAGCAAAGTACTGAGGATCCGTGGACGTT
CGGTGGAGGGACCAAGCTCGAGATCAAAGGAGGTGGTGGATCCGATATCA
AACTGCAGCAGTCAGGGGCTGAACTGGCAAGACCTGGGGCCTCAGTGAAG
ATGTCCTGCAAGACTTCTGGCTACACCTTTACTAGGTACACGATGCACTG
GGTAAAACAGAGGCCTGGACAGGGTCTGGAATGGATTGGATACATTAATC
CTAGCCGTGGTTATACTAATTACAATCAGAAGTTCAAGGACAAGGCCACA
TTGACTACAGACAAATCCTCCAGCACAGCCTACATGCAACTGAGCAGCCT
GACATCTGAGGACTCTGCAGTCTATTACTGTGCAAGATATTATGATGATC
ATTACTGCCTTGACTACTGGGGCCAAGGCACCACTCTCACAGTCTCCTCA
GTCGAAGGTGGAAGTGGAGGTTCTGGTGGAAGTGGAGGTTCAGGTGGAGT
CGACGACATTCAGCTGACCCAGTCTCCAGCAATCATGTCTGCATCTCCAG
GGGAGAAGGTCACCATGACCTGCAGAGCCAGTTCAAGTGTAAGTTACATG
AACTGGTACCAGCAGAAGTCAGGCACCTCCCCCAAAAGATGGATTTATGA
CACATCCAAAGTGGCTTCTGGAGTCCCTTATCGCTTCAGTGGCAGTGGGT
CTGGGACCTCATACTCTCTCACAATCAGCAGCATGGAGGCTGAAGATGCT
GCCACTTATTACTGCCAACAGTGGAGTAGTAACCCGCTCACGTTCGGTGC
TGGGACCAAGCTGGAGCTGAA
```

Resulting in an amino acid sequence of

GGGGSGGGGSGGGGSDIQLTQSPASLAVSLGQRATISCKASQSVDYDGDS

YLNWYQQIPGQPPKLLIYDASNLVSGIPPRFSGSGSGTDFTLNIHPVEKV

DAATYHCQQSTEDPWTFGGGTKLEIKGGGGSDIKLQQSGAELARPGASVK

MSCKTSGYTFTRYTMHWVKQRPGQGLEWIGYINPSRGYTNYNQKFKDKAT

LTTDKSSSTAYMQLSSLTSEDSAVYYCARYYDDHYCLDYWGQGTTLTVSS

VEGGSGGSGGSGGSGGVDDIQLTQSPAIMSASPGEKVTMTCRASSSVSYM

NWYQQKSGTSPKRWIYDTSKVASGVPYRFSGSGSGTSYSLTISSMEAEDA

ATYYCQQWSSNPLTFGAGTKLEL to which an N-terminal human VH domain generated in vivo in the vertebrate or cell of the invention will be fused in vivo as described above. VH domains for pairing with the encoded VL specific for CD19 can be generated for example by immunising transgenic vertebrates of the invention with human CD19. In vivo recombination of VDJ gene segments of the heavy chain locus in the vertebrate (eg, mouse) genome will then generate an scFv module consisting of a VH selected in vivo in the animal and a VL encoded in the genome of the vertebrate, that is specific for human CD19 connected via a linker to a binding module specific to human CD3 as outlined above.

Immunisation Procedures

Immunisation procedures for CD19 cell surface antigen have been described for the generation of monoclonal antibodies (PEZZUTTO, A., DÖRKEN, B., RABINOVITCH, P. S., LEDBETTER, J. A., MOLDENHAUER, G. and CLARK, E. A., CD19 monoclonal antibody HD37 inhibits anti-immunoglobulin-induced B cell activation and proliferation. J. Immunol.; Pezzutto A, Dörken B, Feller A, Moldenhauer G, Schwartz R, Wernet P, et al. HD37 monoclonal antibody: a useful reagent for further characterization of "non-T, non-B" lymphoid malignancies. In: Reinherz E L, Haynes B F, Nadler L M, Bernstein I D, editors. Leukocyte typing II. Proceedings of the 2nd International Workshop on Human Leukocyte Differentiation Antigens; 1984 Sep. 17-20; Boston, USA. New York, Berlin, Heidelberg, Tokyo: Springer-Verlag; 1986. Volume 2. p. 391-402. 138, 2793-2799 (1987).

Screening for CD19-Specific scFvs

Screening for molecules of the invention that are specific for human CD19 can be screened from culture supernatant of hybdridoma cells generated by the fusion of mouse (or other vertebrate) spleenocytes with myeloma lines as described by Köhler and Milstein. This can be achieved for example by screening for binding to primary cells or immortalised cell lines that express human CD19 on the cell surface using flow cytometry or immunoassay techniques such as cell-based ELISA or imaging technqiues such as Li-Cor Odysee™. Equally, bispecifc ELISA and SPR screens can be carried out using recombinant proteins as for example described in Moore et al 2011 (Moore P A, Zhang W, Rainey G J, et al. Application of dual-affinity re-targeting molecules to achieve optimal redirected T-cell killing of B-cell lymphoma. *Blood.* 2011; 117(17):4542-4551). Hybridoma clones positive for binding to human CD19 would be selected and subjected to secondary screening for binding to human CD19 and human CD3 separately using the same technqiues. Functional analysis of these selected clones would involve the CD19-mediated killing of B-cell lymphoma lines or the depletion of B-cells from human PBMC preparations both also described for example in Moore et al 2011.

Example 8: Transgenic Non-Human Vertebrates

Engineering Mouse IgG1 Constant Region (Landing Pad Insertion)

To allow for the in-vivo selection of multivalent (eg, multispecific or bispecific) polypeptide chains having a structure $VH_1$-$L_1$-$VL_1$-$L_2$-$VH_2$-$L_3$-$VL_2$-Hinge-CH2-CH3 as an example, the mouse IgG1 constant region was engineered as detailed below.

Figure 14A:
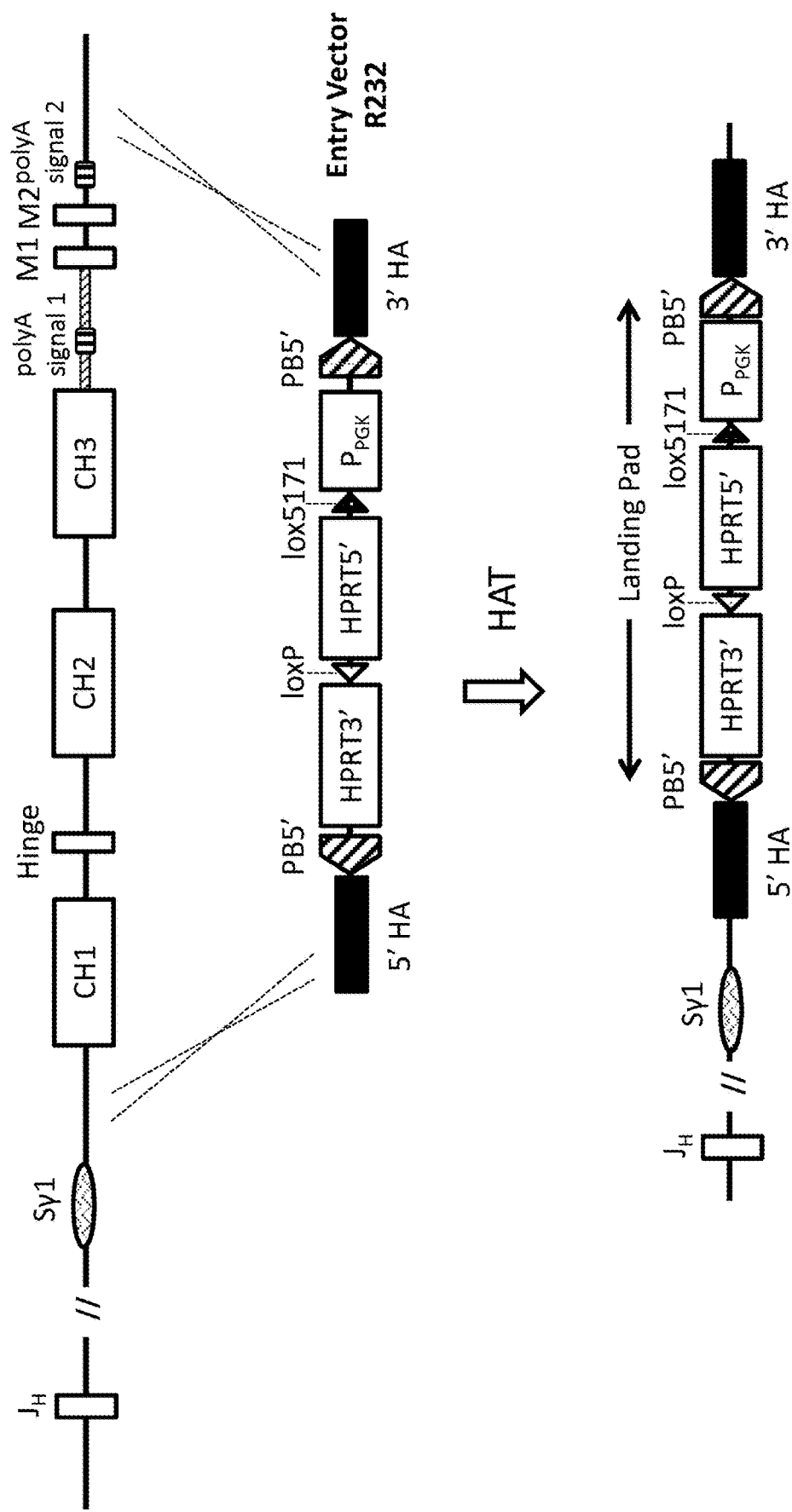
FIGS. 14A and 14B show the detailed method used to construct a non-human vertebrate comprising a transgenic locus for expressing multivalent polypeptides.

An entry vector termed R232 was constructed for targeting into the mouse IgG1 constant region containing features detailed in FIG. 14A using standard molecular biology techniques unless otherwise stated. Once the targeting vector is inserted into the IgG1 constant region, it acts as a landing pad for inserting any DNA fragments via RMCE, which could be for example a gene or multiple genes, Binding Modules such as antibody single variable domain(s) (dAbs), ScFv(s), peptides etc.

Mouse 129 BAC bMQ263j18 purchased from Source BioScience LifeSciences containing IgG1 constant region was used to retrieve by recombineering the 5' and 3' homology arms (HA). The 5'-HA was 2707 bp and the 3'-HA was 3001 bp and retrieval was done in plasmid pBR322. The oligos used for retrieval contained incorporated restriction sites to facilitate downstream cloning. The 5'-HA contained restriction sites NotI and MluI, whereas the 3'-HA contained restriction sites EcoRI and KpnI. The respective homology arms were cloned sequentially into vector R3, which contained an inactive piggyBAC transposon element with two PB5'LTRs and within it a PGK promoter and HPRT gene split into two portions (5'HPRT and 3'HPRT). The 3'-HPRT portion was flanked by loxP and mutant lox5171 sites. Cloning of the 5' and 3'-HA into R3 yielded the entry vector R232.

The entry vector was prepared for targeting into ES cells by linearizing with NotI restriction enzyme. Approximately 10 µg of linearised R232 plasmid DNA was used for targeting into ES cells containing human VDJ gene segments at an IgH locus. Targeted ES clones were selected on medium containing hypoxanthine-aminopterin-thymidine (HAT) and correctly targeted clones were genotyped by PCR.

Binding Module Vector Construction

The binding module vector was constructed using standard molecular cloning techniques unless otherwise stated. The IgG1 constant region containing the Hinge, CH2, CH3, M1 and M2 domains was retrieved from BAC bMQ263j18 by recombineering. scFv from the bispecific single chain antibody construct comprising binding domains specific for human CD3 and human CD19 as documented in WO2004/106381, was used as a fixed binding module against CD3. The overall binding module structure was similar to that of construct 2 (Sequence ID no. 1; protein ID no. 2) documented in WO2004/106381 except the variable heavy chain for CD19 was not included and the variable light chain for CD19 was replaced with a single rearranged common light chain. It was documented in EP2505654 that mice genetically engineered to express reverse chimeric immunoglobulin heavy chains associated with a single rearranged light chain (e.g. $V_k1$-39/J or $V_k3$-20/J), when immunised with an antigen of interest, generated B cells that comprised a diversity of human V segment rearrangements and expressed a diversity of high-affinity antigen specific antibodies. To this end, we used a rearranged $V_k1$-39$J_k5$ in the absence of a VH to form part of the binding module for a second antigen (this would combine with the VH produced by rearrangement of the human variable region gene segments at the 5' of the locus). Downstream of the fixed CD3 binding domain, intronic sequence located between mouse IgG1 CH1 and hinge domains was included to allow splicing of the CD3 binding domain to the hinge domain and thus the rest of the IgG1 constant region. The binding module domains and the intronic DNA was synthetically constructed through GeneArt (Invitrogen), which had the following structure:

$L_1$-$VL_{(Vk1\text{-}39Jk5)}$-$L_2$-$VH_{(CD3)}$-$L_3$-$VL_{(CD3)}$-Intronic-Seq $L_1$ is linker 1:

```
GGGGSGGGGSGGGGS encoded by GGTGGTGGTGGTTCTGGCGGCGG
CGGCTCCGGTGGTGGTGGTTCT
```

L₂ is linker 2:

SGGGGS encoded by TCCGGAGGTGGTGGATCC

L₃ is linker 3:

VEGGSGGSGGSGGSGGVD encoded by

GTCGAAGGTGGAAGTGGAGGTTCTGGTGGAAGTGGAGGTTCAGGTGGAGT

CGAC

VL$_{(Vk1-39Jk5)}$:

DIQMTQSPSSLSASVGDRVTITCRASQSISSYLNWYQQKPGKAPKLLIYA

ASSLQSGVPSRFSGSGSGTDFTLTISSLQPEDFATYYCQQSYSTPPITFG

QGTRLEIKRK

Encoded by

Gacatccagatgacccagtctccatcctccctgtctgcatctgtaggaga cagagtcaccatcacttgccgggcaagtcagagcattagcagctatttaa attggtatcagcagaaaccagggaaagcccctaagctcctgatctatgct gcatccagtttgcaaagtggggtcccatcaaggttcagtggcagtggatc tgggacagatttcactctcaccatcagcagtctgcaacctgaagattttg caacttactactgtcaacagagttacagtaccccctccgatccacccttcggc caagggacacgactggagattaaacgtaag

VH$_{(CD3)}$:

DIKLQQSGAELARPGASVKMSCKTSGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSS

Encoded by

GATATCAAACTGCAGCAGTCAGGGGCTGAACTGGCAAGACCTGGGGCCTC

AGTGAAGATGTCCTGCAAGACTTCTGGCTACACCTTTACTAGGTACACGA

TGCACTGGGTAAAACAGAGGCCTGGACAGGGTCTGGAATGGATTGGATAC

ATTAATCCTAGCCGTGGTTATACTAATTACAATCAGAAGTTCAAGGACAA

GGCCACATTGACTACAGACAAATCCTCCAGCACAGCCTACATGCAACTGA

GCAGCCTGACATCTGAGGACTCTGCAGTCTATTACTGTGCAAGATATTAT

GATGATCATTACTGCCTTGACTACTGGGGCCAAGGCACCACTCTCACAGT

CTCCTCA

VL$_{(CD3)}$:

DIQLTQSPAIMSASPGEKVTMTCRASSSVSYMNWYQQKSGTSPKRWIYDT

SKVASGVPYRFSGSGSGTSYSLTISSMEAEDAATYYCQQWSSNPLTFGAG

TKLELK

Encoded by

GACATTCAGCTGACCCAGTCTCCAGCAATCATGTCTGCATCTCCAGGGGA

GAAGGTCACCATGACCTGCAGAGCCAGTTCAAGTGTAAGTTACATGAACT

GGTACCAGCAGAAGTCAGGCACCTCCCCCAAAAGATGGATTTATGACACA

TCCAAAGTGGCTTCTGGAGTCCCTTATCGCTTCAGTGGCAGTGGGTCTGG

GACCTCATACTCTCTCACAATCAGCAGCATGGAGGCTGAAGATGCTGCCA

CTTATTACTGCCAACAGTGGAGTAGTAACCCGCTCACGTTCGGTGCTGGG

ACCAAGCTGGAGCTGAAA

Figure 14B:
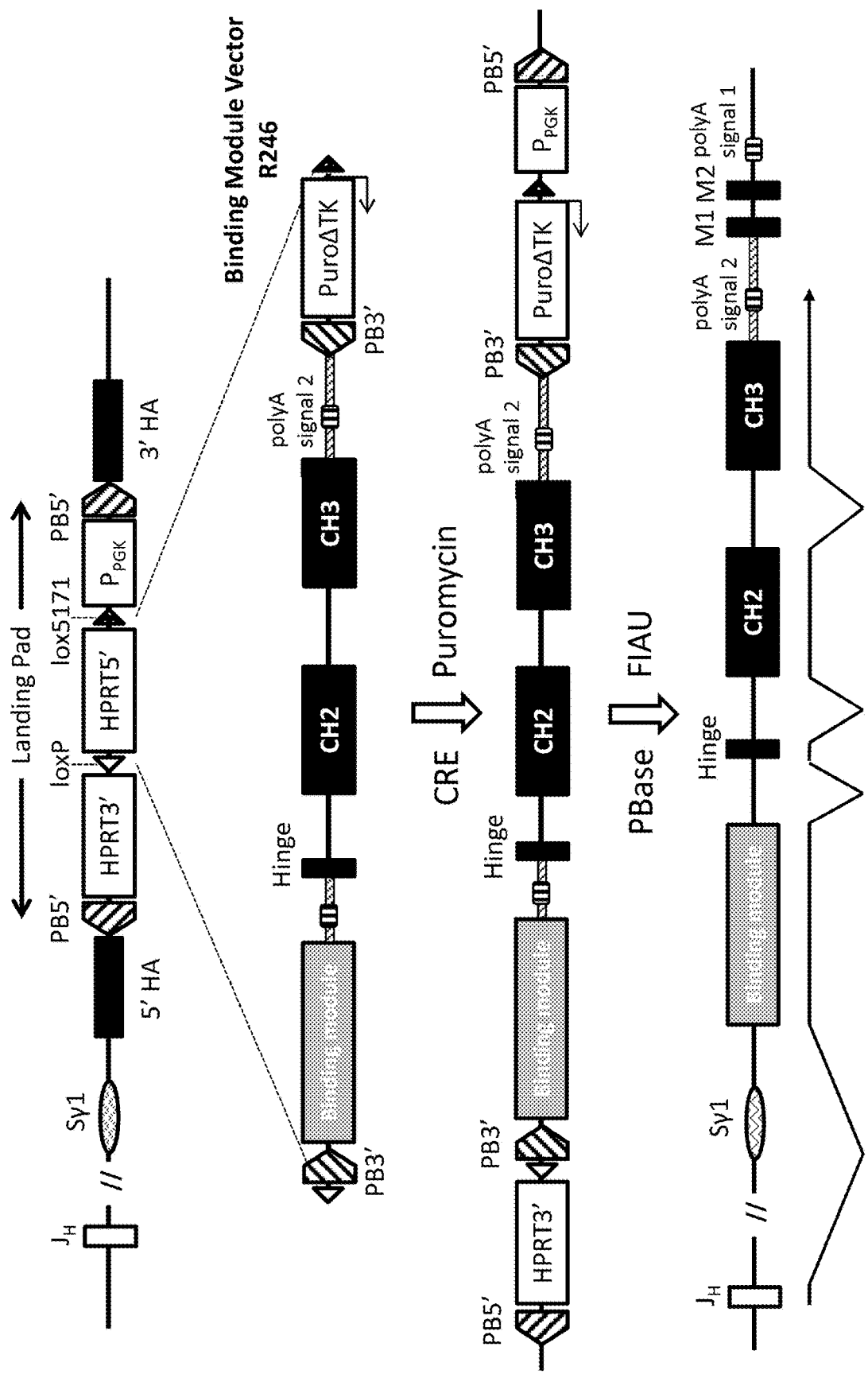

The retrieved mouse IgG1 constant region containing hinge, CH2, CH3, M1 and M2 was cloned downstream of the synthetically constructed binding module domains via NdeI and MluI restriction sites. The resulting binding module and IgG1 constant region was cloned as a single fragment into vector R217 via HindIII and MluI and in between two PB 3'LTRs, which also contained puro-delta-TK selection cassette and compatible lox sites to the entry vector to allow RMCE. The final structure of the binding module is shown in FIG. 14B and is referred to as R246.

Targeting of the binding module vector R246 into ES cells containing the landing pad was achieved by RMCE with transient expression of Cre recombinase and selection of clones in medium containing puromycin. Correctly targeted binding module vector in ES cells replaced the landing pad and reconstitutes two functional piggyBAC transposons at the 5' and 3' ends to the inserted binding module. The two functional transposons flank the modifying elements and the selection cassettes and thus these were conveniently excised simultaneously by transient expression of hyper-piggyBac transposase. Targeting of the binding module vector and the subsequent double excision were analysed sequentially by PCR.

Progeny mice were generated using standard procedures from the ES cells.

Bispecific Transcripts Amplification from Chimeric Mice

Figure 15B:
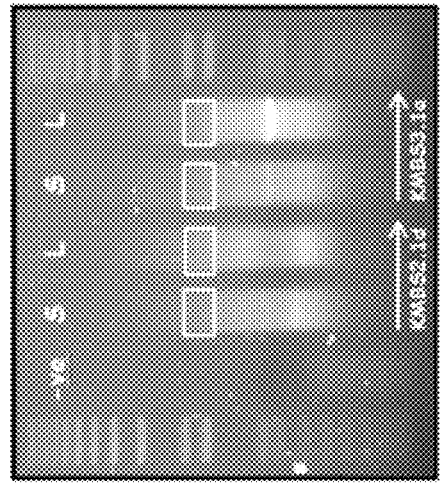
Figure 15D:
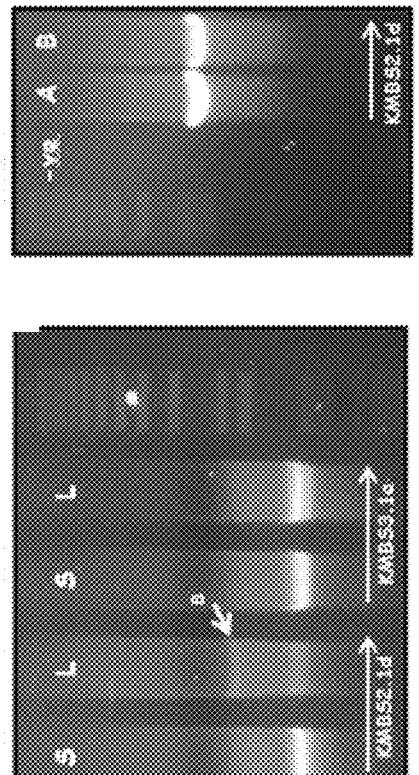
Figure 15A:
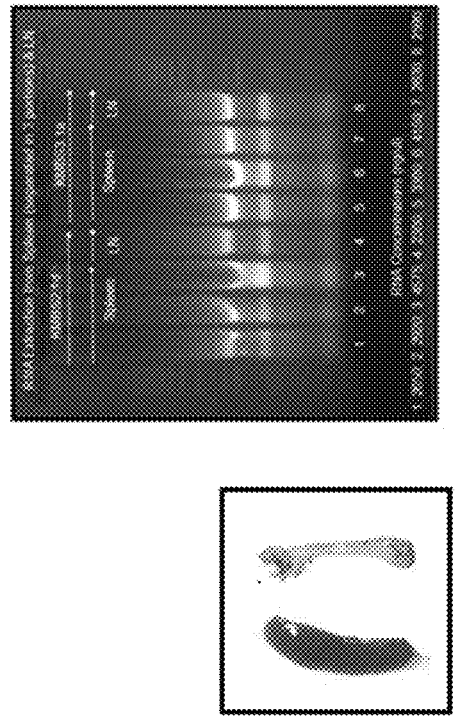

Two chimeric mouse (Table 2) were sacrificed 25 days after birth and their spleen and lymph nodes were collected and total RNA was extracted using Trizol reagent (Life Technologies) according to the manufacturer's protocol (FIG. 15a).

TABLE 2

Details of chimeric bispecific transgenic mice

| Details | Mouse 1 | Mouse 2 |
| --- | --- | --- |
| Mouse ID | KMBS2.1d | KMBS3.1a |
| Gender | Female | Male |
| Age | 25 Days | 25 Days |
| % Chimerism | 70% | 80% |
| Tissues Obtained | Spleen/Lymph Node | |

Figure 15C:
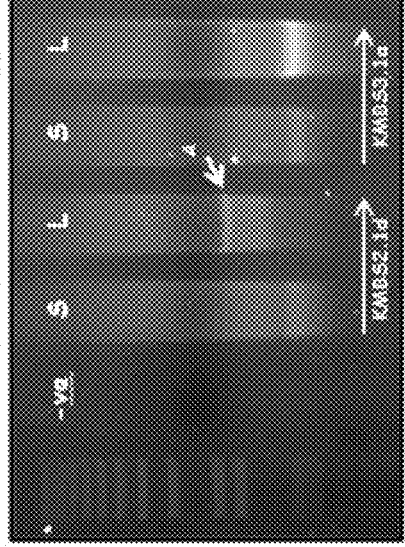

The spleen was sectioned into 3 equal portions from which total RNA was extracted. A reverse primer specific for mouse IgG1 CH2 domain was used for first strand cDNA synthesis from approx 5 µg total RNA with 5'-RACE second generation kit (Roche). The cDNA was purified with High Pure PCR Purification Kit (Roche). Poly(A) tailing was added to the first-strand cDNA using recombinant terminal transferase and dATP according to the manufacturer's protocol. The dA-tailed cDNA was used directly for PCR amplification using oligo dT-anchored primer and an internal reverse primer 1 specific for mouse IgG1 CH2 domain (1$^{st}$ round single semi-nested PCR) (FIG. 15B). A second round of PCR was carried out using 1 μl of gel extracted first round PCR product as template using the same nested oligo as the first round PCR ($2^{nd}$ round single semi-nested PCR) or using a further internal reverse primer 2 ($2^{nd}$ round double semi-nested PCR) specific for mouse CH2 domain and a PCR anchor primer (FIG. 15C). PCR products corresponding to the expected size of the bispecific transcript (approx. 1.7 kb) was gel extracted and the DNA purified using Qiagen gel extraction kit. A third round of PCR was carried out using a further internal reverse primer 3 ($3^{rd}$ round triple semi-nested PCR) specific for CH2 domain (FIG. 15D) to reduce the likelihood of amplifying any non-specific DNA fragments.

Results

Bispecific Antibody Transgenic Mice Generation

A transgenic mouse containing inserted human VDJ genes was further engineered. The IgG1 constant region was replaced initially by targeting in a landing pad. The landing pad facilitated the insertion of a binding module via RMCE containing the following structure $L_1$-$VL_1$-$L_2$-$VH_2$-$L_3$-$VL_2$-Hinge-CH2-CH3-Intronic-Seq-M1-M2, which lacked CH1 domain. To allow RNA splicing of V genes selected in-vivo to linker 1 ($L_1$), a splice acceptor was placed at the 5' end of $L_1$. In addition, the intragenic region located between the endogenous mouse IgG1 CH1 and hinge, was engineered between the $VL_2$ and hinge region within the binding module to allow correct splicing of the two domains. Furthermore to allow universal selection and rearrangement of VH genes to $L_1$ and thus heavy and light chain pairing, a common light chain was used ($Vk_1$-39/$Jk_5$) as $VL_1$.

Young naïve chimeric mice (25 days old) were analysed for mRNA transcripts corresponding to the expected size of novel bispecific antibodies using 5'-RACE. Using three rounds of sequential semi-nested PCR on cDNA synthesised from total RNA harvested from spleen and bone marrow using primers specific for IgG1 CH2 domain, transcripts with size corresponding to the expected size of novel bispecific antibodies (approx. 1.7 kb) could be detected in RNA extracted from lymph node of mouse KMBS2.1d. These transcripts were distinct in size from those amplified from the germ line allele (approx. 850 bp) (FIG. 15).

FIG. 16 shows a gel of the PCR product digested with SalI. Bands corresponding to the expected size of bispecific antibody transcripts could be seen. Sequencing will be carried out to further confirm the results.

The inventors believe that they have provided a method for generating products of guided selection that are stable and that can be generated in vivo via natural selection, VDJ rearrangement and class-switch recombination, and further wherein the constant region can be altered without adversely affecting VDJ rearrangement and class-switch recombination in the absence of a CH1 domain.

The invention claimed is:

1. A mouse comprising B cells whose genomes comprise:
(i) an antibody heavy chain locus comprising (in 5' to 3' direction) a rearranged or unrearranged variable region, a first switch, a mu constant region, a second switch and a non-mu constant region lacking a CHI gene segment;
(ii) a functional antibody light chain locus for expressing light chains;
    wherein the immature B cells of said mouse can express IgM antibodies comprising IgM-type heavy chains and light chains;
    wherein the heavy chain locus of said B cells is capable of undergoing isotype switching to produce non-mu antibodies comprising one or more non-mu-type heavy chains lacking a CH1 domain; and
said genomes further comprising:
    (a) a site specific recombinase sequence inserted in operable linkage to an AICDA gene promoter, such that the promoter controls expression of the site specific recombinase sequence, and
    (b) site specific recombination elements flanking at least the light chain J region gene segment(s) or the light chain constant region gene segment, wherein the flanking site specific recombination elements are in the same orientation or are in opposing orientation;
wherein mature B cells of said mouse express the site specific recombinase and delete or invert the light chain sequences flanked by the site specific recombination elements, thereby inactivating the light chain locus such that functional light chains are not expressed after isotype switching to said non-mu antibodies in the mature B cells, and wherein non-mu heavy chains are expressed by the mature B cells in the absence of light chain expression.

2. The mouse of claim 1, wherein said site specific recombinase sequence is encodes CRE.

3. The mouse of claim 1, wherein said site specific recombinase sequence encodes CRE and wherein said site specific recombination elements flanking at least the light chain J region gene segment(s) or the light chain constant region gene segment are lox sites.

4. The mouse of claim 3, wherein said light chain locus comprising said flanking lox sites is a kappa light chain locus.

5. The mouse of claim 3, wherein said light chain locus comprising said flanking lox sites is a lambda light chain locus.

6. The mouse of claim 1, wherein the AICDA gene promoter is endogenous.

* * * * *

UNITED STATES PATENT AND TRADEMARK OFFICE
CERTIFICATE OF CORRECTION

PATENT NO. : 10,667,501 B2
APPLICATION NO. : 14/543359
DATED : June 2, 2020
INVENTOR(S) : Volker Germaschewski et al.

Page 1 of 1

It is certified that error appears in the above-identified patent and that said Letters Patent is hereby corrected as shown below:

In the Claims

In Claim 2 (Column 181, Line 5), delete the word "is"

Signed and Sealed this
Fourteenth Day of July, 2020

Andrei Iancu
*Director of the United States Patent and Trademark Office*